(12) United States Patent
Goto

(10) Patent No.: US 7,298,878 B2
(45) Date of Patent: Nov. 20, 2007

(54) IMAGE DIAGNOSIS SUPPORTING DEVICE

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 703 days.

(21) Appl. No.: 10/312,779

(22) PCT Filed: Jul. 2, 2001

(86) PCT No.: PCT/JP01/05703

§ 371 (c)(1),
(2), (4) Date: Apr. 1, 2003

(87) PCT Pub. No.: WO02/02002

PCT Pub. Date: Jan. 10, 2002

(65) Prior Publication Data

US 2003/0179915 A1    Sep. 25, 2003

(30) Foreign Application Priority Data

| Jun. 30, 2000 | (JP) | ............................. 2000-198736 |
| Oct. 16, 2000 | (JP) | ............................. 2000-314550 |
| Jan. 10, 2001 | (JP) | ............................. 2001-002673 |
| Mar. 1, 2001 | (JP) | ............................. 2001-57226 |
| Jun. 21, 2001 | (JP) | ............................. 2001-187969 |

(51) Int. Cl.
*G06K 9/00* (2006.01)

(52) U.S. Cl. .......................... 382/128; 382/190; 378/21

(58) Field of Classification Search ................ 382/128, 382/129, 130, 131, 132, 133, 168, 190–194, 382/203, 256, 260, 274, 276, 291, 297, 305, 382/181; 600/425, 300; 358/520; 378/21, 378/4
See application file for complete search history.

(56) References Cited

U.S. PATENT DOCUMENTS

| 5,235,510 | A | * | 8/1993 | Yamada et al. | ............. 600/300 |
| 5,506,913 | A | * | 4/1996 | Ibison et al. | ................. 382/132 |
| 5,781,315 | A | * | 7/1998 | Yamaguchi | ................. 358/520 |
| 5,807,256 | A | * | 9/1998 | Taguchi et al. | ............. 600/425 |
| 6,441,821 | B1 | * | 8/2002 | Nagasawa | .................... 345/426 |
| 6,542,771 | B2 | * | 4/2003 | Saotome et al. | ............ 600/425 |
| 6,748,099 | B1 | * | 6/2004 | Kawata | ....................... 382/132 |

* cited by examiner

*Primary Examiner*—Seyed Azarian
(74) *Attorney, Agent, or Firm*—Antonelli, Terry, Stout & Kraus, LLP.

(57) ABSTRACT

An image diagnosis supporting device operates, through digitizing, to apply predetermined image processing to a medical image and to generate a multi-valued image having discrete multiple values. At least one decision making processing routine is then executed on the multi-valued image and/or the medical image; and, from among shadows in the processed image, a focus candidate shadow which is likely to indicate a diseased site is extracted. The extracted focus candidate shadow is then displayed in the medical image so that it is easily identifiable.

51 Claims, 80 Drawing Sheets

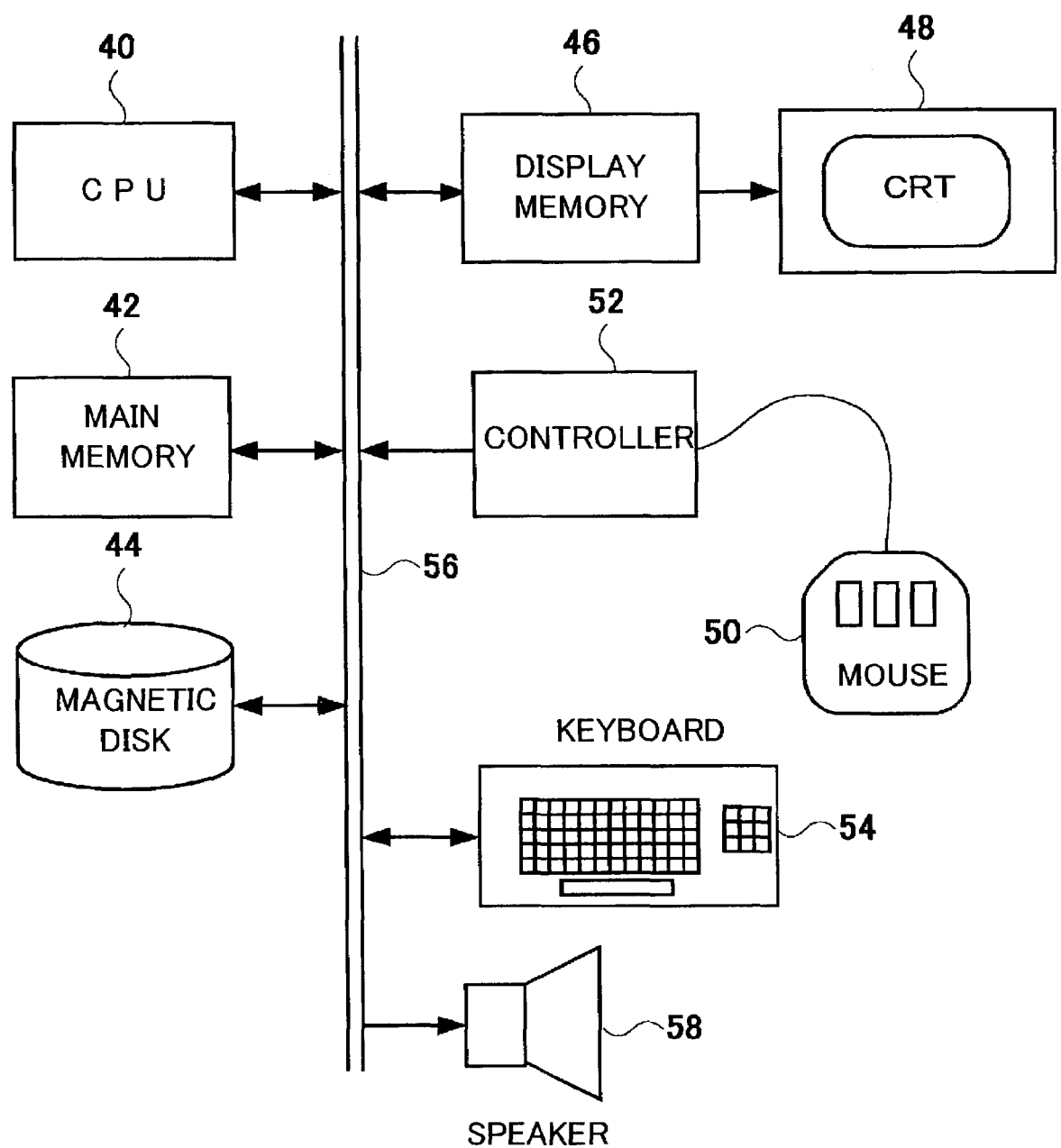

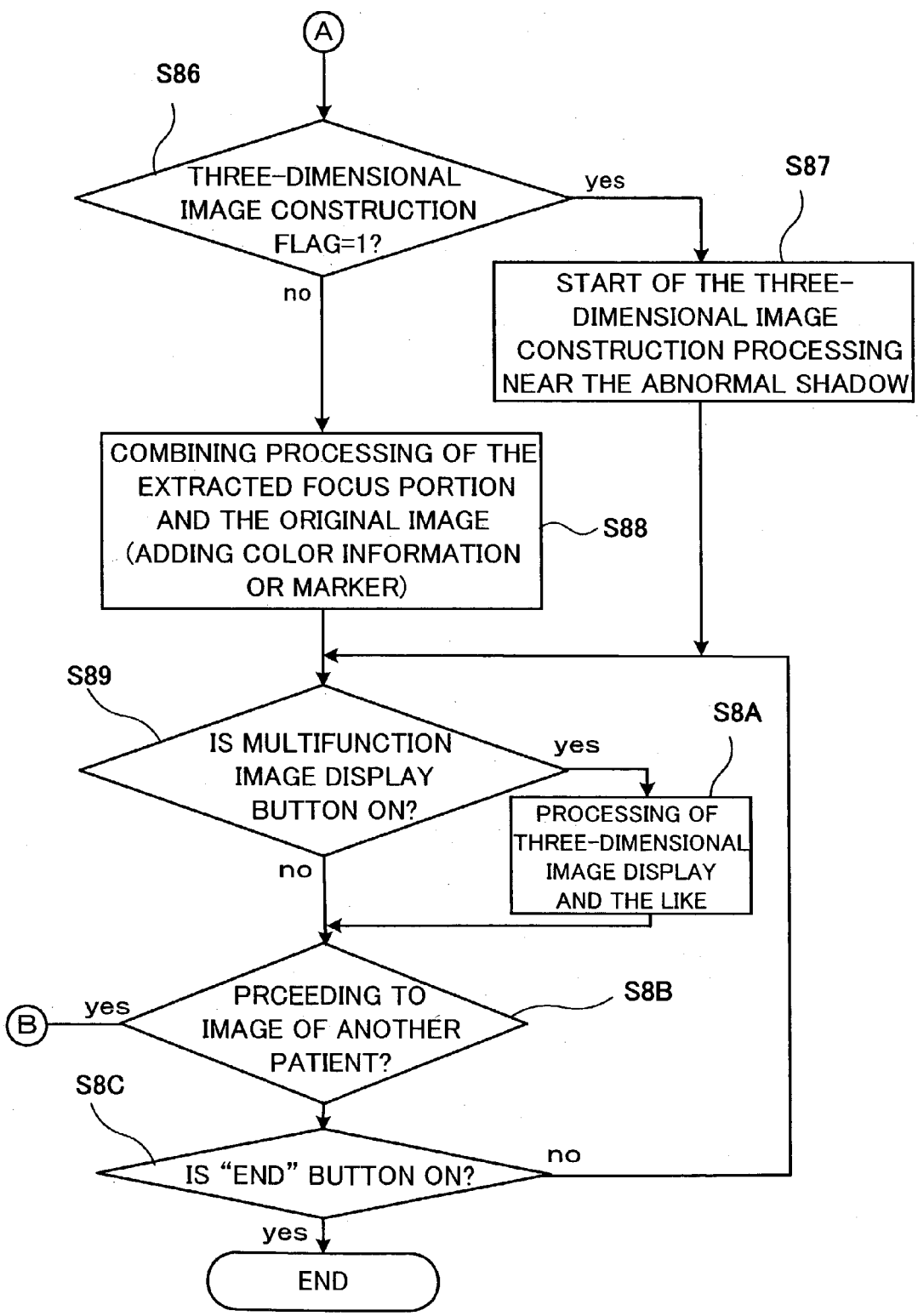

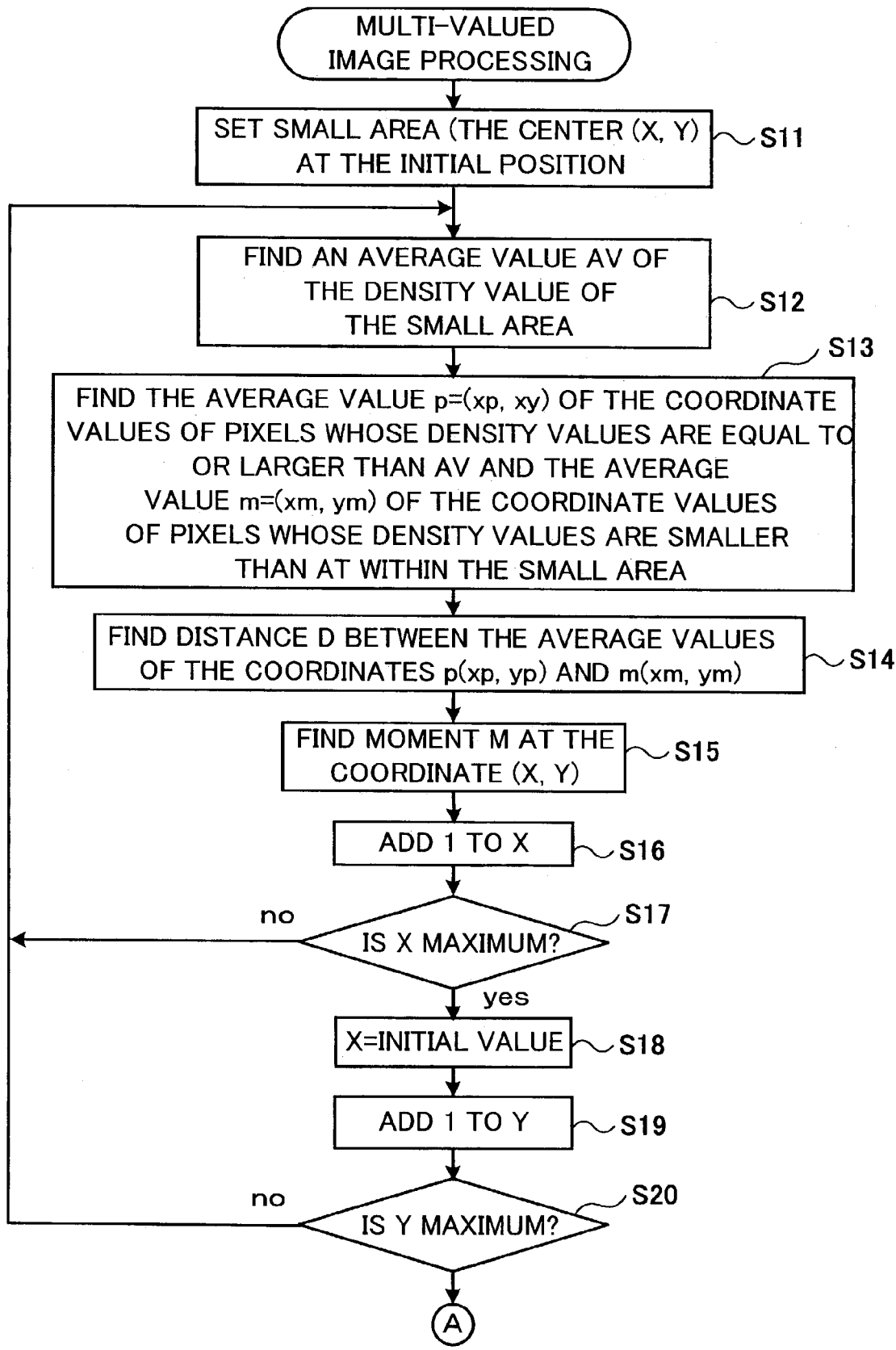

~21

22 SHADOW

HIGH DENSITY

HIGH DENSITY

23 SHADOW

LOW DENSITY

FIG. 16(a-1)
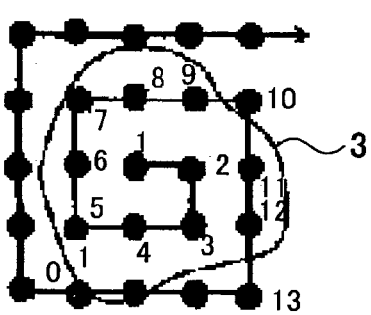
FIG. 16(a-2)
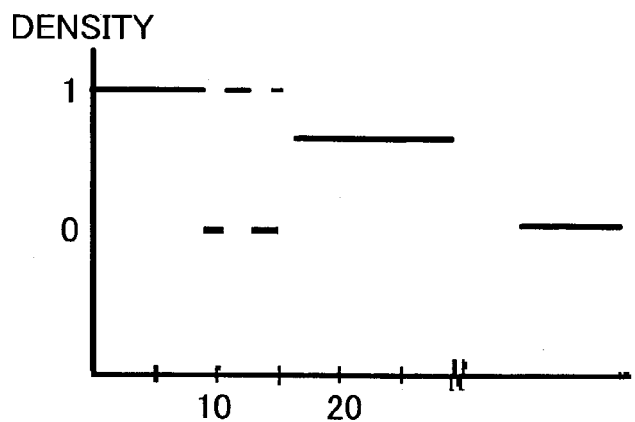
FIG. 16(b-1)
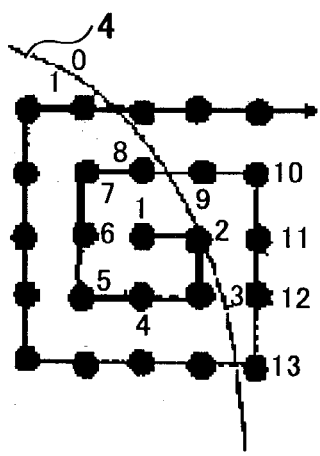
FIG. 16(b-2)
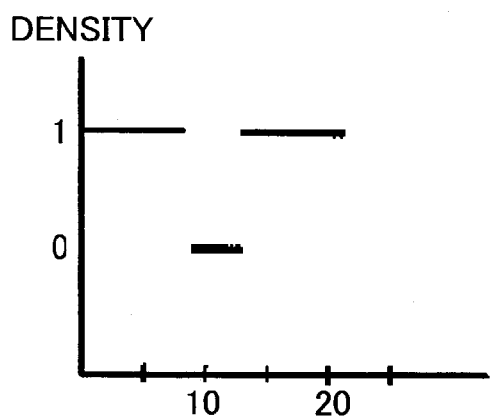
FIG. 16(c-1)
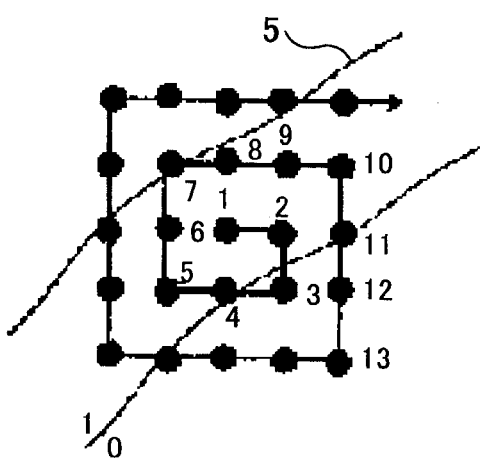
FIG. 16(c-2)
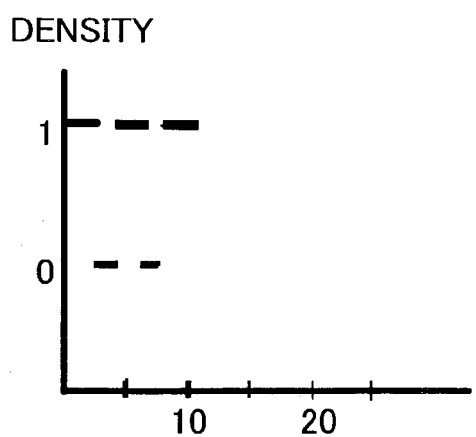

T% OF BOUDARY OF THE SHADOW

472 BLOOD VESSEL SHADOW

471 BLOOD VESSEL SHADOW

470 FOCUS CANDIDATE SHADOW

CUTTING LENGTH

MINIMUM LENGTH OF MOVING RADIUS

| RUN LENGTHS | NUMBER |
|---|---|
| 1 | 15 |
| 2 | 53 |
| 3 | 44 |
| 4 | 21 |
| 5 | 16 |
| 6 | 8 |
| 7 | 2 |
|  |  |
|  |  |

SPECULA TYPE CANCER SHADOW

711

712

RECORD A PARTICULAR VALUE ON p3 ~ p4.

IMAGE DIAGNOSIS SUPPORTING DEVICE

TECHNICAL FIELD

The present invention relates to an image diagnosis supporting device, which extracts a shadow that serves as a focus candidate (a possibly diseased portion) from a medical image by computerized image processing and displays the extracted shadow as is a focus candidate so that it can be identified.

BACKGROUND OF THE INVENTION

A computerized image diagnosis supporting device analyzes shadows in a medical image by using a computer, and displays a medical image containing a focus candidate shadow selected from the shadows, thereby presenting such medical image to a doctor who has been requested to make a diagnosis. The term "medical image" used herein covers photographic images photographed with medical image diagnosis devices, such as CT devices, MRI devices and ultrasonic diagnosis devices, as well as difference images between past images and current images and the like. As to the method of selecting a focus candidate, several examples associated with medical images of lung areas have been reported in meetings and the like. Among the reports, there is a method of discriminating between a blood vessel shadow having an elongated shape and a cancer shadow having a shape close to that of a circle in a medical image of a lung area, for example, a "Quoit Filter" (refer to Journal of Computer Aided Diagnosis of Medical Images, Vol. 9, Page 21, November 1999). During a diagnosis of a medical image of a lung area, since the medical image contains not only a shadow of a cancer candidate, but also shadows such as blood vessels, cross sections of blood vessels and cross sections of bronchi, and various shadows have various sizes and shapes, it is desirable that only the shadow of the cancer candidate be extracted from the other shadows and be presented to the doctor.

However, the above-described image diagnosis supporting device is difficult to use, because a lot of time-consuming work is required to adjust the parameters for specifying the sizes and shapes of various shadows.

An object of this invention is to provide an image diagnosis supporting device that is capable of reducing the computing time of a computer by handling shadows of different sizes and shapes in an integrated manner when a decision as to whether a shadow is a focus candidate of a medical image is to be automatically made by the use of the computer.

Another object of this invention is to provide an image diagnosis supporting device that is capable of easily and instantaneously displaying a shadow which seems to be an extracted focus candidate.

SUMMARY OF THE INVENTION

To achieve the above object, an image diagnosis supporting device according to this invention includes digitizing means for applying predetermined image processing to a medical image and for generating a multi-valued image, and extracting means for executing at least one decision process on the multi-valued image and/or the medical image generated by the digitizing means and for extracting a shadow which seems to be a candidate for a focus, which device identifiably displays in the medical image the focus candidate shadow extracted by the extracting means.

In addition, since the probability that the focus candidate shadow is a focus (focus certainty) can be determined, when the focus candidate shadow is displayed by being enclosed with a marker or the like, the marker is given a size or a thickness corresponding its focus certainty.

For example, markers are displayed in different colors in the order of the highness of the focus certainty, like red, yellow and blue, or are flash-displayed in such a manner as to blink their luminance, or are displayed in a combined manner of display in different colors and flash display.

BRIEF DESCRIPTION OF DRAWINGS

FIG. 1 is a schematic block diagram of the hardware to which this invention is applied;

FIGS. 2a and 2b, when combined, comprise a main flowchart of the process of focus candidate extraction and display;

FIG. 5 is a detailed flowchart showing the first half of Step S81 of FIG. 2a;

FIG. 6 is a detailed flowchart showing the second half of Step S81 of FIG. 2a;

FIG. 9 is a detailed flowchart showing Step S83 of FIG. 2a;

FIGS. 16(a-1), 16(a-2) through 16(c-1), 16(c-2) are conceptual diagrams of sampling points by each of the search methods of FIGS. 15 and 16;

FIGS. 71a and 71b are diagrams showing a specific example of the case where a focus candidate shadow is simply displayed in the state of being enclosed with a marker, and a specific example of the case where a CT image in an area enclosed with a marker is displayed in an emphasized state, respectively;

BEST MODE FOR CARRYING OUT THE INVENTION

Figure 2A:
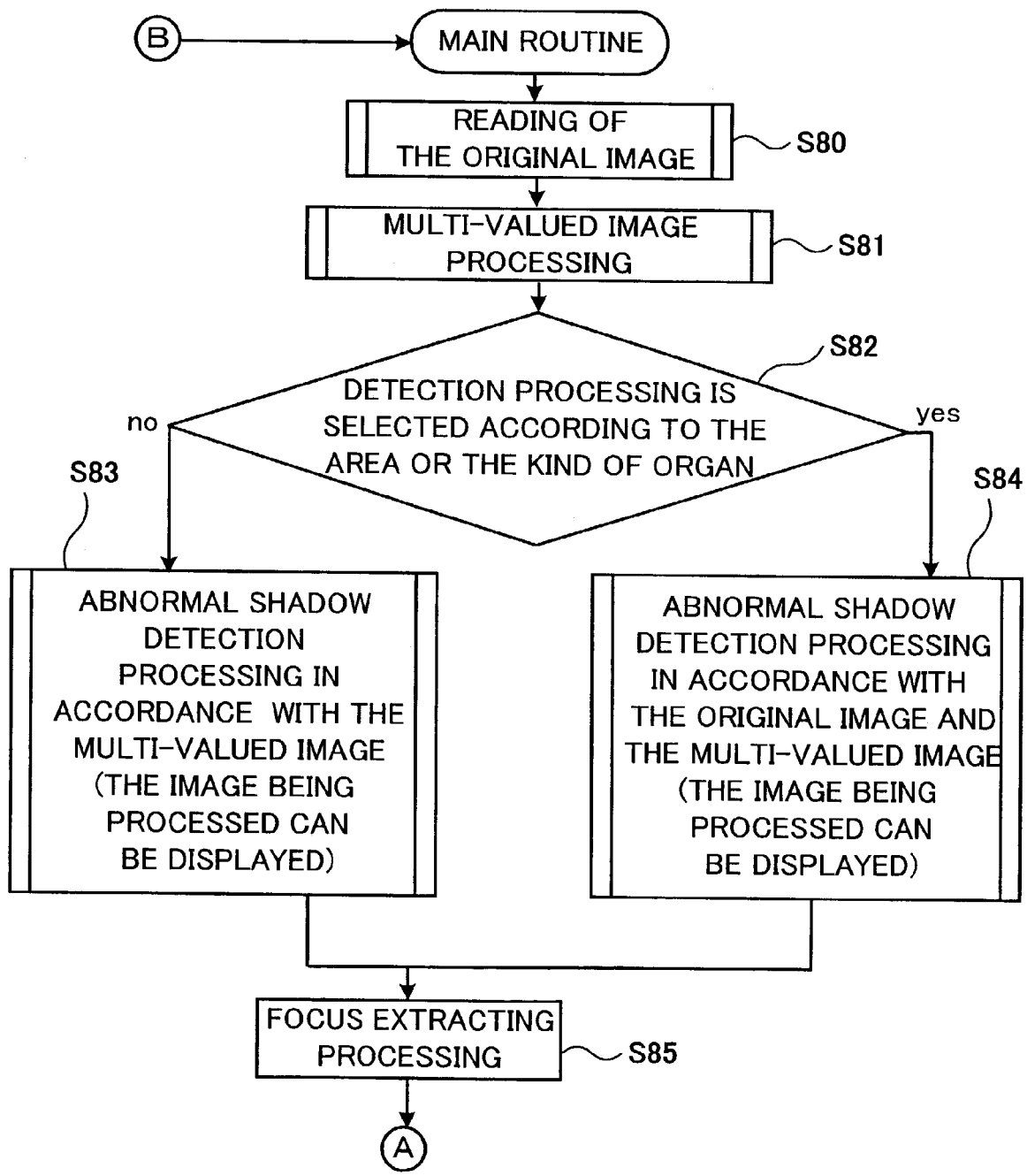

Preferred embodiments of an image diagnosis supporting device according to this invention will be described with reference to the accompanying drawings.

FIG. 1 is a block diagram showing the overall hardware construction of an image diagnosis supporting device to which this invention is applied. This image diagnosis supporting device displays extracted focus candidate shadows on the basis of a plurality of tomographic images (such as CT images) that are collected from a target area of a sample by means of, for example, an X-ray CT device. The image diagnosis supporting device selectively displays, in addition to focus candidate shadows, shadows of high certainty from among extracted focus candidate shadows or the like, or displays halfway images during this processing.

This image diagnosis supporting device is made up of a central processing unit (CPU) 40 which controls the operation of each constituent element, a main memory 42 in which a control program for the device is stored, a magnetic disk unit 44 in which a plurality of tomographic image data and a computer program and the like are stored, a display memory 46 which temporarily stores image data to be displayed, a CRT display 48 which serves as a display device to display an image on the basis of image data read out from this display memory 46, a mouse 50 for manipulating software switches on a screen, a controller 52 for the mouse 50, a keyboard 54 provided with keys and switches for setting various parameters, a speaker 58, and a common bus 56 which connects the above-described constituent elements to one another.

In the illustrated example, only the magnetic disk unit 44 is connected as a storage device other than the main memory unit 42, but in addition to this magnetic disk 44, a floppy disk drive, a hard disk drive, a CD-ROM drive, a magneto-optical disk (MO) drive, a ZIP drive, a PD drive, a DVD drive and the like may also be connected. Furthermore, the image diagnosis supporting device may also be connected to various communication networks, such as a LAN (local area network), the Internet and a telephone line via a communication interface which, is not shown, so that the image diagnosis supporting device can transmit and receive image data and program data to and from other computers. In addition, the inputting and outputting of image data may also be implemented in such a manner that a medical image diagnosis device, such as an X-ray CT device and an MRI device, capable of collecting tomographic images of samples, is connected to the above-described LAN and the like.

Figure 3:
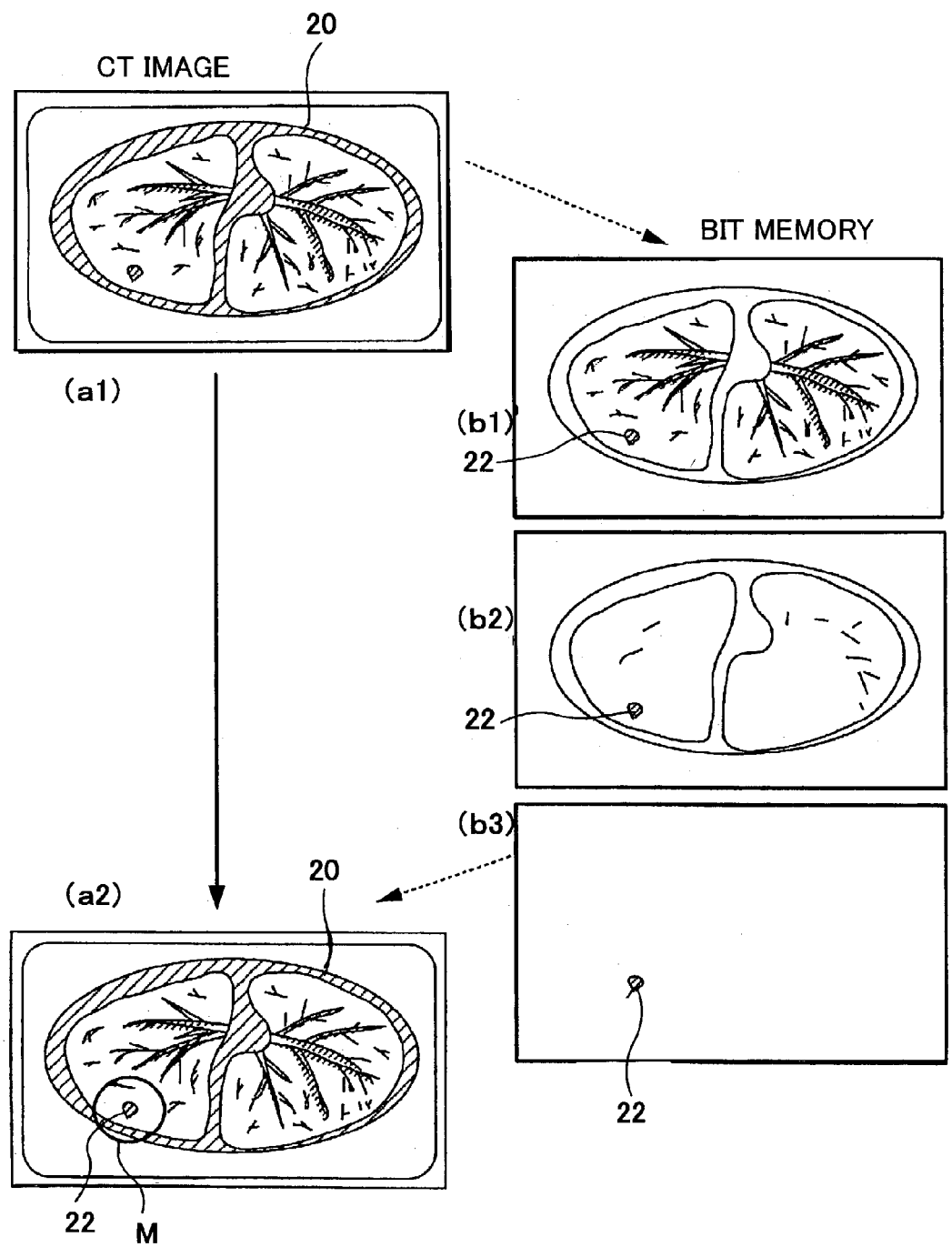
FIG. 3 is an image processing flow diagram showing the processing of a CT image according to the flowchart of FIGS. 2a and 2b.
Figure 4:
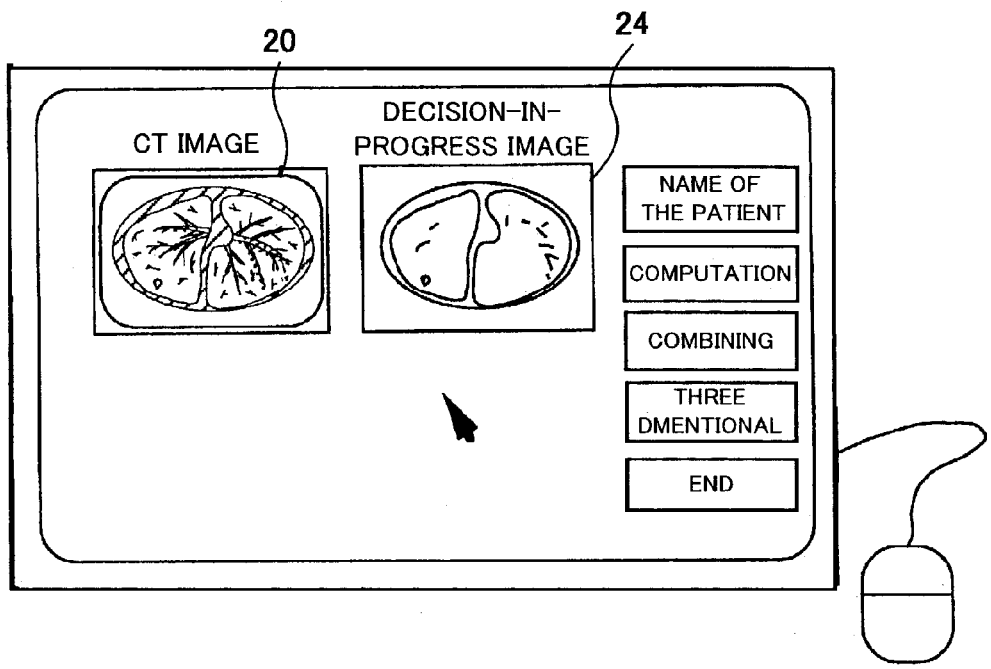
FIG. 4 is a diagram showing one example of a display on the CRT of FIG. 1.

An operational example of the image diagnosis supporting device shown in FIG. 1 will be described below with reference to the accompanying drawings. FIG. 2 is a flowchart showing one example of a process to be executed by the image diagnosis supporting device. The CPU 40 shown in FIG. 1 operates in accordance with this main flowchart. FIG. 3 is a view showing how an CT image is processed according to this main flowchart. FIG. 4 is a view showing one example of a display picture on the CRT display 48. This main flowchart is activated when an operator inputs the name of a patient, who is a target of focus candidate extraction and display processing, in a field "Name of Patient" on the display picture shown in FIG. 4 and clicks a button "COMPUTE". Details of the processing indicated by this flowchart will be described below in the order of the steps thereof.

[Step S80] The CPU 40 reads from the magnetic disk unit 44 a CT image 20 (FIG. 3 at (a1)) of the patient corresponding to the patient name shown in FIG. 4 from among CT images of the patient photographed by a CT device.

[Step S81] The CPU 40 applies digitization processing to a diagnostic target organ in the read CT image, and generates a multi-valued image as shown in FIG. 3 at (b1). Details of this digitization processing will be described later.

[Step S82] To execute optimum detection processing corresponding to the area of the diagnostic target organ or the kind of organ, the CPU 40 determines the area or the kind of organ and makes a decision as to whether to proceed to Step S83 or Step S84.

[Step S83] The CPU 40 applies various kinds of image processing to the multi-valued image shown in FIG. 3 at (b1), selects a focus candidate shadow and detects a shadow inferred to be a focus candidate, i.e., an abnormal shadow 22. This abnormal shadow detection processing detects the abnormal shadow 22 without using the original CT image, on the basis of only the multi-valued image generated in Step S81. Details of this will be described later. By implementing abnormal shadow detection processing on the basis of a multi-valued image as in this embodiment, it is possible to shorten the time required for computer operations and the like, and it is also possible to ease the burden of computer processing.

[Step S84] The CPU 40 applies various kinds of image processing to the CT image of FIG. 3 as seen at (a1) and the multi-valued image of FIG. 3 as seen at (b1), and selects a focus candidate shadow and detects a shadow inferred to be a focus candidate, i.e., an abnormal shadow 22.

Incidentally, a decision-in-progress image 24 indicative of the progress of the abnormal shadow detection processing in each of Steps S83 and S84 is displayed in parallel form by the side of the CT image 20 of FIG. 3 as seen at (a1) on the CRT display 48, as shown in FIG. 4. Incidentally, when the button "COMBINE" shown in FIG. 4 is clicked, the decision-in-progress image 24 is combined with the CT image 20 in response to the click, and the result is displayed. The displayed contents of the decision-in-progress image 24 are sequentially changed in accordance with the processing of data on the multi-valued image (i.e., according to the stage of extraction of a focus candidate shadow). When the number of extracted abnormal shadows which are detected through the abnormal shadow detection processing is larger than a predetermined number, the CPU 40 may also provide a display indicative of decision disabled and bring the processing to an end. The result is constantly recorded on the magnetic disk. Details of this abnormal shadow detection processing will be described later.

[Step S85] The CPU 40 leaves as a focus portion a focus candidate which has been determined to be an abnormal shadow in the above-described Step S83 or S84, or deletes a focus candidate which has not been so determined in the above-described Step S83 or S84.

[Step S86] The CPU 40 determines whether the three-dimensional image structuring button 3D shown in FIG. 4 has been clicked, i.e., whether the three-dimensional image structuring flag is "1" or "0", and proceeds to Step S87 in the case of "1" (yes). In the case of "0" (no), the CPU 40 proceeds to Step S88. Incidentally, the three-dimensional image structuring flag can be set to "1" or "0" if the operator arbitrarily clicks the three-dimensional image structuring button of FIG. 4 as the occasion demands.

[Step S87] The processing of Step S87 is executed in the case where the decision made in Step S86 is yes. The CPU 40 starts structuring processing for a three-dimensional image from a plurality of CT images near the abnormal shadow. The structuring processing for a three-dimensional image is executed in parallel with the processing of Step S88, but after the structuring processing for a three-dimensional image has been completed, the CPU 40 may also proceed to Step S88 to execute the processing of Step S88.

[Step S88] In order to enable the abnormal shadow to be easily identified, the CPU 40 performs a combining processing to display the CT image of FIG. 3 as seen at (a1) with color information added thereto, to display the abnormal shadow enclosed with a marker M, or to display a colored extracted focus portion or a marker in the original image (CT image). In FIG. 3 at (a2), there is displayed one example of a combined image in which the abnormal shadow is enclosed with the marker M.

[Step S89] The CPU 40 determines whether a multifunction image display button has been turned on, and if the button has been turned on (yes), the CPU 40 proceeds to Step S8A. If the button has not been turned on (no), the CPU 40 proceeds to Step S8B.

[Step S8A] Since the multifunction image display button is in the "on" state, the CPU 40 displays the three-dimensional image structured in Step S87.

[Step S8B] The CPU 40 determines whether an instruction to perform the same focus candidate extracting and displaying processing on an image of another patient has been given by the operator. If the CPU 40 determines that an image of another patient is to be displayed (yes), the CPU 40 returns to Step S80 and repeatedly executes the same processing. If the CPU 40 determines that an image of another patient is not to be displayed (no), the CPU 40 proceeds to Step S8C.

[Step S8C] The CPU 40 determines whether the "END" button shown in FIG. 4 has been turned on by the operator. If the CPU 40 determines that the button has not been turned on (no), the CPU 40 returns to Step S89 and continues normal image display or multifunction image display. If the CPU 40 determines that the button has been turned on (yes), the CPU 40 brings the processing to an end.

Figure 6:
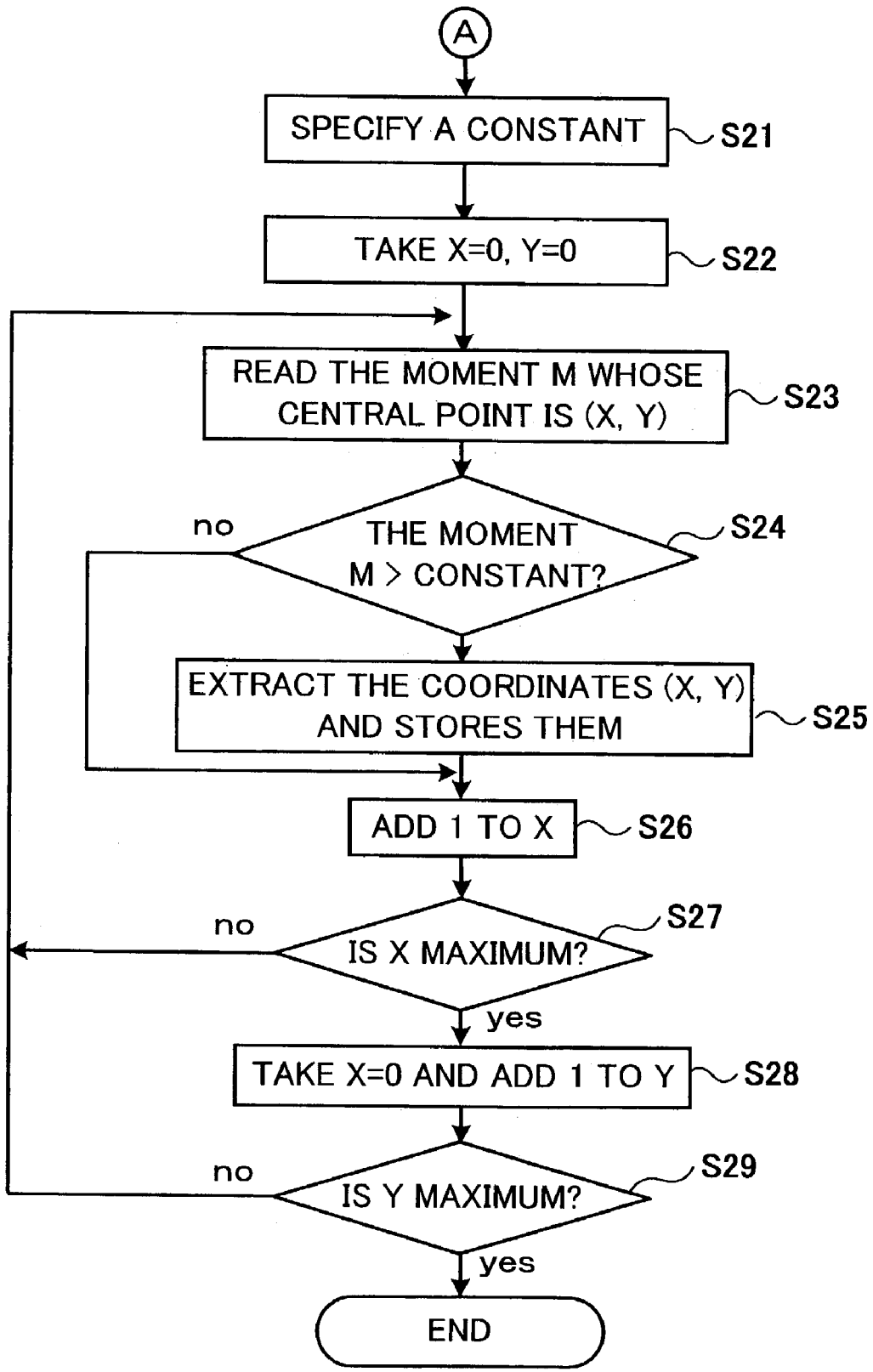

The multi-valued image processing of Step S81 of FIG. 2 is performed on the basis of the CT image 20 shown in FIG. 3. This multi-valued image processing is, as shown in FIG. 3, intended to apply predetermined thresholding processing to a result obtained by calculating a standard deviation and the like of the original CT image 20 and produce a multi-valued image as shown in FIG. 3 at (a1). FIGS. 5 and 6 are flowcharts showing details of the multi-valued image processing for the diagnostic target organ in Step S81 of FIG. 2. The most basic binary image processing in the multi-valued image processing will be described hereinbelow.

Figure 7:
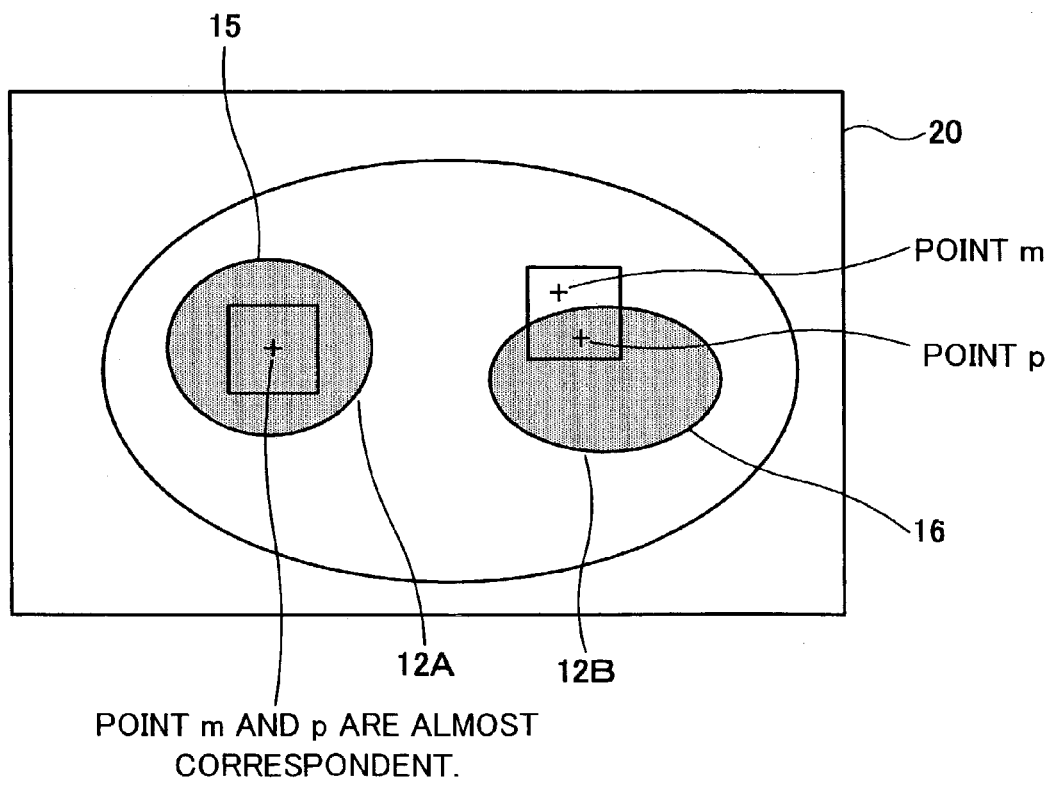
FIG. 7 is a diagram showing a principle view of the multi-valued image processing of FIGS. 5 and 6.

Conventionally, a method of finding a difference between each CT image has been used as one of the image processing methods for emphasizing and displaying shadows. For example, the difference in CT value between pixels at the same address (x, y) is found between two adjacent CT images each having an image size of 512×512, and this difference in CT value is stored at the address (x, y) in the memory, whereby an emphasized image whose shadow is emphasized is obtained. There is also a method using standard deviation (inclusive of variance). These methods do not particularly emphasize the vicinity of the boundary of a shadow, and they extract neither the boundary (edge) of a shadow, nor a shadow only. On the other hand, this embodiment extracts a shadow in a CT image (particularly, the vicinity of the boundary of the shadow), or adopts multi-valued image processing, which enables an extracted shadow to be displayed with emphasis. FIG. 7 is a view for theoretically explaining this multi-valued image processing. Details of the processing indicated by this main flowchart will be described below in the order of the steps thereof.

[Step S11] The CPU 40 sets a particular area of predetermined shape to be the initial position on the CT image. For example, as shown in FIG. 7, the CPU 40 sets particular areas (small areas) 12A and 12B each having a square shape of 10×10 pixels within the CT image 20 (a tomographic image of the sample), and sets the areas 12A and 12B at an initial position at the top left corner of the CT image 20. If the coordinates of the central position of each of these small areas 12A and 12B are (X, Y), the coordinates (X, Y) are respectively set to (0, 0). Incidentally, in FIG. 7, the small area 12A is set inside a shadow 15, and the small area 12B is set to overlap the boundary (edge) of a shadow 16. Each of these small areas is not limited to a size of 10×10 pixels, and they may also have, for example, a rectangular shape, a diamond shape or a circular shape, other than a square shape. If the central position of such a small area differs from the weighted center position of the same, the weighted center position is given priority, but either of the central position or the weighted center position may be selected for priority on a case-by-case basis.

[Step S12] The CPU 40 finds an average value AV of the density value (CT value) of the small area. The obtained average value AV exhibits a high value if the small area exists in the shadow 15 like the small area 12A of FIG. 7, a low value if the small area does not overlap a shadow, or an approximately middle value if the small area overlaps the shadow 16 like the small area 12B.

[Step S13] The CPU 40 finds the average p (xp, yp) of the coordinate values of pixels whose density values are not smaller than the average density value AV within the small area, as well as an average m (xm, ym) of the coordinate values of pixels whose density values are smaller than the average density value AV. In the case of the small area 12A of FIG. 7, average values pA and mA are approximately near the center of the small area 12A, and the coordinate positions of both average values pA and mA approximately coincide with each other. On the other hand, in the case of the small area 12B, an average value pB is approximately near the center of the portion of the small area 12B that is superposed on the shadow 16, and an average value mB is approximately near the center of the portion of the small area 12B that is not superposed on the shadow 16, and the coordinates of both average values pB and mB are removed from each other.

[Step S14] The CPU 40 determines the distance D between the coordinates (xp, xy) of the average value p and the coordinates (xm, xm) of the average value m. In the case of the small area 12A of FIG. 7, since the average values pA and mA are the same, the distance D becomes "0". In the case of the small area 12B, since the average value pB and the average value mB are spaced from each other, the distance D becomes a corresponding distance DB. Namely, this distance D tends to be large in the case where the small area is located near the edge of the shadow, or to be small in the case where the small area does not overlap the shadow.

[Step S15] To make the above-described tendency more remarkable, in this step S15, the CPU 40 finds M=g·f(D) as a moment M at the central coordinates (X, Y) of the small area on the basis of the distance D found in Step S14. This moment M is a value related to (X, Y). For example, letting Np be the number of pixels whose density values are not smaller than the above-described average value AV within the small area, and letting Nm be the number of pixels whose density values are smaller than the average value AV, each of the moments M1 to M3 found on the basis of the following equations is defined as the moment M in Step S15:

the moment M1 is M1=Np×Nm×D;

the moment M2 is M2=Nor×D, (where Nor is the larger of Np and Nm); and the moment M3 is M3=an existing variance×D, (where D may be the δ-th power of a value of about 1-3.)

In general, a computation including D is effective. In addition, even in the decision processing which will be described later, a computation result including D relative to a focus area can be used for decision.

[Step S16] The CPU 40 adds 1 to the central coordinate X of the small area in order to move the small area in the X direction of the image.

[Step S17] The CPU 40 determines whether the value of the coordinate X of the center of the small area is a maximum (a position where the small area is moved beyond the right end of the image), and if the CPU 40 determines that the value is a maximum (yes), the CPU 40 proceeds to Step S17. If the CPU 40 determines that the value is not a maximum (no), the CPU 40 returns to Step S12, where the CPU 40 repeats the processing of Step S12 to Step S17 until the value of the central coordinate X becomes a maximum.

[Step S18] Since it has been determined in the above-described step S17 that the central coordinate X of the small area is a maximum, the CPU 40 returns the central coordinate X to an initial value (normally, "0") in order to return the small area to the left end of the image.

[Step S19] The CPU 40 adds "1" to the central coordinate Y of the small area in order to move the small area in the Y direction of the image.

[Step S20] The CPU 40 determines whether the value of the coordinate Y of the center of the small area is a maximum (a position where the small area is moved beyond the right end of the image), and if the CPU 40 determines that the value is a maximum (yes), the CPU 40 brings the processing to an end, and proceeds to Step S21 of FIG. 6 via a connector A. If the CPU 40 determines that the value is not a maximum (no), the CPU 40 returns to Step S12, where the CPU 40 repeats the processing of Step S12 to Step S20 until Y becomes a maximum. In this manner, the CPU 40 scans the small area from the top left to the bottom right of the CT image 20 and sequentially calculates the moment M at the central coordinate position of the small area.

A method of extracting pixels located in a shadow or near the boundary of the shadow from each CT image 20 by using the moment M obtained in this manner will be described below in accordance with the flowchart shown in FIG. 6.

[Step S21] The CPU 40 reads a constant inputted from the keyboard by the operator, or a constant stored in advance in the magnetic disk 44 or the like, as a threshold for determining whether each pixel of the CT image 20 is in a shadow or near the boundary of the shadow, and specifies the read constant as a constant.

[Step S22] In order to set a pixel which is a decision target (a decision target pixel) in the initial position which is the top left corner of the CT image 20, the CPU 40 set the coordinates (X, Y) of the decision target pixel) to (0, 0).

[Step S23] The CPU 40 reads the moment M obtained in Step S15 of FIG. 5 as to a small area centered about the coordinates (X, Y) of the decision target pixel.

[Step S24] The CPU 40 determines whether the read moment M is larger than the constant specified in Step S21. If the CPU 40 determines that the read moment M is larger (yes), the CPU 40 proceeds to Step S25, whereas if the CPU 40 determines that the read moment M is not larger (no), the CPU 40 jumps to Step S26.

[Step S25] The fact that it has been determined in Step S24 that the moment M is larger than the constant means that the decision target pixel corresponding to the coordinates (X, Y) corresponds to the shadow or the boundary of the shadow. Accordingly, in this step, the CPU 40 extracts the coordinates (X, Y) and stores them in the memory (the main memory 42 or the magnetic disk unit 44). Specifically, if the CPU 40 has determined in Step S24 that the moment M is larger than the constant (yes), the CPU 40 sets a binary high level "1" to the coordinates (X, Y). On the other hand, if the CPU 40 determines in Step S24 that the moment M is not larger than the constant (no), the CPU 40 sets a binary low level "0" to the coordinates (X, Y). In this manner, each set of coordinates is set to either of a low level "0" or a high level "1" and is binarized. By binarizing each set of coordinates in this manner, it is possible to express each set of coordinates by one bit, whereby it is possible to simplify the following processing.

[Step S26] The CPU 40 adds "1" to the coordinate X in order to move the coordinates of the decision target pixel in the X direction.

[Step S27] The CPU 40 determines whether the value of the coordinate X of the decision target pixel is a maximum (a position beyond the right end of the image), and if the CPU 40 determines that the value is a maximum (yes), the CPU 40 proceeds to Step S28. If the CPU 40 determines that the value is not a maximum (no), the CPU 40 returns to Step S23, where the CPU 40 repeats the processing of Step S233 to Step S26 until X becomes a maximum.

[Step S28] Since the CPU 40 has determined in the above-described step S27 that the coordinate X of the decision target pixel is a maximum, the CPU 40 resets the coordinate X to "0" in order to return the decision target pixel to the left end, and adds "1" to the coordinate Y of the decision target pixel in order to move the decision target pixel in the Y direction.

[Step S29] The CPU 40 determines whether the coordinate Y of the decision target pixel is a maximum (a position beyond the bottom end of the image), and if the CPU 40 determines that the value is a maximum (yes), the CPU 40 brings the processing to an end. If the CPU 40 determines that the value is not a maximum (no), the CPU 40 returns to Step S23, where the CPU 40 repeats the processing of Step S23 to Step S28 until Y becomes a maximum.

In this manner, the CPU 40 scans the decision target pixel from the top left to the bottom right of the CT image 20 and makes a decision as to whether the decision target pixel corresponds to the shadow or the boundary of the shadow. Through the above-described processing, the central point (X, Y) of the small area having the moment M larger than the constant, i.e., the coordinate point of the pixel lying in the shadow or the boundary of the shadow, is sequentially stored in the memory (the main memory 42 or the magnetic disk unit 44). Incidentally, in the description of FIGS. 5 and 6, reference has been made to binarization using a low level "0" and a high level "1", but the CT image 20 can be digitized with an arbitrary number of values by specifying a plurality of constants in Step S21. For example, it is possible to digitize the CT image with four values by specifying three constants C1, C2 and C3 and determining to which of the following cases the moment M corresponds: the case where the moment M is smaller than the constant C1, the case where the moment M is not smaller than the constant C1 and is smaller than the constant C2, the case where the moment M is not smaller than the constant C2 and is larger than the constant C3, and the case where the moment M is not smaller than the constant C3. In the case of four-value digitization, one pixel is expressed by two bits. Incidentally, if the CT image is to be digitized with yet another number of values, a plurality of constants may be similarly specified so that the CT image can be digitized on the basis of the constants.

Figure 8A:
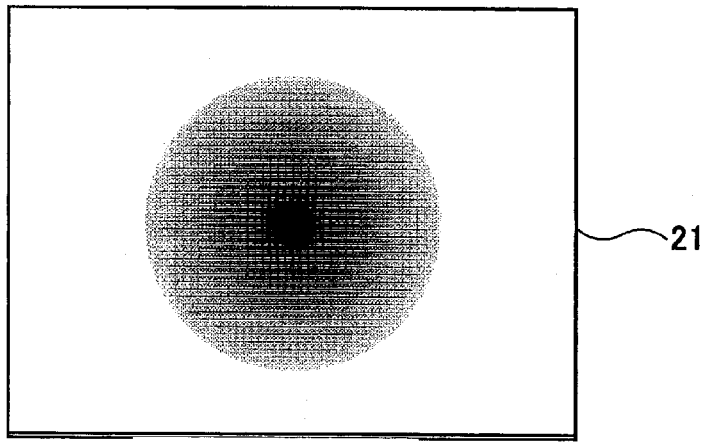
FIGS. 8a to 8c are diagrams showing the concept of shadow extraction.
Figure 8B:
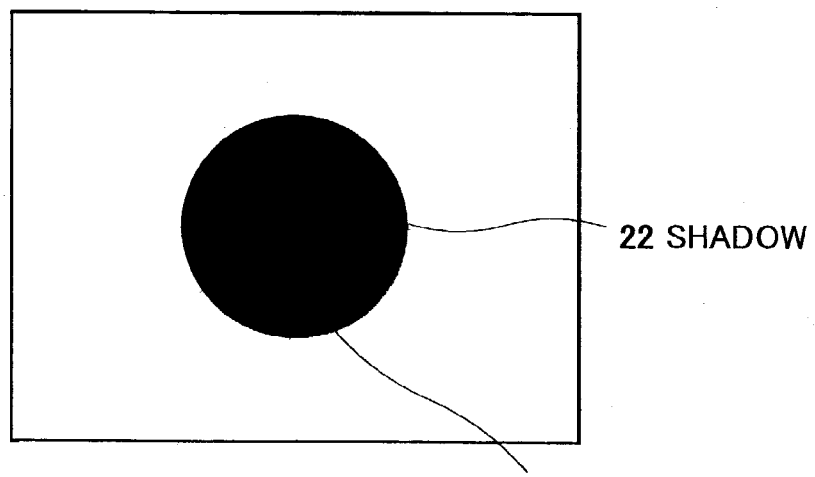
Figure 8C:
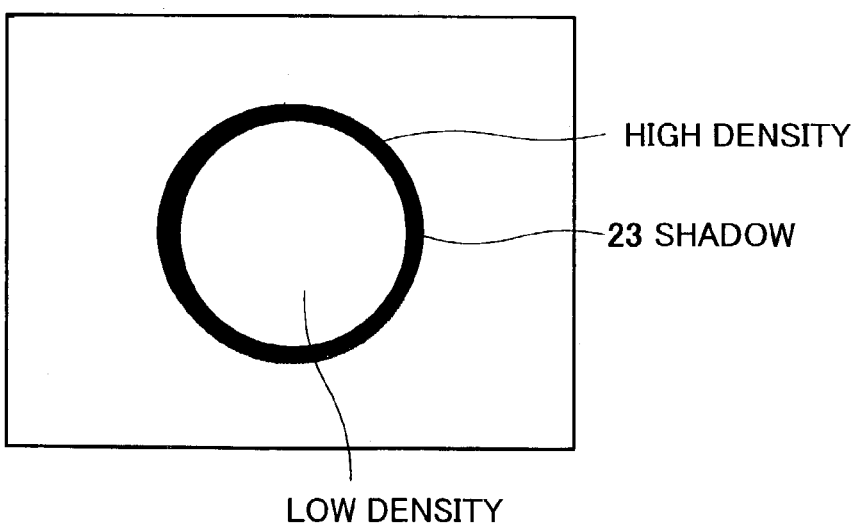

FIGS. 8*a* to 8*c* show the concept of how a shadow is extracted by the above-described method of extracting a pixel located in a shadow or near the boundary of the shadow. When the above-described processing is executed on a CT image 21 having a circular shadow which, as shown in FIG. 8*a*, exhibits the highest CT value near the center of the shadow and gradually decreases in CT value in the radius direction, a shadow 22 of a multi-valued image, the boundary of which is clear, as shown in FIG. 8*b*, is stored in the memory and is also displayed on the CRT display 48. In addition, by increasing the constant to be specified in Step S21, a ring-shaped shadow in which a boundary 23 of the shadow is emphasized, as shown in FIG. 8*c* is extracted. Accordingly, by variously changing the constant to be specified in Step S21, it is possible to extract only the boundary of the shadow or to extract the entire shadow. In addition, the boundary, etc., of the shadow extracted in this manner can also be displayed with emphasis.

The abnormal shadow detection processing of Step S83 of FIG. 2*a* is performed by using the multi-valued image generated by the above-described multi-valued image processing. In addition, the abnormal shadow detection processing of Step S84 of FIG. 2*a* is performed by using this multi-valued image and the CT image 20, which is the original image. In the case where abnormal shadow detection processing is performed by using a multi-valued image like that used in Step S83, it is desirable to perform the abnormal shadow detection processing by using a binary image and a multi-valued image digitized with a larger number of values (for example, an eight-valued image or a sixteen-valued image). In the following description, reference will be made to a case where abnormality detection processing is performed by using a binary image and the CT image 20. Incidentally, in the case where the abnormal shadow detection processing is to be performed by using only a multi-valued image like in Step S83 of FIG. 2*a*, it is similarly possible to cope with the abnormal shadow detection processing by reading the CT image 20 as the multi-valued image.

Figure 9:
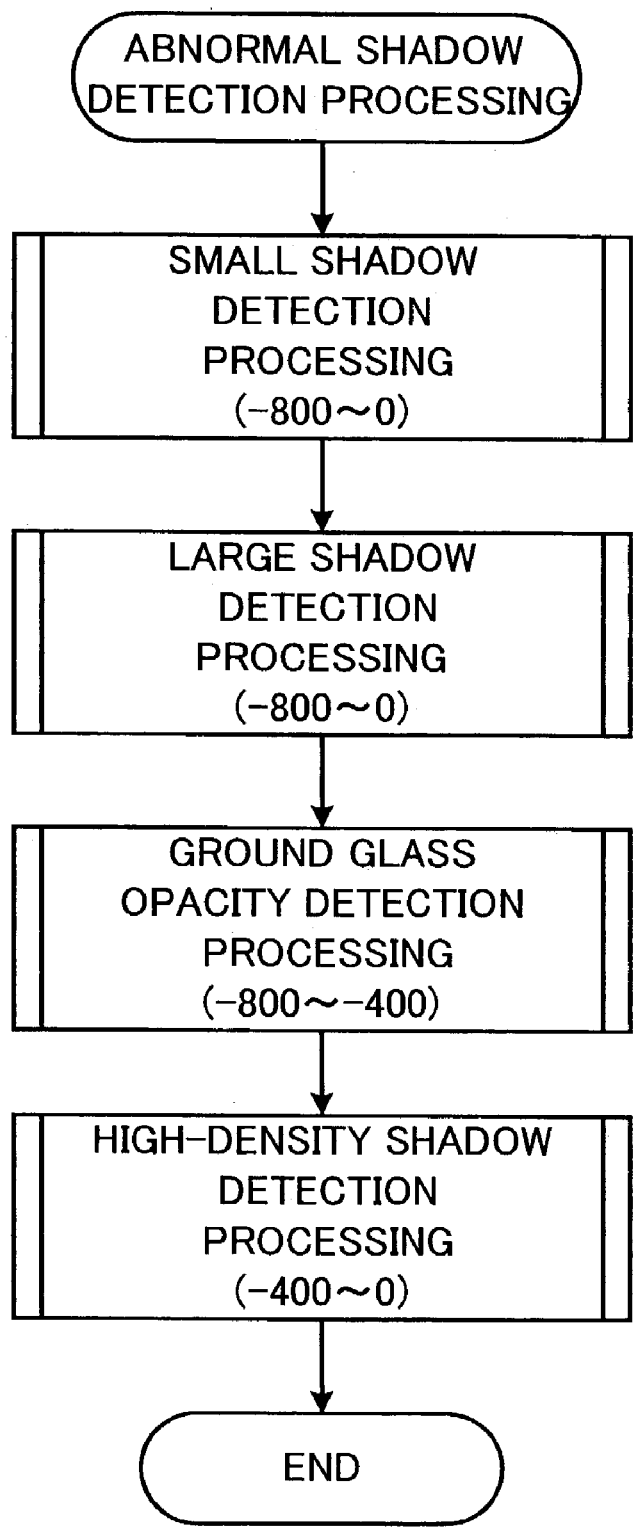

FIG. 9 is a view showing the main flowchart of the abnormal shadow detection processing. The abnormal shadow detection processing of FIG. 9 extracts only pixels belonging to the range of predetermined CT values (pixel values) from a medical image and generates a medical image for a decision target, according to a parameter indicative of the kind of shadow, such as a small shadow, a large shadow, a ground glass opacity or a high-density shadow. Namely, there are kinds of shadows, such as a small shadow, a large shadow, a ground glass opacity and a high-density shadow. It is empirically confirmed that each of the shadows distinctively appears in a predetermined pixel value range within a medical image. For example, small shadows and large shadows remarkably appear in the range of pixel values (CT values) from −800 to 0, ground glass opacities in the range of from −800 to −400, and high-density shadows in the range of from −400 to 0. Accordingly, in this embodiment, only pixels belonging to a predetermined range of pixel values are extracted from a medical image according to the kind of shadow, a new target medical image is generated, and extracting processing for a focus candidate shadow is performed on the basis of the new target medical image. In addition, in the case of ground glass opacities, since a focus occurs in many cases in the periphery of a lung region, it is effective to perform separate processing methods on a central portion and on a peripheral portion.

Small shadow detection processing performs abnormal shadow detection processing on a shadow in a decision target medical image made up of pixels which belong to the range of CT values from −800 to 0 within the CT image 20. Large shadow detection processing performs abnormal shadow detection processing on a shadow in a decision target medical image made up of pixels which belong to the range of CT values from −800 to 0. Glass-shaped shadow detection processing performs abnormal shadow detection processing on a shadow in a decision target medical image made up of pixels which belong to the range of CT values from −800 to −400. High-density shadow detection processing performs abnormal shadow detection processing on a shadow in a decision target medical image made up of pixels which belong to the range of CT values from −400 to 0. Incidentally, the multi-valued image extracting processing of Step S81 of FIG. 2a may be performed on the basis of this target medical image, so that the abnormal shadow detection processing of Step S83 and Step S84 of FIG. 2a is performed by using the obtained multi-valued image. Accordingly, in the following description, the term "CT image" includes this target medical image and a multi-valued image, and the terms "pixel value" and "density value" include pixel values in a multi-valued image.

Figure 10:
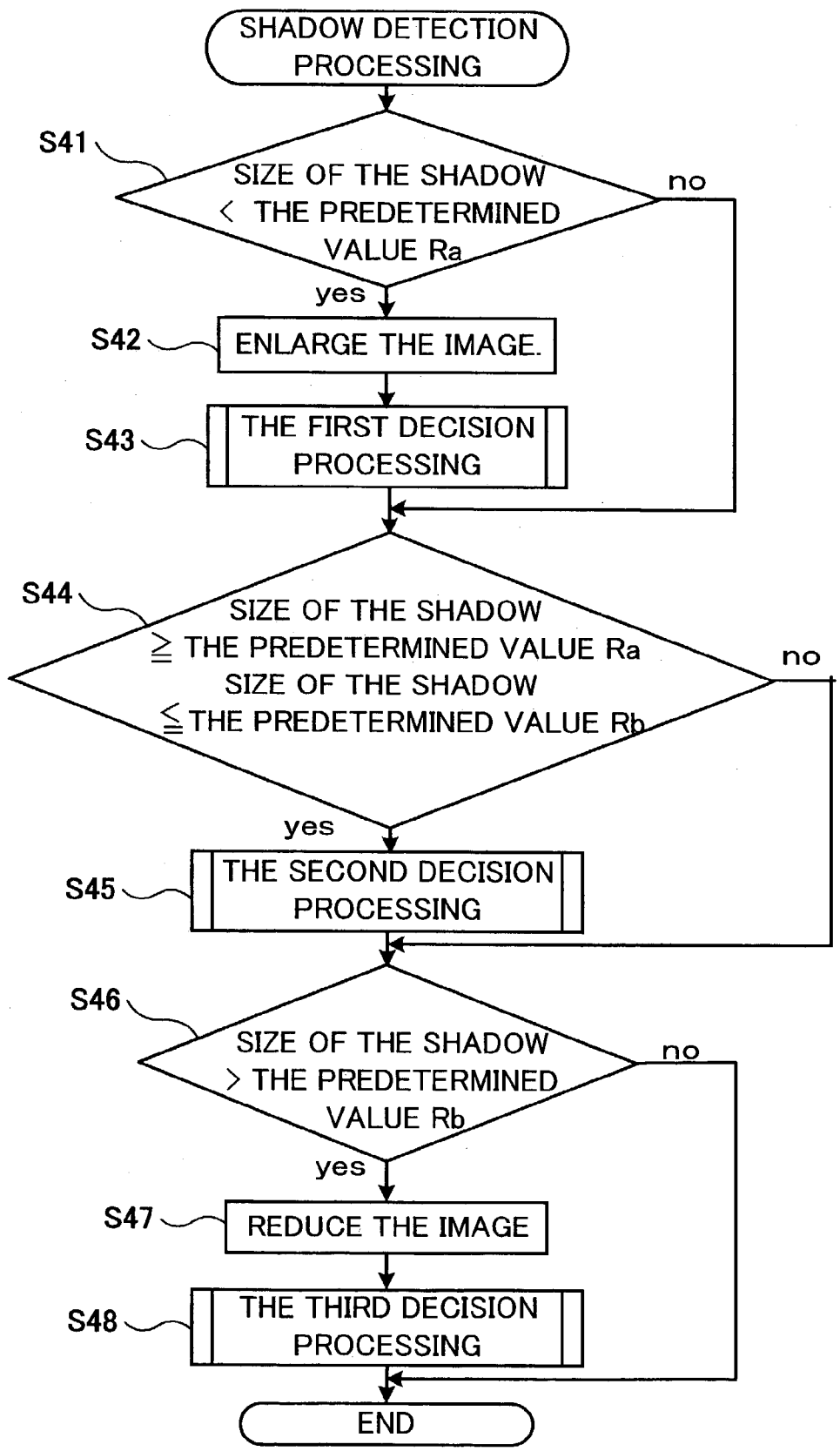
FIG. 10 is a flowchart showing details of the shadow extraction processing of FIG. 9.

FIG. 10 is a view showing details of each of these types of shadow detection processing. The types of shadow processing executed in the abnormal shadow detection processing shown in FIG. 9 are approximately common to one another except that predetermined values Ra and Rb used in Steps S41, S44 and S46 differ among the types of shadow processing. The size of a shadow is expressed by the number of pixels which constitute the shadow. There exist various focus shadows of different sizes, such as small shadows, large shadows, ground glass opacitys or high-density shadows. In the case where decision processing is performed on these shadows, similar processing is executed on each of the shadows by using a parameter corresponding to the size of each of the shadows. However, in the case where a shadow itself is small or large, or where shadows appear at different locations, there occurs the problem that if the same decision processing is performed with the same parameter, the accuracy becomes lower. Therefore, it is necessary to increase or decrease a parameter according to the size of each shadow. In this embodiment, if a shadow is smaller than the predetermined value Ra, the image of the shadow is enlarged; whereas, if a shadow is larger than the predetermined value Rb, the image of the shadow is reduced, whereby the image of the shadow is converted into a shadow having a size which enables decision processing to be most efficiently performed on the shadow, and the decision processing is performed on the converted shadow. Details of this shadow detection processing will be described below, step by step.

[Step S41] The CPU 40 determines whether the size (in this case, the number of pixels) of a shadow, which constitutes a detection target, is smaller than the predetermined value Ra; and, if the CPU 40 determines that the size of the shadow is smaller (yes), the CPU 40 proceeds to Step S42; whereas, if the CPU 40 determines that the size of the shadow is not smaller (yes), the CPU 40 jumps to Step S44.

[Step S42] Since it has been determined in Step S41 that the size of the shadow is smaller, the CPU 40 enlarges the shadow image to a size corresponding to a parameter to be used in the first decision processing of Step S43. In this case, the pixel value between each pixel is determined by interpolation processing.

[Step S43] The CPU 40 executes the first decision processing on the shadow that was enlarged in Step S42.

[Step S44] The CPU 40 determines whether the size of the shadow, which constitutes a decision target, is not smaller than the predetermined value Ra and not larger than the predetermined value Rb or more, i.e., whether the size of the shadow is within a predetermined range. If the CPU 40 determines that the size of the shadow is within the predetermined range (yes), the CPU 40 proceeds to Step S45; whereas, if the CPU 40 determines that the size of the shadow is not within the predetermined range (no), the CPU 40 jumps to Step S46.

[Step S45] The CPU 40 executes second decision processing on the shadow whose size is within the predetermined range of Step S44.

[Step S46] The CPU 40 determines whether the size of the shadow extracted according to each CT value is larger than the predetermined value Rb; and, if the CPU 40 determines that the size of the shadow is larger (yes), the CPU 40 proceeds to Step S47; whereas, if the CPU 40 determines that the size of the shadow is not larger (no), the CPU 40 brings the processing to an end and proceeds to the next shadow decision processing shown in FIG. 9.

[Step S47] Since the CPU 40 determines in Step S46 that the size of the shadow is larger than the predetermined value Rb, the CPU 40 reduces the image of the shadow to a size corresponding to a parameter to be used in the third decision processing of Step S48.

[Step S48] The CPU 40 executes the third decision processing on the shadow that has been reduced in Step S47, and then proceeds to the shadow decision processing shown in FIG. 9 (large-shadow detection processing, ground glass opacity detection processing or high-density shadow detection processing). Incidentally, although the number of pixels are used as the size of the shadow, the maximum diameter or the minimum diameter of the shadow may also be used. In this case, it is preferable to set a minimum diameter of about 7 mm to the predetermined value Ra and a maximum diameter of about 21 mm to the predetermined value Rb.

Figure 11:
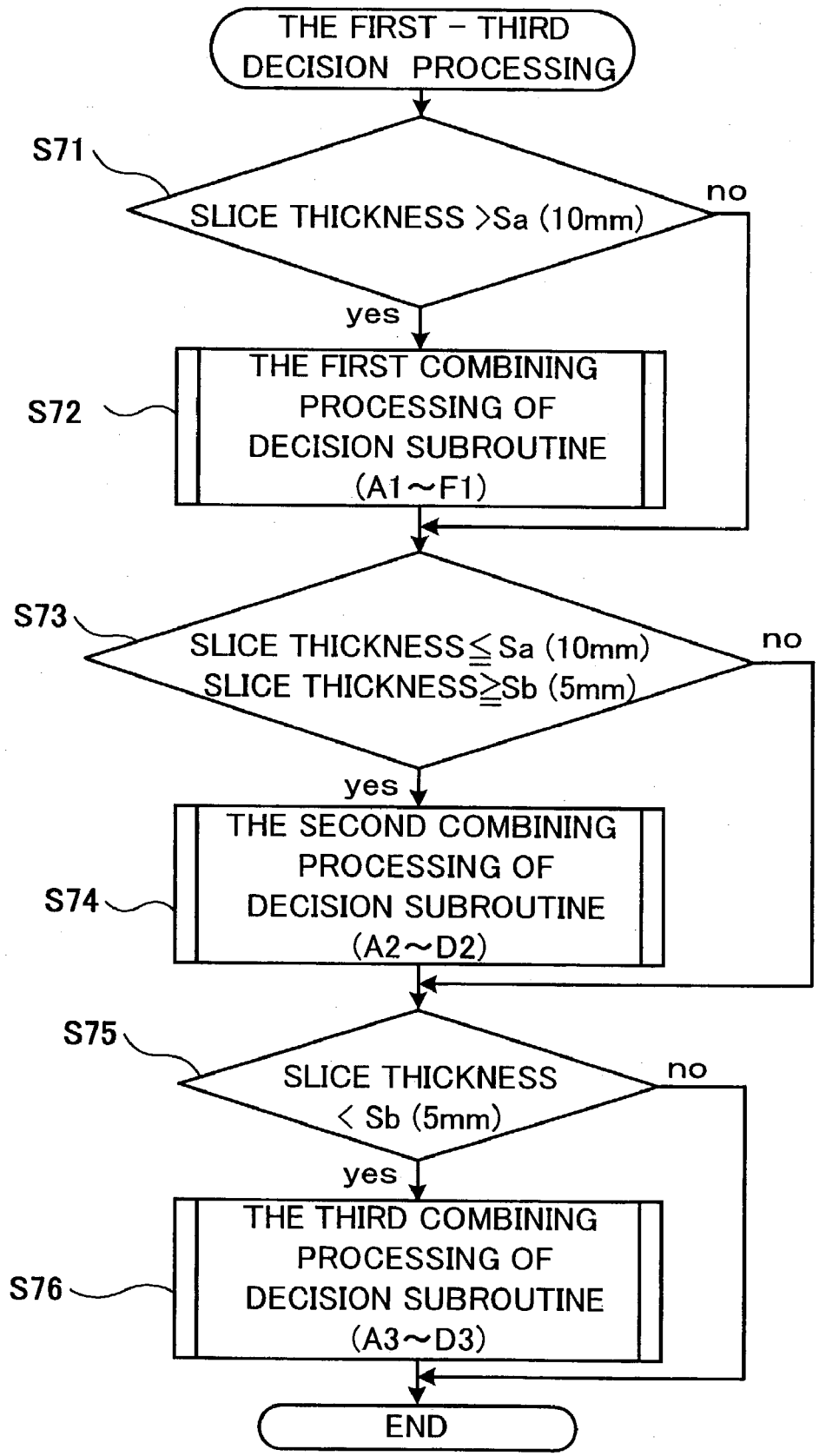
FIG. 11 is a flowchart showing details of the first to third decision processings of Steps S43, S45 and S45 of FIG. 10.

FIG. 11 is a flowchart showing details of the first to third decision processing of Steps S43, S45 and S48 of FIG. 10. The first to third decision processing are approximately common to one another except that various different parameters are used in the respective decision making subroutines of Steps S72, S74 and S76. The first decision processing is executed on an image which has been enlarged by Step S42 of the shadow decision, processing shown in FIG. 10. The second decision processing is executed on an image whose shadow size has been determined as accommodated within a predetermined range, by Step S44 of the shadow decision processing shown in FIG. 10. The third decision processing is executed on an image which has been reduced by Step S47 of the shadow decision processing shown in FIG. 10. In each of the first to third decision processing, a combination of decision making subroutines is changed according to the slice thickness of each CT image.

In a medical image, a shadow such as a cancer, a blood vessel, a cross section of a blood vessel, a cross section of a bronchus and the like are photographed together. As the slice thickness of a medical image is made different, a particular shadow of the shadows contained in the medical image becomes clear or obscure. For example, if the slice thickness is small, a shadow corresponding to a blood vessel extremely diminishes and becomes difficult to recognize. As the slice thickness increases, the shadow of the blood vessel clearly appears. Accordingly, in the case where the slice thickness is small, it is necessary to make a decision as to whether the shadow is a blood vessel shadow or a focus candidate shadow. Contrarily, in the case where the slice thickness is large, it is possible to clearly identify the shadow of a blood vessel, so that decision processing is not needed. In addition, in the case where a shadow is bound to a lung wall, as shown in FIG. 44, it is desirable to change processing according to the location where the shadow is present.

Thus, processing is performed with a plurality of specialized decision making subroutines, and, finally, a logical OR operation is carried out with respect to all the subroutine results. This embodiment is provided with first combined processing including decision processing E1 and E2 necessary for shadow decision in the case of a small slice thickness, as well as second and third combined processing, not including the decision processing E1 and E2. One of these first to third processes are appropriately selected according to slice thicknesses Sa and Sb. Details of the first to third decision processing will be described below in the order of the steps thereof.

[Step S71] The CPU 40 determines whether the slice thickness of the CT image 20 is larger than the predetermined value Sa (for example, 10 mm). If the CPU 40 determines that the slice thickness is larger (yes), the CPU 40 proceeds to the next step S72, whereas if the CPU 40 determines that the slice thickness is not larger (no), the CPU 40 jumps to Step S73.

[Step S72] The CPU 40 executes the first combined processing, combining decision making subroutines A1 to F1.

[Step S73] The CPU 40 determines whether the slice thickness of the CT image 20 is not larger than the predetermined value Sa and not smaller than the predetermined value Sb, i.e., within a predetermined range. If the CPU 40 determines that the slice thickness is within the predetermined range (yes), the CPU 40 proceeds to Step S74; whereas, if the CPU 40 determines that the slice thickness is not within the predetermined range (no), the CPU 40 jumps to Step S75.

[Step S74] The CPU 40 executes the second combined processing made up of a combination of the decision making subroutines A2 to D2. In this second combined processing, decision making subroutines corresponding to the decision making subroutines E1 and F1 are not executed. The decision making subroutines E1 and F1 constitute processing for determining whether a shadow is a shadow corresponding to a blood vessel; and, in the case of small slick thickness, a shadow corresponding to a blood vessel diminishes greatly and the decision making subroutines E1 and F1 are unable to recognize such shadows. Accordingly, in this step, the decision making subroutines are not executed. Incidentally, it goes without saying that the CPU 40 may execute the decision making subroutines E2 and F2 similarly to Step S72.

[Step S75] The CPU 40 determines whether the slice thickness of the CT image 20 is smaller than the predetermined value Sb. If the CPU 40 determines that the slice thickness is smaller (yes), the CPU 40 proceeds to the next step S76; whereas, if the CPU 40 determines that the slice thickness is not smaller (no), the CPU 40 brings the processing to an end and proceeds to Step S44 or S46 of FIG. 10.

[Step S76] The CPU 40 executes the third combined processing made up of a combination of decision making subroutines A3 to D3. In this third combined processing, decision making subroutines corresponding to the decision making subroutines E1 and F1 are not executed. Similarly to the case of the above-described step, since the decision making subroutines E1 and F1 constitute processing for determining whether a shadow is a shadow corresponding to a blood vessel, decision making subroutines related to the decision making subroutines E1 and F1 are not executed. Incidentally, it goes without saying that the CPU 40 may execute the decision making subroutines E3 and F3 similarly to the case of Step S72.

Figure 12:
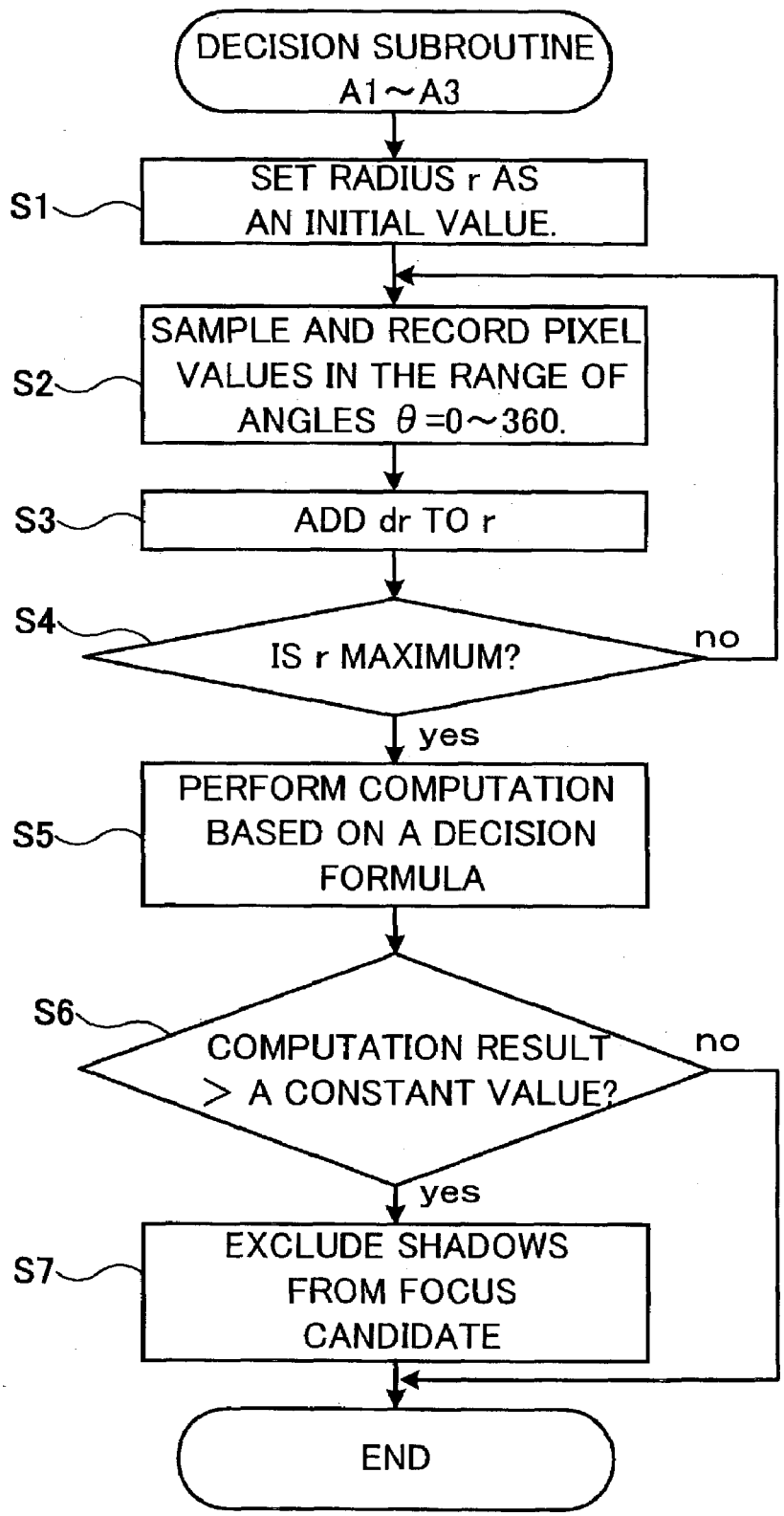
FIG. 12 is a flowchart showing details of decision making subroutines A1 to A3 of Steps S72, S74 and S75 of FIG. 11.
Figure 13A:
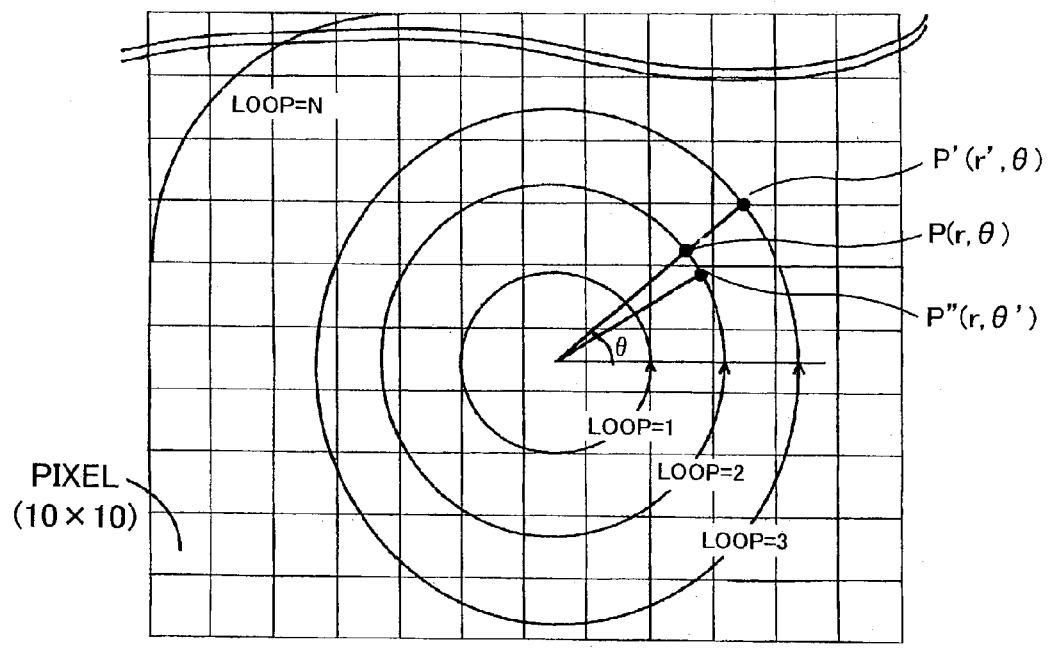
FIG. 13a is a conceptual diagram showing the manner of imaginary loops set on a CT image.
Figure 13B:
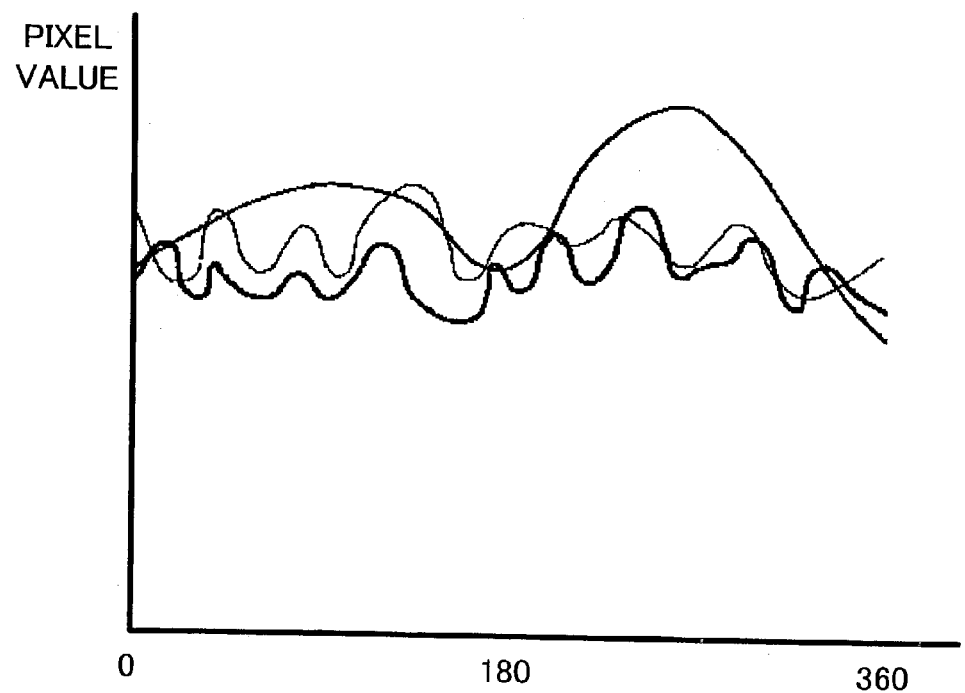
FIG. 13b is a graph showing pixel values of each of the imaginary loops in the processing of FIG. 12.

The respective decision making subroutines A1 to A3 that are executed in Steps S72, S74 and S76 of FIG. 11 will be described below. FIG. 12 is a flowchart showing details of each of the decision making subroutines A1 to A3. FIGS. 13a and 13b are provided to conceptually show the manner of processing each of these decision making subroutines A1 to A3, in which FIG. 13(a) is a diagram showing the manner in which imaginary loops are set on a CT image, while FIG. 13(b) is a graph showing the pixel values of each of the imaginary loops. In general, although there are some exceptions, the correlation of densities of a shadow located on a loop of radius r from the central position of the shadow exhibits a tendency to become larger in a focus shadow than in a blood vessel cross-sectional shadow. To use this tendency in shadow decision processing, the correlation of density variations of a shadow between adjacent loops spaced a small radius dr apart from each other is found. Namely, it is known that the density of a shadow greatly differs between the vicinity of the center of the shadow and the vicinity of the periphery thereof, so that if the correlation of density values only between adjacent loops is found, it is impossible to find an accurate correlation between both. In this embodiment, the correlation of density variations of the shadow is found. Incidentally, the vicinity of the central position of the shadow is determined on the basis of the multi-valued image (b1) of FIG. 3, and the determined center of the shadow is applied to the CT image 20 of FIG. 3, as seen at (a1), and then the density on each loop is found. Incidentally, in the case of the Step S83 of FIG. 2a, multi-valued information indicative of a multi-valued image other than a binary image is used in place of the CT image 20. Details of these decision making subroutines A1 to A3 will be described below in the order of the steps thereof.

[Step S1] The CPU 40 sets a radius r at which to search a shadow, as an initial value. In FIG. 13a, for example, a value equivalent to about 1.5 times a square-shaped small area of approximately 10×10 pixels is set as the radius r.

[Step S2] The CPU 40 rotates at the radius r by one degree at one time about the vicinity of the center of the shadow, and it samples and records each pixel value in the range of angles θ=0 to 360 degrees. Incidentally, it is preferable to add a constant value for each loop in order to equalize the density average of each loop.

[Step S3] The CPU 40 sets a radius r+d obtained by adding the radius r to the small radius dr, to obtain the radius r of the next loop. In FIG. 13a, for example, a value equivalent to about 1.2 times the above-described small area is set as the small radius dr.

[Step S4] The CPU 40 determines whether the radius r is a maximum, and, if the radius r is not a maximum (no), the CPU 40 jumps to Step S2; whereas, if the radius r is a maximum (yes), the CPU 40 proceeds to Step S5. Incidentally, the maximum radius is a radius which is set in advance according to, for example, the size of a focus target to be extracted and the kinds of first to third decision processing.

[Step S5] The CPU 40 performs a computation based on a predetermined decision formula. For example, as shown in FIG. 13a, the CPU 40 determines the density differences between pixels at a point P (r, θ) and pixels at a point P' (r', θ) in the range of 0 to 360 degrees, and determines the sum of the absolute values of the density differences. Namely, the CPU 40 finds the correlation of densities between adjacent loops on the basis of the following formula (1):

$$\Sigma |\text{density difference between pixels at the same angle on adjacent loops}| \quad (1)$$

As described above, the correlation of shadows between adjacent loops is larger in a focus shadow than in a blood vessel cross-sectional shadow, so that the computation result of the above formula (1) tends to be smaller in a focus shadow than in a blood vessel cross-sectional shadow. This fact can also clearly understood from each curve shown in FIG. 13b. Specifically, the curve (solid line) of a loop=1 and the curve (dotted line) of a loop=2 show similar density variations, and, therefore, it can be said that the correlation therebetween is extremely large. On the other hand, the curve (dotted line) of the loop=2 and the curve (dot-dashed line) of a loop=3 show utterly different density variations, and therefore, it can be said that the correlation therebetween is small. Incidentally, the computing formula for finding the correlation between adjacent loops is not limited to the above-described formula (1).

On the other hand, although there are some exceptions, the magnitude of a shadow variation in the same loop is smaller in a focus shadow than in a blood vessel cross-sectional shadow. To use this fact in shadow a decision, as shown in FIG. 13a, the CPU 40 determines the density differences between pixels at the point P (r, θ) and pixels at a point P''' (r, θ'') in the range of 0 to 360 degrees, and determines the sum of the absolute values of the density differences. Namely, the CPU 40 finds the correlation of densities between adjacent pixels on the same loop on the basis of the following formula (2):

$$\Sigma |\text{density difference between adjacent pixels on the same loop}| \quad (2)$$

As described above, although there are some exceptions, the magnitude of a shadow variation in the same loop is smaller in a focus shadow than in a blood vessel cross-sectional shadow, so that the computation result of the above formula (2) tends to be smaller in a focus shadow than in a blood vessel cross-sectional shadow. This fact can also clearly understood from each curve shown in FIG. 13b. Namely, it can be said that the curve (solid line) of the loop=1 and the curve (dotted line) of the loop=2 show small density variations, whereas the curve (dot-dashed line) of the loop=3 shows large density variations. Incidentally, a computing formula for finding the correlation between adjacent pixels on the same loop is not limited to the above-described formula (2).

In this embodiment, the following formula (3), made up of a combination of the above formula (1) and the above formula (2), is used:

$$\prod_{i=1}^{N} \left( \text{constant} \times \sum_{0}^{359} |A| \cdot \sum_{0}^{359} |B| \right), \quad (3)$$

where A: density difference between pixels at the same angle on adjacent loops i and i+1; and
B: density difference between adjacent pixels on the same loop i.

The computation result of this formula (3) shows a tendency for a focus shadow to be smaller than a blood vessel cross-sectional shadow. Accordingly, it is possible to make a decision to exclude from focus candidates a shadow whose computation result obtained from the formula (3) is larger than a constant value. Incidentally, a threshold to discriminate between a focus candidate shadow and a normal shadow (the constant of the formula (3)) is experimentally found, and the threshold is previously recorded in the magnetic disk unit 44 and the like and is used when necessary by being read therefrom.

Although in the formula (3), summation is found after the absolute values have been found, the following decision formula (4) of finding the absolute values after having performed the summation may also be used:

$$\prod_{i=1}^{N} \left( \text{constant} \times \left| \sum_{0}^{359} A \right| \cdot \left| \sum_{0}^{359} B \right| \right). \quad (4)$$

[Step S6] The CPU 40 determines whether the computation result obtained from the decision formula (3) or (4) is larger than a constant value. If the CPU 40 determines that the computation result is larger (yes), the CPU 40 proceeds to Step S7; whereas, if the CPU 40 determines that the computation result is not larger (no), the CPU 40 brings the processing to an end and proceeds to the next subroutines B1 to B3.

[Step S7] The CPU 40 excludes from focus candidate shadows the result of the decision in Step S6, i.e., a shadow whose computation result obtained from the decision formula (3) or (4) is determined to be larger than the constant value (computation result>constant value), and proceeds to the next subroutines B1 to B3.

In the above description of the decision making subroutines A1 to A3, reference has been made to the case where the center of a shadow is determined on the basis of the multi-valued (binary) image (b1) shown in FIG. 3 and the center of the shadow is applied to the CT image 20, thereby finding densities on a plurality of concentric loops about the center to make a decision as to whether the shadow is a focus candidate shadow. This decision method is merely one example, and various other modifications are available. Some modifications will be described below.

Figure 14A:
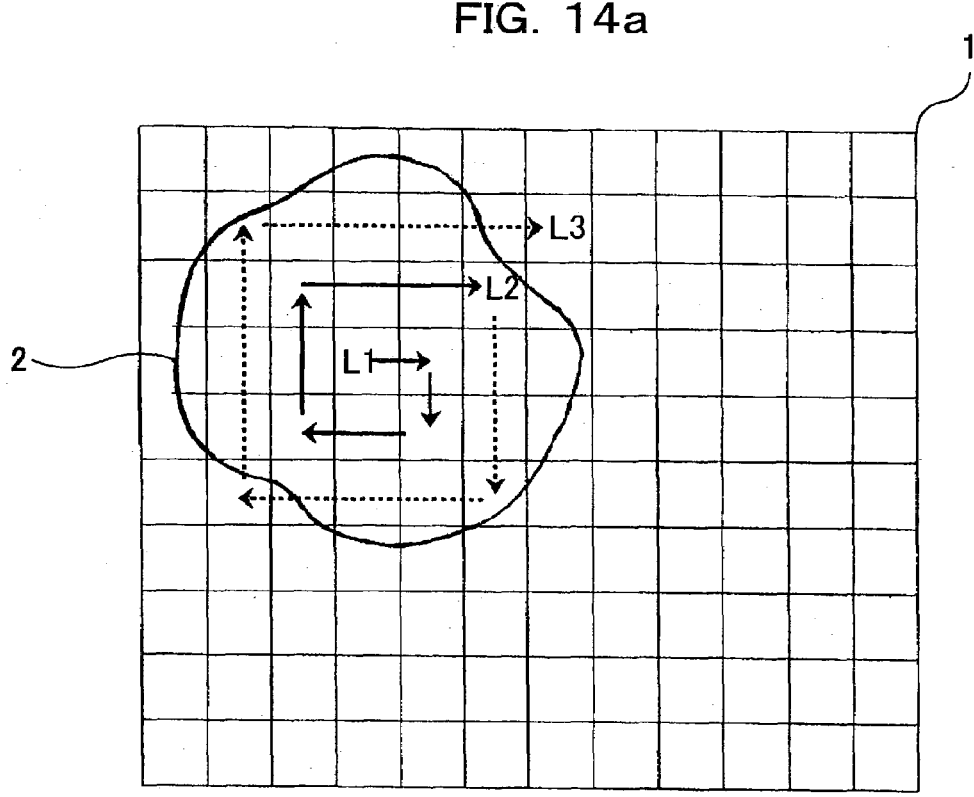
FIGS. 14a and 14b are a conceptual diagram showing a method of searching for a pixel whose density is to be found, spirally from the central position of a shadow.
Figure 14B:
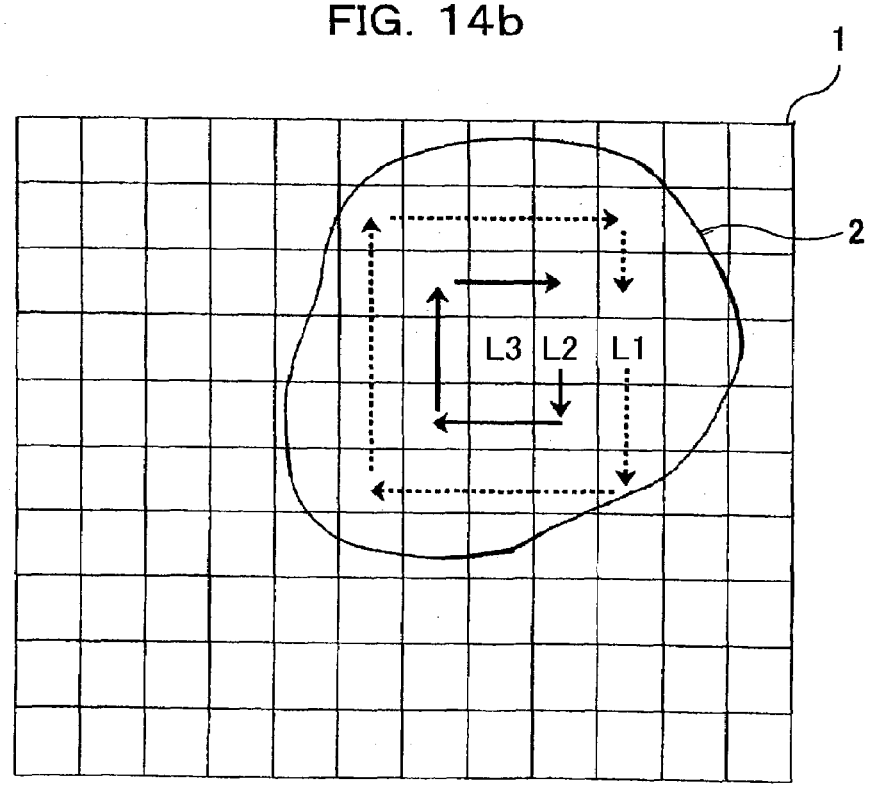
Figure 15A:
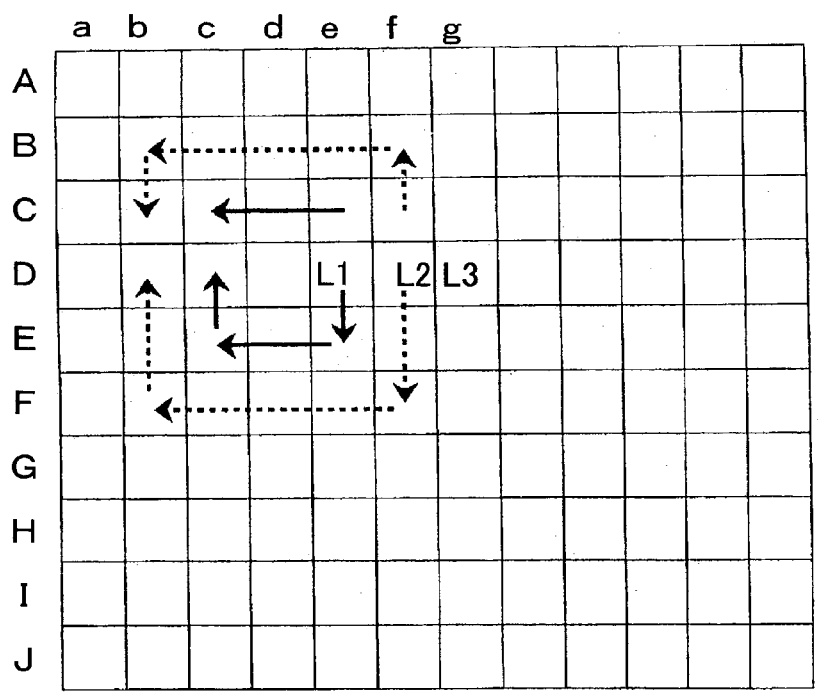
FIGS. 15a and 15b are conceptual diagrams showing another method of searching for a pixel whose density is to be found, spirally from the central position of a shadow.
Figure 15B:
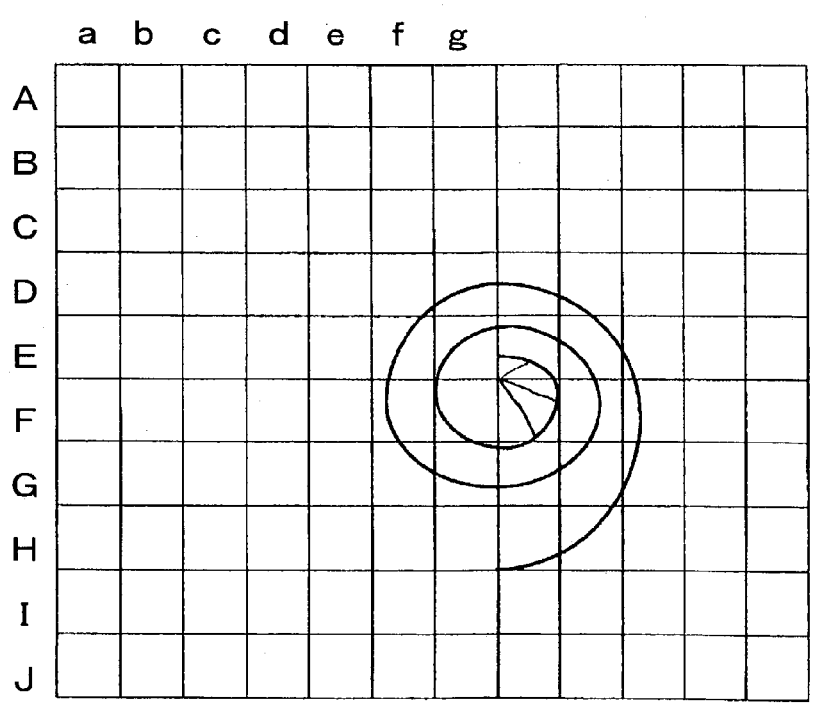

FIGS. 14a, 14b and 15a, 15b are views showing the concepts of several methods for searching for a pixel whose density is to be found, spirally from the central position of a shadow. As shown in FIG. 14a, a corresponding pixel for finding the density of a shadow is identified by selecting the vicinity of the center of a shadow 2 as a reference point and making a spiral search along loops L1, L2 and L3, which rotate clockwise from the reference point toward the edge of the shadow 2. Namely, the CPU 40 makes a search in the order indicated by solid-line arrows along the first loop L1; then it makes search in the order indicated by dotted-line arrows along the second loop L2; and subsequently it makes search in a similar manner along the third loop L3 and the following loops (not shown), thereby identifying the corresponding pixel. Incidentally, the starting point of the search and the direction of the search are not limited; and, as shown in FIG. 14b, a search may be concentrically made along the loops L1, L2 and L3 from the edge of the shadow 2 toward the vicinity of the center of the shadow 2. In addition, the search order of one loop is not limited; and, as shown in FIG. 15a, as to the loop L2, a search may also be made in the order of Df→Ff→Fb→Db and then in the order of Cf→Bf→Bb→Cb. Incidentally, the capital alphabetical letters indicative of the above-described search order indicate the y coordinate of the CT image 20, and the small alphabetical letters indicate the x coordinate of the same. Furthermore, as shown in FIG. 15b, while a radius is rotationally continuously increased, passage points may also be used as search point pixels.

FIGS. 16(a-1) to 16(c-2) conceptually show sampling points in the search methods shown in FIGS. 14a, 14b and 15a, 15b, show data at the sampling points in the pattern of values "0" and "1". Specifically, in each of FIGS. 16(a-1) to 16(c-1), black dots indicate sampling points in each of shadows 3-5, respectively. Incidentally, the shadows 3-5 correspond to an binary image of FIG. 16(b-1), and any pixel value on each of the shadows is "1" and the other pixel values are "0". Numbers attached to the black dots indicate the order of search. The density values of the pixels on the shadows 3-5 that are sampled in accordance with this search order are shown as graphs in FIGS. 16(a-2) to 16(c-2). As is apparent from FIGS. 16(a-2) to 16(c-2), the density value of each of the sampling points assumes a pattern made of "0" and "1". The CPU 40 makes a decision as to whether the shadow is a focus candidate shadow, on the basis of this pattern. For example, if the state in which the density value at each sampling point is "1" continuously exists from 1 to 9, as shown in FIG. 16(a-1), the shadow is determined as a focus candidate shadow. If, as shown in FIG. 16(b-2), the state in which the density value at each sampling point is "1" continuously exists from 1 to 8 and the state in which the density value at each sampling point is "0" continues from 9 to 13, the shadow is determined as not being a focus candidate shadow. If, as shown in FIG. 16(c-2), the state in which the density value is "1" and the state in which the density value is "0" are repeated at short cycles, the shadow is determined as not being a focus candidate shadow. Incidentally, it is preferable to make this decision with values previously learned on the basis of actual focus shadows.

Figure 17A:
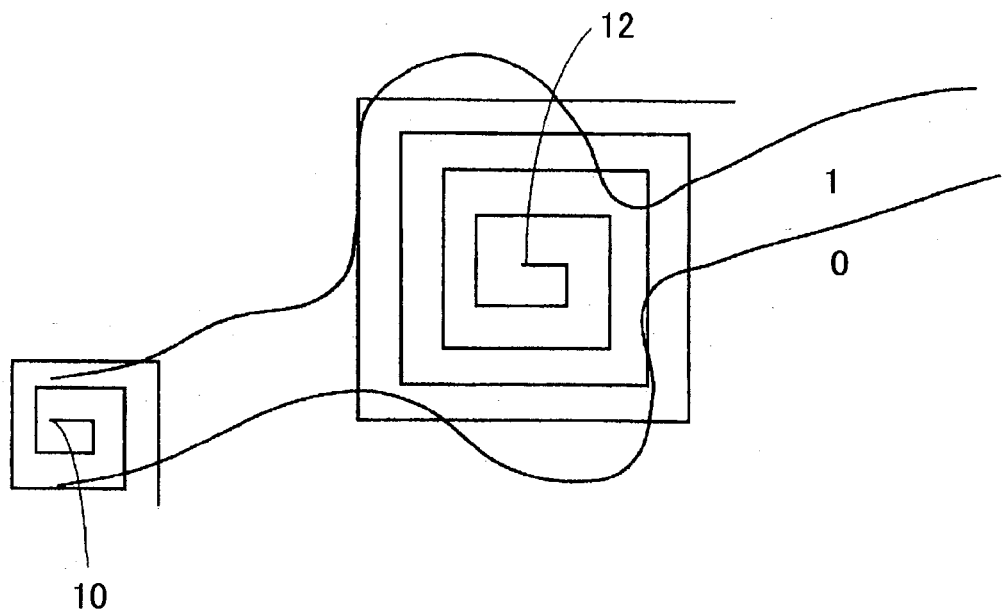
FIGS. 17a and 17b are conceptual diagrams of a method of converting the shape of a shadow in a multi-valued image into the degree of density.
Figure 17B:
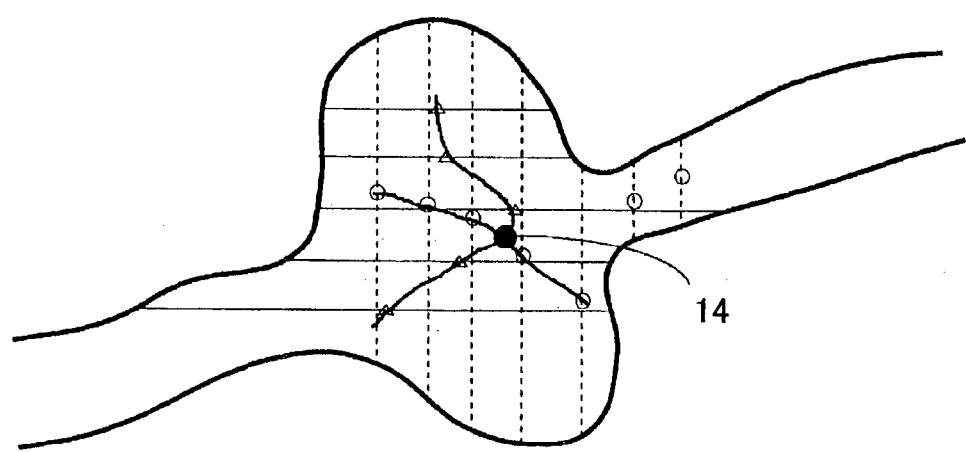

A method of converting the shape of a shadow in a multi-valued image into the degree of density shall here be explained. FIGS. 17a and 17b are diagrams showing the concept of this converting method. As shown in FIG. 17a, when the case where a point 10 is selected as the starting point of a search is compared with the case where a point 12 is selected as the starting point of a search, the number of loop turns required to search for a point indicative of a pixel value of zero is larger in the case where the point 12 is selected as the starting point of the search. Accordingly, by selecting a value proportional to this number of loop turns as the density of the shadow, it is possible to convert the shadow shape of the multi-valued image into density values. Incidentally, in the above-described embodiment, the weighted center portion of a shadow is adopted as the starting point of a search (the center of the shadow), but as shown in FIG. 17b, an intersection point 14 of a curve connecting dots (the circular dots shown in FIG. 17b) indicating the center of the vertical length lines of a shadow and a curve connecting dots (the triangular dots shown in FIG. 17b) indicating the center of the horizontal length lines of a shadow can also be selected as the center of the shadow. The starting point of a search may also be the center of a circle inscribed in a shadow in addition to the weighted center position of the shadow. In other words, the starting point of a search needs only to be near the center of the shadow. Each of the decision making subroutines may also be executed on the basis of densities converted in this manner.

In addition, since the surroundings of an area to be extracted can be viewed, the above-described method can also be used to make a decision as to whether an area to take a value larger than a particular CT value surrounds the area to be extracted.

Figure 18:
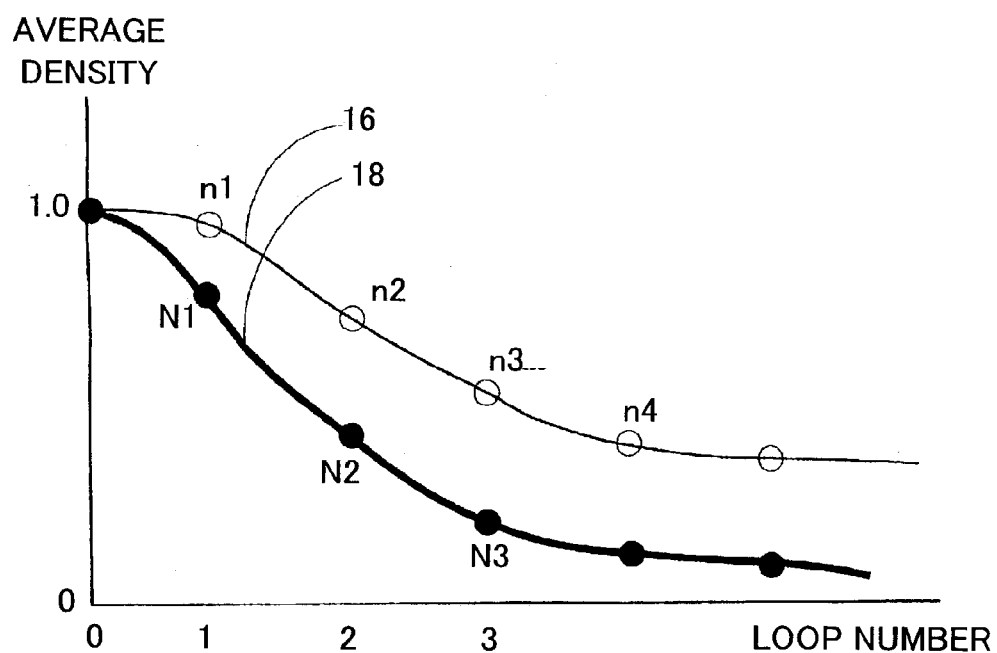
FIG. 18 is a graph showing a method of determining whether a shadow is a focus candidate shadow or a normal shadow.

FIG. 18 is a view showing a method of determining whether a shadow is a focus candidate shadow (cancer shadow) or a normal shadow. In the graph shown in FIG. 18, the horizontal axis represents the number of loop turns by which a search is made spirally or concentrically, while the vertical axis represents the average value of the densities at sampling points in each loop. The average value of densities is found on the basis of a multi-valued image as shown in FIGS. 16(a-1) to 16(c-1). Incidentally, such average value may also be found on the basis of the original CT image and be normalized. In general, the density of a shadow tends to be high near the center of the shadow and to become lower toward the periphery thereof. Accordingly, as shown in FIG. 18, as the number of loop turns increases like points n1, n2, n3, n4 . . . , or points N1, N2, N3, N4 . . . , the average of densities shows a tendency to decrease gradually. Incidentally, in FIG. 18, a curve 16 represented by the points n1, n2, n3, n4 . . . relates to a cancer shadow, while a curve 18 represented by the points N1, N2, N3, N4 . . . relates to a blood vessel cross-sectional shadow. As is apparent from this figure, the cancer shadow 16, which is a focus candidate shadow, is smaller than the blood vessel cross-sectional shadow 18 in the rate of diminishing as the number of the loop is higher. Accordingly, a multiplicity of curve data are measured by using actual cancer shadows in advance, and the measured results are stored in the magnetic disk unit or the like as reference data in advance, and a decision is made as to whether each shadow is a focus candidate shadow, on the basis of these reference data.

Figure 19:
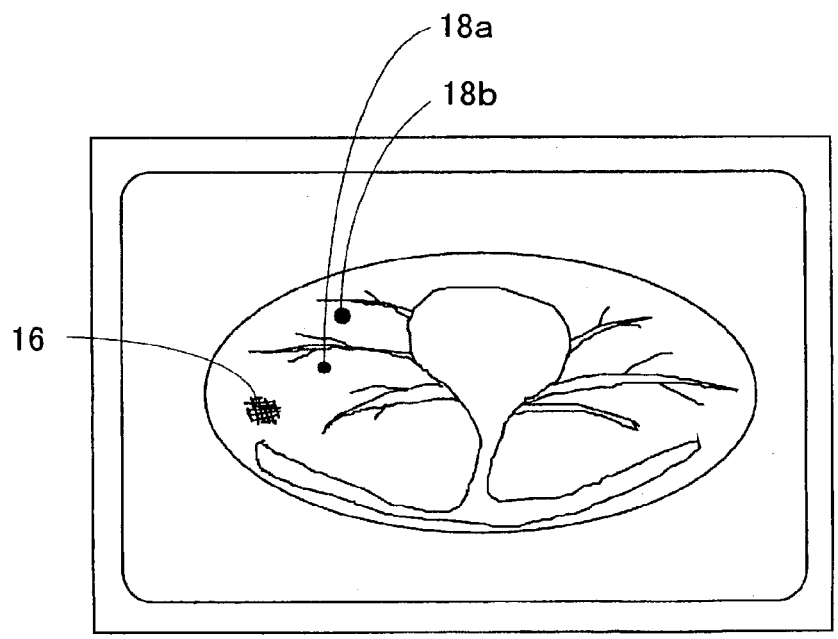
FIG. 19 is a diagram showing one example of a CT image in which a focus shadow and a normal shadow exist.

FIG. 19 is a view showing one example of a CT image in which a focus shadow and a normal shadow exist. In the case where the CPU 40 is to discriminate between shadows 16a, 18a and 18b, as shown in FIG. 19, the CPU 40 makes a search spirally from the vicinity of the center of each of the shadows 16a, 18a and 18b and finds an average density value for each loop. The CPU 40 compares each data on the average density value with each reference data of FIG. 18, and makes a decision as to whether the average density value coincides with any one of the reference data. For example, in the case where the data of the average density value of the shadow 16 coincides with the curve 16 of FIG. 18, the shadow 16 is presented to a doctor as a candidate for a cancer shadow. The data of the average density value of each of the shadows 18a and 18b approximately coincides with the curve 18 of FIG. 18, but does not coincide with any of the reference data. In this case, the shadows 18a and 18b are deleted from focus candidate shadows, and are not presented to the doctor. Incidentally, the following formula (5) is used to make a decision as to whether the data of the average density data coincides with the reference data:

$$\Sigma |Ni-ni| < \text{constant value}. \quad (5)$$

When the above formula (5) is satisfied, the two curves are regarded as coincident with each other. In the formula (5), Ni is an average density value as to actually searched sampling points of a loop number i, and ni is an average density value (reference data) in a cancer shadow of the loop number i. The above absolute value may also be raised to the δ-th power (δ=1 to 2). Incidentally, the decision formula is not limited to this one, and the following formula (6) may also be used:

$$\Pi |Ni-ni| < \text{constant value}. \quad (6)$$

Although the above-described example has referred to an examination of a known cancer shadow, another method may be used in which reference data on normal shadows of blood vessel cross sections are prepared; and, when a shadow coincides with the reference data, the shadow is excluded from focus candidates. Furthermore, it is also possible to discriminate between shadows by not only the shape fitting between the number of loop turns and the curve of a graph of an average density value for each loop, but also the shape fitting with the curve of a graph of loop number and maximum value for each loop.

Figure 20A:
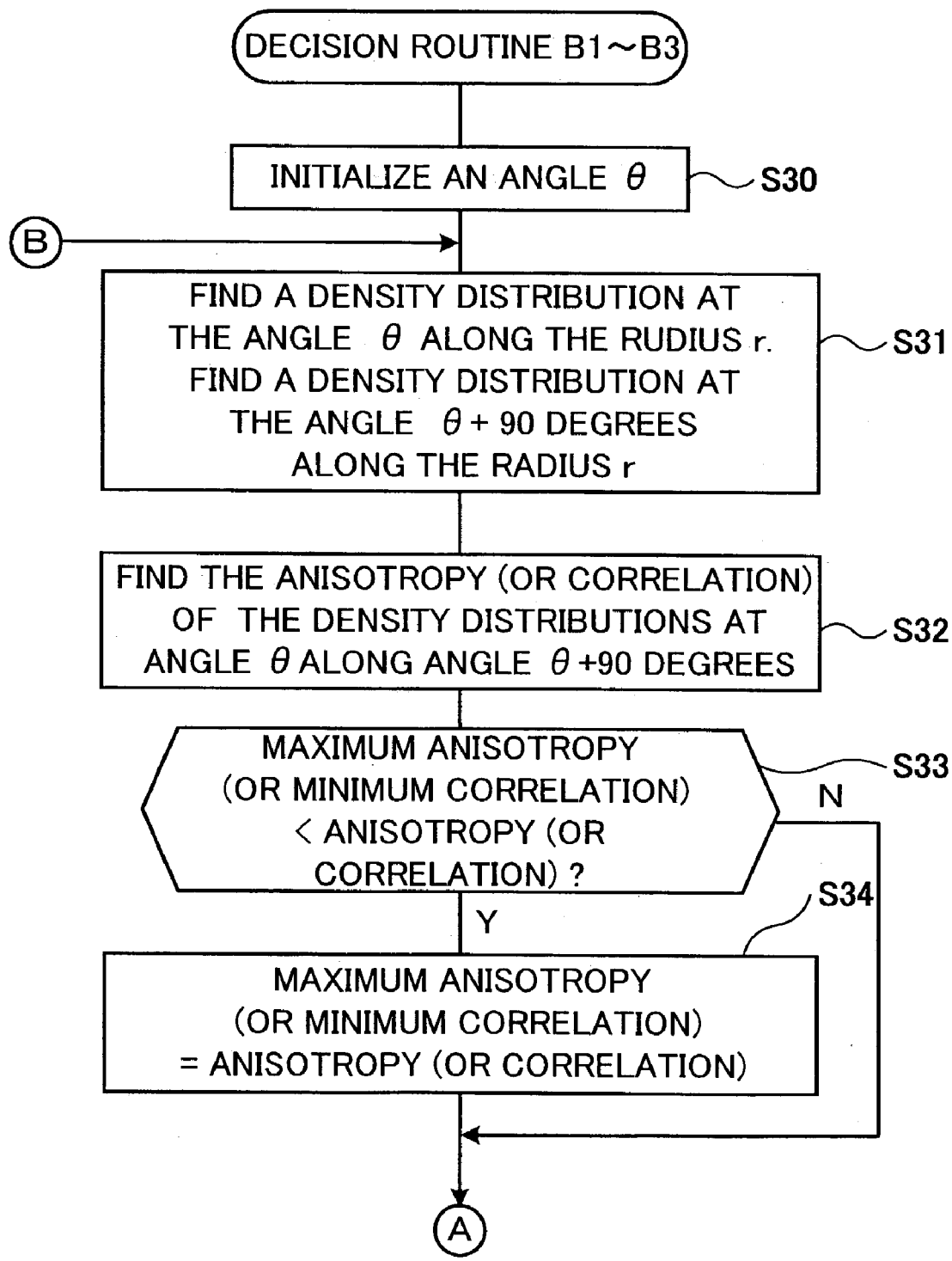
FIGS. 20a and 20b, when combined, comprise a detailed flowchart of each of the decision making subroutines B1 to B3 of Steps S72, S74 and S75 of FIG. 11.
Figure 20B:
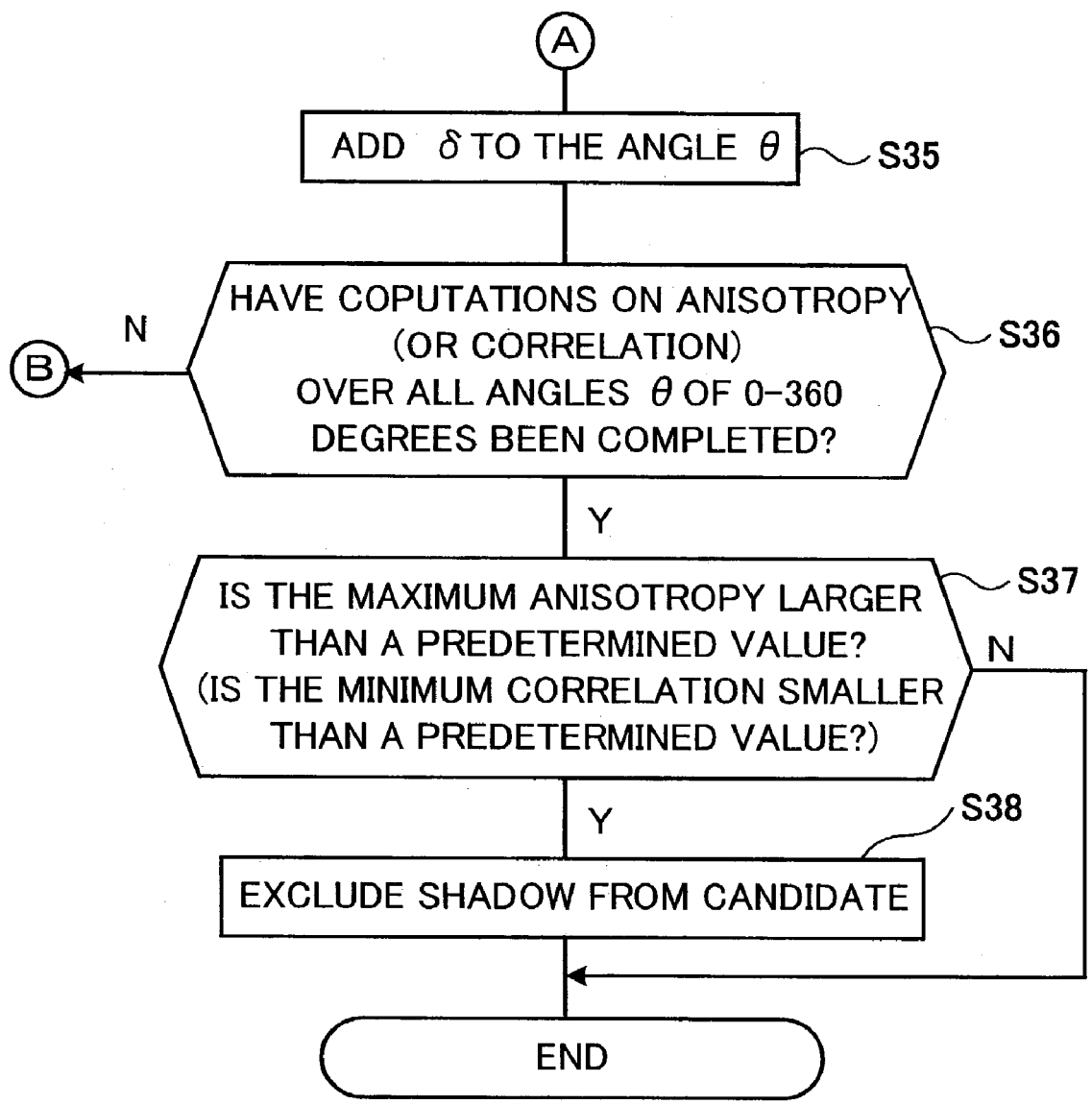
Figure 21A:
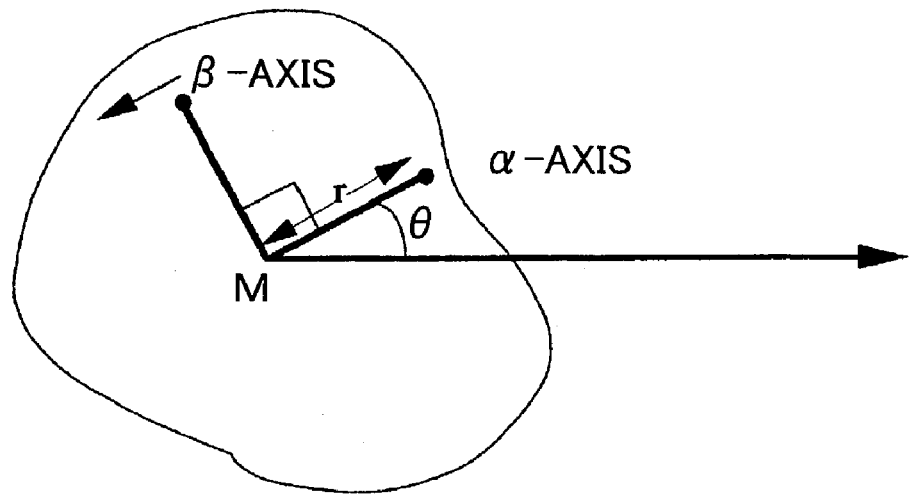
FIG. 21a is a conceptual diagram of the case of abnormal shadow.
Figure 21B:
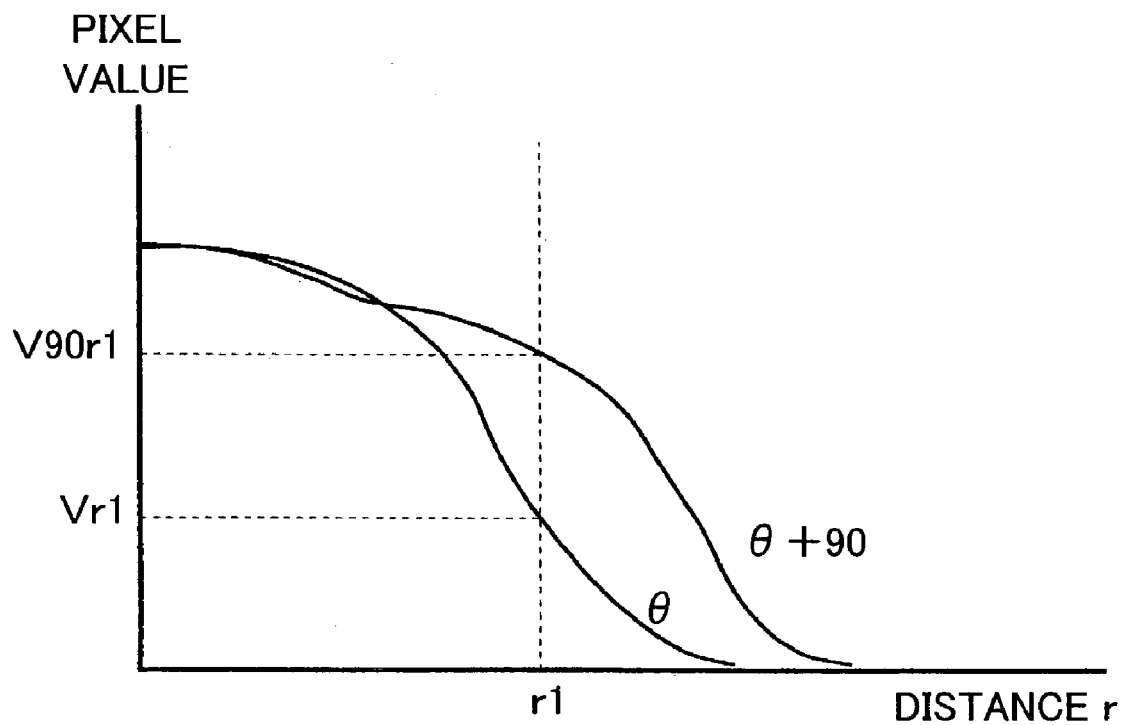
FIG. 21b is a graph showing the pixel values in each of the decision making subroutines B1 to B3 of FIGS. 20a and 20b.

The decision making subroutines B1 to B3 executed in Steps S72, S74 and S76 of FIG. 11 will be described below. FIGS. 20a and 20b constitute a flowchart showing details of each of the decision making subroutines B1 to B3 for identifying a shadow on the basis of the anisotropy of the shadow. FIGS. 21a, 21b and 22a, 22b are views conceptually showing the manner of processing of each of these decision making subroutines B1 to B3. FIGS. 21a, 21b relate to the case of a focus shadow, and FIGS. 22a, 22b relate to the case of a blood vessel cross-sectional shadow. Details of these decision making subroutines B1 to B3 will be described below in the order of the steps thereof.

[Step S30] The CPU 40 initializes an angle θ to, for example, θ=0 degrees. In each of FIGS. 21a and 22a, the angle θ=0 is a line which is shown by an arrow extending from a central position M of a shadow in the rightward horizontal direction.

[Step S31] The CPU 40 determines a density distribution Vr of the shadow located on an α axis at the angle θ and at a radius r from the center M of the shadow, and a density distribution V90r of the shadow located on an β axis at the angle θ+90 degrees and at the radius r.

[Step S32] In the case of FIG. 21a, since the positions of the radius r on the α axis and the β axis lie inside the shadow, the density distributions Vr and V90r assume an equal value. On the other hand, in the case of FIG. 22a, the position of the radius r on the α axis lies outside the shadow and the position of the radius r on the β axis lies inside the shadow, so that the density distributions Vr and V90r assume remarkably different values. Accordingly, the CPU 40 can make a comparison decision as to these values and determines whether the shadow is a focus candidate shadow. Specifically, in this step S32, the CPU 40 will substitute the density distribution Vr located at the radius r on the α axis at the angle θ and the density distribution V90r located at the radius r on the β axis at the angle θ+90 degrees into the following formula (7) to find the anisotropy (or else correlation) of the shadow:

$$90\text{-degree anisotropy } (\theta) = \sum_{r=r0}^{r=\max} |V90r - Vr|. \quad (7)$$

In the above formula (7), after the absolute value has been found, summation processing is performed. A formula such as that which finds an absolute value after having performed summation processing can also be used as a formula which expresses anisotropy. Although FIG. 21a shows the case where the radius r is a positive value, the radius r may also be a negative value. A correlation may also be found with respect to only a radius r1 in each of FIGS. 21b and 22b. In this case, since the lengths differ, a correlation of average values is found. Furthermore, the angle θ of the 90-degree anisotropy (θ) found by the above formula (7) may also be varied in the range of 0-360 degrees to find the anisotropy expressed by the following formula (8):

$$\text{anisotropy} = \sum_{0}^{359} 90\text{-degree anisotropy } (\theta). \quad (8)$$

Otherwise, the anisotropy expressed by the following formula (9) may also be found instead of the above formula (8):

$$\text{anisotropy} = \prod_{0}^{359} 90\text{-degree anisotropy } (\theta). \quad (9)$$

[Step S33] The CPU 40 determines whether the anisotropy (or correlation) found in Step S32 is larger than the maximum anisotropy (or the minimum correlation) found in the past. If the CPU 40 determines that the anisotropy (or correlation) is larger than the maximum anisotropy (or the minimum correlation) (yes), the CPU 40 proceeds to Step S34; whereas, if the CPU 40 determines that the anisotropy (or correlation) is not larger than the maximum anisotropy (or the minimum correlation) (no), the CPU 40 jumps to Step S35. Incidentally, even in the case where this processing is in the initial cycle and the maximum anisotropy (or the minimum correlation) does not exist, the CPU 40 proceeds to Step S34.

[Step S34] The CPU 40 sets the anisotropy (or correlation) found in Step S33 as the maximum anisotropy (or the minimum correlation), and updates the value of the maximum anisotropy (or the minimum correlation).

[Step S35] The CPU 40 adds a small angle δ to the angle θ to set the angle θ to an angle (θ+δ). Incidentally, the small angle δ is, for example, one degree, but may also be another value.

[Step S36] The CPU 40 determines whether computations on anisotropy (or correlation) over all angles θ of 0-360 degrees have been completed. If the CPU 40 determines that the computations have been completed (yes), the CPU 40 proceeds to Step S37; whereas, if the CPU 40 determines that the computations have not been completed (no), the CPU 40 returns to Step S31 and repeats similar processing until the angle θ reaches 360 degrees.

[Step S37] The CPU 40 determines whether the maximum anisotropy is larger than a predetermined value (the minimum correlation is smaller than a predetermined value). If the CPU 40 determines that the maximum anisotropy is larger (the minimum correlation is smaller), the CPU 40 proceeds to Step S38, whereas if the CPU 40 determines that the maximum anisotropy is not larger (the minimum correlation is not smaller), the CPU 40 proceeds to the next subroutines C1 to C3. Incidentally, a decision comparison constant in each of the steps is a value determined according to the conditions (such as slice thickness and tube current) of photography with an X-ray CT device, and may also be automatically selected.

Figure 22A:
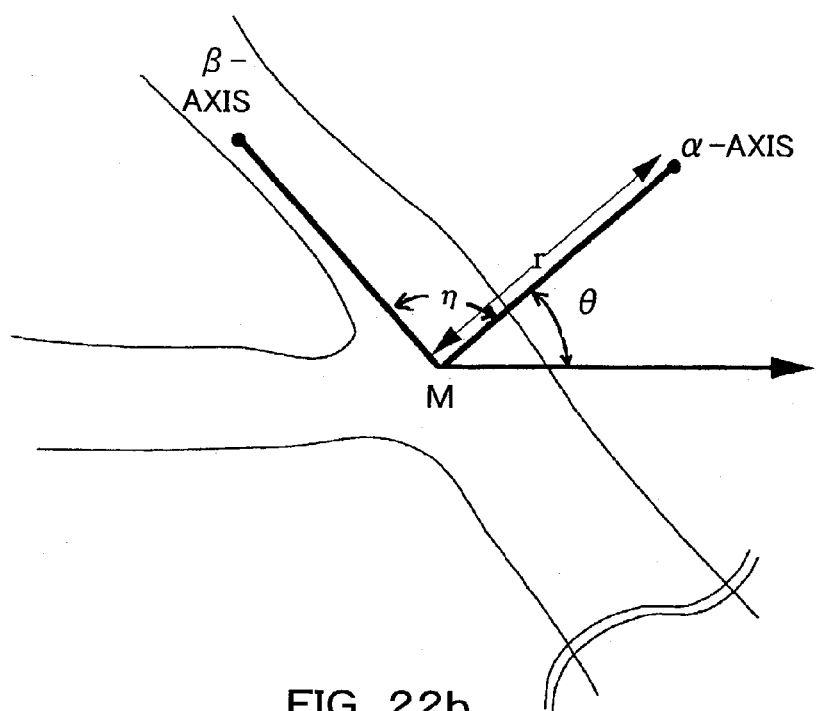
FIG. 22a is a conceptual diagram of the case of a blood vessel cross-sectional shadow.
Figure 22B:
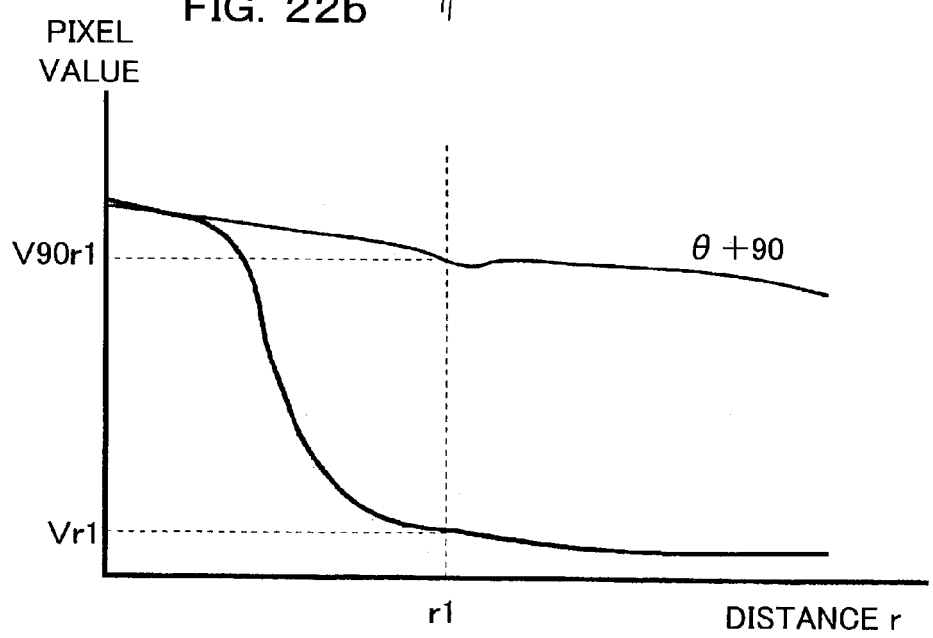
FIG. 22b is a graph showing the pixel values in each of the decision making subroutines B1 to B3 of FIGS. 20a and 20b.

[Step S38] Since it has been determined in Step S37 that the maximum anisotropy is larger than the predetermined value (the minimum correlation is smaller than the predetermined value), the CPU 40 excludes the shadow from focus candidate shadows, and proceeds to the next subroutines C1 to C3. In the case where the above-described anisotropy is calculated on an actual focus shadow, such as a cancer shadow, the value of the anisotropy tends to be small (large in the case of the correlation). Accordingly, shadows other than a focus candidate shadow can be effectively excluded by these decision making subroutines C1 to C3. Specifically, actual focus shadows in many cases exhibit shapes close to circles, as shown in FIG. 21a, and as shown in FIG. 21b, the density difference between a density distribution Vr1 of the shadow located at the radius r1 at the angle θ and a density distribution V90r1 of the shadow located at the radius r1 at the angle θ+90 degrees is comparatively small, and the anisotropy of the shadow tends to be small. On the other hand, blood vessel cross-sectional shadows are elongated, as shown in FIG. 22a, and, as shown in FIG. 22b, the density difference between the density distribution Vr1 of the shadow located at the radius r1 at the angle θ and the density distribution V90r1 of the shadow located at the radius r1 at the angle θ+90 degrees is comparatively large, and the anisotropy of the shadow tends to be large. Accordingly, the CPU 40 can easily discriminate between a focus shadow and a blood vessel shadow by a value indicative of the anisotropy found by the above formula (8) or (9).

Incidentally, although the above formula (7) uses the absolute value of the difference between the density distribution V90r and the density distribution Vr, this invention is not limited to this example, and the absolute value may be raised to the δ-th power (δ=2 to 4). In addition, the correlation is not limited to density distribution, and may also be a correlation of computation results, such as a density gradient correlation. In addition, since the computation result of the above formula (8) or (9) is in general a large value, the computation result may also be multiplied by a predetermined constant, so that it can be rounded off to a small value that is easy to handle. Moreover, although a correlation angle of 90 degrees is an angle most effective in making a decision, this invention is not limited to 90 degrees, and an appropriate angle within the range of 90 degrees±30 degrees may be selected as a correlation angle, so that the anisotropy thereof may be found. Furthermore, the computation result of the above formula (8) or (9) (for example, 90-degree anisotropy) may be used to calculate a standard deviation or the like, and the standard deviation or the like can also used for decision. This invention may use any formula that can find a correlation of shadow densities in two directions spaced substantially 90 degrees apart, and is not limited to the above formula (8) or (9), and may also use the above formula (7).

Figure 23A:
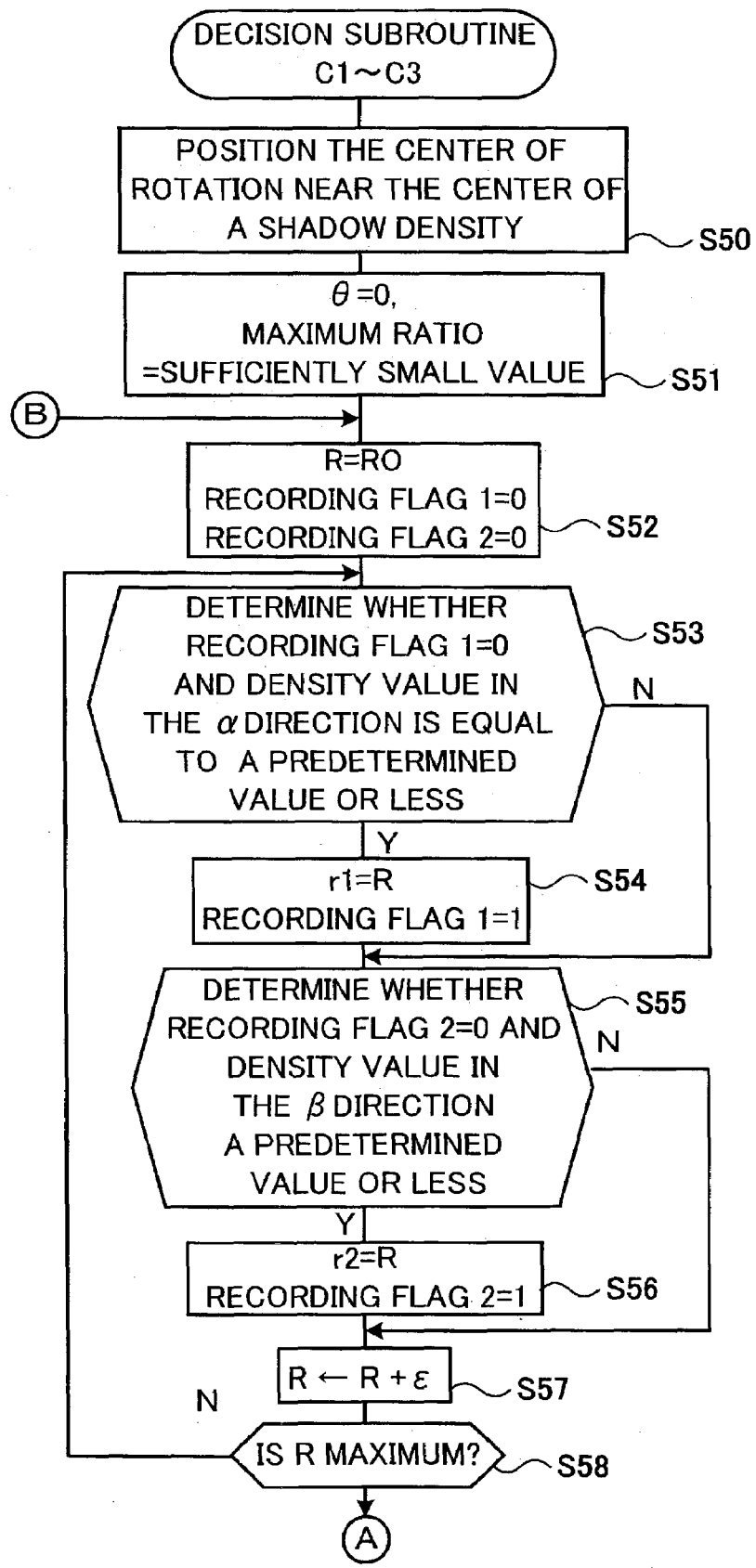
FIGS. 23a and 23b, when combined, comprise a detailed flowchart of each of the decision making subroutines C1 to C3 of Steps S72, S74 and S76 of FIG. 11.
Figure 23B:
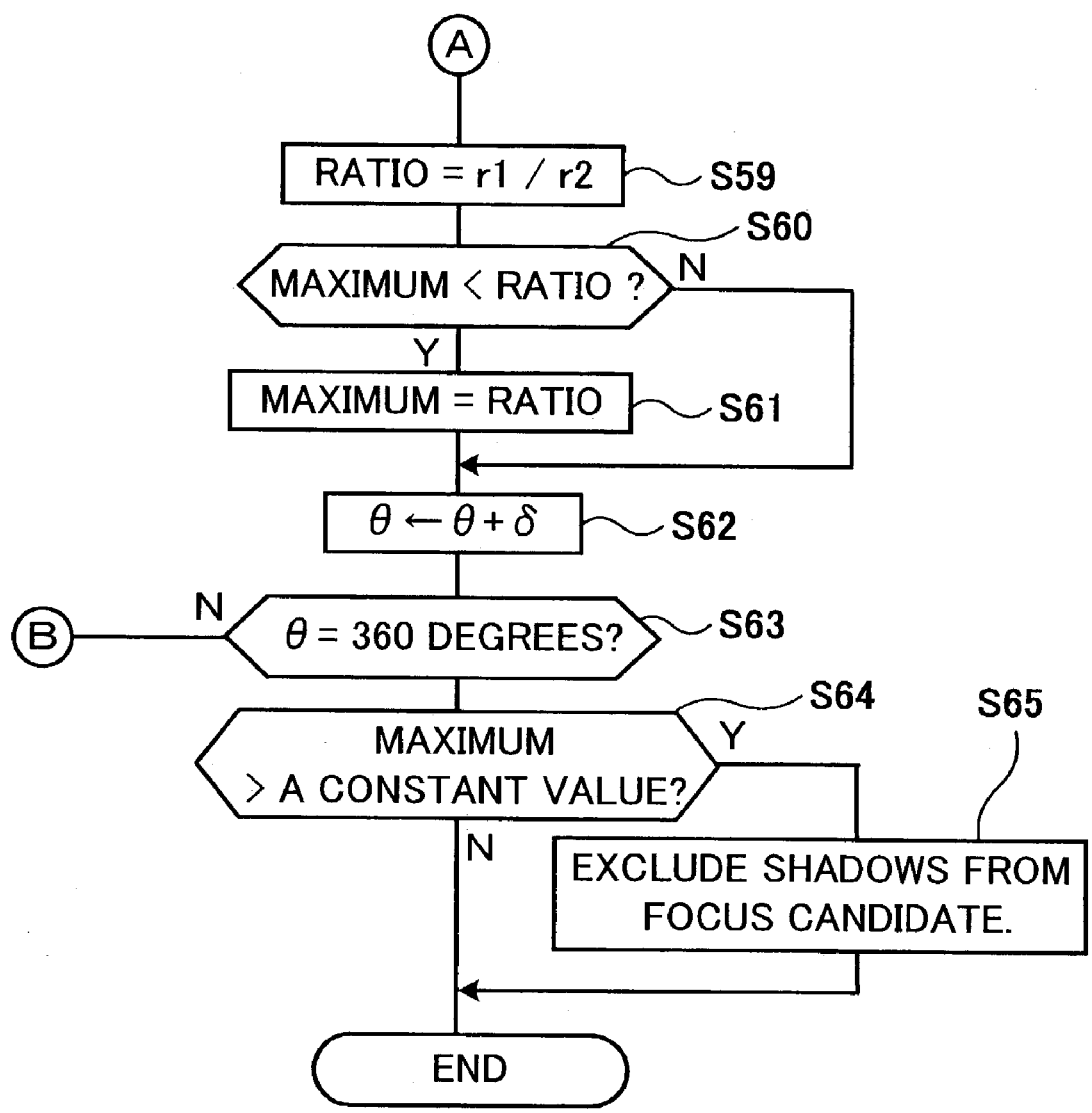
Figure 24A:
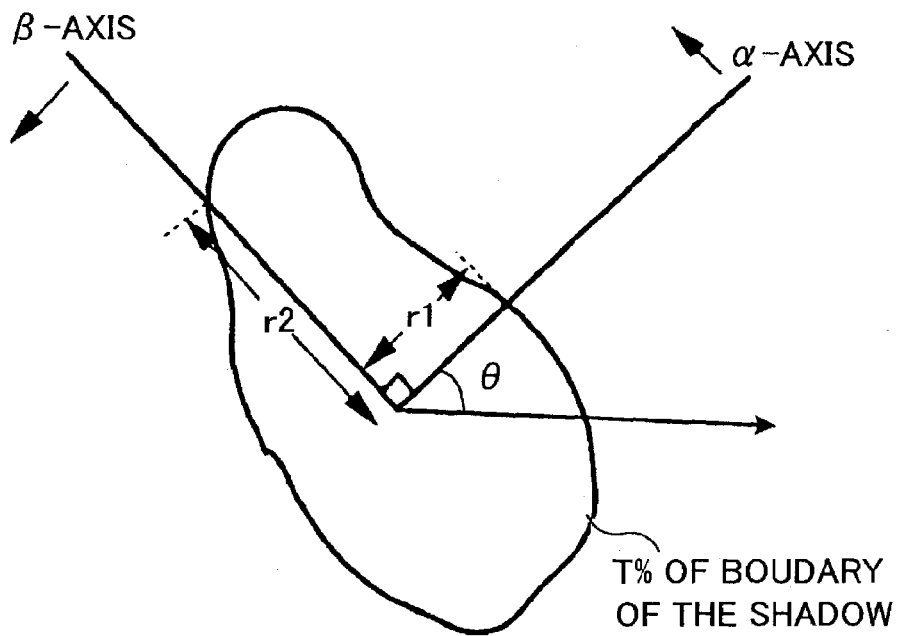
FIG. 24a is a conceptual diagram and FIG. 24b is a graph of the processing of the decision making subroutines C1 to C3 of FIG. 23.
Figure 24B:
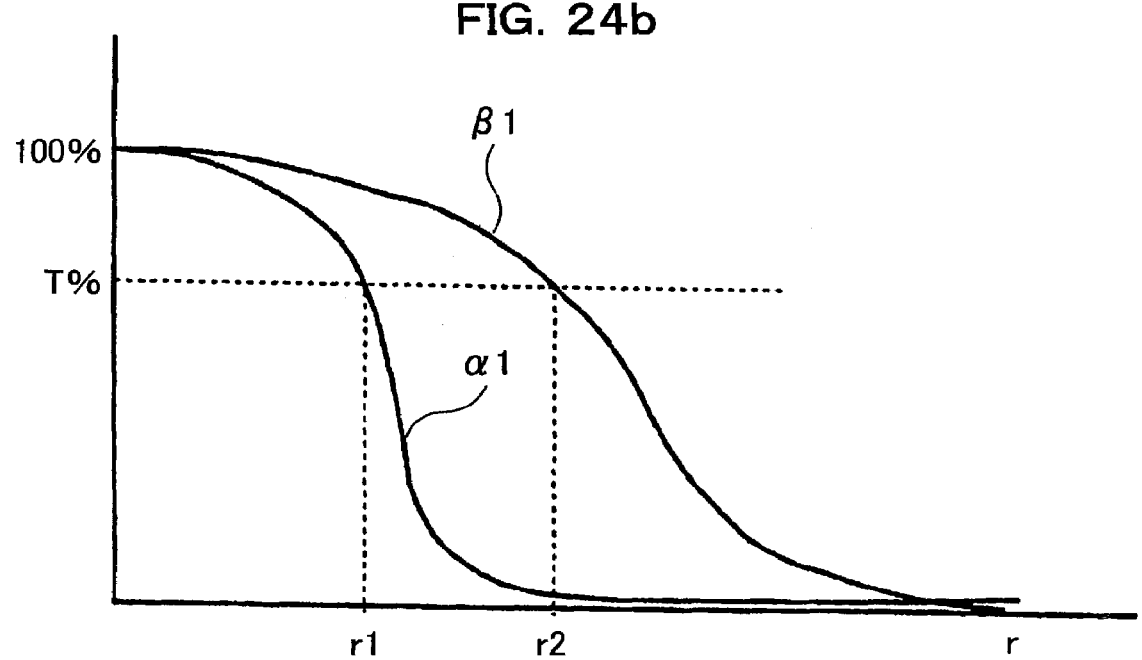

The decision making subroutines C1 to C3 executed in Steps S72, S74 and S76 of FIG. 11 will be described below. FIGS. 23a, 23b constitute a flowchart showing details of each of the decision making subroutines C1 to C3 for identifying a shadow on the basis of the ratio of the long radius to the short radius of the shadow. FIGS. 24a, 24b conceptually show the manner of processing of each of these decision making subroutines C1 to C3. Although the above-described decision making subroutines B1 to B3 identify a shadow by using the anisotropy of each of shadow density distributions in two directions spaced substantially 90 degrees apart, these decision making subroutines C1 to C3 identify a shadow by using the ratio of lengths of a shadow in two directions spaced substantially 90 degrees apart. Details of these decision making subroutines C1 to C3 will be described below in the order of the steps thereof.

[Step S50] The CPU 40 positions the center of rotation near the center of a shadow density. Namely, as shown in FIG. 24a, the CPU 40 sets the center of rotation of the α axis and the β axis with radii of predetermined lengths to the center M of the shadow. In the case of a focus shadow, since a plurality of peaks generally appear in its density distribution, the vicinity of the center of the shadow is set as the average position of this plurality of peaks. Incidentally, as described previously, on the basis of a binary-image shadow obtained by binarizing the shadow, the center-weight position of the shadow may be set as the central coordinates, or the position found in FIG. 17b may also be set as the central coordinates.

[Step S51] The CPU 40 initializes the angle θ to, for example, θ=0 degrees, and initializes the maximum ratio of lengths of the shadow in two directions spaced substantially 90 degrees apart to, for example, "1". The angle θ=0 is shown by an arrow extending from the center M of the shadow in the rightward horizontal direction in FIG. 24a.

[Step S52] The CPU 40 initializes a radius R to a small radius R0 near 0, and initializes both a first recording flag 1 and a second recording flag 2 to "0".

Through the next steps S53 to S58, as shown in FIG. 24a, the CPU 40 finds the radius r1 on the α axis extending from the center M, which is the reference of the shadow, and where angle θ is given different values and a radius r2 on the β axis at the angle θ+90 degrees. The respective radii r1 and r2 represent the distances from the origin M to the boundary of the shadow, and this boundary is determined by finding the initial positions where the values of density curves α1 and β1 reach about T % of the density value at the origin, as shown in FIG. 24b. Incidentally, the value of T % can be arbitrarily set, and is herein set to T=75%. It goes without saying that CT values or values of a multi-valued image themselves can also be used instead of percent.

[Step S53] The CPU 40 determines whether the first recording flag 1 is "0" and the density value of a pixel at the radius R in the direction of the α axis is a predetermined value or less. If the CPU 40 determines that the density value is not larger than the predetermined value (Yes), the CPU 40 proceeds to Step S54; whereas, if the CPU 40 determines that the density value is larger than the predetermined value (No), the CPU 40 jumps to Step S55. Incidentally, this predetermined value is a value obtained by multiplying the density value of the shadow at the origin by the above-described value T. Namely, in this step, the CPU 40 determines whether a pixel at the radius R lies on the boundary (edge) of the shadow.

[Step S54] Since it has been determined in Step S53 that the density value of the pixel at the radius R in the direction of the α axis is not larger than the predetermined value, this radius R indicates the distance from the origin M to the boundary of the shadow. Accordingly, the CPU 40 selects this radius R as the radius r1 and sets "1" to the first recording flag 1, to define the radius r1.

[Step S55] The CPU 40 determines whether the second recording flag 2 is "0" and whether the density value of a pixel at the radius R in the direction of the β axis is a predetermined value or less. If the CPU 40 determines that the density value is not larger than the predetermined value (Yes), the CPU 40 proceeds to Step S56; whereas, if the CPU 40 determines that the density value is larger than the predetermined value (No), the CPU 40 jumps to Step S57.

[Step S56] Since it has been determined in the above step S55 that the density value of the pixel at the radius R in the direction of the β axis is not larger than the predetermined value, this radius R indicates the distance from the origin M to the boundary of the shadow. Accordingly, the CPU 40 selects this radius R as the radius r2 and sets "1" to the second recording flag 2, to define the radius r2.

[Step S57] The CPU 40 adds a small distance ϵ to the radius R to set the radius R to a radius (R+ϵ). Namely, the CPU 40 performs the processing of increasing the radius R by the small increment ϵ.

[Step S58] The CPU 40 determines whether the radius R is a predetermined maximum value (for example, the maximum radius of a shadow which is a decision target), and, if the CPU 40 determines that the radius R is not the maximum value (No), the CPU 40 returns to Step S53; whereas, if the CPU 40 determines that the radius R is the maximum value (Yes), the CPU 40 returns to Step S59. The CPU 40 can find the radius r1 on the α axis at the angle θ and the radius r2 on the β axis at the angle θ+90 degrees by repeating the processing of Steps S54 to S58. Incidentally, in the description of this step, reference has been made to the case where the CPU 40 leaves the loop of Steps S53 to S58 depending on the size of the radius R; however, instead of this step S58, the CPU 40 can be made to leave the loop according to whether both the first recording flag 1 and the second recording flag 2 are "1".

[Step S59] The CPU 40 finds the ratio of the radius r1 to the radius r2: r1/r2. In this step, the ratio=r1/r2 is found, but since the ratio is made to be not smaller than 1, the larger of the radius r1 and the radius r2 is made the numerator and the smaller is made the denominator.

[Step S] The CPU 40 determines whether the ratio found in Step S59 is larger than a maximum ratio, and if the CPU 40 determines that the ratio is larger (Yes), the CPU 40 proceeds to Step S61; while, if the CPU 40 determines that the ratio is not larger (No), the CPU 40 jumps to Step S62.

[Step S61] Since the ratio found in Step S59 is larger than the maximum ratio, the CPU 40 sets that ratio to be the new maximum ratio. Incidentally, since the value "1" defined as the maximum ratio in Step S51 is set in advance, the initially found ratio is recorded as the maximum ratio.

[Step S62] The CPU 40 adds the small angle δ to the angle θ to set the angle θ to the angle (θ+δ). Incidentally, the small angle δ is, for example, one degree, but may also be another value.

[Step S63] The CPU 40 determines whether the angle θ in Step S62 has reached 360 degrees, and if the CPU 40 determines that the angle θ is smaller than 360 degrees (No), the CPU 40 jumps to Step S52; whereas, if the CPU 40 determines that the angle θ=360 degrees (Yes), the CPU 40 proceeds to Step S64. In this manner, it is possible to find the maximum ratio of the radius r1 to the radius r2 where the angle θ is varied from 0 to 360 degrees.

[Step S64] The CPU 40 determines whether the maximum ratio is larger than a predetermined constant, and if the CPU 40 determines that the maximum ratio is larger (Yes), the CPU 40 proceeds to Step S65; whereas, if the CPU 40 determines that the maximum ratio is not larger (No), the CPU 40 proceeds to the next decision making subroutines D1 to D3.

[Step S65] Since it has been determined in Step S64 that the maximum ratio is larger than the predetermined constant, the CPU 40 excludes the shadow from focus candidate shadows and proceeds to the next decision making subroutines D1 to D3. In this manner, the CPU 40 varies the angle θ in the range of 0 to 360 degrees, and if the maximum ratio of the radius r1 and the radius r2 obtained at this time is larger than the predetermined constant, the CPU 40 excludes the shadow from focus candidate shadows. This is because focus candidates are small in anisotropy and approximately close to circular shapes and the ratios of their radii r1 to their radii r2 are in many cases smaller than the predetermined constant. Incidentally, although each of FIGS. 21b, 22b and 24b shows only anisotropy in the positive direction on the α axis, the case of anisotropy in the negative direction is also included in this invention.

In the above-described embodiment, reference has been made to the case where anisotropy (correlation) is found by using shadow density distributions in two directions spaced substantially 90 degrees apart or the ratio of the lengths of shadows in two directions spaced substantially 90 degrees apart, but anisotropy may also be found by using other methods. For example, anisotropy (correlation) may also be found by causing the α axis and the β axis shown in FIG. 22a to move like the long hand and the short hand of a clock. In this case, assuming that the α axis and the β axis are the short hand and the long hand, respectively, while the α axis is making one rotation, the β axis makes several hundred rotations. In FIG. 22a, the α axis and the β axis are shown to be perpendicular to each other, but this angle may be made an arbitrary angle η. First, a density distribution in the direction of the α axis is found by determining the angle θ, then the angle is changed by η to find a density distribution in the direction of the β axis, and subsequently the anisotropy (correlation) of both density distributions is found. In the case where both the α axis and the β axis are superposed on a blood vessel shadow, the anisotropy is small and pixel values along the α axis and β axis are large, and the distribution of the pixel values is flat. On the other hand, if the shadow is circular, such features are not observed, and pixel values along the α axis and β axis are large and their distribution is flat. Accordingly, if a case of small anisotropy is discovered, it can be inferred that the angle η at this time is the branching angle of a blood vessel. For example, in FIG. 22a, when the angle η is about 180 degrees and about 45 degrees, the anisotropy becomes small, so that the shadow is inferred to be a blood vessel and can be excluded from focus candidate shadows.

Figure 25:
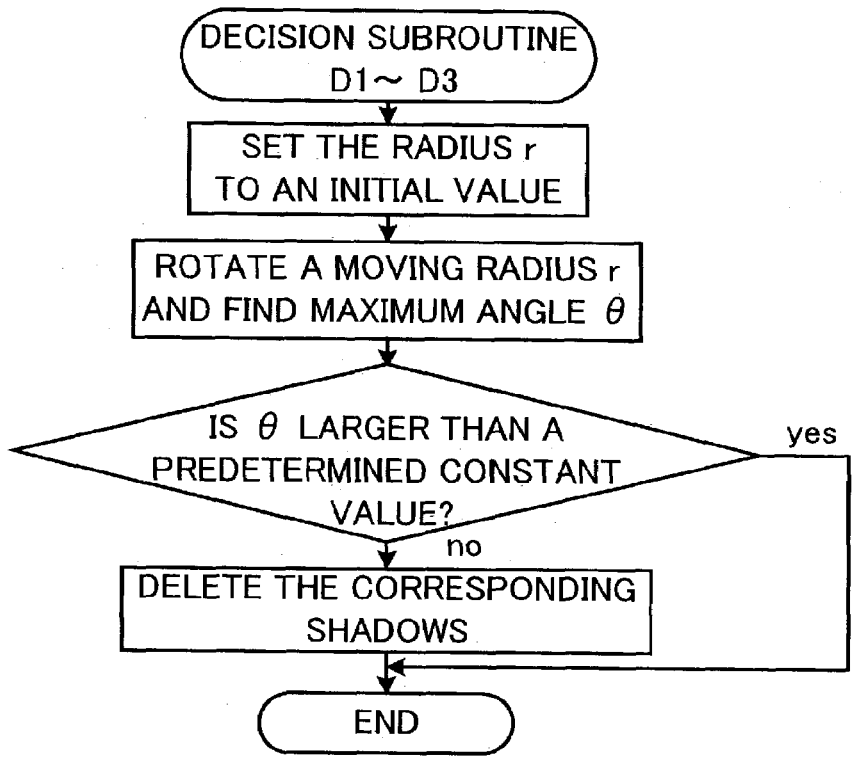
FIG. 25 is a detailed flowchart of each of decision making subroutines D1 to D3 of Steps S72, S74 and S76 of FIG. 11.
Figure 26A:
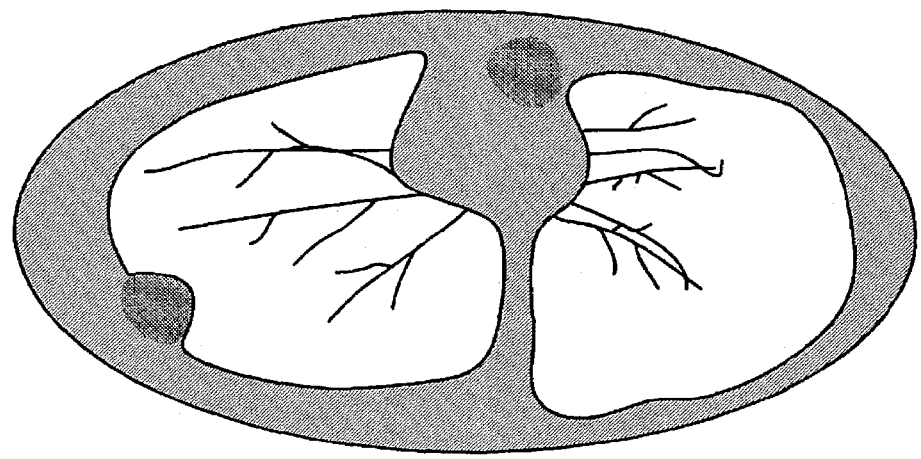
FIGS. 26a to 26d are conceptual diagrams of the processing of the decision making subroutines D1 to D3 of FIG. 25.
Figure 26B:
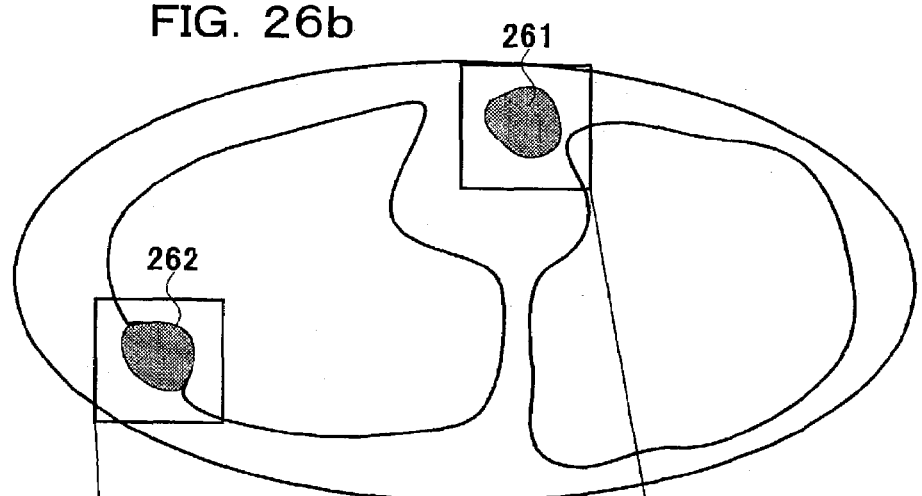
Figure 26C:
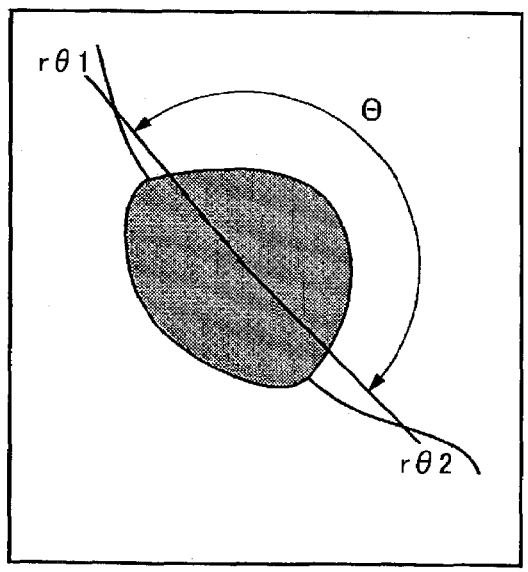
Figure 26D:
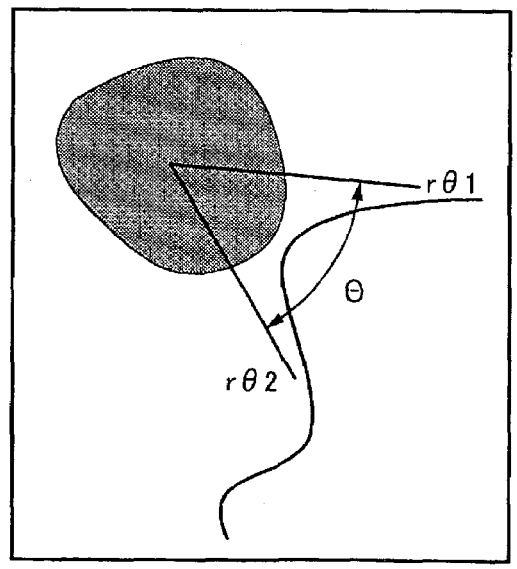

The decision making subroutines D1 to D3 executed in Step S72, S74 and S76 of FIG. 11 will be described below. FIG. 25 is a flowchart showing details of each of the decision making subroutines D1 to D3. FIGS. 26a to 26d conceptually show the manner of processing of each of these decision making subroutines D1 to D3, of which FIG. 26a is a view showing one example of a CT image. FIG. 26b is a view showing one example of a binary image obtained by binarizing this CT image. FIGS. 26c and 26d are views showing on an enlarged scale a part of this binary image, and which show how a decision is made by each of the decision making subroutines D1 to D3. By applying the binary image processing shown in FIGS. 5 and 6 to the CT image shown in FIG. 26a, shadows 261 and 262, which seem to be focus candidates, are extracted in the binary image shown in FIG. 26b. Since these shadows 261 and 262 are the same in size and shape, it is difficult to discriminate between the shadows 261 and 262 by means of the above-described decision. However, since the shadow 262 appears on a wall portion of the shadow, the possibility that the shadow 262 is a cancer shadow is high. The shadow 261 appears in the inside of the shadow, and the possibility that the shadow 261 is a focus candidate is low. For this reason, in the decision making subroutines D1 to D3, a decision is made as to whether a shadow is located on a wall portion, and, on the basis of the result of this decision, a decision is made as to whether the shadow is a focus candidate shadow. In the case where a shadow exists near a wall, as a rotating radius passes through the wall, the pixel values of the shadow that cross the radius sharply vary, and the resultant high variation appears at two locations of radii. Accordingly, in the case where the shadow is in contact with the wall, an angle of elevation θ of the radii at these two locations is larger than a reference value, so that the shadow is identified as a focus candidate shadow. On the other hand, in the case where the shadow is inside the wall, the angle of elevation θ of the radius is smaller than the reference value, so that the shadow is not identified as a focus candidate shadow. Details of these decision making subroutines D1 to D3 will be described below step by step.

[Step S91] The CPU 40 sets the radius r used to search a shadow to an initial value. The radius R in this processing is made to be a value corresponding to the size of each shadow. For example, about 1.5 times the maximum diameter of a shadow, which is a target is set to be the initial value of the radius r.

[Step S92] The CPU 40 rotates a moving radius r by about 5 degrees at one time in the range from θ=0 degrees to θ=360 degrees, and finds density distributions V0 to V355 of the shadow located at the distance r from the center of the shadow and at the respective angles, and applies predetermined computations on these density distributions V0 to V355. Then, if the moving radius of radius r crosses the boundary of the shadow at two or more radii θ1 and θ2, the CPU 40 finds a maximum angle Θ between radii θ1 and θ2. The radii θ1 and θ2 are determined in the following manner. The CPU 40 subtracts the density distribution V(θ+5) at an angle (θ+5) which is 5 degrees larger than a certain angle θ, from a density distribution Vθ at the angle θ; and, if the difference is a positive value and the absolute value is larger than a predetermined value, the CPU 40 sets the larger angle (θ+5) to be θ1. In FIGS. 26c and 26d, a moving radius rθ1 corresponds to the moving radius at the angle θ1. On the other hand, in the case where the CPU 40 subtracts the density distribution V(θ+5) from the density distribution Vθ, if the difference is a negative value and the absolute value is larger than the predetermined value, the CPU 40 sets the smaller angle θ to be θ2. In FIGS. 26c and 26d, a moving radius rθ2 corresponds to the moving radius at the angle θ2. After the angle θ1 and the angle θ2 have been found in this manner, the CPU 40 defines, as the maximum angle Θ, the angle formed by the moving radius rθ1 at the angle θ2 in the clockwise direction relative to the moving radius rθ2 at the angle θ2. Incidentally, this method of finding the maximum angle Θ is merely one example, and it goes without saying that the maximum angle Θ can be found by other methods. In addition, although the description has been made in connection with the case where the moving radius is rotated 5 degrees at one time, this case is not limiting, and it goes without saying that the angle of rotation may be changed in increments ranging from 1 degree to 10 degrees.

[Step S93] The CPU 40 determines whether the maximum angle Θ found in Step S93 is larger than a predetermined constant value, and, if the CPU 40 determines that the maximum angle Θ is larger (yes), the CPU 40 proceeds to the next decision making subroutines E1 to E3; whereas, if the CPU 40 determines that the maximum angle Θ is not larger (no), the CPU 40 proceeds to Step S94. The constant value is herein made 90 degrees. This is because the maximum angle Θ is near 180 degrees in the case of a focus shadow which appears on a wall portion. Accordingly, in such a case, the shadow is left as a focus candidate shadow and is subjected to the processing of the next decision making subroutine.

[Step S94] Since it has been determined by the decision in Step S93 that the maximum angle Θ is smaller than the predetermined constant value, the CPU 40 excludes the shadow from focus candidate shadows and proceeds to the next decision making subroutines E1 to E3. In many cases, a focus shadow, such as a cancer shadow, appears on a wall portion, but a normal shadow does not appear on a wall portion. Therefore, through this processing, a shadow which does not exist on a wall portion is efficiently excluded from focus candidate shadows.

Figure 27:
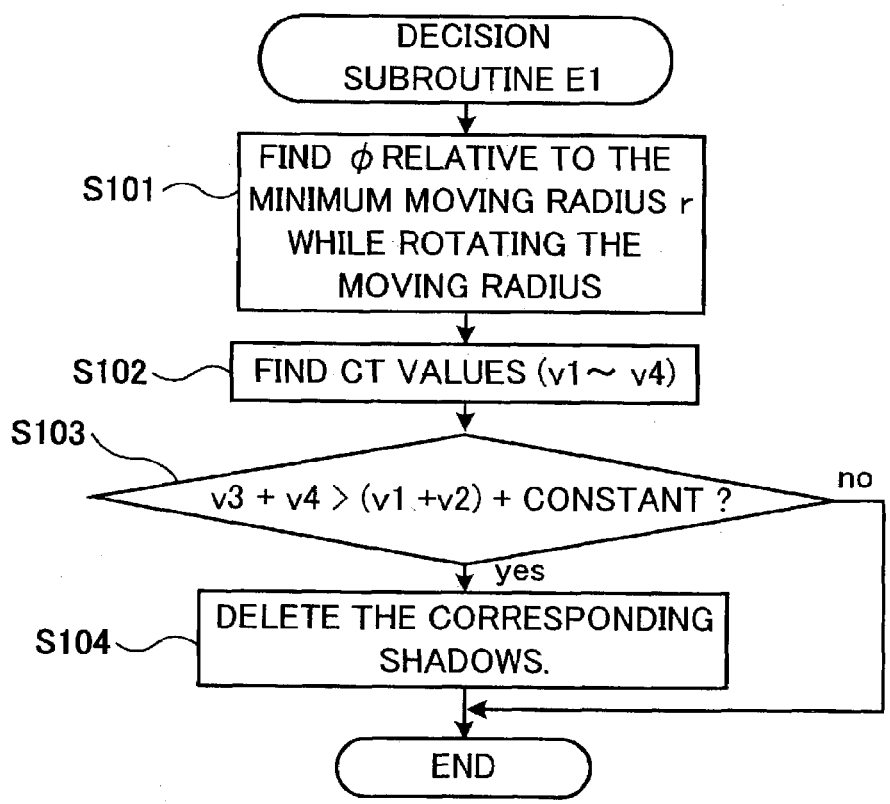
FIG. 27 is a detailed flowchart of a decision making subroutine E1 of Step S72 of FIG. 11.
Figure 28A:
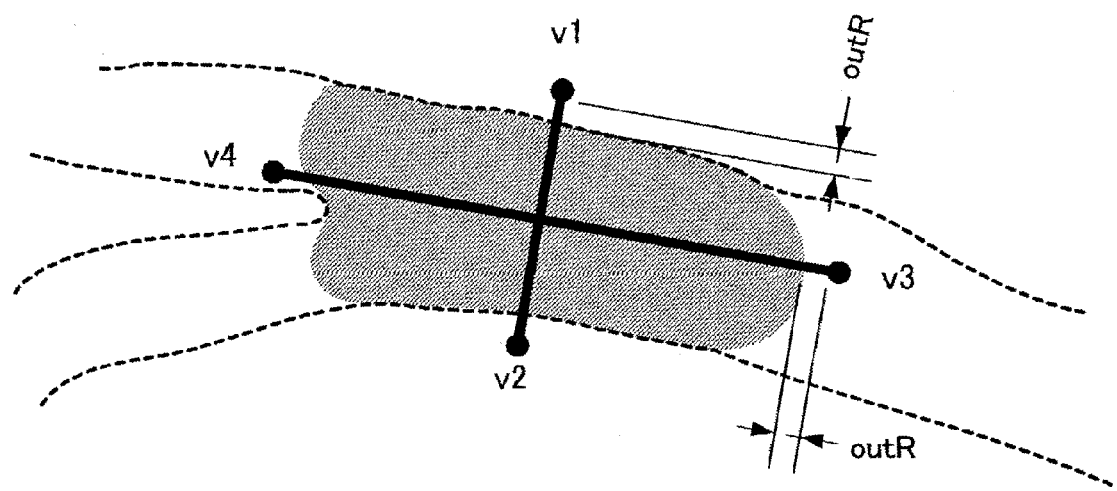
FIGS. 28a and 28b are conceptual diagrams of the processing of the decision making subroutine E1 of FIG. 27.
Figure 28B:
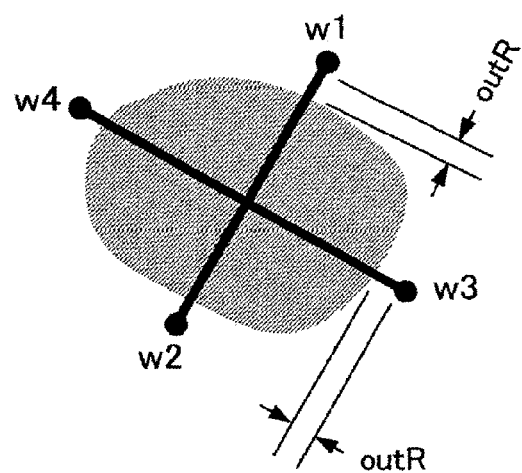

The decision making subroutine E1 executed in Step S72 of FIG. 11 will be described here. FIG. 27 is a flowchart showing details of the decision making subroutine E1. FIGS. 28a, 28b conceptually show the manner of processing of this decision making subroutine E1. FIG. 28a shows processing for a blood vessel cross-sectional shadow generated by applying the binary image processing of FIGS. 5 and 6, and FIG. 28b shows processing for a focus shadow. When the binary image processing of FIGS. 5 and 6 is applied to a CT image to exclude the shadow of a blood vessel portion thinner than a predetermined value, the shadow of the remaining portion becomes a shadow which seems to be a focus shadow, as shown in FIG. 28a. Therefore, the blood vessel cross-sectional shadow shown in FIG. 28a must be excluded from focus candidates. For this reason, in this decision making subroutine E1, this blood vessel cross-sectional shadow is extracted and excluded. Namely, to exclude such a blood vessel cross-sectional shadow from focus candidates, the CPU 40 finds a long diameter and a short diameter of the shadow from the minimum value and the maximum value of the portion of the rotating straight line which intersects the shadow, and samples pixel values which are respectively located a predetermined distance outward from the shadow along extensions of the long diameter and the short diameter. In the case of the blood vessel cross-sectional shadow, the pixel value on the extension of the long diameter and the pixel value on the extension of the short diameter indicate clearly different values. In the case of the focus shadow, both pixel values indicate approximately the same value. Accordingly, on the basis of this fact, it is possible to determine whether the shadow is a focus candidate shadow. Details of this decision making subroutine E1 will be described below, step by step.

[Step S101] The CPU 40 finds the angle Θ relative to the minimum moving radius while rotating the moving radius. The CPU 40 positions the middle point of the straight line of predetermined length to be close to the center of the shadow density, and sets the middle point of the straight line to be the center of rotation and rotates the straight line about the center of rotation by about 1 degree at one time in the range from θ=0 degrees to θ=360 degrees. During this time, the CPU 40 sequentially calculates the length of the portion of the radius which crosses the shadow at each of the angles, and finds an angle Φ of the minimum value of the moving radius. Incidentally, this processing is performed on shadows of multi-valued images. The incremental angle of rotation is not limited to 1 degree, and may be other angles.

[Step S102] This processing is performed on a CT image which is not yet subjected to multi-valued image processing. The CPU 40 finds density values (CT values) v1 and v2 at two points located a predetermined distance "outR" outward from the shadow along the extension of the moving radius at the angle Φ, and finds density values (CT values) v3 and v4 at two points located a predetermined distance outR outward from the shadow along the extension of a moving radius perpendicular to the moving radius at the angle Φ.

[Step S103] The CPU 40 substitutes the density values found in the previous step S102 into the following formula (10) or (11):

$$v3+v4 > ((v1+v2)+\text{constant}),\qquad(10)$$

$$v3+v4 > ((v1+v2)\times\text{constant})\qquad(11)$$

If the CPU 40 determines that the formula (10) or (11) is satisfied (yes), the CPU 40 proceeds to Step S104, whereas if the CPU 40 determines that the formula (10) or (11) is not satisfied (no), the CPU 40 brings the processing to an end and proceeds to the next decision making subroutine F1. In the case of the blood vessel cross-sectional shadow shown in FIG. 28(*a*), the density values (CT values) v1 and v2 at the two points located the predetermined distance outR outward from the shadow along the extension of the moving radius at the angle Φ become extremely small values. On the other hand, the density values v3 and v4 at the two points located the predetermined distance outR outward from the shadow along the extension of the moving radius perpendicular to the moving radius at the angle Φ become comparatively large values, because the density values v3 and v4 are located on the blood vessel cross-sectional shadow. Accordingly, in the case of the blood vessel cross-sectional shadow shown in FIG. 28*a*, the above-described formula (10) or (11) is satisfied. On the other hand, in the case of the focus shadow shown in FIG. 28*b*, since the density values v1 to v4 become approximately the same value, the above-described formula (10) or (11) is not satisfied.

[Step S104] Since it has been determined by the decision in Step S103 that the above-described formula (10) or (11) is satisfied, the CPU 40 excludes the shadow from focus candidate shadows, and proceeds to the next subroutine F1. Through this processing, the blood vessel cross-sectional shadow, which is generated by the multi-valued image processing of FIGS. 5 and 6 and seems to be a focus shadow, is effectively excluded from focus candidate shadows. Incidentally, in the above-described step S102, the density values v3 and v4 are found at the two points located a predetermined distance outR outward from the shadow along the extension of the moving radius perpendicular to the moving radius at the angle Φ. However, as a result of Step S101, an angle Φ relative to the maximum value of the moving radius may also be used, so that the density values v3 and v4 may be found at two points located at the predetermined distance outR outward from the shadow along the extension of a moving radius at that angle Φ. In addition, although in the above-described embodiment the density values v1 and v2 are determined from the moving radius of minimum value, the density values v1 and v2 may instead be determined from the moving radius of maximum value so that the density values v3 and v4 may be determined from the moving radius perpendicular to the moving radius of maximum value.

Figure 29:
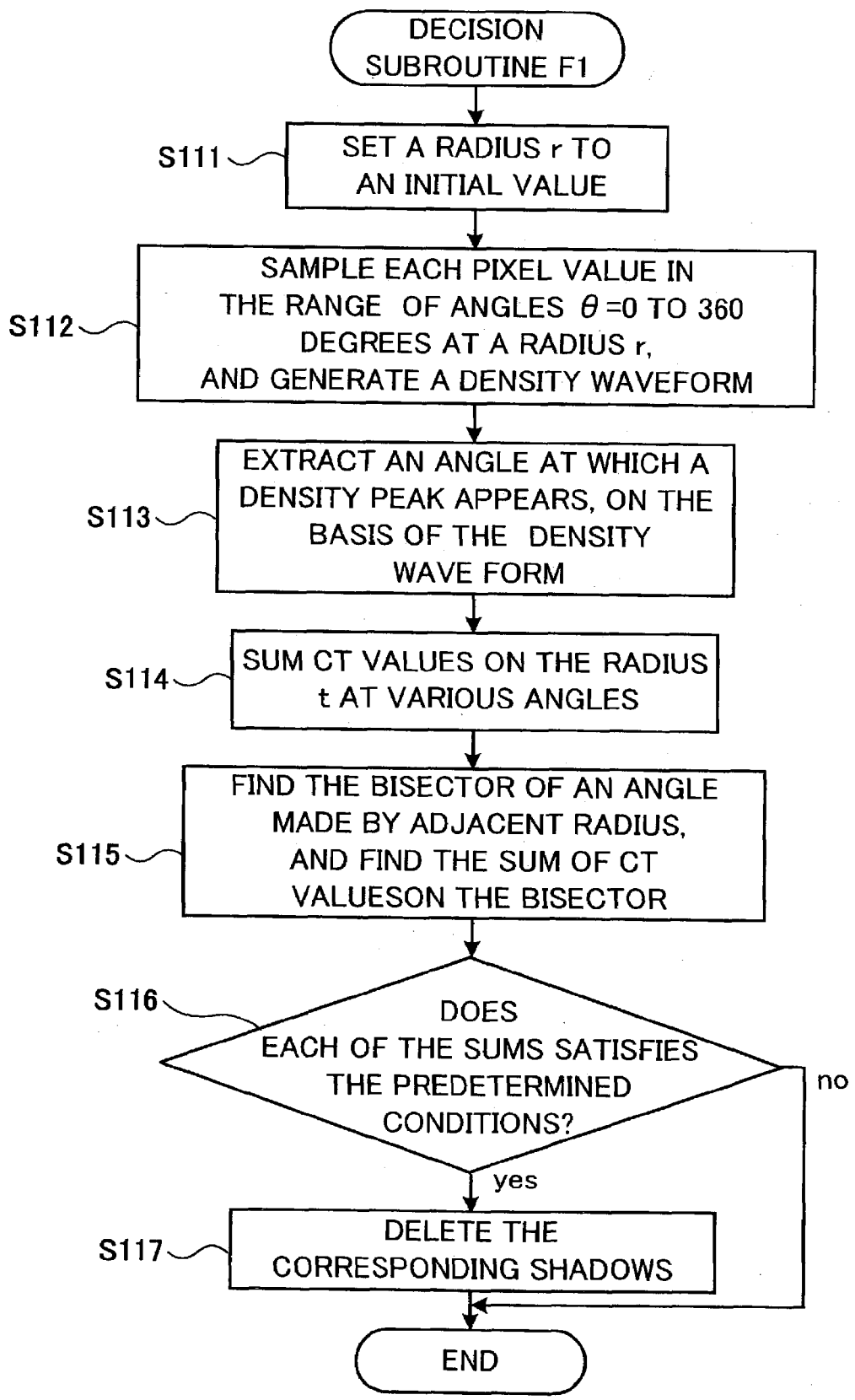
FIG. 29 is a detailed flowchart of a decision making subroutine F1 of Step S72 of FIG. 11.
Figure 30A:
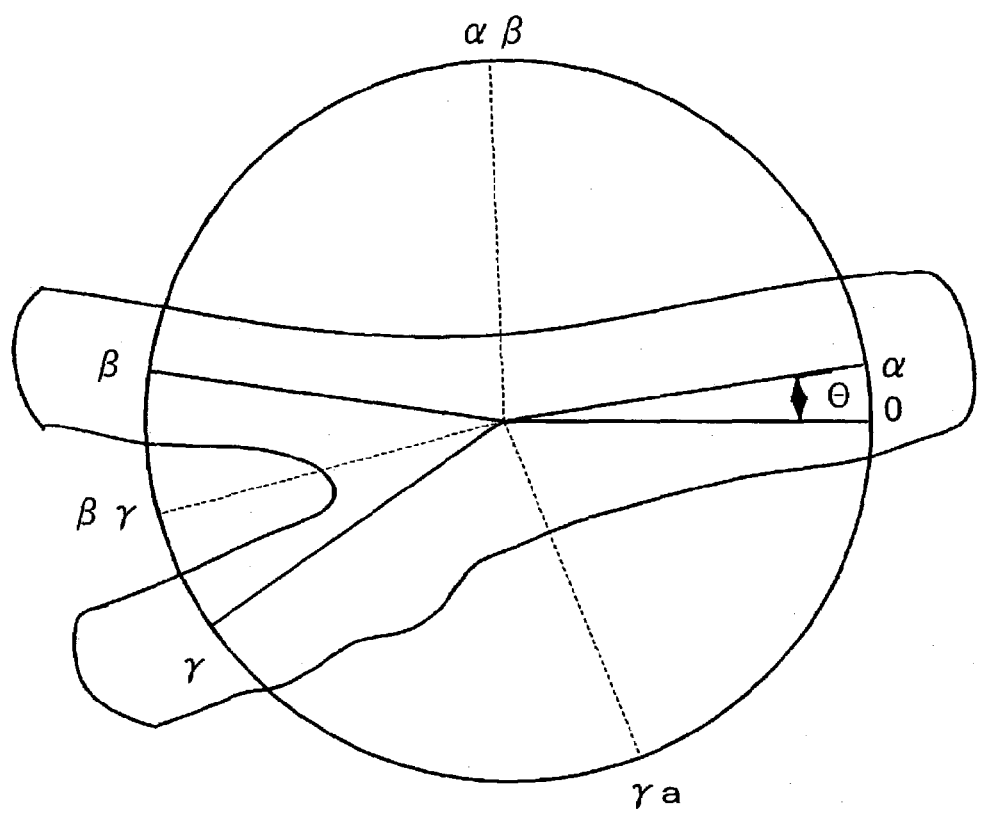
FIG. 30a is a conceptual diagram and FIG. 30b is a graph of the processing of the decision making subroutine F1 of FIG. 29.
Figure 30B:
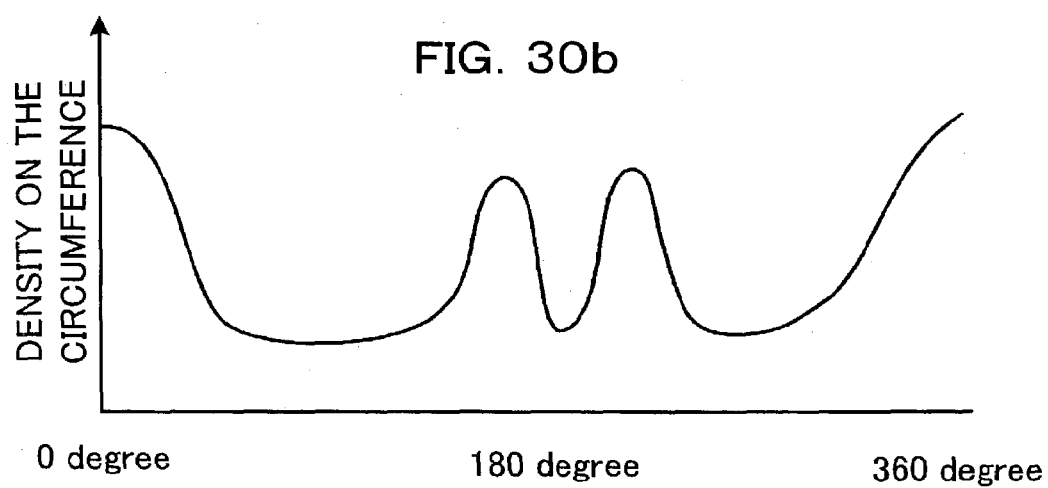

The decision making subroutine F1 executed in Step S72 of FIG. 11 will be described below. FIG. 29 is a flowchart showing details of the decision making subroutine F1. FIGS. 30*a* and 30*b* conceptually show the manner of processing of this decision making subroutine F1. FIG. 30*a* shows processing for a blood vessel cross-sectional shadow generated by applying the multi-valued image processing of FIGS. 5 and 6, and FIG. 30*b* shows the density distribution generated in the course of the processing for this blood vessel cross-sectional shadow. Similarly to the above-described decision making subroutine E1, the decision making subroutine F1 performs the processing of extracting and excluding a blood vessel cross-sectional shadow. Details of this decision making subroutine E1 will be described below in the order of the steps thereof.

[Step S111] The CPU 40 sets a radius r at which to search a shadow at an initial value. For example, the radius r is set to about 7 mm in the case of the first decision processing of FIG. 10 which is performed when the size of the shadow is smaller than the predetermined value Ra, or the radius r is set to about 20 mm in the case of the second decision processing of FIG. 10, which is performed when the size of the shadow is not smaller than the predetermined value Ra and is smaller than the predetermined value Rb, or the radius r is set to about 30 mm in the case of the third decision processing of FIG. 10, which is performed when the size of the shadow is larger than the predetermined value Rb. These values are parameter values which can be variously modified.

[Step S112] The CPU 40 rotates at the radius r by increments of one degree about a point in the vicinity of the center of the shadow, and samples each pixel value in the range of angles θ=0 to 360 degrees and generates a density waveform, as shown in FIG. 30*b*. FIG. 30*b* shows the result obtained by sampling density values at the position of the radius r from the shadow center of the blood vessel cross-sectional shadow shown in FIG. 30*a*.

[Step S113] The CPU 40 extracts an angle at which a density peak appears, on the basis of the density waveform generated in Step S113. For example, the CPU 40 differentiates the density waveform, and extracts an angle relative to the case where the differential value is "0", as an angle at which a density peak appears. In the case of a blood vessel cross-sectional shadow, since the density near the axis of a blood vessel shows a maximum value, an angle at which a density peak appears and the longitudinal direction of the blood vessel are approximately coincident with each other. In the case of FIGS. 30*a* and 30*b*, the angles Θ at which density peaks appear are α=10 degrees, β=170 degrees and γ=210 degrees.

[Step S114] The CPU 40 sums CT values on the radius r at various angles. In FIG. 30*a*=, since density peaks respectively appear at the three angles α, β and γ, the CPU 40 finds the sums of CT values on the radius r at the respective angles α, β and γ. The sum of CT values on the radius at the angle α is sum(α), the sum of CT values on the radius at the angle β is sum(β), and the sum of CT values on the radius at the angle γ is sum(γ).

[Step S115] The CPU 40 finds the bisector of an angle made by adjacent radii, and finds the sum of CT values on the bisector. In the case of FIG. 30*a*, since the angles at which the respective density peaks appear are the three angles α, β and γ, the bisectors of the radii which are adjacent to each other at the respective angles are a bisector αβ formed between the angle α and the angle β, a bisector βγ formed between the angle β and the angle γ, and a bisector γα formed between the angle γ and the angle α. The CPU 40 finds the sum of CT values on the bisector αβ, the bisector βγ and the bisector γα. The sum of the CT values on the bisector αβ is sum(αβ), the sum of the of the CT values on the bisector αβ is sum(αβ), the sum of CT values on the bisector βγ is sum(βγ), and the sum of the CT values on the bisector γα is sum(γα).

[Step S116] The CPU 40 determines whether each of the sums found in the above-described Steps S114 and S115 satisfies the following predetermined conditions. If the CPU 40 determines that the following predetermined conditions are satisfied (yes), the CPU 40 proceeds to the next step S117; whereas, if the CPU 40 determines that the following predetermined conditions are not satisfied (no), the CPU 40 brings the processing to an end, and proceeds to Step S73 of FIG. 11. In this step, any one of the following predetermined conditions are used.

(Predetermined Condition 1)

$$\text{sum}(\alpha\beta) \times \text{constant} < \text{sum}(\alpha),$$

$$\text{sum}(\alpha\beta) \times \text{constant} < \text{sum}(\beta),$$

$$\text{sum}(\beta\gamma) \times \text{constant} < \text{sum}(\beta),$$

$$\text{sum}(\beta\gamma) \times \text{constant} < \text{sum}(\gamma),$$

$$\text{sum}(\gamma\alpha) \times \text{constant} < \text{sum}(\gamma), \text{ and}$$

$$\text{sum}(\gamma\alpha) \times \text{constant} < \text{sum}(\alpha).$$

In the case where all of the above-described condition formulas are satisfied, the predetermined condition 1 is determined as satisfied.

(Predetermined Condition 2)

$$\text{sum}(\alpha\beta) + \text{constant} < \text{sum}(\alpha),$$

$$\text{sum}(\alpha\beta) + \text{constant} < \text{sum}(\beta),$$

$$\text{sum}(\beta\gamma) + \text{constant} < \text{sum}(\beta),$$

$$\text{sum}(\beta\gamma) + \text{constant} < \text{sum}(\gamma),$$

$$\text{sum}(\gamma\alpha) + \text{constant} < \text{sum}(\gamma), \text{ and}$$

$$\text{sum}(\gamma\alpha) + \text{constant} < \text{sum}(\alpha).$$

In the case where all of the above-described condition formulas are satisfied, the predetermined condition 2 is determined as satisfied.

(Predetermined Condition 3)

$$\text{average}(\alpha\sim\beta) + \text{constant} < \text{sum}(\alpha),$$

$$\text{average}(\alpha\sim\beta) + \text{constant} < \text{sum}(\beta),$$

$$\text{average}(\beta\sim\gamma) + \text{constant} < \text{sum}(\beta),$$

$$\text{average}(\beta\sim\gamma) + \text{constant} < \text{sum}(\gamma),$$

$$\text{average}(\gamma\sim\alpha) + \text{constant} < \text{sum}(\gamma), \text{ and}$$

$$\text{average}(\gamma\sim\alpha) + \text{constant} < \text{sum}(\alpha).$$

In the case where all of the above-described condition formulas are satisfied, the predetermined condition 3 is determined as satisfied. In the above condition formulas, the term "average($\alpha\sim\beta$)" indicates the average value of the CT values contained in a sector from the angle $\alpha$ to the angle $\beta$, and the term "average($\alpha$)" indicates the average value of the CT values on the radius r at the angle $\alpha$. Accordingly, in this case, it is necessary to newly add processing for finding the average values. Incidentally, it goes without saying that, in Step S116, the CPU 40 may determine whether all of these conditions 1 to 3 are satisfied.

[Step S117] The CPU 40 excludes from focus candidate shadows the shadow which has been determined as satisfying the predetermined condition, as a result of the decision of Step S116, brings this processing to an end, and proceeds to Step S73 of FIG. 11.

In the above-described manner, the shadows other than the focus candidate shadow 22 shown (b1) to (b3) in FIG. 3 are sequentially deleted, and only the focus candidate shadow 22 is finally left as shown at (b3) in FIG. 3. This focus candidate shadow 22 is the final selected image (FIG. 3 at (b3)), and is combined with the original CT image 20 (FIG. 3 at (a1)), so that the final combined image shown in FIG. 3 at (a2) is displayed on the CRT display 48. On the image shown in FIG. 3 at (a2), the focus candidate shadow 22 is enclosed with the circular marker M so that the operator's attention is drawn to the focus candidate shadow 22. Incidentally, only the focus candidate shadow 22 need be displayed in color or in a painted-out state. Images which are subjected to the extraction processing of sequentially excluding non-candidate shadows to select the focus candidate shadow 22 are actually displayed in greater numbers than those shown in FIG. 3 at (b2) and 3 at (b3). FIG. 3 merely shows part of the images displayed actually.

Figure 31:
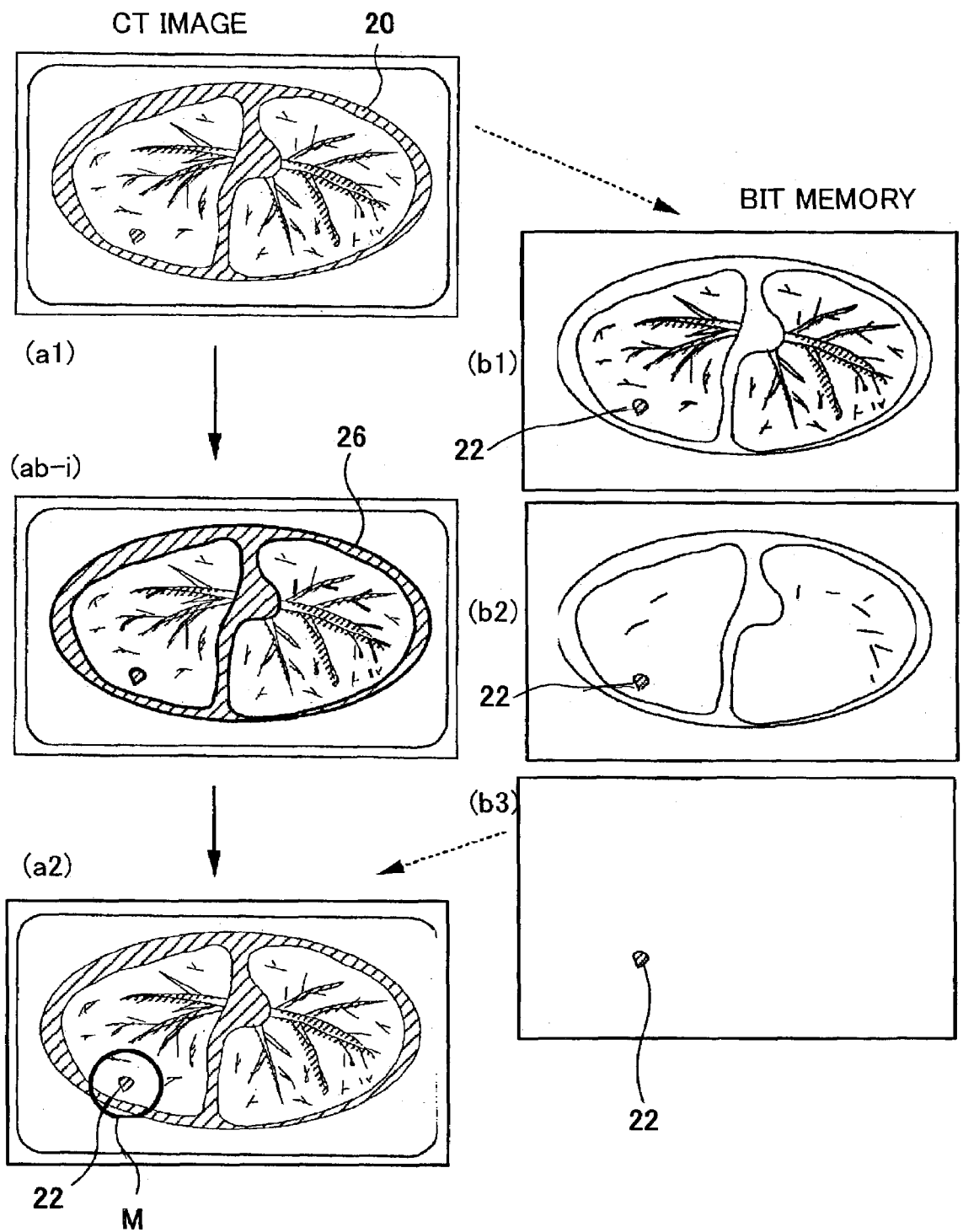
FIG. 31 is an image processing flow diagram, representing a modification of FIG. 3, showing the case where a CT image and images being processed on a bit memory are displayed in a combined form.
Figure 32:
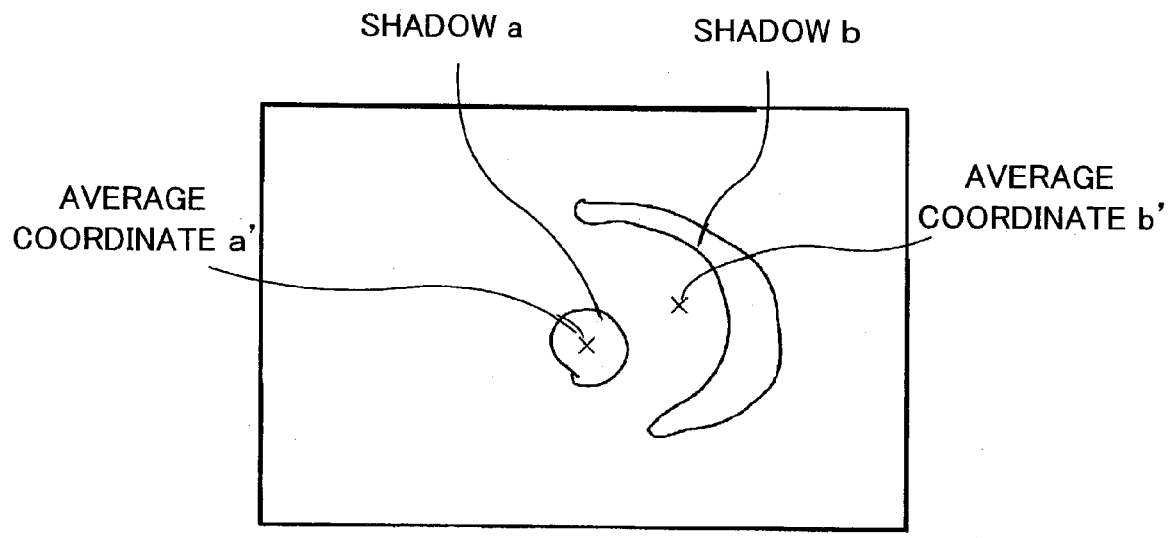
FIG. 32 is a diagram showing another example of extracting a normal shadow to be excluded from focus candidate shadows.
Figure 33:
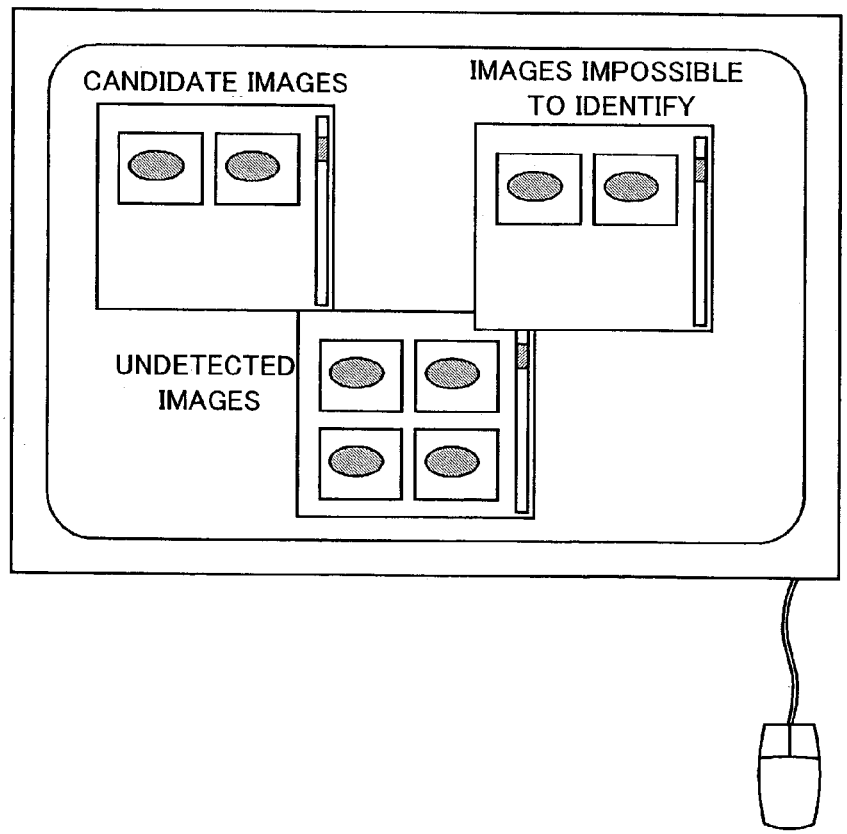
FIG. 33 is a diagram showing an example of the display of all images and focus candidate images in separate windows in a classified manner.
Figure 83:
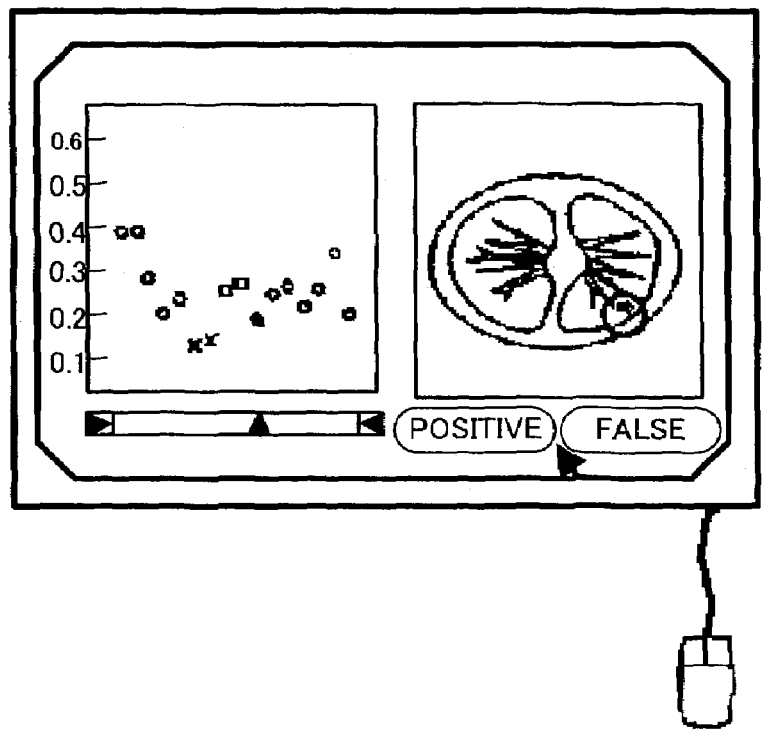
FIG. 83 is a diagram showing one example of a display picture which accompanies the processing of FIGS. 80a to 80c.

FIG. 31 is a view of a modification of the display picture of FIG. 3, and shows the case where a CT image and images being processed on a bit memory are displayed in combined form. Specifically, FIG. 3 sequentially displays images which are being subjected to the extraction processing of sequentially excluding non-candidate shadows to select the focus candidate shadow 22; however, in FIG. 31, the original CT image 20 is combined with each of images which are being processed as shown in FIG. 3 at (b1) to 3 at (b3), and a resultant combined image 26 is sequentially displayed. Since the combined image is displayed in this manner, the operator (doctor) can serially observe the process of sequentially excluding non-candidate shadows from the CT image 20 and selecting the focus candidate shadow. Incidentally, the method of extracting and selecting a focus candidate shadow is not limited to this embodiment; and, as shown in FIG. 32 by way of example, there is also a method of finding average coordinates a' and b' of respective shadows a and b and excluding from focus candidate shadows the shadow a or b if the average coordinates a' or b' lie outside that shadow (the shadow b in the example of FIG. 32). Also, a Quoit filter, Mahalanobis distance, Euclidean distance and the like may be used to select a focus candidate shadow. In the case where a focus candidate shadow is presented to the operator (doctor), each image may also be stored in the magnetic disk unit 44 together with information indicative of an undetected image, an image that is impossible to identify, or candidate image so that undetected images, images that are impossible to identify and candidate images may be displayed in separate windows, classified as shown in FIG. 33, in accordance with an instruction from the operator (doctor). The above-described windows respectively display such images, but in the respective windows, image supplementary information for identifying the images, such as the patient names and the patient IDs of the respective images, may also be displayed in list form. In addition, information for identifying the nature of focus candidate shadows, such as a positive indication that shadow is a focus, a nature close to a positive (apparent-positive) and a negative indicating that a focus candidate shadow is not a focus, may also be displayed as image supplementary information. A display example of such image supplementary information is shown in FIG. 83.

Although images are displayed in each of the above-described windows, image supplementary information for identifying the images, such as the patient names and the patient IDs of the respective images, may also be displayed in list form.

Figure 34:
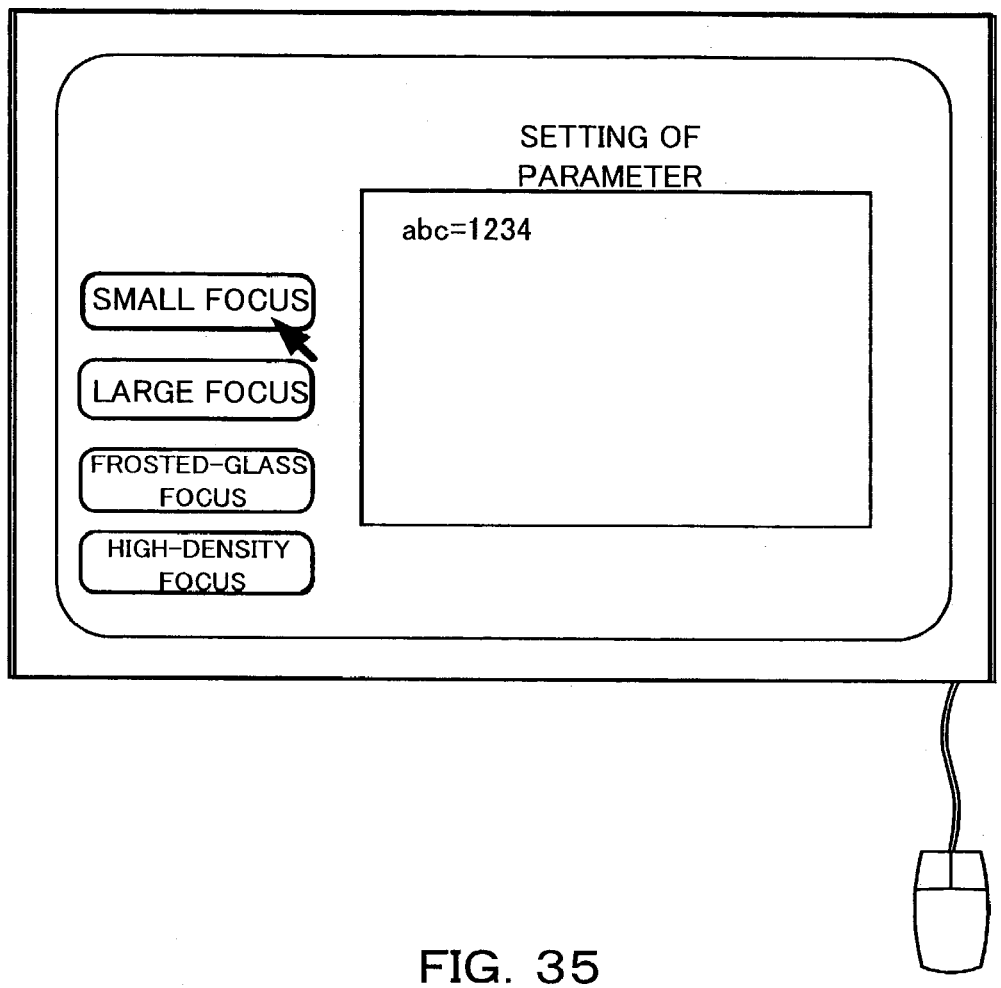
FIG. 34 is a diagram showing one example of a picture for setting the parameters required for the processing of each of the decision making subroutines.

One example of a picture which is displayed on the CRT display 48 in the case where the processing of each of the above-described shadow decisions is executed will be described below. FIG. 34 is a view showing a display for setting the parameters required for the processing of each of the above-described decision making subroutines. Incidentally, there are optimum parameters depending on the sizes of shadows and the states of densities of shadows; and, when a "SMALL FOCUS" button, a "LARGE FOCUS" button, a "FROSTED-GLASS FOCUS" button or a "HIGH-DENSITY FOCUS" button is selected by a mouse cursor, the corresponding optimum parameters are set. When the setting of the parameters with the display of FIG. 34 is completed, a focus candidate extracting and displaying device which is not shown performs sequential or parallel processing in accordance with the main flowchart of FIGS. 2a, 2b by using the parameters set for each of the kinds of shadows, and detects a small focus, a large focus, a ground-glass focus and a high-density focus, and combines each detected shadow with a cross-sectional image of a CT image as shown in FIG. 3 to display the combined image on the CRT display 48.

Figure 35:
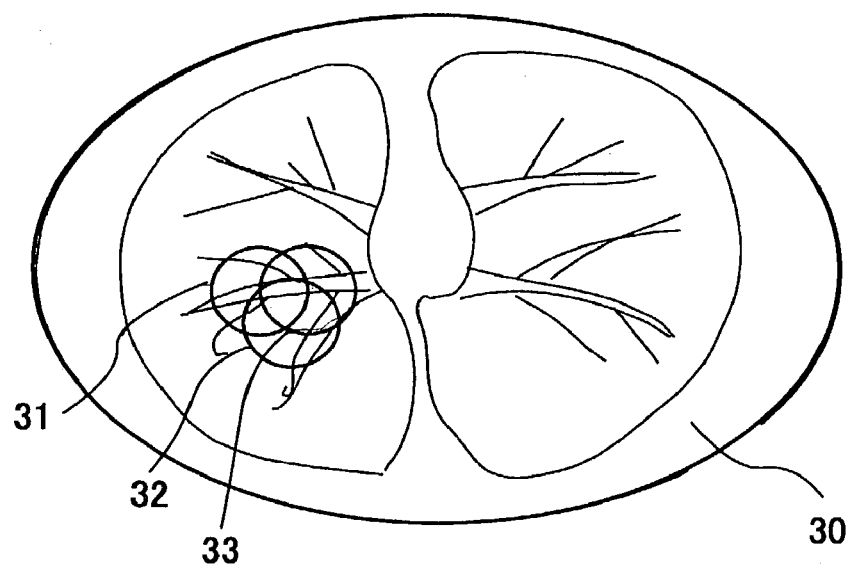
FIG. 35 is a diagram showing an example in which a plurality of circles which enclose a plurality of focus candidate shadows are displayed in a CT image.

A display method of indicating a detected shadow portion to which attention is to be directed by enclosing an area of interest, such as a focus candidate shadow, with a marker (circle) will be described below. As shown in FIG. 35, in the case where focus candidate shadows (not shown) on a medical image 30, such as a CT image, an MRI image and an ultrasonic image, are enclosed with circles 31, 32 and 33, if a plurality of focus candidate shadows are close to one another, the circles overlap and the focus candidate shadows themselves or the peripheries of the focus candidate shadows may become difficult to observe. In this embodiment, instead of overlapping and displaying the plurality of circles 31, 32 and 33, markers are displayed as an aggregation of circular arcs 34, 35 and 36, as shown in FIG. 36b. Specifically, in the case where the circles 31, 32 and 33 which are respectively centered at focus candidate shadows p1, p2 and p3, overlap one another, the circular arcs contained in the overlap are erased and the circles 31, 32 and 33 are drawn as an aggregation of a plurality of circular arcs 34, 35 and 36, as shown in FIG. 36b. Incidentally, since focus candidate shadows are generally small, it is preferable that the diameters of the circles be made about 10 times the diameters of the focus candidate shadows.

Figure 36A:
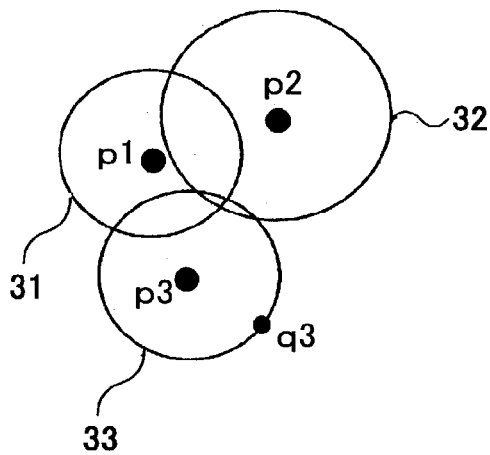
FIGS. 36a and 36b are diagrams conceptually showing a method of processing the plurality of circles shown in FIG. 35, and the drawing of circular arcs so that the circles do not overlap one another, respectively.
Figure 36B:
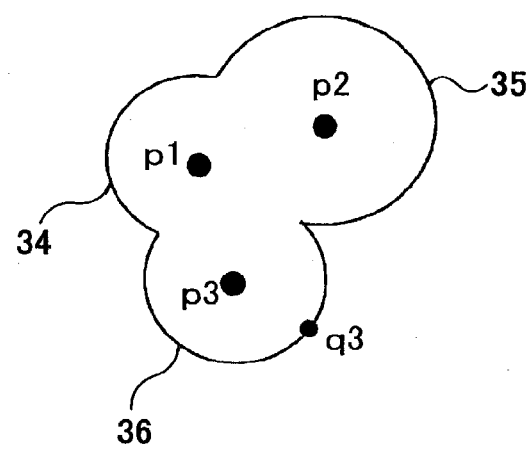
Figure 37:
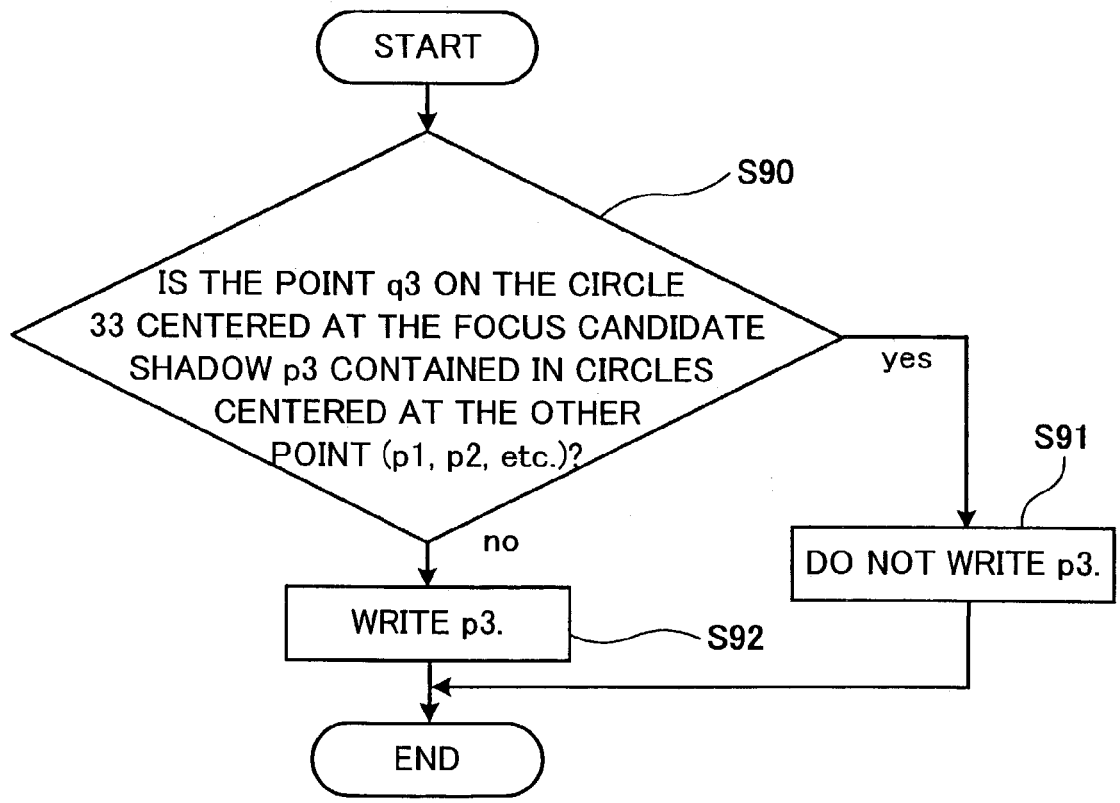
FIG. 37 is a flowchart showing one example of the processing of drawing the circular arcs shown in FIG. 35.

FIG. 37 is a flowchart indicating the processing for erasing the overlap among the above-described plurality of circles and for generating an aggregation of the plurality of circular arcs. Namely, this flowchart shows details of the processing for the case of drawing the point q3 on the circle 33 of FIG. 36a as the point q3 on the circular arc 36 of FIG. 36b.

[Step S72] The CPU 40 determines whether the point q3 on the circle 33 that is centered at the focus candidate shadow p3 is contained in the circles 31 and 32 centered at the other focus candidate shadows (the focus candidate shadows p1 and p2 in FIG. 36a). If the CPU 40 determines that the point q3 is contained (yes), the CPU 40 proceeds to Step S91; whereas, if the CPU 40 determines that the point q3 is not contained (no), the CPU 40 proceeds to Step S92.

[Step S91] Since the CPU 40 has determined in the previous step S90 that the point q3 overlaps the other circles, the CPU 40 brings the processing to an end without drawing the point q3.

[Step S92] Since the CPU 40 has determined in Step S90 that the point q3 does not overlap the other circles, the CPU 40 draws the point q3 and brings the processing to an end. In the case where the CPU 40 draws the circle 33 that is centered at the focus candidate shadow p3, the CPU 40 performs the processing of the above-described steps S90 to S92 on all points on the circle. If the CPU 40 is to draw the circles 31 and 32 that are centered at the focus candidate shadows p1 and p2, the CPU 40 performs similar processing.

In addition, in the extraction process of a focus candidate shadow, by taking the inverse proportion of the results of the decision formulas (1) and (2) of Step S5 of FIG. 12, it is possible to find the probability that the focus candidate shadow is a focus (focus certainty). Therefore, when the above-described circuit is to be displayed, it is possible to reflect the focus certainty by making the size of the circles proportional to the focus certainty or the size of the shadow. Incidentally, the circle may also be displayed as a thick circle or a large circuit, or in different colors (in the order of the highness of the focus certainty like red, yellow and blue), or in flashing manner, in proportion to the focus certainty irrespective of the size of the circle. Furthermore, the markers are not limited to circles, and may also be rectangles or ellipses. In addition, in the case where a focus itself is extracted, a focus candidate shadow itself may be displayed in different colors or in flashing form to attract the operator's attention, or a buzzer or a sound may also be used to attract the operator's attention.

Figure 38:
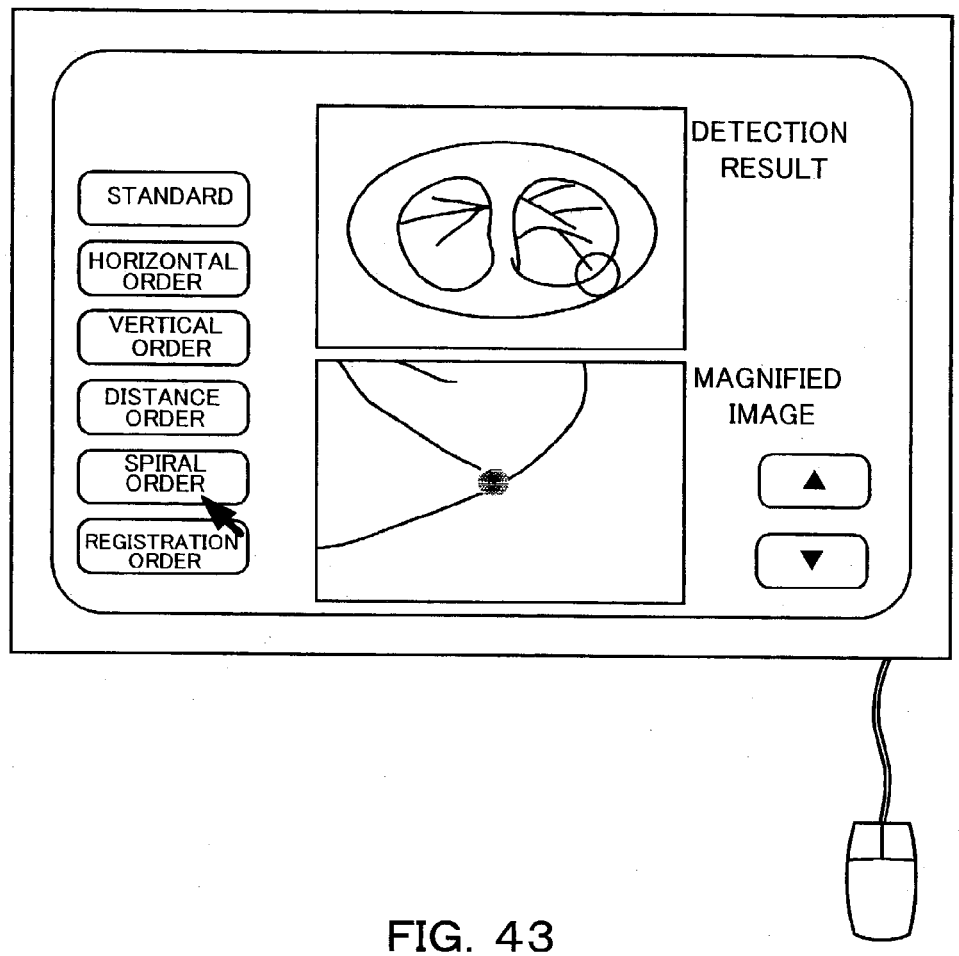
FIG. 38 is a diagram showing one example of a case where a detection result picture, in which a focus candidate shadow is indicated by a marker, and a magnified picture in which the portion of the marker is displayed on a magnified scale, are displayed in one picture at the same time.

A display method for displaying to the operator (doctor) a CT image from which a focus candidate shadow is extracted, together with the above-described marker, will now be explained. FIG. 38 is a view showing one example of a case where a detection result image, in which a focus candidate shadow is enclosed with a marker, and a magnified image, in which the portion within the marker is displayed on a magnified scale, are displayed in one display at the same time. As is apparent from the figure, the detection result image is the picture (a2) of FIG. 3 or FIG. 31, and this magnified image displays the portion within the marker in the detection result image in the state of being magnified at a predetermined magnification. By this magnified display, the operator (doctor) can more accurately observe the focus candidate shadow. The display shown in FIG. 38 is a standard picture which is designed to enable various display modes to be selected by display mode selecting buttons that are arranged in a column at the left-hand end of the picture. These display mode selecting buttons are respectively provided as icons assigned to six kinds of mode, i.e., standard display mode, horizontal order display mode, vertical order display mode, distance order display mode, spiral order display mode and registration order display mode. Although not shown, there also exists a button for displaying/erasing the marker, but the illustration thereof is omitted.

Figure 39:
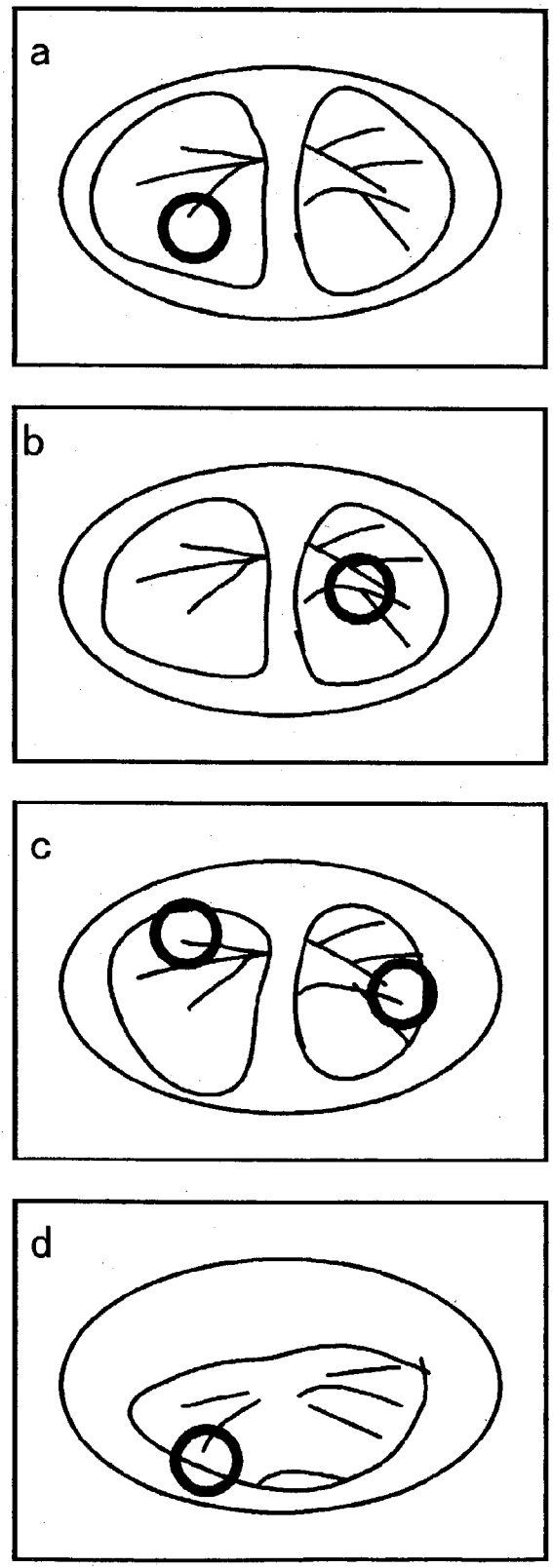
FIG. 39 is a diagram showing one example of a display picture in which images are displayed in the order of execution of extraction of focus candidate shadows.

The standard mode is the mode of displaying images in the order in which extraction processing for focus candidate shadows is performed on the images, as shown in FIG. 39; and, if extraction processing is performed in the order of, for example, images a-d, the images a-d are displayed in that order. Switching of pictures is performed by means of the picture switching buttons shown in FIG. 38 at the bottom right thereof. A picture switching button on which a downward triangle is displayed is a next-picture display button, and a picture switching button on which an upward triangle is displayed is a previous-picture display button. Incidentally, focus candidate shadows exist in the image c at two locations, and, in this case, a marker display switching button is displayed. In addition, a magnification change button for arbitrarily changing the display magnification of a magnified picture is also displayed, but the illustration thereof is omitted herein.

Figure 40A:
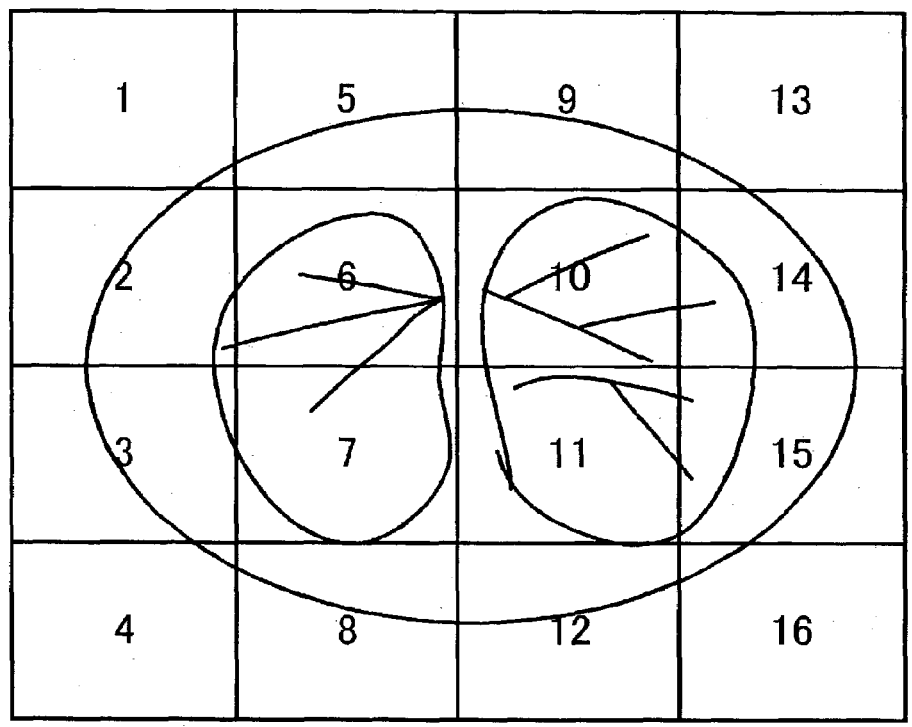
FIGS. 40a and 40b are diagrams showing the state in which a CT image is divided into 16 parts in the horizontal and vertical directions, FIG. 40(a) being a view showing the case where the 16 parts are assigned numbers in order from top left to bottom left, and FIG. 40(b) being a view showing the case where the 16 parts are assigned numbers in order from top left to top right.
Figure 41:
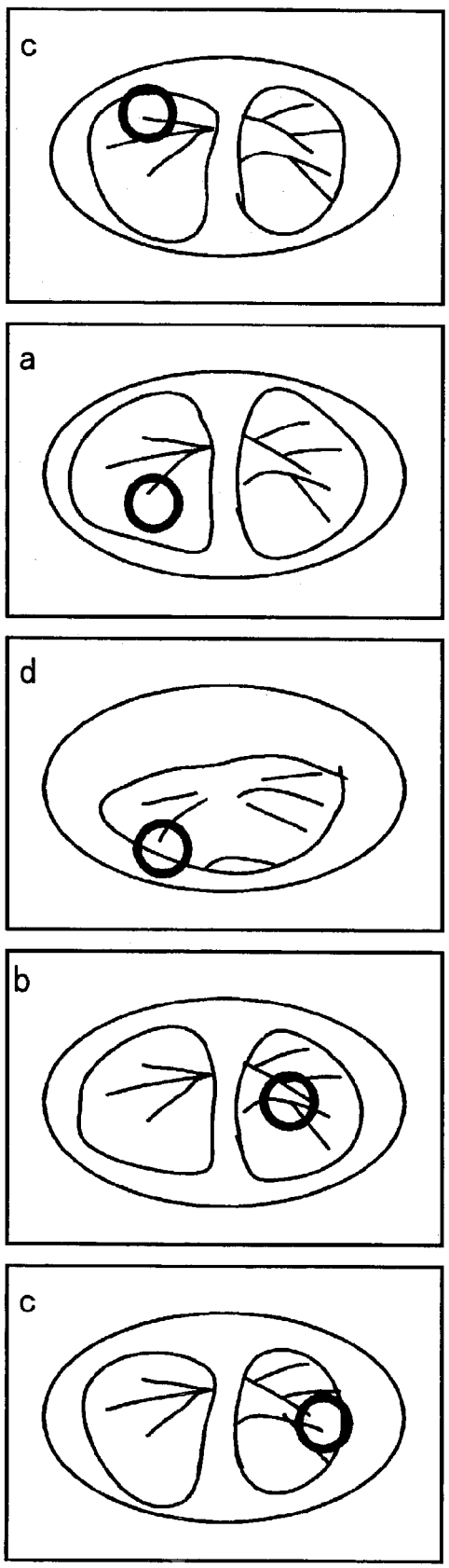
FIG. 41 is a diagram showing one example of a display picture in which a focus candidate shadow is displayed in order from top left to bottom left.

The horizontal order display mode is the mode of dividing a CT image into 16 parts in the horizontal and vertical directions, as shown in FIG. 40a, assigning numbers to the 16 parts in order from top left to bottom left, and displaying focus candidate shadows in the ascending order of the numbers. Accordingly, in the case of a focus-candidate-shadow-extracted image, as shown in FIG. 39, a focus candidate shadow is displayed in order from top left to bottom left as shown in FIG. 41. At this time, the image c of FIG. 39 is displayed separately in the top and bottom sections of FIG. 41.

Figure 40B:
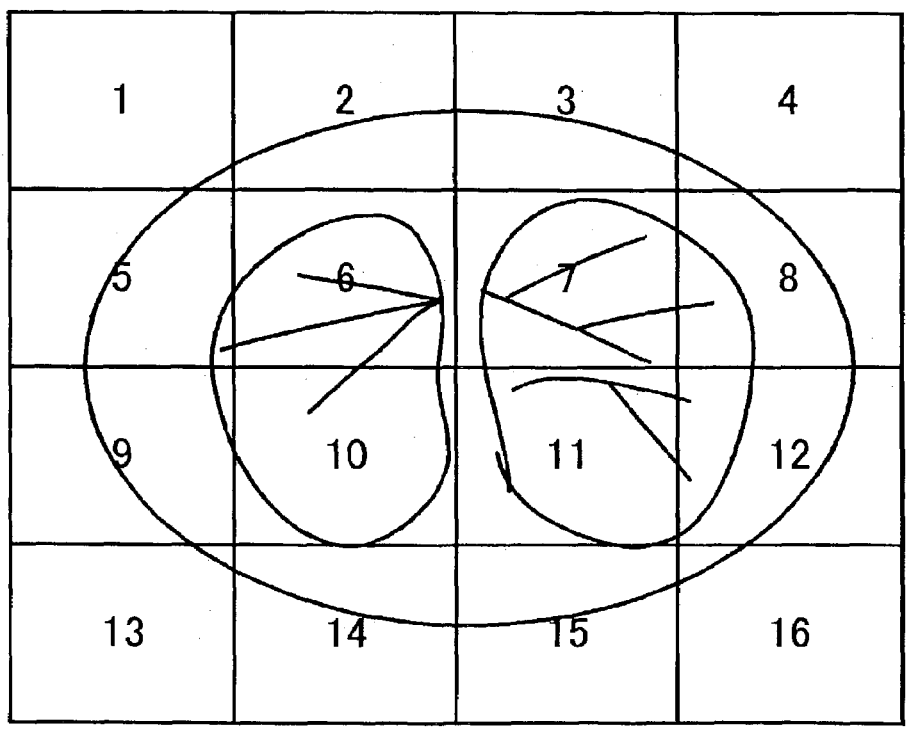
Figure 42:
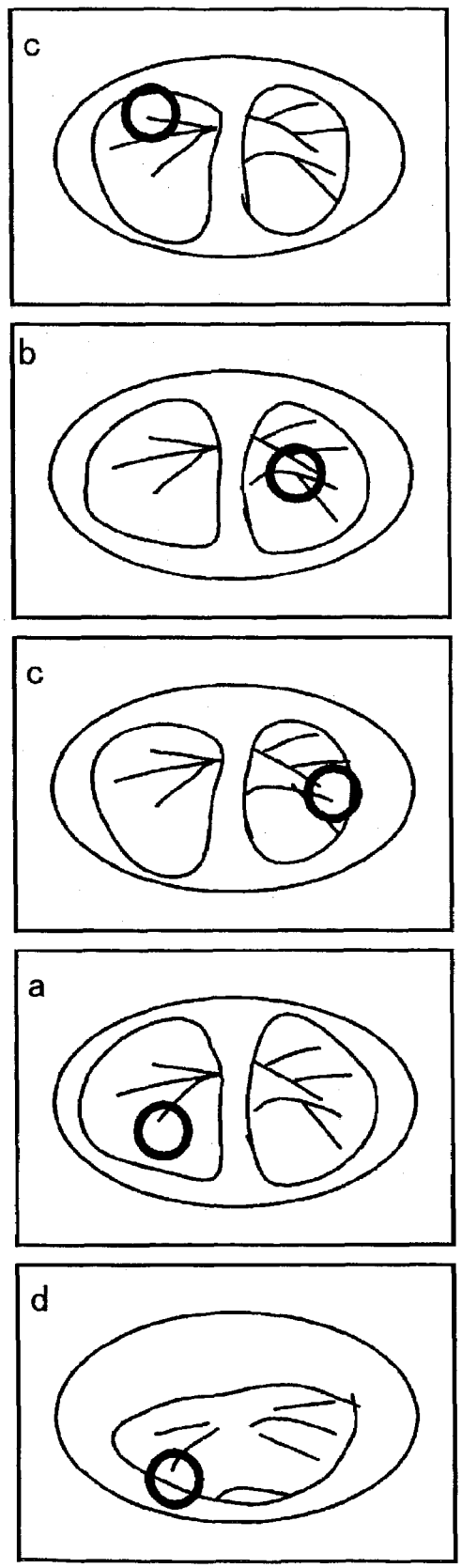
FIG. 42 is a diagram showing one example of a display picture in which a focus candidate shadow is displayed in order from top left to top right.

The distance order display mode is the mode of dividing a CT image into 16 parts in the horizontal and vertical directions, as shown in FIG. 40b, assigning numbers to the 16 parts in order from top left to top right, and displaying focus candidate shadows in the ascending order of the numbers. Accordingly, in the case of a focus-candidate-shadow-extracted image as shown in FIG. 39, a focus candidate shadow is displayed in order from top left to top right, as shown in FIG. 42. Incidentally, images having focus candidate shadows at approximately the same division position like the images a and d are displayed in the order of extraction processing.

Figure 43:
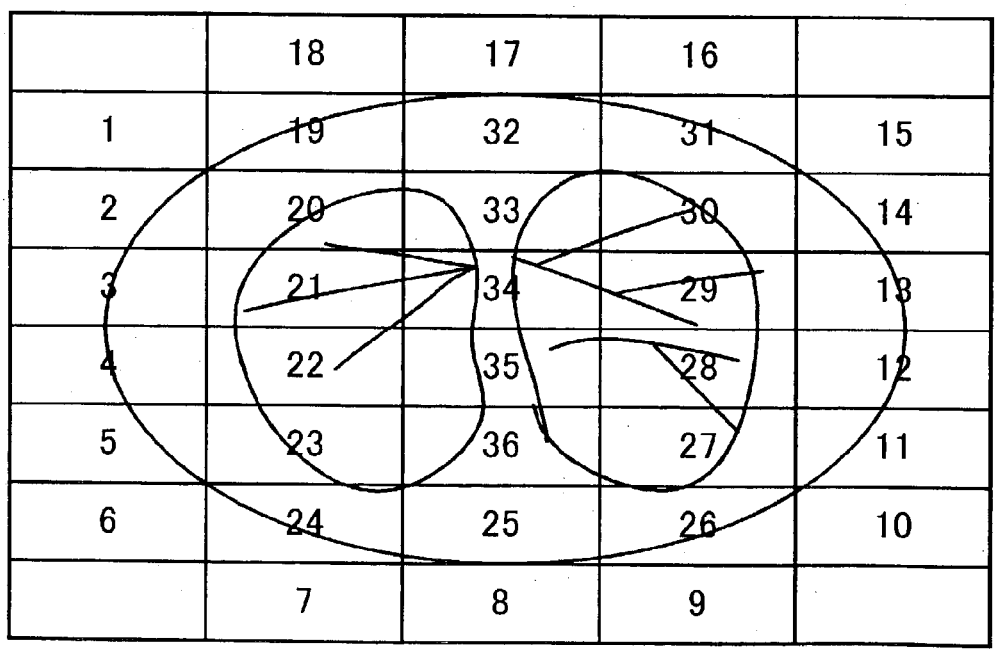
FIG. 43 is a diagram showing the state in which a CT image is divided into 40 areas in the horizontal and vertical directions.

The distance order display mode is the mode of sequentially accessing an image having a focus candidate shadow at the smallest distance to the first displayed focus candidate shadow. The spiral order display mode is the mode of dividing a CT image into 40 parts in the horizontal and vertical directions, as shown in FIG. 43, sequentially assigning numbers to the 40 parts counterclockwise spirally in order from top left to bottom left, and displaying focus candidate shadows in the ascending order of the numbers. The registration order display mode is the mode of displaying images in the order of display registered in advance by an operator. Incidentally, it goes without saying that the above-described horizontal and vertical division number is merely one example and other division numbers may also be adopted. In the case of the spiral order display mode, although images are displayed in order from the outside, images may also be displayed in order from the vicinity of the center toward the outside. The direction of the spiral may be either clockwise or counterclockwise. Furthermore, since the inside of a mark, such as a circle, has a different CT value, the inside of the mark may be set to an area of interest to adjust a display level and a display window and recalculate and modify a display conversion table, thereby easily identifiably displaying the mark.

Incidentally, in the decision making subroutines D1 to D3 of FIG. 25, the CPU 40 makes a decision as to whether a shadow is located on a wall portion, and identifies the shadow on the basis of the decision. However, in the case where a shadow is located on a wall portion and the distance of the contact of the wall and the shadow with each other is long, the possibility that the shadow is not a focus candidate shadow is high. Contrarily, if the distance by which the wall and the shadow are in contact is short, the possibility that the shadow is a focus candidate shadow is high. For this reason, in a modification of the decision making subroutines D1 to D3 of FIG. 25, if the CPU 40 determines from the processing of the decision making subroutines D1 to D3 that a shadow is located on a wall portion, the CPU 40 determines whether the length of contact between the shadow and the wall portion is smaller than a predetermined length. If the CPU 40 determines that the length is smaller, the CPU 40 determines that the shadow is a focus candidate shadow; whereas, if the CPU 40 determines that the length is larger, the CPU 40 excludes the shadow from focus candidate shadows.

Figure 44A:
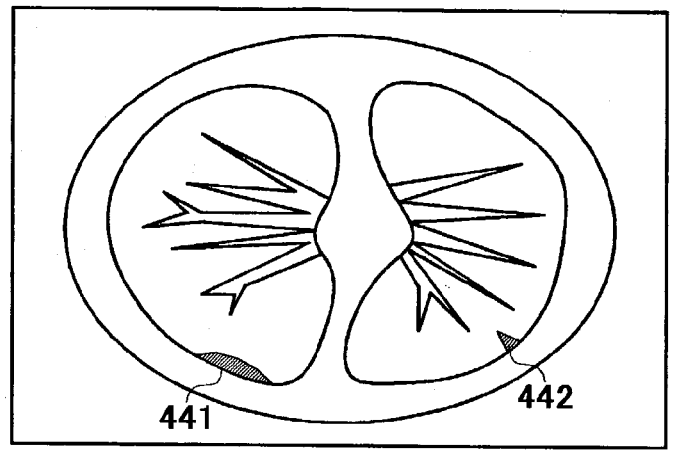
FIGS. 44a to 44c are diagrams showing a specific example in which, in the case where it is determined that a shadow is located on a wall portion, a decision is made as to whether the shadow is a focus candidate shadow, on the basis of the length of contact between the shadow and the wall portion.
Figure 44B:
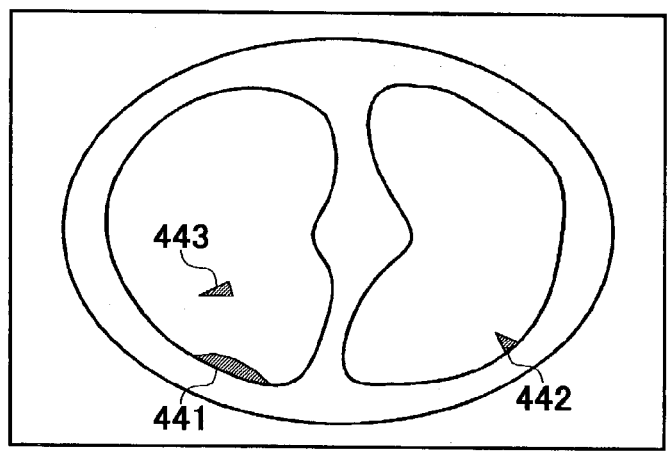
Figure 44C:
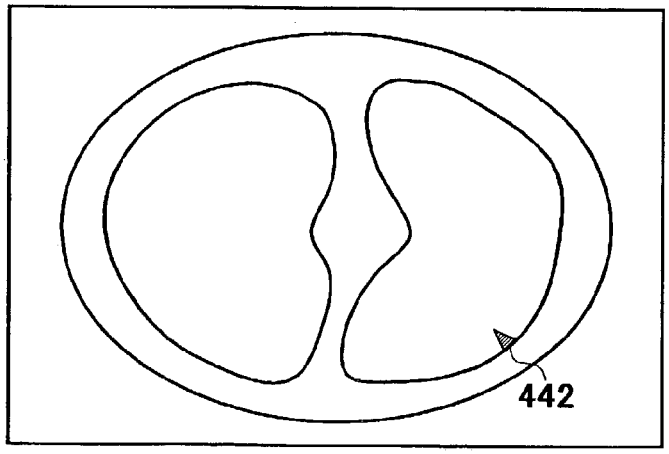

FIGS. 44a to 44c show a specific example in which, when the CPU 40 determines that a shadow is located on a wall portion, the CPU 40 determine whether the shadow is a focus candidate shadow from the length of contact between the shadow and the wall portion. As shown in FIG. 44a, in a CT image, shadows 441 and 442 exist in contact with a wall portion. By applying the multi-valued image processing and the predetermines decision process of FIGS. 5 and 6 to the CT image as shown in FIG. 44a, the shadows 441 and 442, as well as a shadow 443, all of which seem to be focus candidates, are extracted in a multi-valued image, as shown in FIG. 44b. Both of these shadows 441 and 442 are in contact with the wall portion and the shadow 443 is not in contact therewith, so that although the shadow 443 is excluded by the decision making subroutine of FIG. 25, the CPU 40 cannot discriminate between the shadows 441 and 442. However, since the distance by which the shadow 442 is in contact with the wall portion is smaller than that of the shadow 441, the possibility that the shadow 442 is a focus shadow is high. Accordingly, the CPU 40 finds the distances by which the respective shadows 441 and 442 are in contact with the wall portion, and determines whether each of the distances is smaller than a predetermined value, and determines on the basis of the result of the decision whether each of the shadows is a focus candidate. Therefore, since the distance by which the shadow 441 is in contact with the interior wall portion is larger than the predetermined value, the CPU 40 determines that the shadow 441 is not a focus candidate shadow. On the other hand, since the distance by which the shadow 442 is in contact with the wall portion is substantially smaller than the predetermined value, the CPU 40 determines that the shadow 442 is a focus candidate shadow, and, as shown in FIG. 44c, only the shadow 442 is finally extracted as a focus candidate shadow.

Figure 45A:
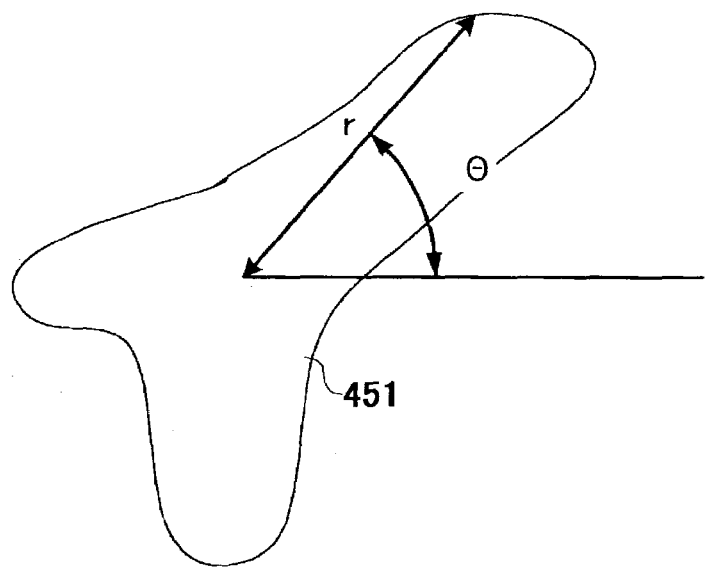
FIGS. 45(a) to 45(c) comprise a diagram and graphs showing another embodiment of the decision making subroutine.
Figure 45B:
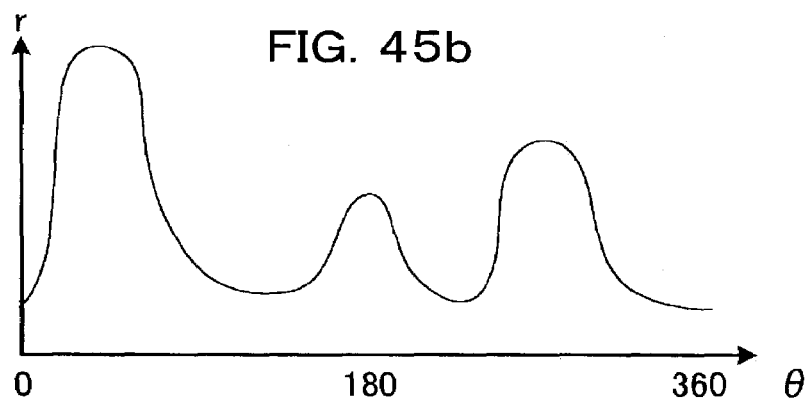
Figure 45C:
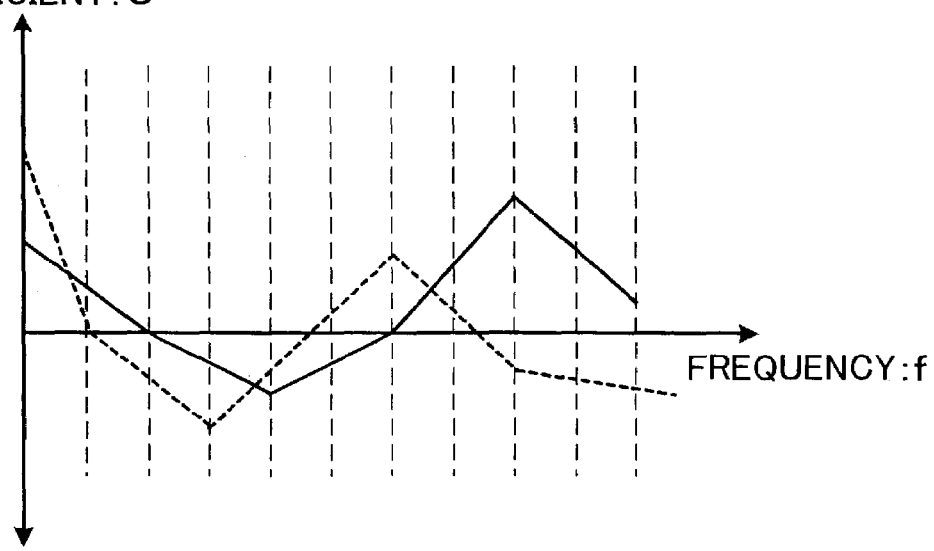

Referring to FIG. 45a, the CPU 40 rotates a radius of predetermined length by about one degree at one time about a point in the vicinity of the center of a shadow 451 in the range of angle θ from 0 degrees to 360 degrees. During this time, the CPU 40 finds the length r at which the radius crosses the edge of the shadow at each angle. On the basis of this length r, as shown in FIG. 45b, the CPU 40 plots a curve against the horizontal axis showing the angle θ and against the vertical axis showing the length r of the radius, and performs Fourier expansion on the curve. On the basis of this Fourier-expanded result, the CPU 40 generates a broken-line graph in which the horizontal axis shows frequency f and the vertical axis shows the Fourier coefficient C, as shown in FIG. 45c. On the basis of this broken-line graph, the CPU 40 determines whether the shadow is a focus shadow. Namely, in this broken-line graph, a Fourier coefficient at a frequency f0 is C0, a Fourier coefficient at a frequency f1 is C1, and a Fourier coefficient at a frequency f2 is C2. Therefore, the CPU 40 represents each of the Fourier coefficients as Ci and each of the frequencies as Fi, and finds the absolute value |fi×Ci| of the product of Ci and fi; and, further, it finds the summation Σ|fi×Ci| of the absolute value |fi×Ci|. The CPU 40 divides the summation Σ|fi×Ci| by the absolute value |Ci| of the Fourier coefficient Ci, to calculate a determined value ff. This determined value ff is expressed by the following expression:

$$ff = \Sigma|fi \times Ci|/\Sigma|Ci|.$$

The CPU 40 determines whether the shadow is a focus candidate shadow, according to whether this determined value ff is smaller than a predetermined value. In the case where the shadow is a blood vessel cross-sectional shadow 451, as shown in FIG. 45a, the Fourier coefficients of high-order frequency components are large in the Fourier expansion. In contrast, if the shadow is like a focus candidate shadow, low-order frequency components are contained in large quantities and high-order frequency components are small in the Fourier expansion. Accordingly, the CPU 40 can determine on the basis of the value of the determined value ff whether the shadow is a focus candidate shadow or a blood vessel cross-sectional shadow. Incidentally, instead of this determined value ff, a particular |fi×Ci| may also be used as a determined value.

Figure 46A:
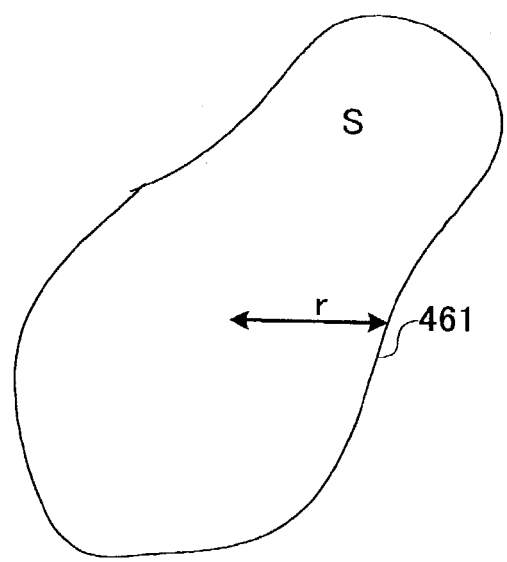
FIGS. 46a to 46d are diagrams showing yet another embodiment of the decision making subroutine.
Figure 46B:
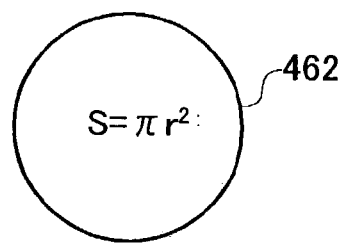
Figure 46C:
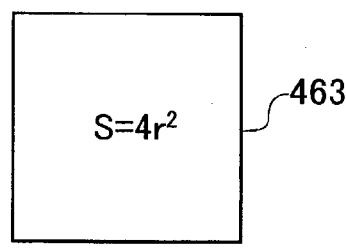
Figure 46D:
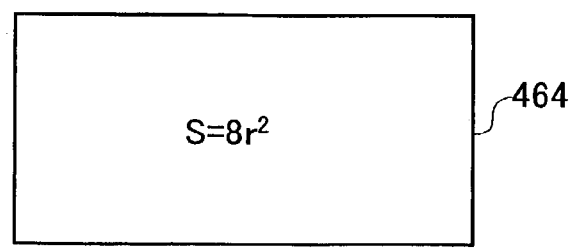

FIGS. 46a to 46d show another embodiment of the decision making subroutine. In FIG. 46a, the CPU 40 rotates a radius of predetermined length by about one degree at one time about the vicinity of the center of a shadow 461 in the range of angles from θ=0 degrees to θ=360 degrees. During this time, the CPU 40 determines a length of the portion of the radius up to the edge of the shadow at each angle. The minimum value of the determined lengths is set as r. Namely, a short radius r of the shadow 461 is found. The area (the number of constituent pixels) S of the shadow 461 is divided by this short radius r. Namely, $S/r^2$ is found. The CPU 40 compares this value with a predetermined value and determines whether the shadow is a focus shadow. Namely, as shown in FIG. 46*b*, if a shadow 462 is a circle, the value of $S/r^2$ is π. As shown in FIG. 46*c*, if a shadow 463 is a square, the value of $S/r^2$ is 4. As shown in FIG. 46*d*, if a shadow 464 is a rectangle consisting of two squares, the value of $S/r^2$ is 8. Therefore, the shadow 464 having the rectangular shape as shown in FIG. 46*d* must be excluded from focus candidate shadows. Accordingly, when the value of $S/r^2$ is smaller than 8, the shadow is selected as a focus candidate shadow, whereas when the value of $S/r^2$ is not smaller than 8, the shadow is excluded from focus candidate shadows. Incidentally, these values are one example; and in actual practice, different numerical values may be used. Incidentally, as the above-described short radius r, a value r obtained by dividing the area S of a shadow by a maximum radius rm of the shadow may also be used as an effective short radius r.

Figure 47A:
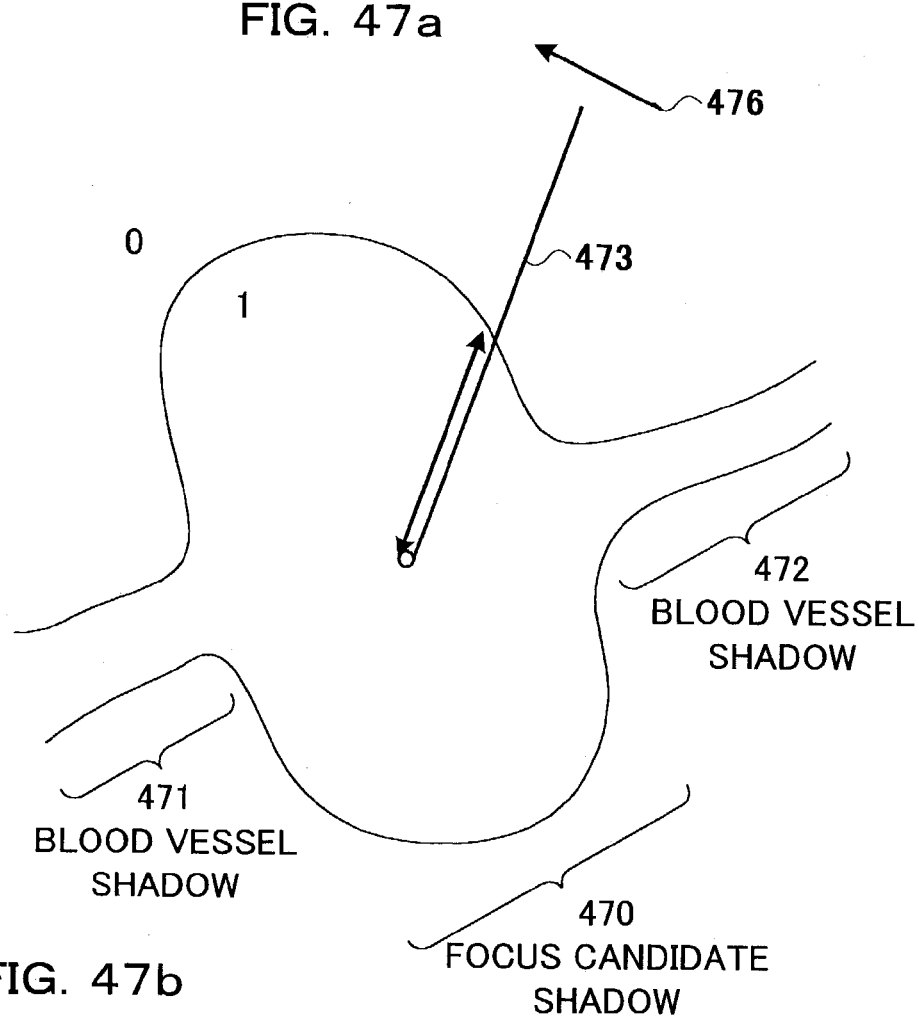
FIGS. 47a and 47b are conceptual diagrams of the state where, when a comparatively large focus candidate shadow and blood vessel shadows overlap one another, the blood vessel shadows are excluded by cutting.

Incidentally, in the above-described embodiment, the binary image processing of FIGS. 5 and 6 is applied to a CT image to perform the processing of excluding the shadow of a blood vessel portion that is thinner than a predetermined value. This processing extracts and deletes a shadow having a predetermined number of pixels or less in the horizontal (X axis) or vertical (Y axis) direction, and so a comparatively large blood vessel which does not conform to this condition is not excluded. Even in the case of the shadow of such a blood vessel portion, an elongated shadow as shown in FIG. 28*a* can be effectively excluded by the decision making subroutine E1 of FIG. 27. However, there is a case where, if a comparatively large focus candidate shadow 470 and blood vessel shadows 471 and 472 overlap, as shown in FIG. 47*a*, these blood vessel shadows 471 and 472 cannot be excluded. For this reason, in this embodiment, the blood vessel shadows 471 and 472, as shown in FIGS. 47*a*, 47*b* are removed by cutting through using the cutting processing shown in FIG. 48.

First of all, in the first step S481, the CPU 40 applies the binary image processing of FIGS. 5 and 6 to a CT image, and removes the shadow of a blood vessel portion that is thinner than a predetermined value. After this processing, in Step S482, the CPU 40 finds a temporary weighted center position of the shadow shown in FIG. 47*a*. The weighted center position may be found by using the above-described various methods. In Step S483, the CPU 40 finds a minimum length Rmin of a moving radius 473 in the shadow while rotating the moving radius 473 in the direction of an arrow 476. When the minimum length Rmin is found, in Step S484, the CPU 40 determines, as a cutting length L, a value obtained by multiplying this minimum length Rmin by a constant. Therefore, the cutting length L=Rmin×constant. When the cutting length L is found, in Step S485, the CPU 40 executes cutting of the shadows of the blood vessel portions on the basis of this cutting length L. The cutting of the shadows of the blood vessel portions is performed as shown in FIG. 47*b*. First, the CPU 40 sets decision areas 474 and 475, each made of the number of pixels corresponding to the cutting length L in the horizontal (X axis) direction or the vertical (Y axis) direction, and determines whether any of the shadows 470 to 472 is smaller than the decision areas 474 and 475.

Figure 47B:
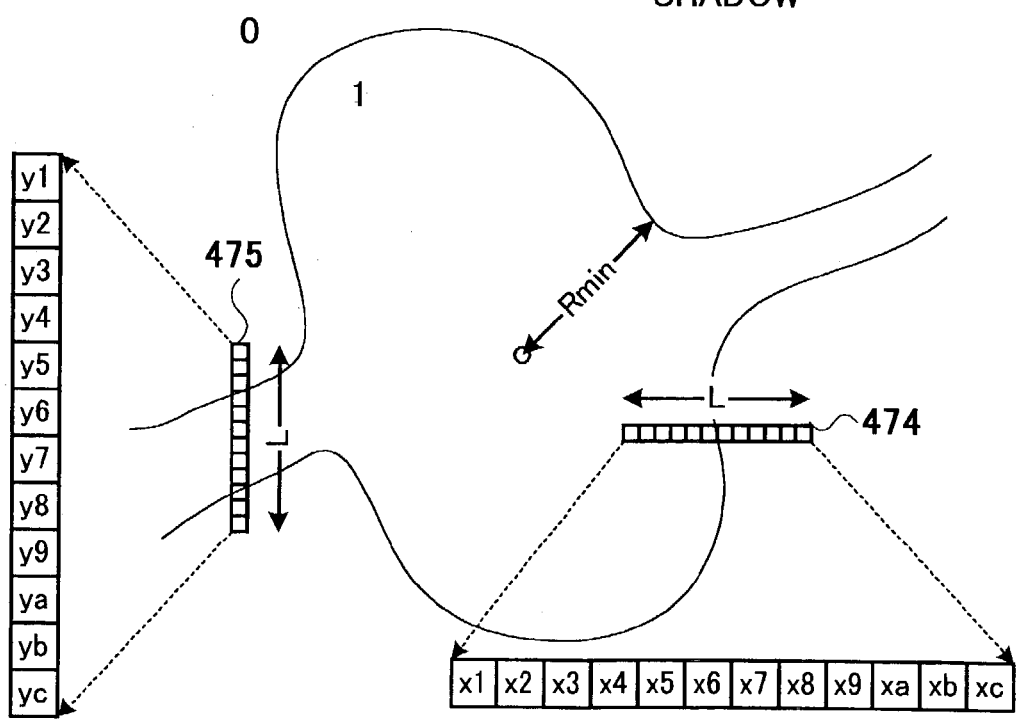
Figure 48:
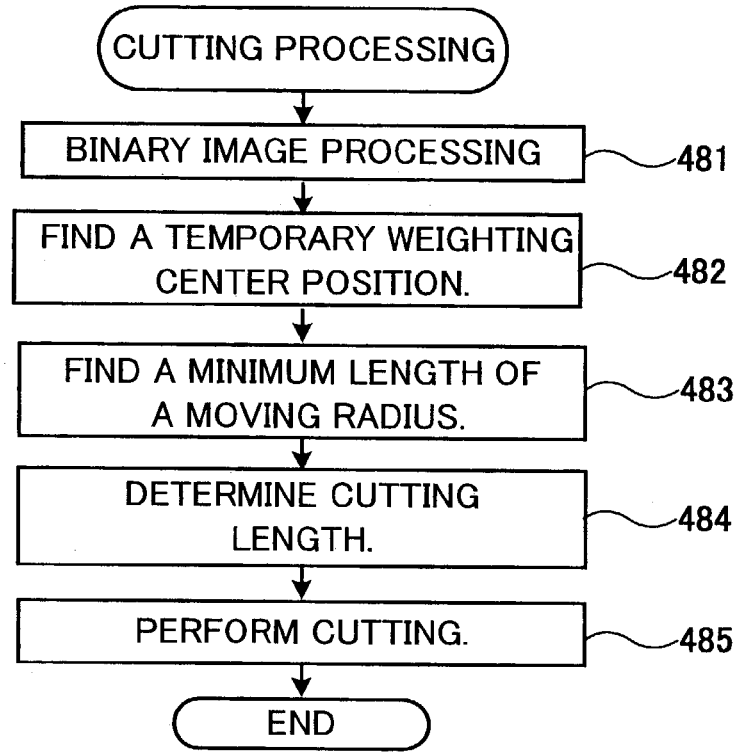
FIG. 48 is a flowchart showing details of the blood vessel cutting processing of FIGS. 47a and 47b.
Figure 49A:
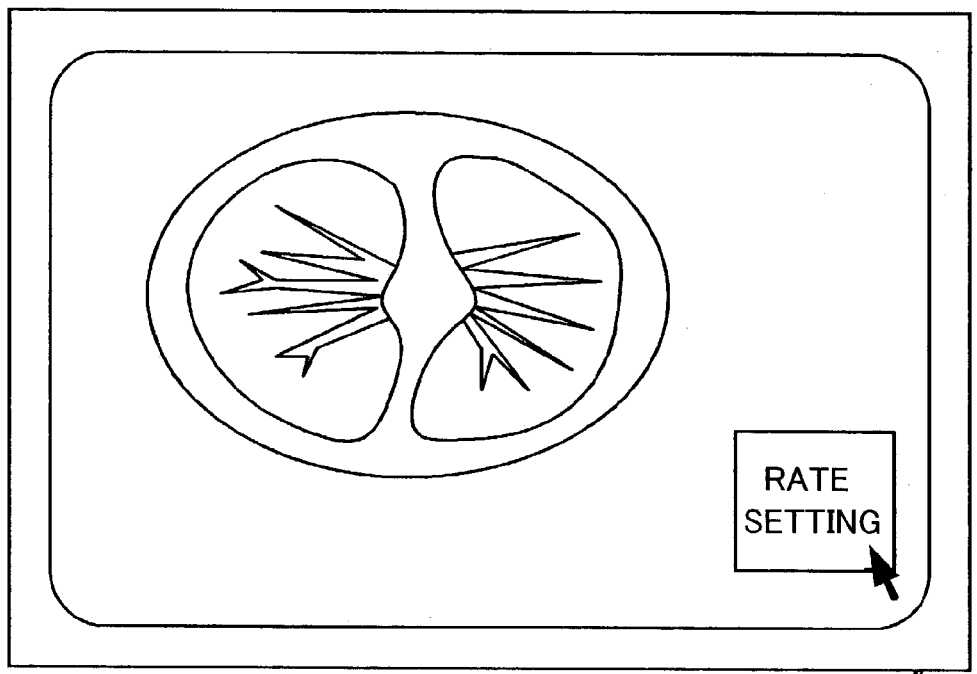
FIG. 49a is a diagram and FIG. 49b is a graph showing a specific example of setting a cutting length in FIG. 48.
Figure 49B:
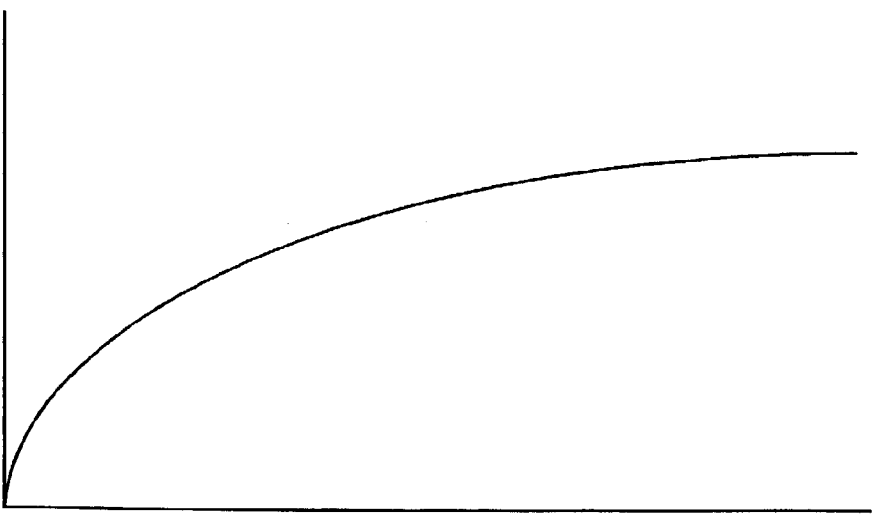

In the case of FIG. 47(*b*), the number of pixels of the cutting length L is assumed to be about 12 pixels. In the case of the horizontal decision area 474, the pixel value of a pixel x1 is "1" and the pixel value of a pixel xc is "0". Accordingly, this decision area 474 does not become a cutting target, and the pixels x1 to xc remain unchanged. On the other hand, in the case of the vertical decision area 475, since the pixel values of a pixel y1 and a pixel yc are both "0", the shadow 471 located in this decision area 475 becomes a cutting target, and the pixel values of the pixels y1 to yc are converted to "0". The CPU 40 executes the above-described cutting processing around the shadows 470 to 472. In this manner, the blood vessel shadows 471 and 472 are cut from the shadows shown in FIG. 47*a*, and only the focus candidate shadow 470 is left. Incidentally, a constant for determining the cutting length L is preferably in the range of 0.5-1.5. In FIG. 47*b*, the case where the constant is 1 has been described. In addition, the setting of this constant can also be arbitrarily changed by clicking a rate setting button with a mouse cursor, as shown in FIG. 49*a*. Furthermore, as shown in FIG. 49*b*, the cutting length may also be found on the basis of predetermined function processing with respect to the horizontal axis showing the minimum length Rmin of a moving radius and the vertical axis showing the cutting length.

Figure 50A:
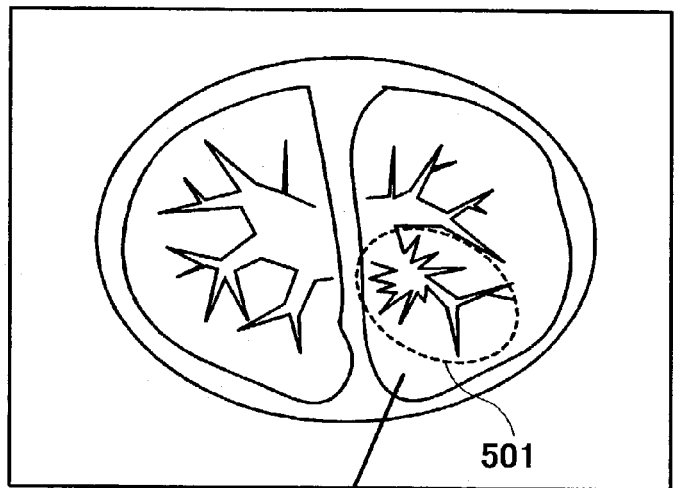
FIGS. 50a and 50b are diagrams showing a first modification of the decision making subroutine.
Figure 50B:
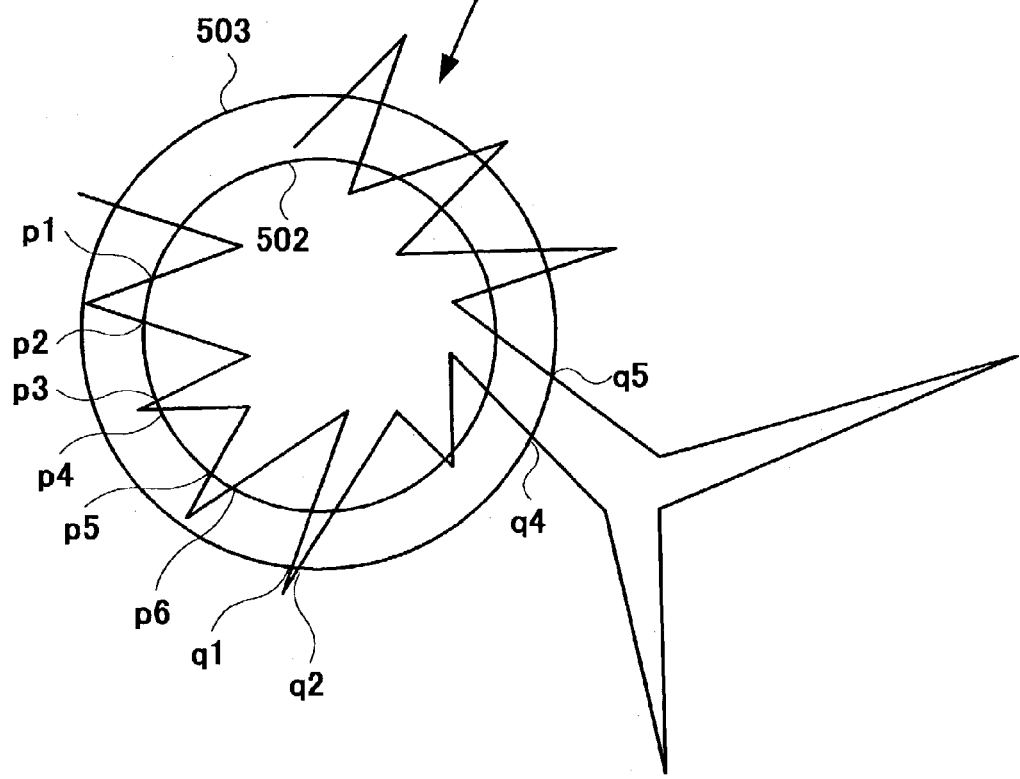

FIGS. 50*a* and 50*b* show a first modification of the decision making subroutine. The decision making subroutine of FIGS. 50*a*, 50*b* is performed in place of the decision making subroutine E1 of FIG. 27, the decision making subroutine F1 of FIG. 29 and each of the above-described decision making subroutines, or it is performed in parallel with these decision making subroutines. FIG. 50*a* is a view showing one example of the case where the binary image processing of FIGS. 5 and 6 is applied to a CT image. FIG. 50*b* is a view showing on a magnified scale the portion enclosed with a circle 501 in the image subjected to this binary image processing, and it shows how this decision is made. There is a medical image in which a ground glass opacity focus candidate shadow, which is bound to a blood vessel, exists in its binary image, as shown in FIG. 50*b*. Since this shadow is, as shown, bound to the blood vessel, the shadow has a shape provided with a multiplicity of projections toward its periphery as diagrammatically shown in FIG. 50(B). Therefore, this shadow cannot be easily determined by any of the above-described decision making subroutines.

For this reason, the CPU 40 finds a temporary weighted center position similar to the above-described case. The CPU 40 finds the minimum length of a moving radius in the shadow, while rotating the moving radius about the weighted center position. When this minimum length is found, the CPU 40 draws a circle 502 having a radius determined by adding a predetermined value (a value equivalent to the number of pixels, for example, 1-5 pixels) to the minimum length. The CPU 40 measures the lengths (run lengths) of circular arcs and the number of the circular arcs in which this circle 502 and the shadow are superposed on each other. For example, in the case of FIG. 50*b*, the respective run lengths of the circular arcs are found so that the run length of a circular arc p1p2 between an intersection point p1 and an intersection point p2 is defined as "3", the run length of a circular arc p3p4 between an intersection point p3 and an intersection point p4 is defined as "1", and the run length of a circular arc p5p6 between an intersection point p5 and an intersection point p6 is defined as "2". After the measurement of the run lengths and the counting of the number of the circular arcs have been completed, the CPU 40 draws another circle 503 having a radius determined by adding another predetermined value to the circle 502, and similarly counts the run lengths of circular arcs and the number in which this circle 503 and the shadow are superposed on each other. In FIG. 50b, only intersection points q1 and q2 are shown as the intersection points of the circle 503 and the shadow.

Figures 51A, 51B:
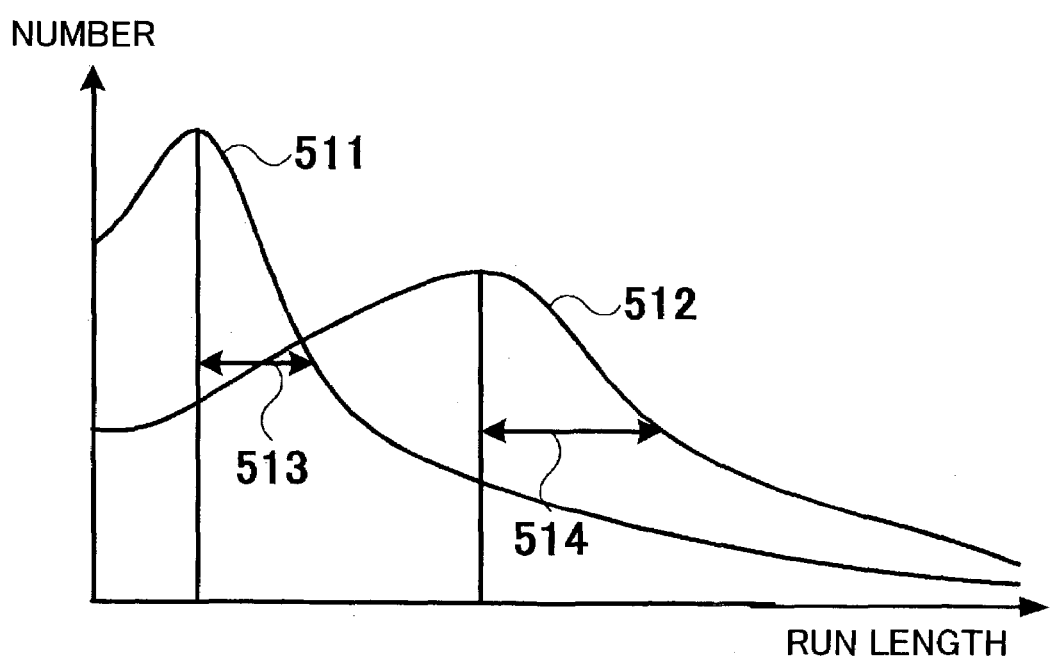
FIG. 51a is a table and FIG. 51b is a graph showing the result of counting.

In this manner, the CPU 40 gradually increases the radius of the circle and counts the run lengths of circular arcs and the number thereof. FIGS. 51a and 51b show the result of this counting. FIG. 51a schematically shows a count memory which uses run lengths as its addresses, and FIG. 51b shows characteristic curves plotted against the horizontal axis representing the run lengths of arcs and the vertical axis representing the number of arcs, the run lengths and the number of arcs being the contents of the count memory. In the case of FIG. 51a, the count memory shows values, such as 15 circular arcs, each having a run length of "1", and 53 circular arcs, each having a run length of "2". A characteristic curve which corresponds to these values is a characteristic curve 511 in FIG. 51b. Accordingly, in the case where the shadow is a focus candidate shadow, since the number of portions projecting outward from the shadow is extremely large, the shadow exhibits the feature that an extremely large number of circular arcs of short run length exist, and the number of circular arcs of long run length is small. On the other hand, in the case where the shadow is not a focus candidate shadow, the shadow has a shape as shown by a characteristic curve 512 and exhibits the feature that circular arcs of short run length exist and circular arcs of long run length exist by approximately the same number, unlike the case of the focus candidate shadow. Accordingly, the CPU 40 can make a decision as to whether the shadow is a focus candidate shadow, by identifying the shadow by using the position of a peak (in the run length) of such a characteristic curve. In addition, the CPU 40 may make a decision as to the shadow by using the shape of a distribution of the characteristic curve, i.e., half-value widths 513 and 514 and the like. Furthermore, the CPU 40 may provide the value of a run length to the input of a neural network or the like, and make a decision as to the shadow by using the output of the neural network. In addition, although in the above-described embodiment the circular arc lengths obtained in the case where a focus candidate shadow and a circle overlap are used, circular arc lengths obtained where a focus candidate shadow and a circle do not overlap may be used, and further, a combination of both circular arc lengths may also be used. Run lengths may also be found on the basis of whether a CT value is larger or smaller than a threshold value or whether a density gradient is larger or smaller than a threshold value.

Figure 52A:
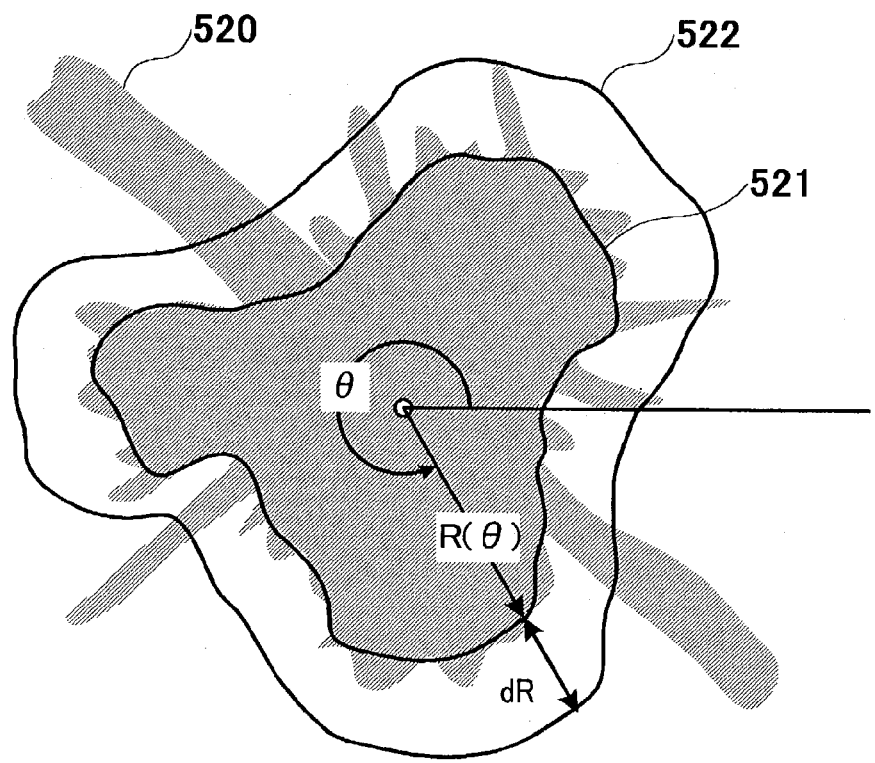
FIG. 52a is a diagram and FIG. 52b is a graph showing a modification of the decision making subroutine of FIGS. 50a and 50b.
Figure 52B:
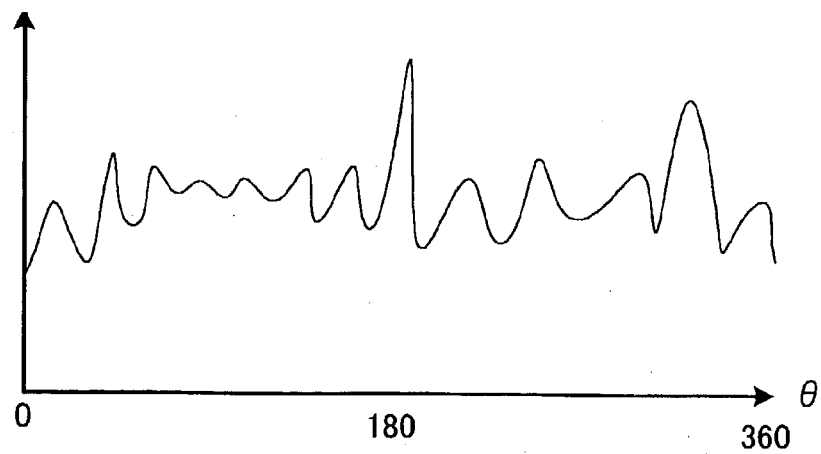

Incidentally, although in FIG. 50 a circle is used to count run lengths and the number of arcs, a closed curve corresponding to the shape of a shadow may be generated in the following manner to count run lengths and the number thereof on the basis of this closed curve. Namely, in the case of a shadow 520, as shown in FIG. 52a, the CPU 40 rotates a radius of predetermined length by increments of one degree about a point at the vicinity of the center of the shadow 520 in the range of an angle θ from 0 degrees to 360 degrees. During this time, the CPU 40 finds a length R at which the radius crosses the edge of the shadow at each angle. Incidentally, if a plurality of intersection points of the radius and the edge of the shadow exist, the CPU 40 selects the shortest radius. The CPU 40 plots a curve with the horizontal axis showing the angle θ and the vertical axis showing the length R of the radius calculated in this manner. This curve may be as shown in FIG. 52b. This curve becomes a curve whose apexes and valleys are alternately repeated. Accordingly, the CPU 40 finds the positions of the respective valleys (the angle θ), and marks them onto the shadow display. The positions of the respective valleys are discrete on the shadow. Therefore, the CPU 40 generates a closed curve 521, as shown in FIG. 52a, by performing the processing of interpolation between each of the valleys by means of a spline curve or the like. When the closed curve 521 is found, the CPU 40 counts the lengths of short curve segments (run lengths) in portions in each of which this closed circle 521 and the shadow 520 are superposed on each other, as well as the number of the curve segments, similar to the above-described case of FIGS. 50a, 50b. After the measurement of the run lengths and the counting of the number of curve segments have been completed as to the circle 521, the CPU 40 draws a closed curve 522 formed by adding a predetermined value dR to the radius R(θ) of the closed curve 521, and similarly counts the run lengths and the number of curve segments in the circle 522. In this manner, the CPU 40 gradually increases the predetermined value dR and sequentially counts the run lengths and the number of the curve segments. Accordingly, since a count memory and characteristic curves similar to those shown in FIGS. 51a, 51b are obtained, the CPU 40 can make a decision as to whether the shadow is a focus candidate shadow, similar to the above-described case. In addition, although in the above-described embodiment the lengths of the curve segments obtained in the case where a focus candidate shadow and a circle overlap are used, the lengths of curve segments obtained in the case where a focus candidate shadow and a circle do not overlap may be used, and, further, a combination of both may also be used. Curve segments may also be found on the basis of whether a CT value is larger or smaller than a threshold value or whether a density gradient is larger or smaller than a threshold value.

In the above description, curve segments of a closed curve are used as a feature by which the decision is made, but a Fourier transform of shadow densities applied to a closed curve can also be used.

Figure 53A:
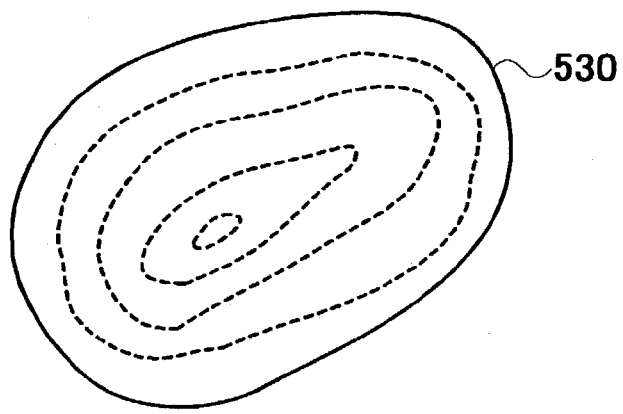
FIGS. 53a to 53c are diagrams showing the first half of a second modification of the decision making subroutine.
Figure 53B:
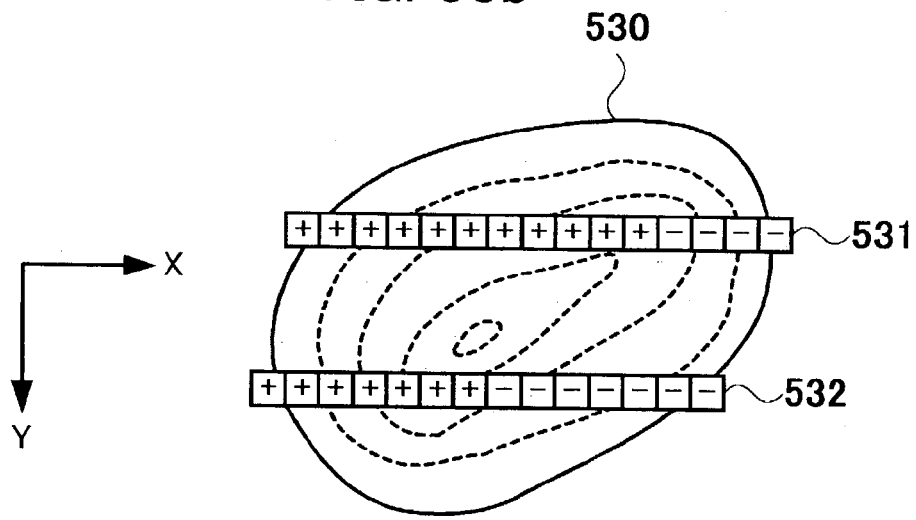
Figure 53C:
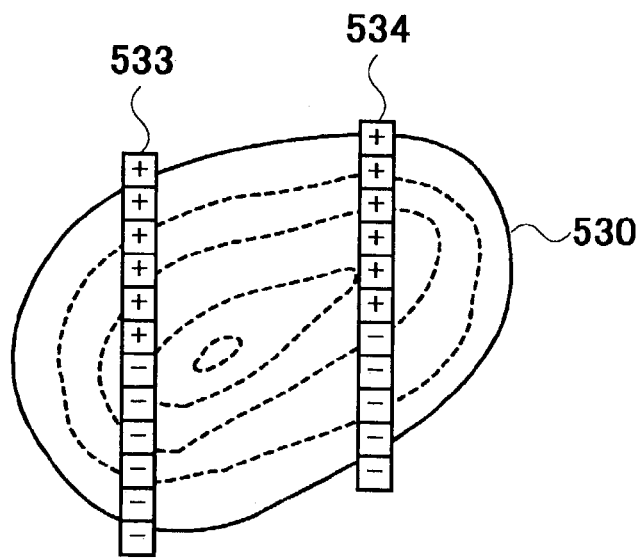
Figure 54A:
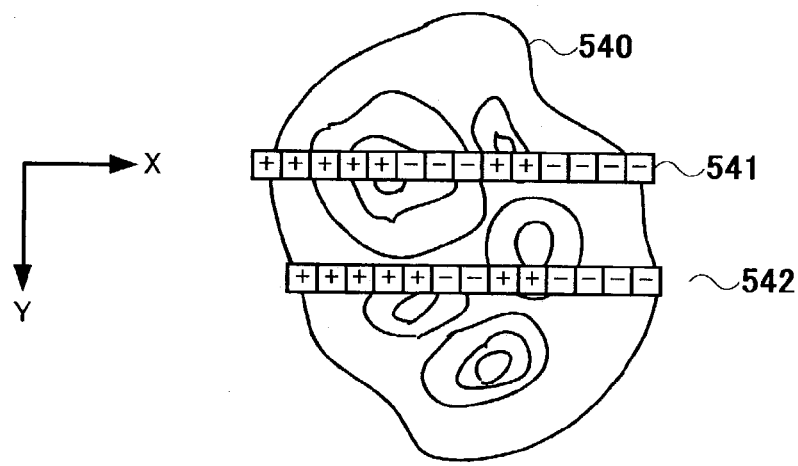
FIGS. 54a to 54c are diagrams showing the second half of the second modification of the decision making subroutine.
Figure 54B:
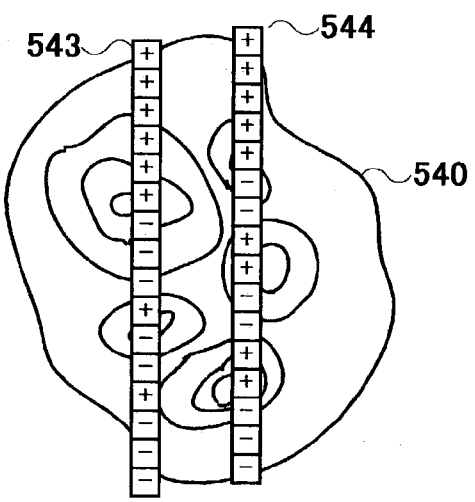
Figure 54C:
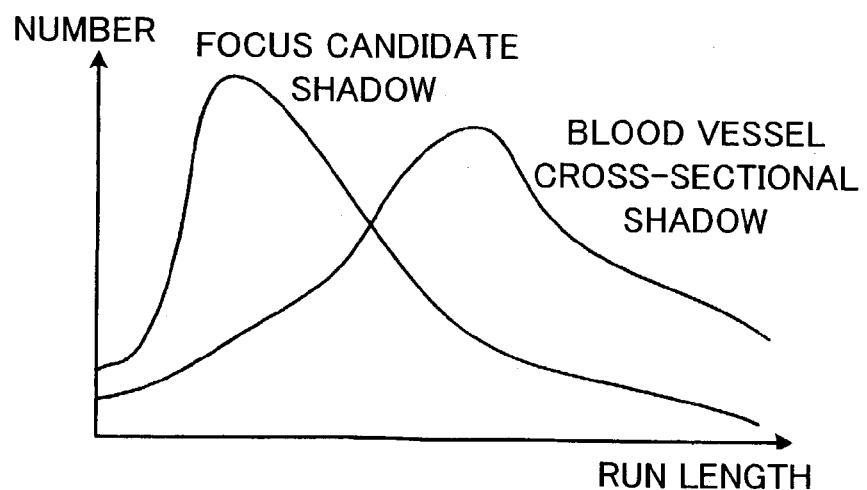

FIGS. 53 and 54 are views showing a second modification of the decision making subroutine. The decision making subroutines of FIGS. 53a to 53c and 54a to 54c are performed in place of the decision making subroutine E1 of FIG. 27, the decision making subroutine F1 of FIG. 29 and each of the above-described decision making subroutines, or they are performed in parallel with these decision making subroutines. FIGS. 53a to 53c shows processing to be performed on a blood vessel cross-sectional shadow generated by applying the binary image processing of FIGS. 5 and 6 to a CT image, and FIGS. 54a to 54c shows processing to be performed on a focus candidate shadow. There is a case where even if the binary image processing of FIGS. 5 and 6 is applied to a CT image to remove the shadow of a blood vessel portion that is thinner than a predetermined value, there may remain a blood vessel cross-sectional shadow 530 which seems to be a focus shadow, as shown in FIG. 53a. Accordingly, the blood vessel cross-sectional shadow 530 as shown in FIG. 53a must be excluded from focus candidates. For this reason, in this modification of the decision making subroutine, this blood vessel cross-sectional shadow 530 is extracted and excluded. Namely, to exclude the blood vessel cross-sectional shadow 530 from focus candidates, notice is taken of the density distribution in the shadow. Namely, in the case of the shadow 530 of a blood vessel cross-section, in a liver or the like, the contours of density in the shadow exhibit a simple form having one peak, as shown in FIG. 53a. On the other hand, in the case of a focus candidate shadow 540, as shown in FIG. 54a, there appear complicated contours having a plurality of peaks in the shadow. Accordingly, as to these shadows, the CPU 40 finds continuous segments (run lengths) along which there are continuously positive or negative values of density gradient, obtains a subtraction result, or performs a differential or other processing between the CT values of one pixel and the pixel adjacent in the x axis direction from left to right and in the y axis direction from top to bottom, as shown in FIGS. 53*b* and 53*c* and FIGS. 54*a* and 54*b*. For example, as shown in FIG. 53*b*, the CPU 40 computes the density gradient of each pixel in order from the left-hand side, on a straight area 531 along a shadow in the X axis direction. Assuming that the density of an original image, such as a CT image corresponding to the shadow 530 of FIG. 53*b* is f[y][x], a density gradient g[y][x] of each pixel is found by a difference between the previous and next pixels, as expressed by the following formula:

$$g[y][x]=f[y][x+1]-f[y][x-1].$$

When the computation of the density gradients in the straight area 531 is completed in this manner, the CPU 40 sequentially shifts this straight area in the y axis direction to compute density gradients. FIG. 53*b* diagrammatically shows the density gradients in the X axis direction in the case of each of the straight areas 531 and 532. FIG. 53*c* diagrammatically shows the density gradients in the Y axis direction in the case of each of the straight areas 533 and 534. The CPU 40 finds the positive and negative run length segments in each of the straight lines on the basis of these density gradients. For example, in the case of the straight area 531, the positive run length is "11" and the negative run length is "4". In the case of the straight area 532, the positive run length is "7" and the negative run length is "7". In the case of the straight area 533, the positive run length is "6" and the negative run length is "6". In the case of the straight area 532, the positive run length is "6" and the negative run length is "5". In this manner, the CPU 40 counts the positive and negative run lengths over the whole of the shadow 530. The CPU 40 similarly finds the density gradients of each straight area of the focus candidate shadow 540 as shown in FIGS. 54*a* and 54*b*, and counts positive and negative run lengths on the basis of the density gradients. In the case of a straight area 541 of FIG. 54*a*, the positive run lengths are "11" and "2" and the negative run lengths are "3" and "4". In the case of a straight area 542, the positive run lengths are "5" and "2" and the negative run lengths is "2" and "4". In the case of a straight area 543, as seen in FIG. 4*b*, the positive run lengths are "6", "1" and "1" and the negative run lengths are "3", "2" and "3". In the case of a straight area 544, the positive run lengths are "5", "2" and "2" and the negative run lengths are "2", "2" and "3". It can be seen from this fact that the focus candidate shadow has shorter length of each run length segment and greater number of run length segments.

FIG. 54*c* shows the relationship between the length and the number of run length segments which are calculated in the shadow 530*a* of FIG. 53 and the focus candidate shadow 540 of FIG. 54*a*. As is apparent from the curves shown in FIG. 54*c*, the case of the focus candidate shadow exhibits a tendency to have a peak in a number of run length segments where the lengths are comparatively small, while the case of the blood vessel cross-sectional shadow or the like exhibits a tendency to have a peak where the lengths are comparatively large. Accordingly, by utilizing these tendencies, the CPU 40 can efficiently exclude the blood vessel cross-sectional shadow, as shown in FIGS. 53*a* to 53*c*. Incidentally, in the description of this modification, reference has been made to the case where a density gradient is found from the difference between the previous and next pixels, but the density of a pixel may be compared with a predetermined threshold value to determine the density gradient of "+" or "−" according to the magnitude of the density. As this threshold value, the average value of densities in the entire range of a shadow may also be used. Incidentally, in the above-described embodiment, reference has been made to the case where density gradients in the X axis direction and the Y axis direction are calculated, but density gradients as to one arbitrary direction may be found, or density gradients may also be found as to a plurality of directions, such as the X axis direction, the Y axis direction and a direction crossing either of these directions at 45 degrees.

Figure 55:
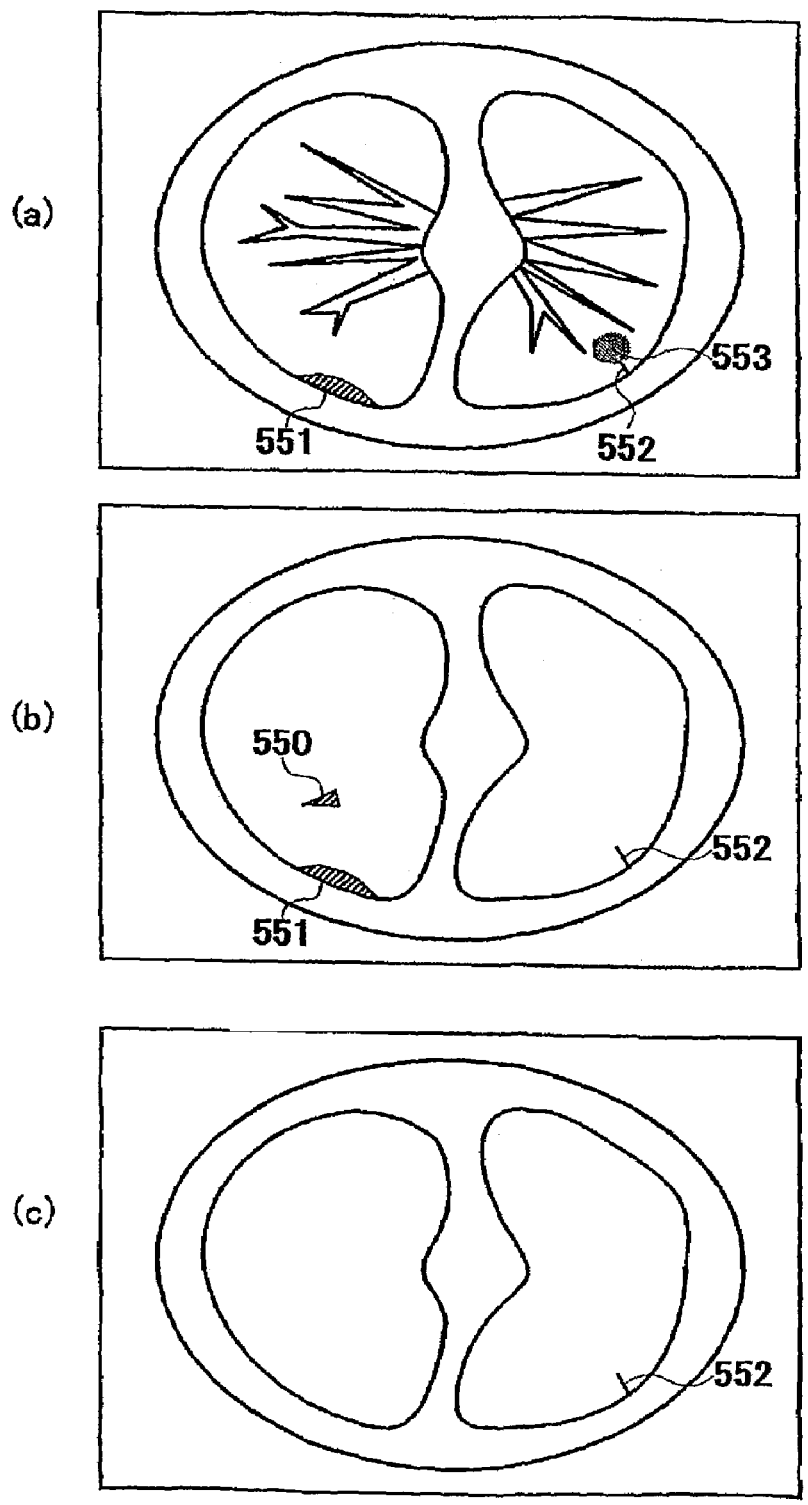
FIG. 55 is a diagram showing a specific example of the case of identifying a cancer-accompanying shadow which accompanies a cancer.
Figure 56:
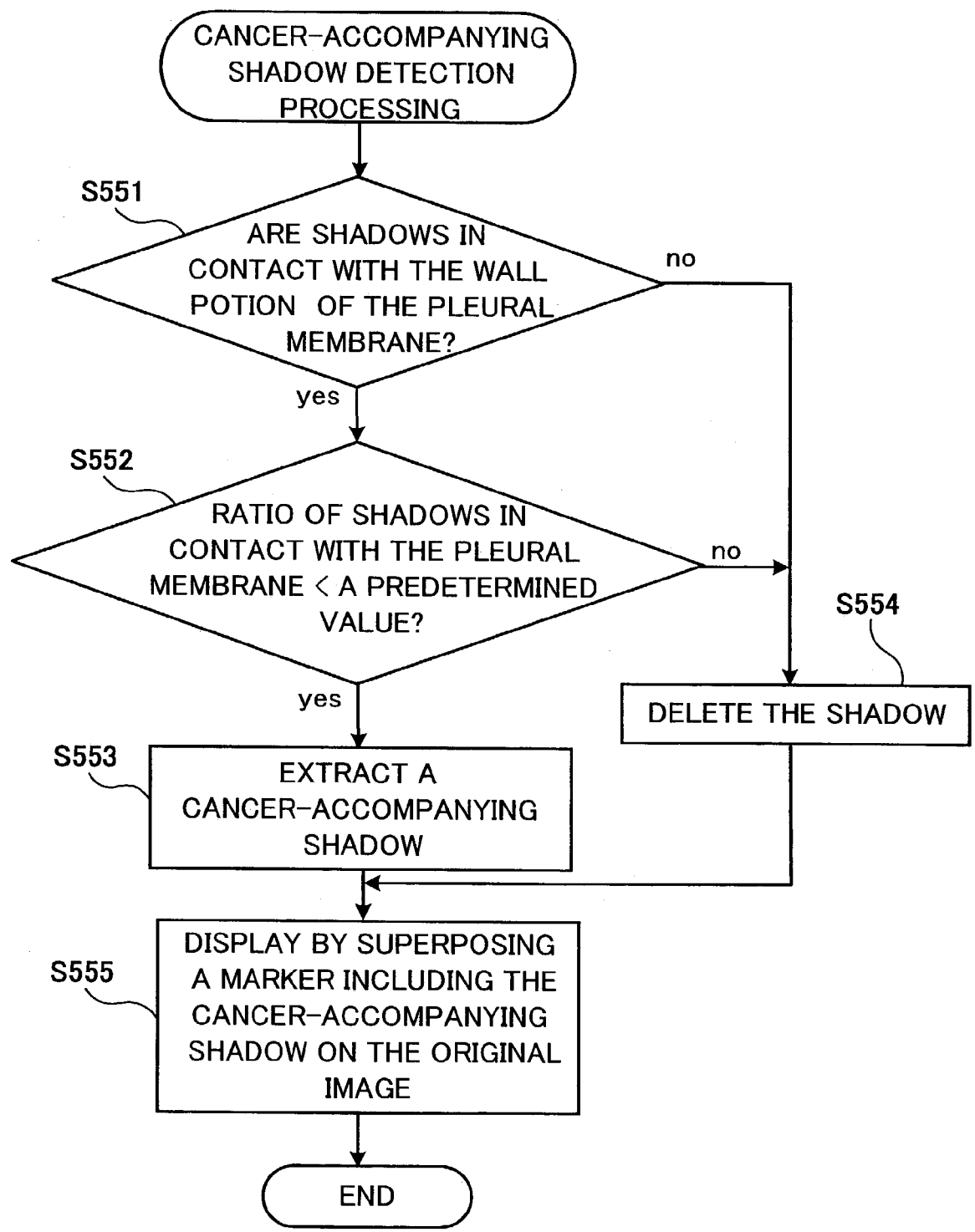
FIG. 56 is a flowchart showing details of cancer-accompanying object detection processing for detecting a cancer-accompanying shadow.

The above description has referred to the case where, in the decision making subroutines D1 to D3 of FIG. 25, a decision is made as to whether a shadow is located on a wall portion; and, further, in FIGS. 44*a* to 44*c*, a decision is made as to whether the shadow is a focus candidate shadow, on the basis of the length of contact between the shadow and the wall portion. However, there is a case where shadows 551 and 552, which are in contact with a wall portion, exist in a CT image, as shown at (a) in FIG. 55. Since the distance of the boundary where the shadow 551 is in contact with the inside of the wall portion is much larger than a predetermined value, it is determined that the shadow 551 is not a focus candidate shadow. However, the shadow 552 is not a shadow of a cancer or the like, but is a cancer-accompanying shadow which is concomitant with a cancer (invagination of a pleural membrane), and the cancer-accompanying shadow is characterized by an elongated shape perpendicular to the pleural membrane. Therefore, the possibility that this shadow 552 is excluded from focus candidate shadows is very high. However, it is known that an indistinct shadow like 553 in the vicinity of a cancer accompanying shadow, for instance, in contact with a tip of the shadow 552, as shown at (a) in FIG. 55, is a focus candidate. This cancer-accompanying shadow 553 cannot be easily extracted by the above-described processing. For this reason, in this embodiment, this cancer-accompanying shadow 552 is extracted, and the cancer-accompanying shadow 552 is displayed in such a manner as to be enclosed with a large marker (a circle or an ellipse), thereby indicating that a shadow acting like a focus exists near the cancer-accompanying shadow 552. In this embodiment, the cancer-accompanying shadow detection processing shown in FIG. 56 is executed to detect such a cancer-accompanying shadow.

[Step S551] First, since a shadow 550 and the shadows 551 and 552, all of which seem to be focus candidate shadows, are extracted in a multi-valued image, as shown at (b) in FIG. 55, the CPU 40 determines whether these shadows 550, 551 and 552 are in contact with the wall portion. If the CPU 40 determines that each of the shadows 550, 551 and 552 is in contact (yes), the CPU 40 proceeds to the next Step S552; whereas, if the CPU 40 determines that a shadow 550, 551 or 552 is not in contact (no), the CPU 40 proceeds to Step S554 and deletes the corresponding shadows. Since the shadow 550 is not in contact, the shadow 550 is excluded from focus candidates through the shadow deletion processing of Step S554.

[Step S552] Then, the CPU 40 determines the proportion in which each of the shadows is in contact with the wall portion of the pleural membrane, i.e., whether each of their contact lengths is smaller than a predetermined value. If the CPU 40 determines that each of the contact lengths is smaller (yes), the CPU 40 proceeds to the next Step S553; whereas, if the CPU 40 determines that part of the contact lengths is not smaller (no), the CPU 40 deletes the corresponding shadow. Since the length of contact of the shadow 551 with the wall portion is larger than the predetermined value, the shadow 551 is deleted through the shadow deletion processing of Step S554. Since the length of contact of the shadow 552 with the wall portion is much smaller than that of the shadow 551, the CPU 40 proceeds to the next Step S553.

[Step S553] The CPU 40 extracts a cancer-accompanying shadow from corresponding shadows. Namely, the shadow 442 of FIG. 44a and the shadow 552 of FIG. 55a corresponds to shadows, each of which is in contact with the wall portion in a proportion smaller than the predetermined value. Among such shadows, a cancer-accompanying shadow is a shadow which is too elongated to be determined as a focus candidate shadow. Therefore, the CPU 40 extracts as a cancer-accompanying shadow a shadow which is in contact with the wall portion in a proportion smaller than the predetermined value and is excluded from focus candidate shadows. Accordingly, as shown at (c) in FIG. 55, the shadow 552 is extracted as a cancer-accompanying shadow. On the other hand, the shadow 442 of FIG. 44a is extracted as a focus candidate shadow.

[Step S554] The CPU 40 determines the shadows which have been determined as "no" in Step S551 and Step S552.

Figure 57:
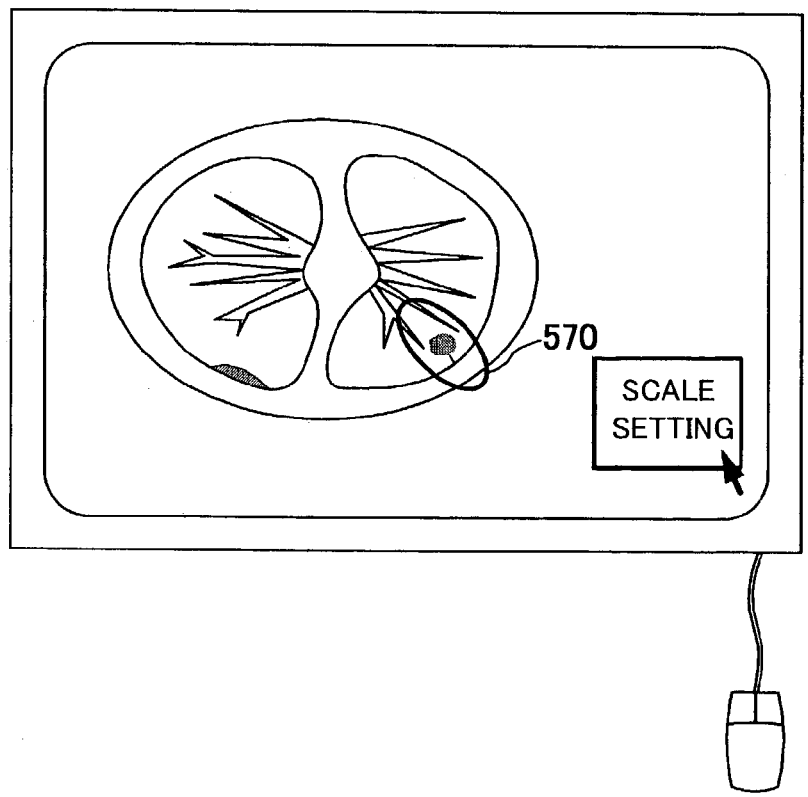
FIG. 57 is a diagram showing one example of a display picture in which the cancer-accompanying shadow detected by the cancer-accompanying object detection processing of FIG. 56 is displayed in the state of overlapping a marker.

[Step S555] The CPU 40 displays a large marker 570 (a circle or an ellipse) in such a manner as to superpose the marker 570 on the original image to enclose the cancer-accompanying shadow detected in Step S553, i.e., a object indicating a focus, as shown in FIG. 57. Incidentally, the size of this marker 570 can be arbitrarily changed by a scale setting button displayed at the bottom right. The doctor can perform an examination as to whether a focus shadow exists by visually inspecting the portion enclosed by this marker 570.

Figure 58A:
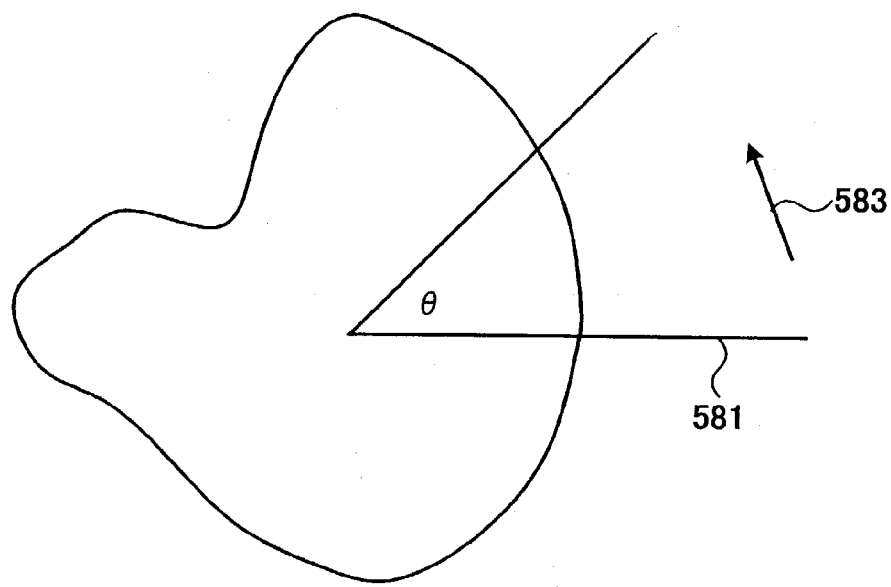
FIG. 58a is a diagram and FIGS. 58b and 58c are graphs showing a third modification of the decision making subroutine.

FIGS. 58a to, 60b are views showing a third modification of the decision making subroutine. The decision making subroutine of FIGS. 58a to 60b is performed in place of the decision making subroutine E1 of FIG. 27, the decision making subroutine F1 of FIG. 29 and each of the above-described decision making subroutines, or it is carried out in parallel with these decision making subroutines. First of all, the CPU 40 applies the binary image processing of FIGS. 5 and 6 to a CT image and finds a temporary weighted center position. The weighted center position may be found by using the above-described various methods. The CPU 40 rotates a radius 581 of predetermined length by increments of 5 degrees in the range of angle θ from 0 degrees to 360 degrees about the temporary weighted center position in the direction of an arrow 583. The increment of rotation may be any appropriate value other than 5 degrees. The CPU 40 finds a variance or standard deviation SDθ of CT values of a shadow located on the radius, while rotating the radius.

Figure 58B:
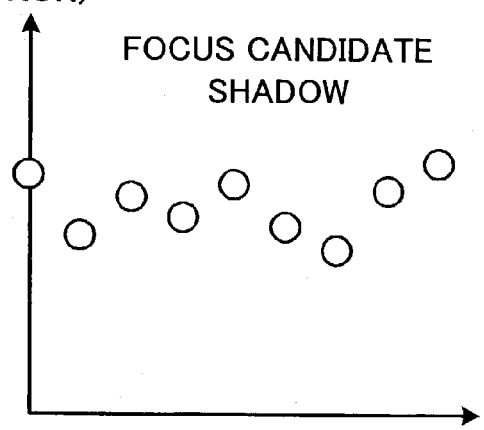
Figure 58C:
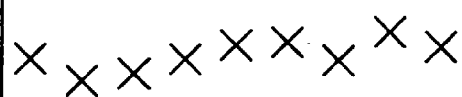

The result obtained in this manner is plotted in graphs as shown in FIGS. 58b and 58c. The variance or standard deviation SDθ of FIG. 58b is that of the focus candidate shadow 540 shown in FIG. 54a. The variance or standard deviation SDθ of FIG. 58c corresponds to the blood vessel cross-sectional shadow 530 shown in FIG. 53a. The focus candidate shadow 540 exhibits complicated contours having a plurality of peaks, as described previously. The variance or standard deviation SDθ assumes various complicated values for the respective angles, as shown in FIG. 58b, according to the complicated contours. On the other hand, the blood vessel cross-sectional shadow 530 exhibits simple contours having one peak. The variance or standard deviation SDθ also assumes simple values which do not greatly vary among the angles, as shown in FIG. 58c. Accordingly, the CPU 40 can determine whether the shadow is a focus candidate shadow or a blood vessel cross-sectional shadow, on the basis of the graphs of the variance or standard deviation SDθ, as shown in FIGS. 58b and 58c.

Figure 59A:
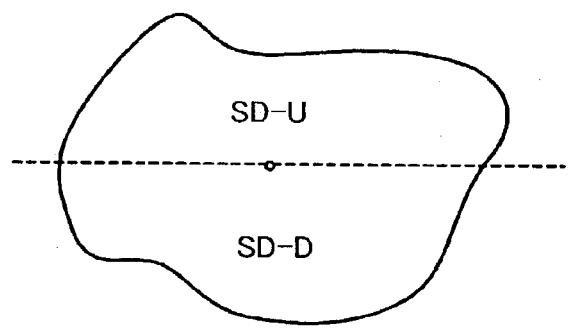
FIGS. 59a to 59c are diagrams showing a modification of the decision making subroutine of FIGS. 58a to 58c.
Figure 59B:
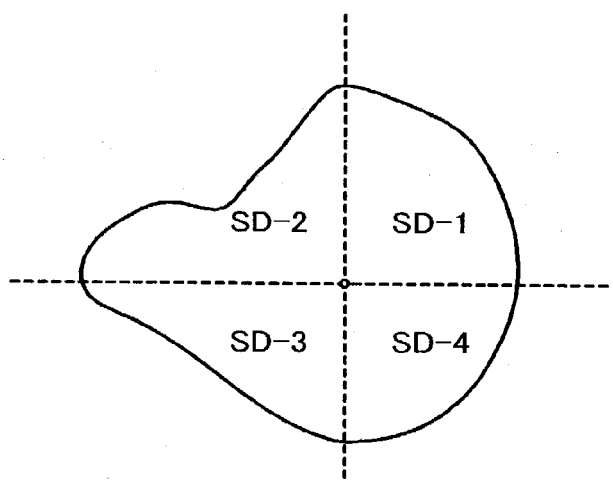
Figure 59C:
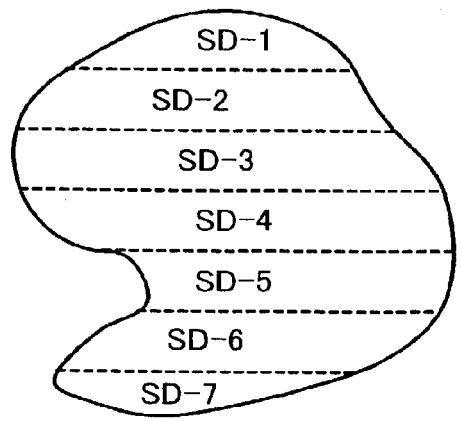

Incidentally, the CPU 40 may also find a secondary variance or standard deviation of the variance or standard deviation SDθ of FIGS. 58b and 58c to determine whether the shadow is a focus candidate shadow or blood vessel cross-sectional shadow, according to whether the secondary variance or standard deviation is larger or smaller than a predetermined value. In addition, as shown in FIGS. 59a to 59c, the CPU 40 may divide each shadow into areas to find a variance or standard deviation as to each of the divided areas. In the case of FIG. 59a, the CPU 40 divides a shadow into upper and lower shadows along a horizontal line passing through the middle of the shadow, and finds a variance or standard deviation SD-U of CT values of the upper shadow and finds a variance or standard deviation SD-D of CT values of the lower shadow; and, further, it finds the secondary variance or standard deviation of both as a key feature to be used for making a decision as to the shadow. Incidentally, the CPU 40 may also use as a key determining feature the difference between the variances or standard deviations SD-U and SD-D of the upper and lower shadows or the absolute value of the difference. In the case of FIG. 59b, the CPU 40 divides a shadow into four quadrants along horizontal and vertical lines passing through the shadow, and finds variance or standard deviations SD-1 to SD-4 of CT values of each of the quadrants as a feature quantity to be used for making a decision as to the shadow. In the case of FIG. 59c, the CPU 40 divides a shadow into areas arranged at equal intervals in the vertical direction, and finds variance or standard deviations SD-1 to SD-7 of CT values of each of the divided areas; and, further, it finds a secondary variance or standard deviation of these variance or standard deviations SD-1 to SD-7 as a key feature quantity to be used for making a decision as to the shadow. Incidentally, the CPU 40 may divide the shadow into areas arranged at equal intervals in the horizontal direction.

Figure 60A:
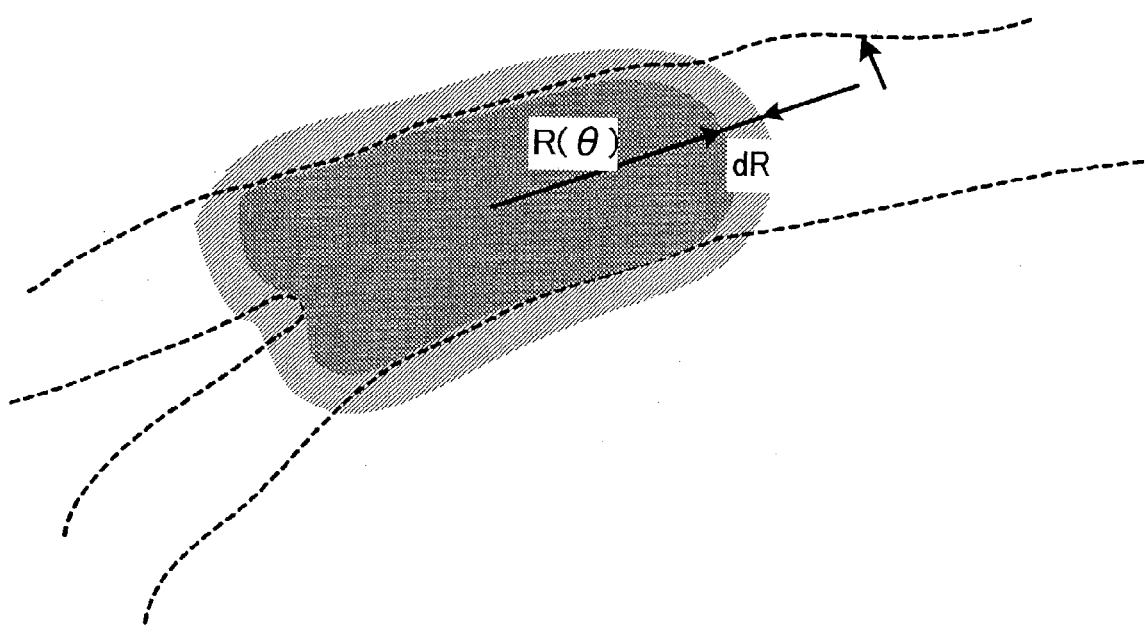
FIGS. 60a and 60b are diagrams showing another modification of the decision making subroutine of FIGS. 58a to 58c.
Figure 60B:
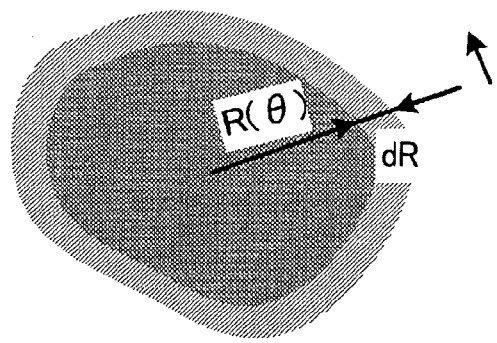

FIGS. 58a to 58c and 59a to 59c show the case where the CPU 40 uses variance or standard deviation of the shadow to make a decision as to whether a shadow is a focus candidate shadow or a blood vessel cross-sectional shadow. As shown in FIGS. 60a and 60b, the CPU 40 may also make a decision as to a shadow by using a variance or standard deviation of the shadow and a variance or standard deviation of a predetermined area along the periphery of the shadow. Namely, in the case where the periphery of a shadow is defined by a moving radius circle R(θ), as shown in FIGS. 60a and 60b, the difference from a variance or standard deviation in the area R(θ) to R(θ)+dR outward by a predetermined distance dR from this moving radius circle R(θ) is found as a feature quantity, whereby it is possible to discriminate between the blood vessel cross-sectional shadow shown in FIG. 60a and the focus candidate shadow shown in FIG. 60b. In the case of the blood vessel cross-sectional shadow shown in FIG. 60a, since the area R(θ) to R(θ)+dR traverses the blood vessel cross-sectional shadow, the variance or standard deviation assumes a comparatively large value. In the case of the focus candidate shadow shown in FIG. 60a, since a substantial part of the area R(θ) to R(θ)+dR traverses a portion where the shadow does not exist, the variance or standard deviation assumes a comparatively small value. Accordingly, the CPU 40 finds the difference between a variance or standard deviation inside of the shadow and the variance or standard deviation in the area R(θ) to R(θ)+dR as a key feature quantity to be used for discriminating between the focus candidate and blood vessel shadow. In addition, the CPU 40 may also set threshold values, respectively, for this key feature and for the variance or standard deviation of the area R(θ) to R(θ)+dR, respectively, to make such a decision. Furthermore, this feature quantity or the variance or standard deviation of the area R(θ) to R(θ)+dR may be used as an input value for Mahalanobis distance, Euclidean distance, neural networks and the like, and the CPU 40 may make such a decision by using the obtained result.

In the above-described embodiment, as a display method for the case where a CT image having an extracted focus candidate shadow and a marker are displayed for the operator (doctor), reference has been made to a method of displaying, at the same time, a detection result image in which a focus candidate shadow is indicated by a marker, as shown in FIG. 38 and a magnified image which shows the marker portion on an magnified scale, as well as a method of providing display in various modes as shown in FIGS. 39 to 43. In these methods, in the case where the operator (doctor) arbitrarily selects a portion desired to be displayed, with a mouse cursor or the like, the CPU 40 may also display focus candidate shadows in the order of their locations relative to the selected portion, from closest to farthest. Details of this focus candidate shadow display processing will be described below with reference to FIGS. 61*a*, 61*b* and 62.

[Step S621] The CPU 40 sequentially displays combined images, each made up of a marker and a tomographic image as shown in FIG. 39, 41 or 42, in accordance with a display mode selected by the standard mode selecting button on the standard picture of FIG. 38.

Figure 61A:
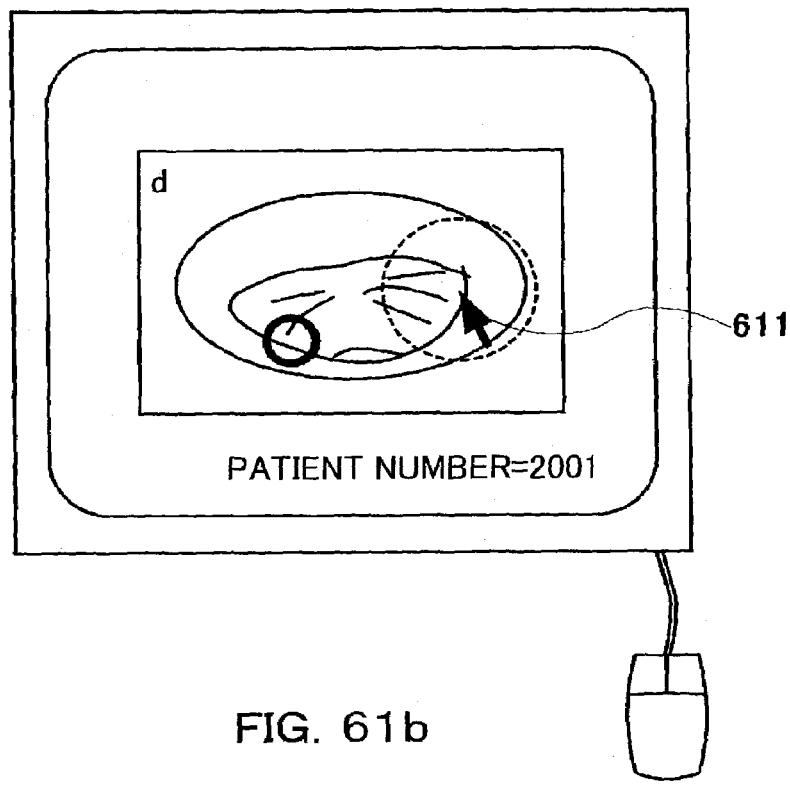
FIGS. 61a and 61b are diagrams showing another embodiment of a focus candidate shadow display in which an arbitrary shadow is displayed with a mouse pointer during the display of a focus candidate shadow.
Figure 62:
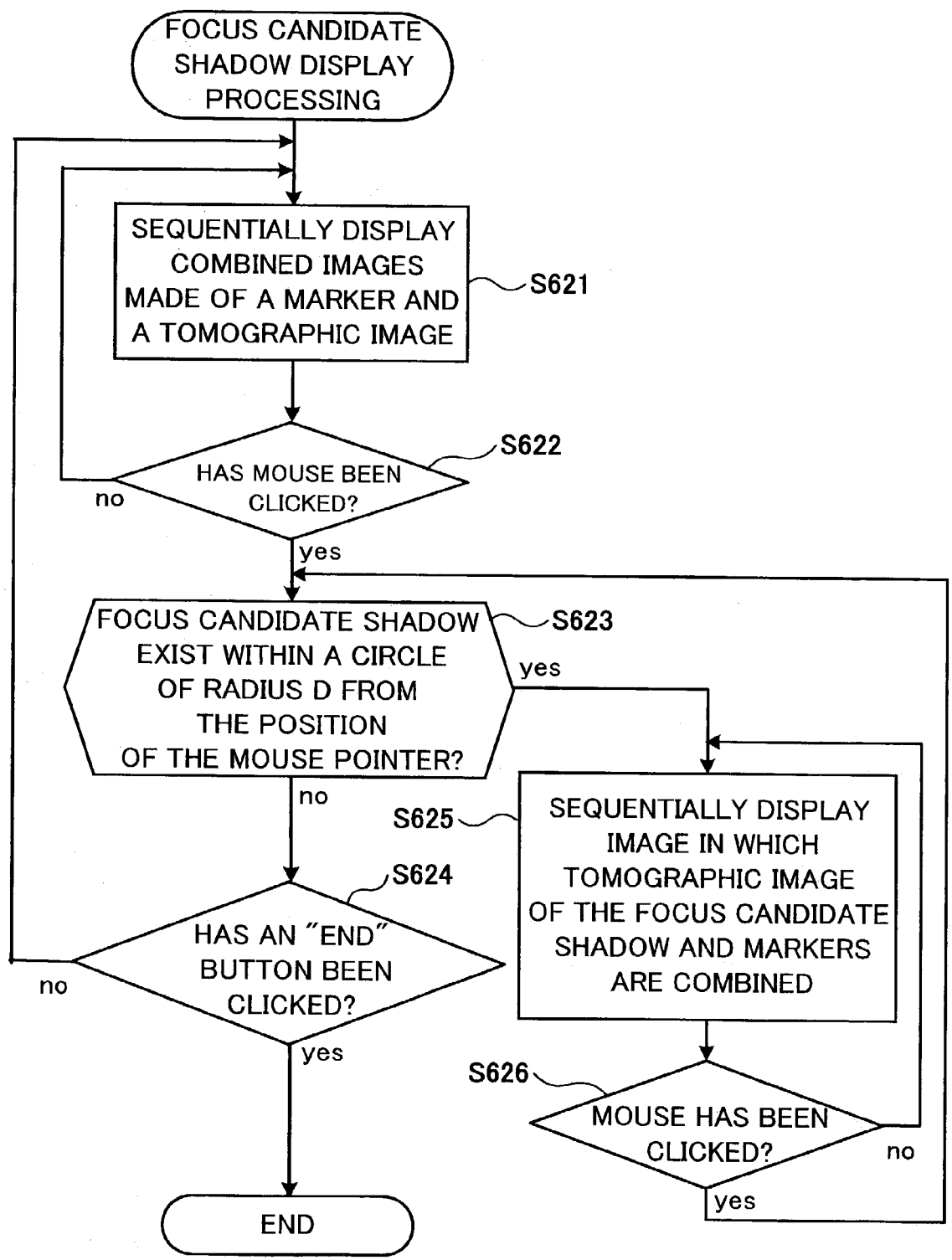
FIG. 62 is a flowchart showing details of the focus candidate shadow display processing of FIGS. 61a and 61b.

[Step S622] The CPU 40 determines whether a mouse has been clicked at an arbitrary position on a combined image being displayed. If the decision result is yes, the CPU 40 proceeds to the next Step S623, whereas if the decision result is no, the CPU 40 returns to Step S621. In Step S621, the display of a combined image according to the display mode is continued. Namely, this means that when a mouse pointer 611 lies at a predetermined position on the combined image as shown in FIG. 61*a*, a decision is made as to whether the button of the mouse has been clicked.

[Step S623] Since it has been determined in Step S622 that the mouse has been clicked, the CPU 40 determines whether a focus candidate shadow exists within a circle of radius D from the position of the mouse pointer. Namely, in the case of FIG. 61*a*, a decision is made as to whether a focus candidate shadow exists within a dashed-line circle of radius D centered at the mouse pointer 611.

[Step S624] Since it has been determined in the decision of Step S623 that a focus candidate shadow does not exist within the circle of radius D centered at the mouse pointer, the CPU 40 displays "No Focus Candidate Shadow Exists". Since a "CONTINUE" button for determining whether the current display is to be continued without modification and an "END" button for bringing display to an end are included in the display, the CPU 40 determines whether this "END" button has been manipulated with a click. If the decision result is yes (the "END" button has been clicked), the CPU 40 brings the processing to an end, whereas if the decision result is no (the "CONTINUE" button has been clicked), the CPU 40 returns to Step S621.

Figure 61B:
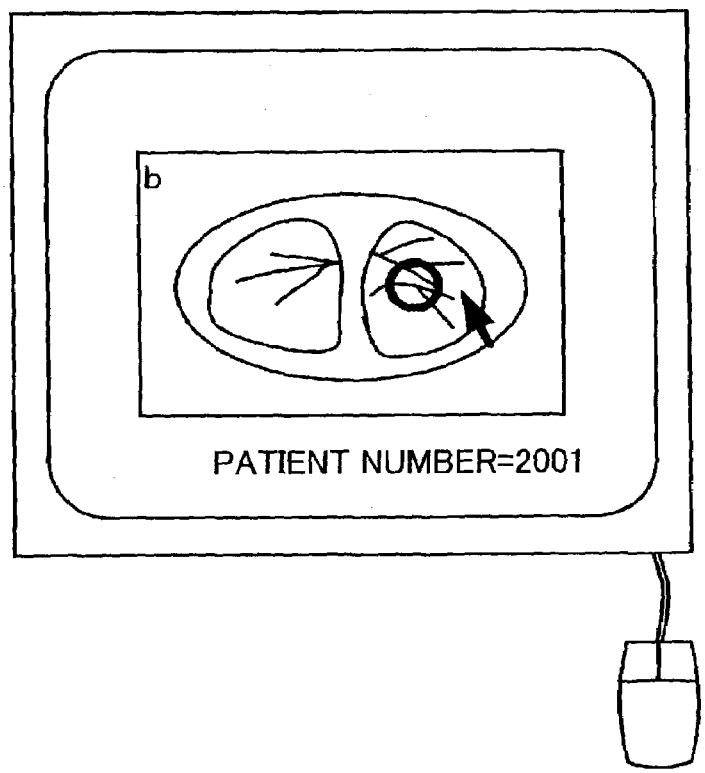

[Step S625] Since it has been determined in the decision of Step S623 that a focus candidate shadow exists within the circle of radius D centered at the mouse pointer, the CPU 40 sequentially displays images in which tomographic images of the focus candidate shadow and markers are combined. In the case of FIG. 61*a*, the focus candidate shadows of the image a and the image c corresponds to the shadow which exists within the dashed-line circle of radius D. The focus candidate shadows of the images b and the images c of FIGS. 41 and 42 correspond to the shadow which exists within the dashed-line circle of radius D. Accordingly, as shown in FIG. 61*b*, the images of the existing focus candidate shadows are sequentially displayed in the circle of radius D. In FIG. 61*b*, the images b of FIGS. 41 and 42 are displayed. Although not shown, a "NEXT button" is displayed, and when it is clicked, the next image c is displayed. There is also a special case where the radius D is set to be larger than such an image, and when a mouse is clicked with no marker being displayed, all corresponding markers are displayed in response to the click.

[Step S626] The CPU 40 determines whether the mouse has been clicked at an arbitrary position on the combined image being displayed. If the decision result is yes (if the mouse is clicked), the CPU 40 returns to the previous Step S623; whereas, if the decision result is no, the CPU 40 returns to Step S625. In Step S625, the display of the focus candidate shadow is continued. When another position is clicked by the mouse pointer, similar processing is performed in this step according to whether a focus candidate shadow exists within a circle of radius D centered at the mouse pointer. In the case where the same position is clicked, similar to the case where the aforementioned "NEXT button" is clicked, the next image c is displayed. To provide such a display, information on x coordinates and y coordinates indicating where extracted focus candidate shadows are located on the image is stored on a predetermined memory space.

Figure 63A:
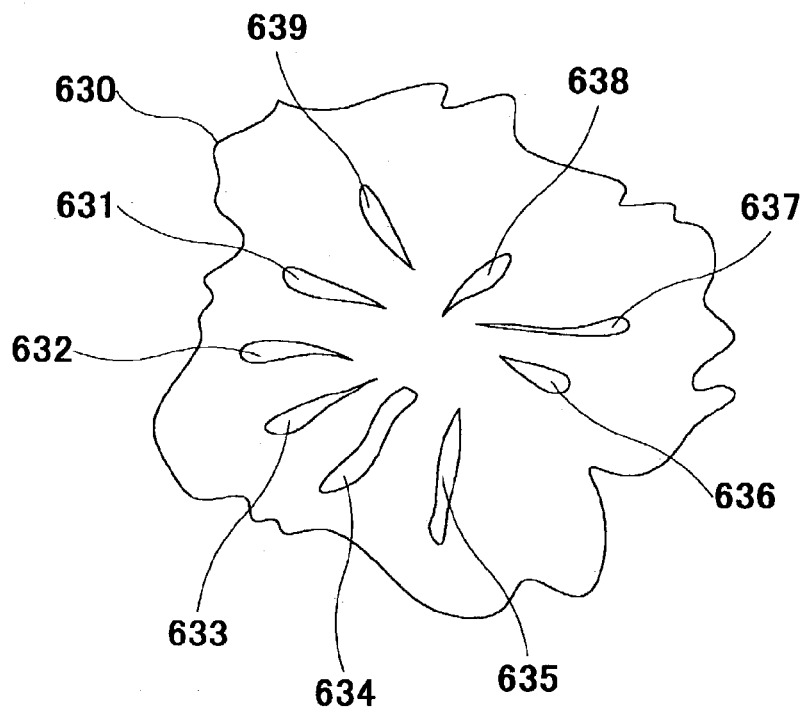
FIGS. 63a and 63b are diagrams showing a fourth modification of the decision making subroutine.

FIG. 63*a*, 63*b* and FIG. 64*a*, 64*b* are views showing a fourth modification of the decision making subroutine. Each of the decision making subroutines of FIG. 63*a*, 63*b* and FIG. 64*a*, 64*b* is performed in place of the decision making subroutine E1 of FIG. 27, the decision making subroutine F1 of FIG. 29 and each of the above-described decision making subroutines, or it is performed in parallel with these decision making subroutines. FIG. 63*a* is a view showing a part of a CT image of the case where a plurality of needle- or line-shaped shadows 631 to 639, called spicules, appear in the periphery of a malignant cancer shadow 630.

Figure 63B:
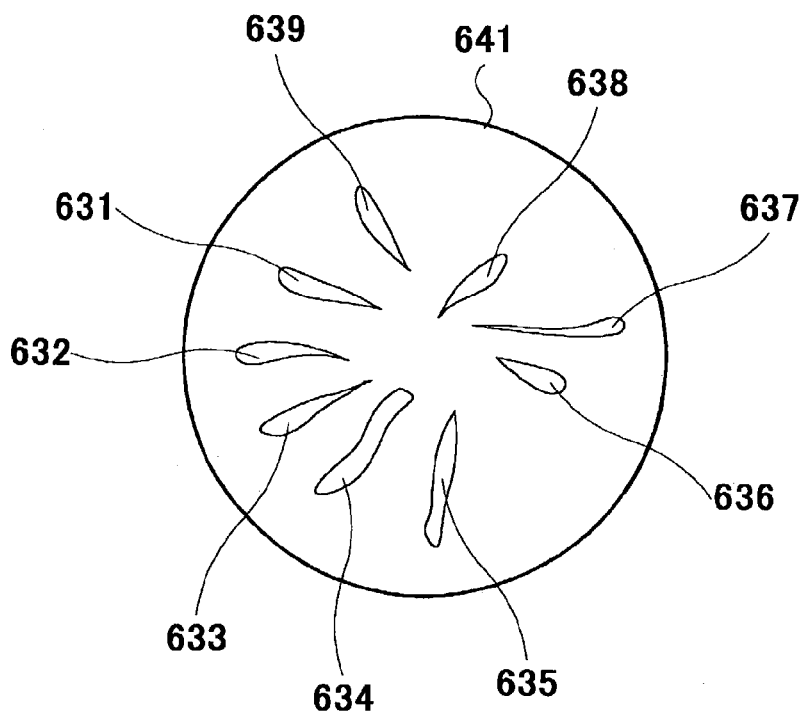

The cancer shadow 630 is a shadow of comparatively low density, and it is difficult to identify. In contrast, the shadows 631 to 639 are shadows of high density and are easy to identify, but they have the disadvantage that they are easily mistaken for shadows of blood vessels. When the binary image processing of FIGS. 5 and 6 is applied to the CT image including the spicules as shown in FIG. 63*a*, the cancer shadow 630 of low density is not extracted and only the needle- or line-shaped shadows 631 to 639 are extracted, as shown in FIG. 63*b*. There is a case where these spicula shadows 631 to 639 are mistaken for the shadow of a blood vessel portion and are excluded. Therefore, it is necessary to determine whether the shadows 631 to 639 shown in FIG. 63*b* are spicula shadows. For this reason, in this embodiment, the CPU 40 discriminates between such spicula shadows and blood vessel shadows; and, in the case of the spicula shadows, the CPU 40 finds the weighted center position of the shadows and displays the weighted center position with a marker.

Figure 64A:
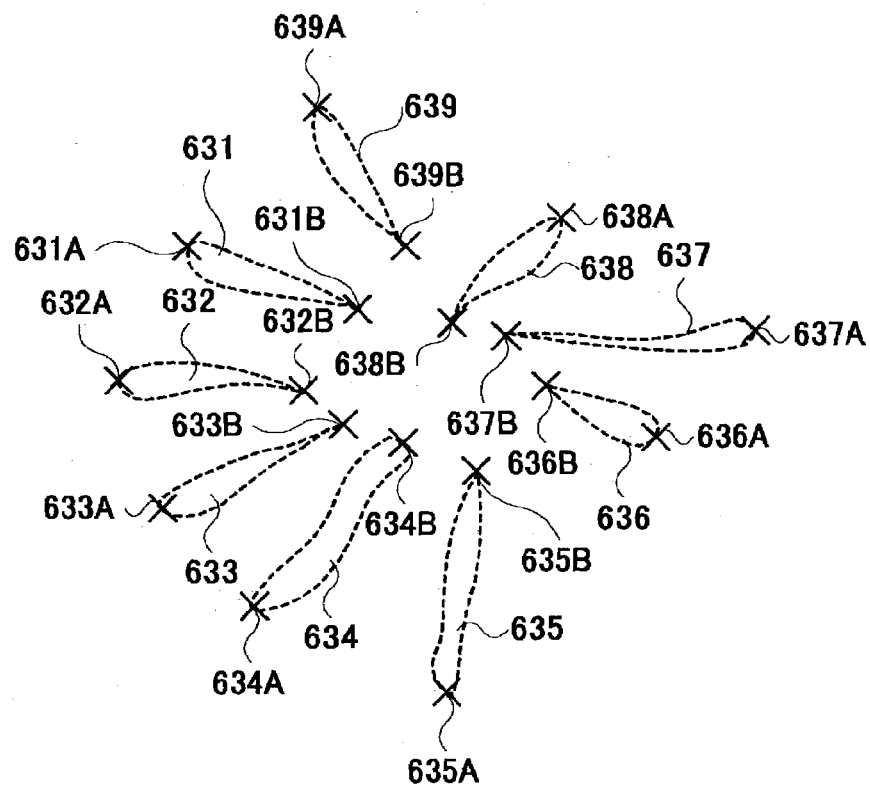
FIGS. 64a and 64b are diagrams showing a specific manner in which needle- or line-shaped shadows called spicules are identified.

First, the CPU 40 applies the binary image processing of FIGS. 5 and 6 to the CT image and finds a temporary weighted center position of the shadows. The weighted center position may be found by using the above-described various methods. The CPU 40 rotates a straight line about the temporary weighted center position and finds a straight line whose portion crossing each the shadows is the longest, i.e., the long length of each of the shadows, and finds the positions (two points) at which this long length line crosses the edge of its shadow. FIG. 64*a* is a view showing the state where the long diameter of each of the shadows 631 to 639 is found and the intersections of the long diameter and each of the shadows are found. As is apparent from FIG. 64*a*, two intersections are found on each of the shadows 631 to 639. Intersections 631A and 631B exist on the shadow 631, and intersections 632A and 632B exist on the shadow 632. Similarly, intersections 633A to 639A and 633B to 639B exist on the respective shadows 633 to 639.

Figure 64B:
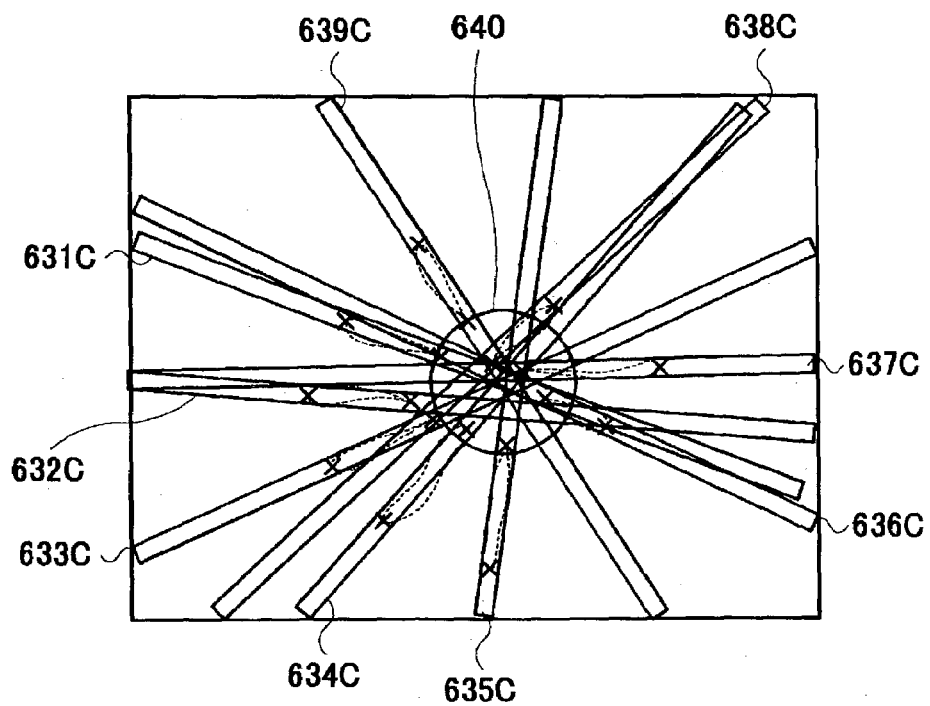

The CPU 40 arranges the thus-obtained intersections 631A to 639A and 631B to 639B on a pixel memory space, as shown in FIG. 64*b*, and assigns straight strips 631*c* to 639*c* of predetermined width, which respectively connect the intersections 631A and 639A to the intersections 631B to 639B, on the pixel memory space cleared to zero. The CPU 40 adds "1" to pixels which correspond to these straight strips 631*c* to 639*c*, for each of the straight strips 631*c* to 639*c*. Namely, the CPU 40 adds "1" to a pixel memory corresponding to an area through which the strip-shaped straight line 631*c* passes, and adds "1" to a pixel memory corresponding to an area through which the straight strip 632*c* passes. Similarly, the CPU 40 adds "1" to a pixel memory corresponding to each of the areas through which the respective straight strips 633*c* to 639*c* pass. In this manner, the values of the respective pixel memories at locations corresponding the areas through which the respective straight strips 631*c* to 639*c* pass are increased.

In the case of FIG. 64*b*, the straight strips 631*c* to 639*c* concentrically pass through a portion enclosed by a circle 640, so that the value of the pixel memory of this portion becomes large. Thus, the CPU 40 extracts a portion in which the value of its pixel memory is, for example, 4 or more, and defines the portion as the weighted center position of the spicula shadows. Incidentally, if portions, in each of which the value of its pixel memory is 4 or more, are close to each other, the portion having the higher value is defined as the weighted center position. When this weighted center position is found, the CPU 40 displays a marker 641 centered about the weighted center position, as shown in FIG. 63*b*. In this manner, a malignant cancer shadow having spicula shadows easily mistaken for blood vessel shadows can be displayed as a focus candidate shadow.

Figure 65:
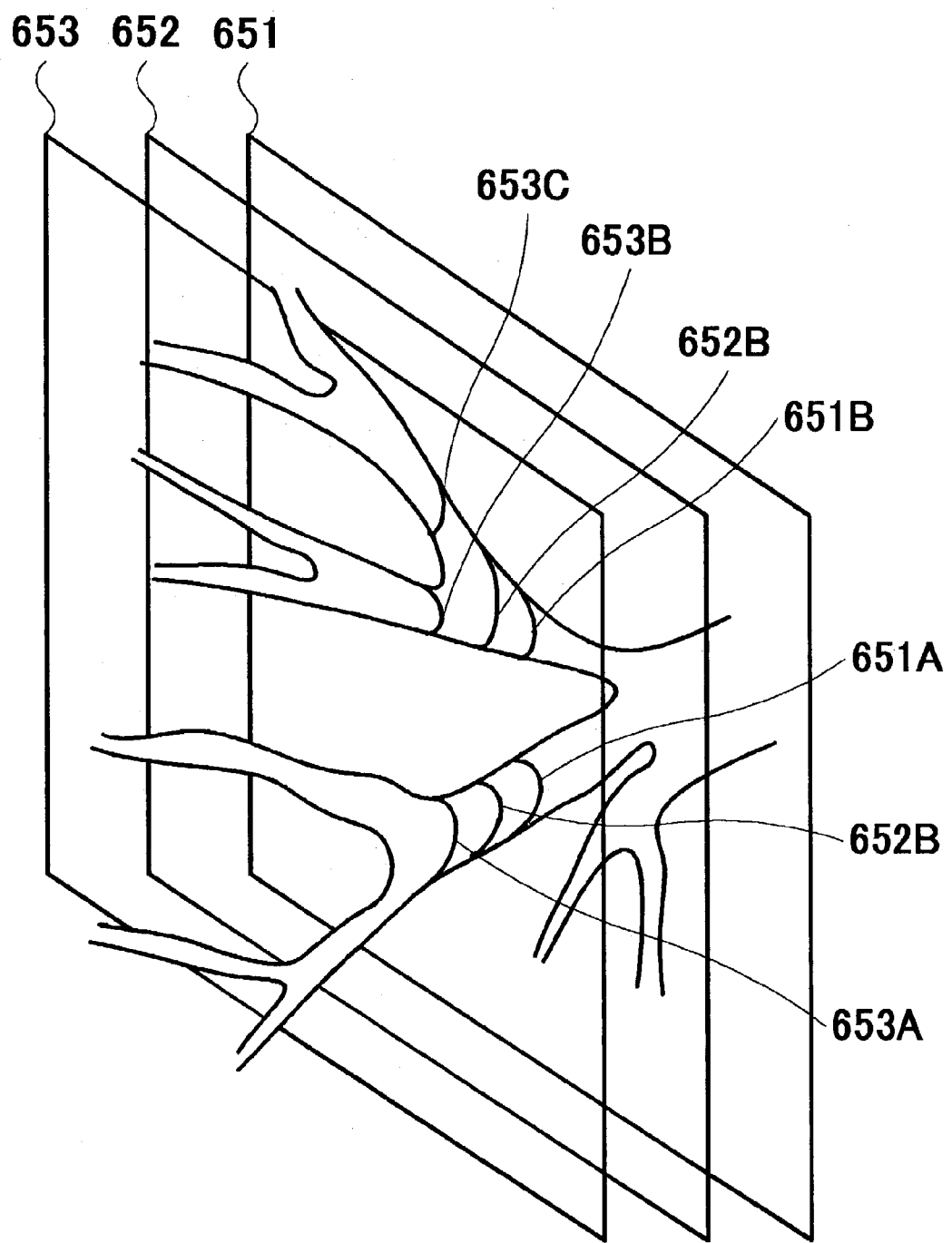
FIG. 65 is a conceptual diagram of a processing method, showing a modification of each of the decision making subroutines of FIGS. 27 and 29.

FIGS. 65 and 66*a* to 66*f* are views showing a modification of each of the decision making subroutine E1 of FIG. 27 and the decision making subroutine F1 of FIG. 29, and they show a processing method for extracting and excluding a blood vessel cross-sectional shadow. The processing of FIGS. 65 and 66*a* to 66*f* may be executed in parallel with the decision making subroutine E1 of FIG. 27 or the decision making subroutine F1 of FIG. 29. Normally, there is a case in which a CT image of a lung portion (lung region) captures part of the blood vessels which extend so as to spread radially. Accordingly, in this embodiment, recognizing that some blood vessels extend radially, the CPU 40 extracts and excludes such blood vessel cross-sectional shadows. Namely, in this embodiment, in the case where blood vessels extend radially as shown in FIG. 65, the CPU 40 compares mutually adjacent tomographic images of predetermined slice thickness to determine whether the tomographic images are blood vessel cross-sectional shadows.

Figure 66A:
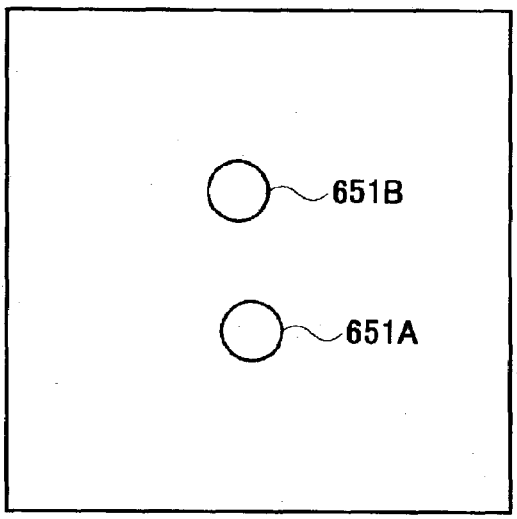
FIGS. 66a to 66f are diagrams showing a specific example of the processing method of FIG. 65.

As to the blood vessels which extend radially, as shown in FIG. 65, tomographic images respectively corresponding to planes 651 to 653 are photographed, as shown in FIG. 65. As to the plane 651, blood vessel cross-sectional shadows 651A and 651B are photographed as tomographic images, as shown in FIG. 66*a*. As to the plane 652, blood vessel cross-sectional shadows 652A and 652B are photographed as tomographic images, as shown in FIG. 66*b*. As to the plane 653, blood vessel cross-sectional shadows 653A, 653B and 653C are photographed as tomographic images, as shown in FIG. 66*c*. In the tomographic images of the radially extending blood vessels, the blood vessel cross-sectional shadows sequentially change in position and size. Accordingly, the CPU 40 superposes mutually adjacent tomographic images, and determines whether the shadows are blood vessel cross-sectional shadows, on the basis of the manner of the changes in the positions and the sizes of the shadows.

Figure 66D:
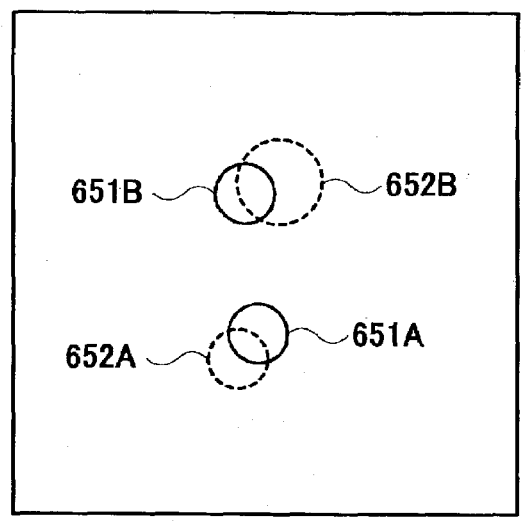
Figure 66B:
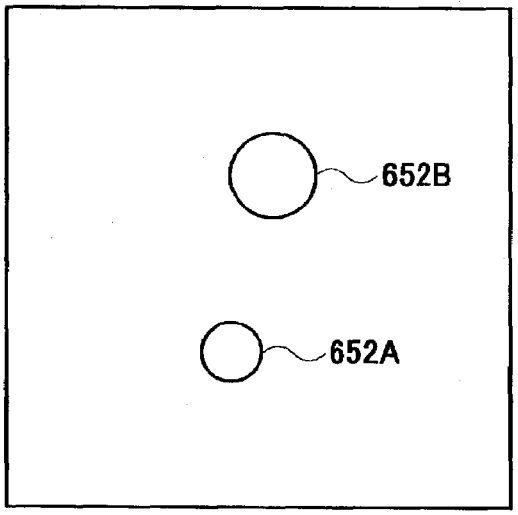
Figure 66E:
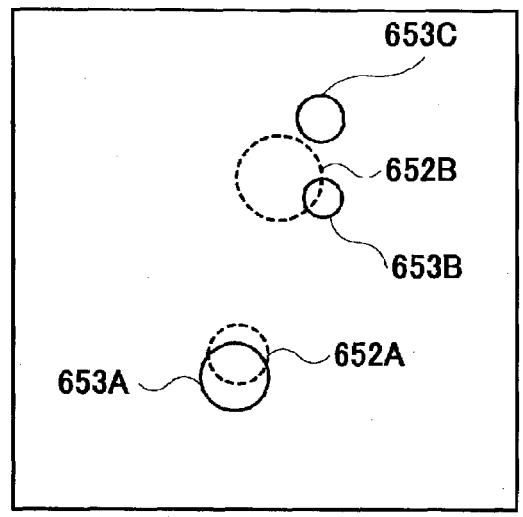
Figure 66C:
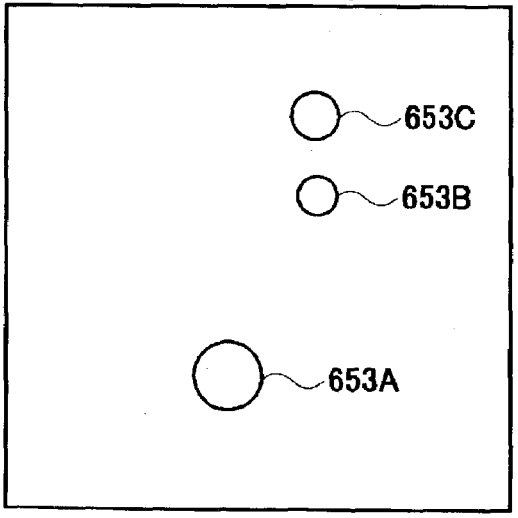
Figure 66F:
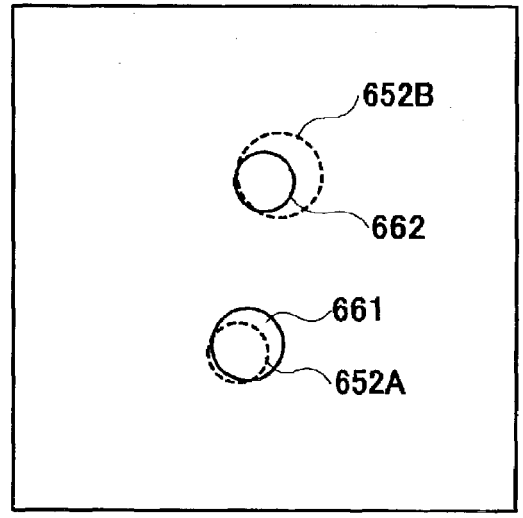

FIG. 66*d* shows tomographic images corresponding to the plane 651 and the plane 652, which are adjacent to each other, i.e., a superposition of FIG. 66*a* and FIG. 66*b*. FIG. 66*e* shows tomographic images corresponding to the plane 652 and the plane 653 which are adjacent to each other, i.e., a superposition of FIG. 66*b* and FIG. 66*c*. For ease of illustration, the blood vessel cross-sectional shadows 652A and 652B of FIG. 66*b* are represented by dashed lines in FIGS. 66*d* and 66*e*. As shown in FIG. 66*a*, the blood vessel cross-sectional shadow 651A and the blood vessel cross-sectional shadow 652A are partly superposed on each other. In addition, the blood vessel cross-sectional shadow 651B and the blood vessel cross-sectional shadow 652B are partly superposed on each other. In the case where the shadows of both tomographic images are partly superposed, both are deleted as blood vessel cross-sectional shadows indicative of part of the radially extending blood vessels. In the case of the blood vessel cross-sectional shadow 652A and the blood vessel cross-sectional shadow 653A of FIG. 66*e*, since they are partly superposed, both shadows are deleted as blood vessel cross-sectional shadows. In the case of the blood vessel cross-sectional shadow 652B and the blood vessel cross-sectional shadows 653B and 653C of FIG. 66*e*, the blood vessel cross-sectional shadows 653B and 653C branch off from the blood vessel cross-sectional shadow 652B, and the blood vessel cross-sectional shadow 653B is partly superposed on the blood vessel cross-sectional shadow 652B, but the blood vessel cross-sectional shadow 653C is not partly superposed on the blood vessel cross-sectional shadow 652B. Accordingly, in this case, the blood vessel cross-sectional shadow 652B and the blood vessel cross-sectional shadow 653B become objects to be deleted as blood vessel cross-sectional shadows, but the blood vessel cross-sectional shadow 653C does not become an object to be deleted. Incidentally, in the case where the respective blood vessel cross-sectional shadows 652A and 652B are superposed on shadows 661 and 662 in proportions more than a predetermined proportion, as shown in FIG. 66*f*, all of these shadows are not detected as focus candidate shadows, and become objects for another decision. Incidentally, these proportions are calculated for the respective shadows, and the area of superposition is divided by the area of each of the superposed shadows, and the larger value is adopted. Namely, in the case of the blood vessel cross-sectional shadow 652A and the shadow 661, the proportion found when the area of their superposition is divided by the area of the blood vessel cross-sectional shadow 652 and the proportion found when the area of the superposition is divided by the area of the shadow 661 differ from each other, and the result of division by the shadow 661 of smaller area is adopted. Incidentally, the proportion of the superposition can be arbitrarily set as a parameter.

Incidentally, in X-ray CT devices and the like, there is a case where data of projection on an area in all directions cannot be obtained and a tomographic image must be reconstructed. This case is called a partial volume effect. Even in a decision as to whether a shadow due to this partial volume effect is mistakenly detected, it is effective to find a correlation of mutually adjacent images. In the case of the partial volume effect, since a shadow of high density is imaged in adjacent areas, the proportion of pixels which assumes a larger value than a preset particular CT value in the previously detected area and the corresponding area (the same position) of its adjacent image can be used for the decision.

Figure 67A:
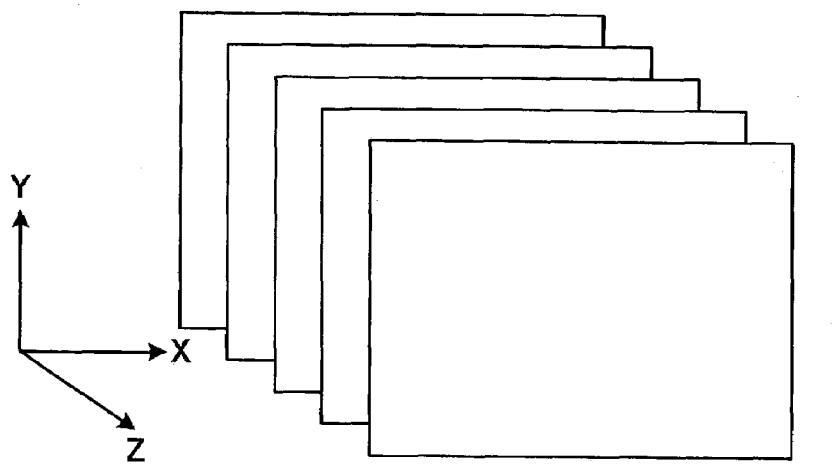
FIGS. 67a to 67d are conceptual diagrams showing a fifth modification of the decision making subroutine.
Figure 67B:
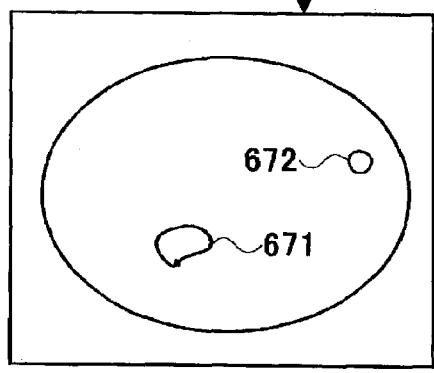
Figure 67D:
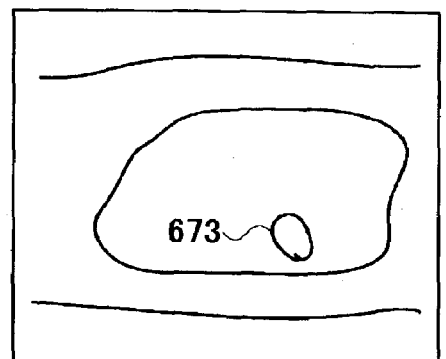
Figure 67C:
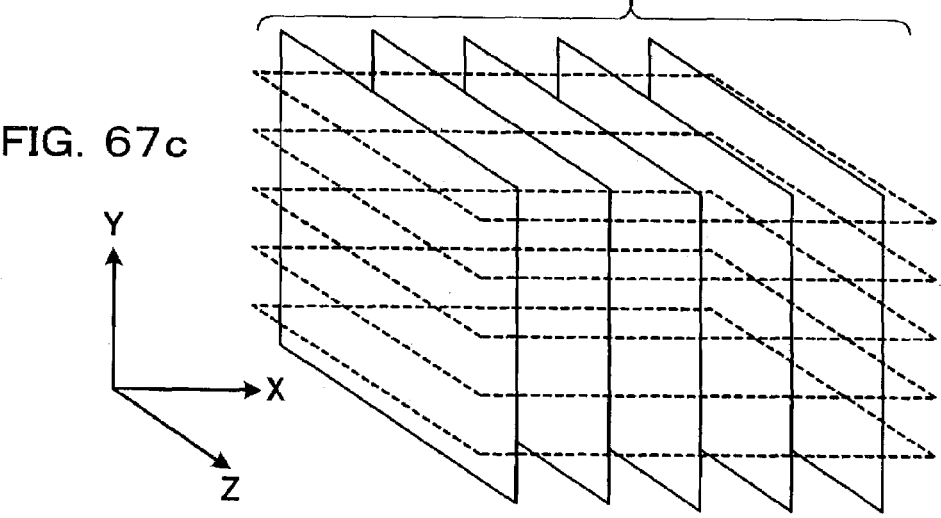

FIGS. 67a to 67d and 68 are views showing a fifth modification of the decision making subroutine. The decision making subroutine of FIGS. 67a to 67d and 68 uses three sets of medical images (axial images, sagittal images and coronal images) which are mutually perpendicular, and detection is made as to an abnormal shadow in each of the three sets of medical images; and, if there is a correlation between positions where detected shadows exist, the shadows are displayed or recorded as focus candidate shadows. FIG. 67a shows the concept of coaxial planes corresponding to coaxial images. FIG. 67b shows one example of a coaxial image corresponding to the coaxial planes shown in FIG. 67a. FIG. 67c shows sagittal planes corresponding to sagittal images as well as coronal planes. In FIG. 67c, the sagittal planes are shown by solid lines, and the coronal planes are shown by dashed lines. FIG. 67d shows one example of a sagittal image corresponding to the sagittal plane shown in FIG. 67c. Incidentally, a coronal image corresponding to the coronal planes is omitted.

Figure 68:
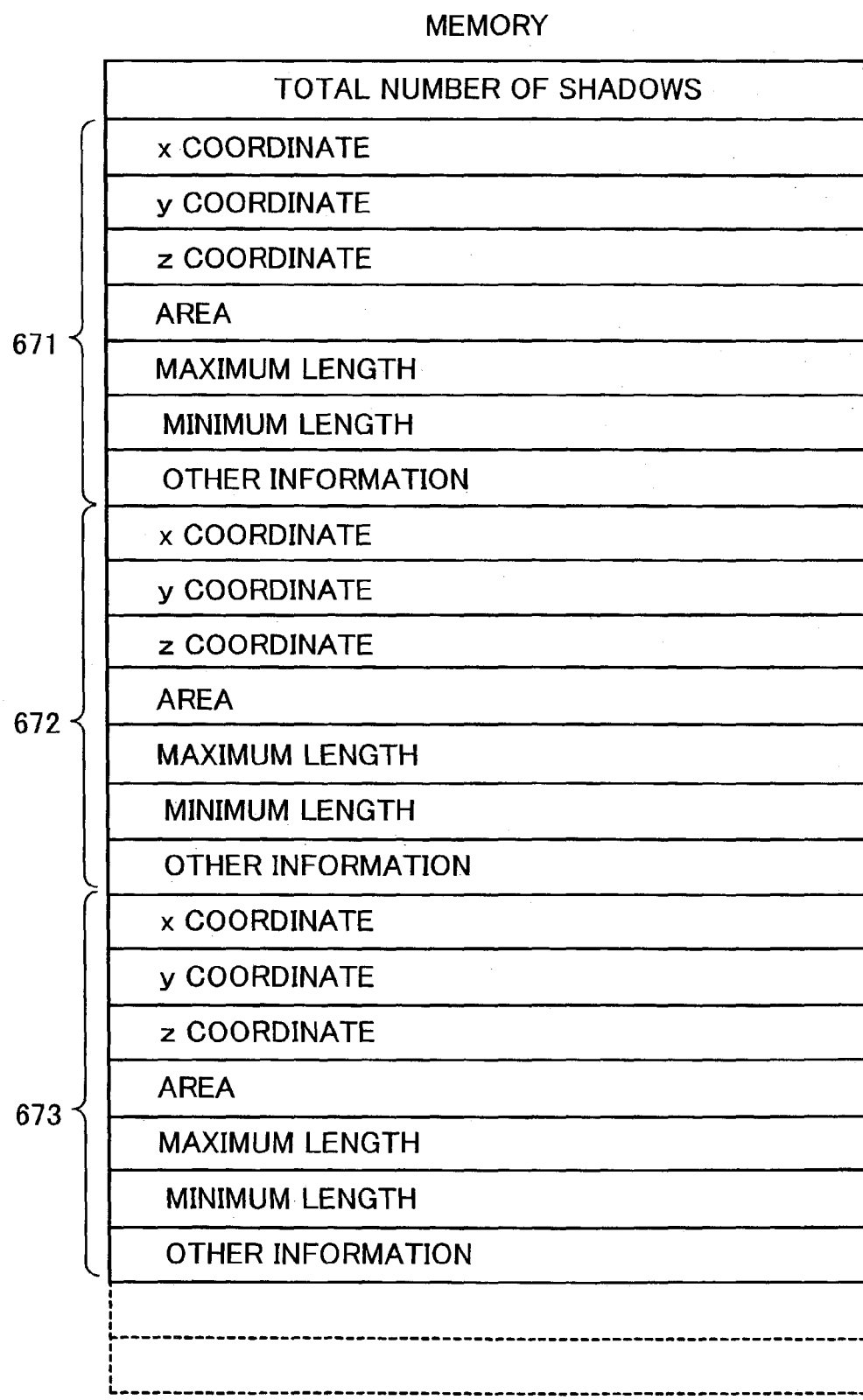
FIG. 68 is a table showing the contents of a memory which stores data, such as position information relating to detected focus candidate shadows.

The CPU 40 executes the above-described decision making subroutine on the basis of two kinds of images, the axial image and the sagittal image. As a result, it is assumed that focus candidate shadows 671 and 672 are detected on the axial image of FIG. 67b and a focus candidate shadow 673 is detected on the sagittal image of FIG. 67d. FIG. 68 shows the contents of a memory which stores data, such as position information as to the detected focus candidate shadows 671 and 673. The data stored in the memory are made up of the total of shadows and information as to each of the shadows. Information as to the focus candidate shadows 671 and 673 is made up, giving the position coordinates (X, Y, Z) of each of the shadows and the area and the maximum and minimum lengths of each of the shadows, as well as other information. The position coordinates of the focus candidate shadow 671 on the axial image are (X1, Y1), and the position coordinates of the focus candidate shadow 672 on the axial image are (X2, Y2). In addition, the position coordinates of the focus candidate shadow 673 on the sagittal plane are (Z1, Y1+δ).

It is assumed here that the z-axis coordinate is not clearly identified on the axial plane and the X-axis coordinate is not clearly identified on the sagittal plane. In this case, when the position coordinates (X1, Y1) of the focus candidate shadow 671 and the position coordinates (Z1, Y1+δ) of the focus candidate shadow 671 are compared with each other, their Y-axis coordinates are found to approximate each other. The Y-axis difference between the focus candidate shadow 671 and the focus candidate shadow 673 is δ. If this difference δ is smaller than a predetermined value Δ, it is determined that both shadows 671 and 673 lie at the same position coordinates and are the same focus candidate shadow, and the shadows 671 and 673 are left as a focus candidate shadow. On the other hand, if the difference δ is smaller than the predetermined value Δ, it is determined that both shadows 671 and 673 lie at different position coordinates, and the shadows 671 and 673 are deleted from focus candidate shadows. Since nothing on the sagittal plane corresponds to the position coordinates (X2, Y2) of the focus candidate shadow 672, the focus candidate shadow 672 in this case is regarded as false and is deleted. Incidentally, in this embodiment, the decision is made according to whether the position coordinates of shadows are the same, but in the case where the position coordinates of shadows are regarded as the same, a decision as to whether both shadows are the same may be made on the basis of the "areas", the "maximum lengths", the "minimum lengths" and the like of the shadows.

Figure 69A:
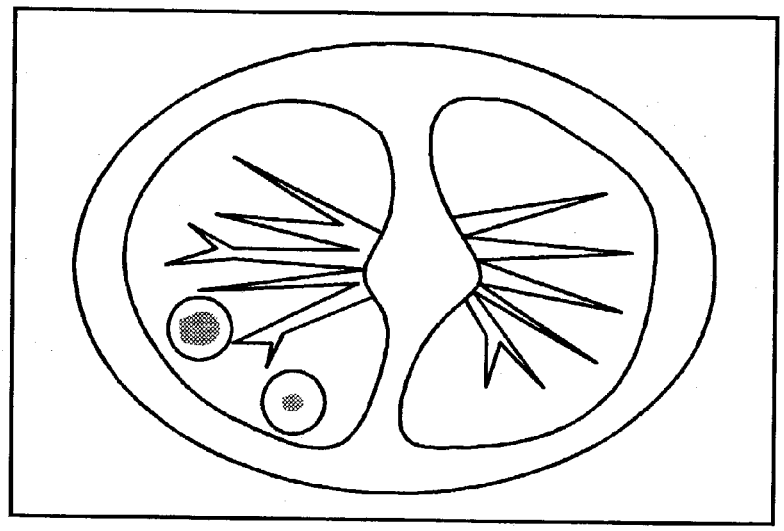
FIGS. 69a and 69b are diagrams showing a specific example in which focus candidate shadows photographed and extracted in the past are displayed together.
Figure 69B:
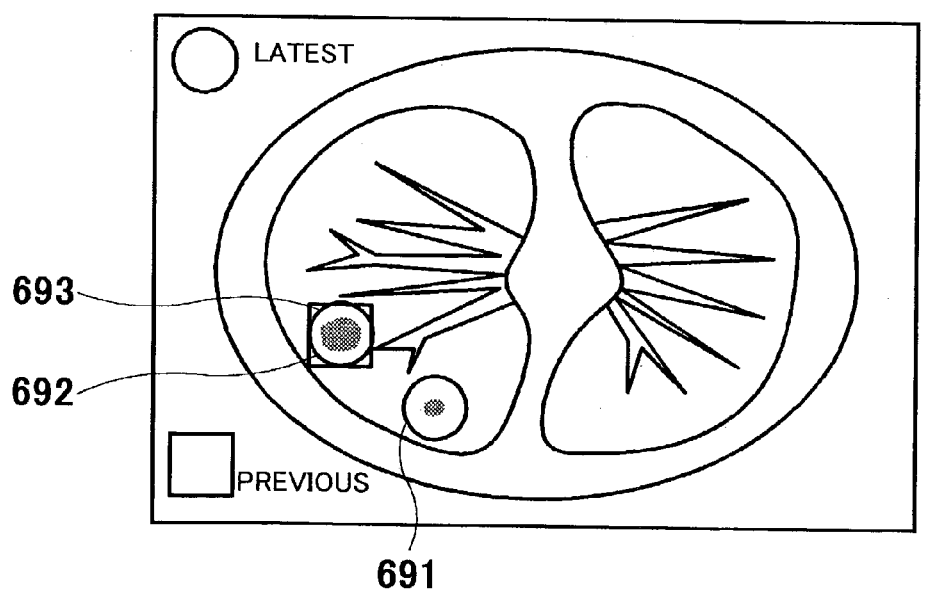

FIG. 69 shows the case where a CT image having an extracted focus candidate shadow and a marker are displayed to the operator (doctor) together with a focus candidate shadow photographed and extracted in the past. FIG. 69a is a view showing one example of a picture which displays focus candidate shadows detected on the basis of a CT image photographed the latest, as well as markers. FIG. 69b shows one example of a picture which displays a marker corresponding to a focus candidate shadow photographed and extracted, for example, one year ago in such a manner that the marker is superposed on the image of FIG. 69a at the same time. In FIG. 69b, the marker corresponding to the focus candidate shadow extracted in the past is shown by a square. In addition, a figure or a character indicating that circular markers 691 and 692 denote the latest photographed objects is displayed at the top left of the picture, while a figure or a character indicating that a square marker 693 denote the past (previous) photographed object is displayed at the bottom left of the picture. Features, such as the coordinates and the size of the focus candidate shadow photographed and extracted in the past, are recorded on a magnetic disk in the format shown in FIG. 68, and a marker corresponding to the past focus candidate shadow may be displayed on the basis of these features. For example, in the case where CT images are photographed and subjected to cancer detection processing at intervals of one year, when the detection result of this year and the detection result of last year are displayed in a superimposed manner, if a shadow newly appears at a location where no shadow existed last year, a doctor can be made to recognize that the possibility that the shadow is that of a cancer is high. Incidentally, the previous date of photography and the like may also be displayed in association with the marker. In addition, if there exist a plurality of dates of photography, the manner of display, such as the colors, the shapes and the like of markers, may also be changed for the respective dates of photography.

Figure 70A:
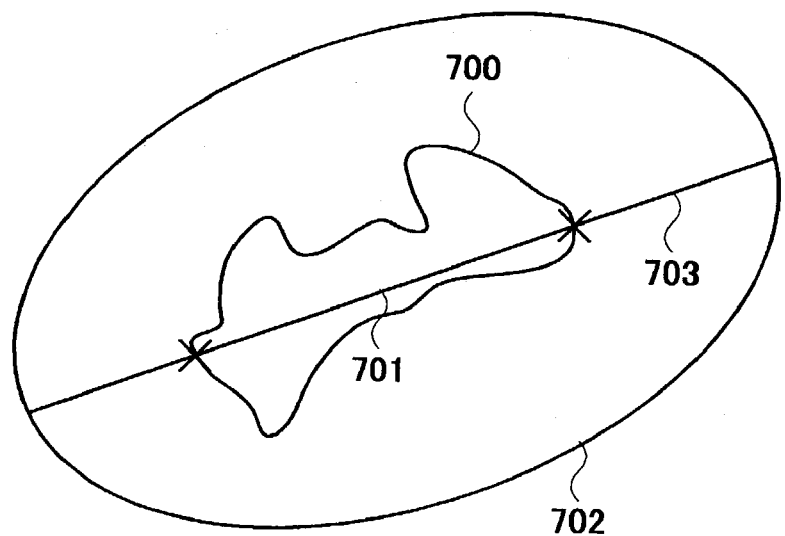
FIGS. 70a and 70 are diagrams showing a modification of the manner of displaying a marker.
Figure 70B:
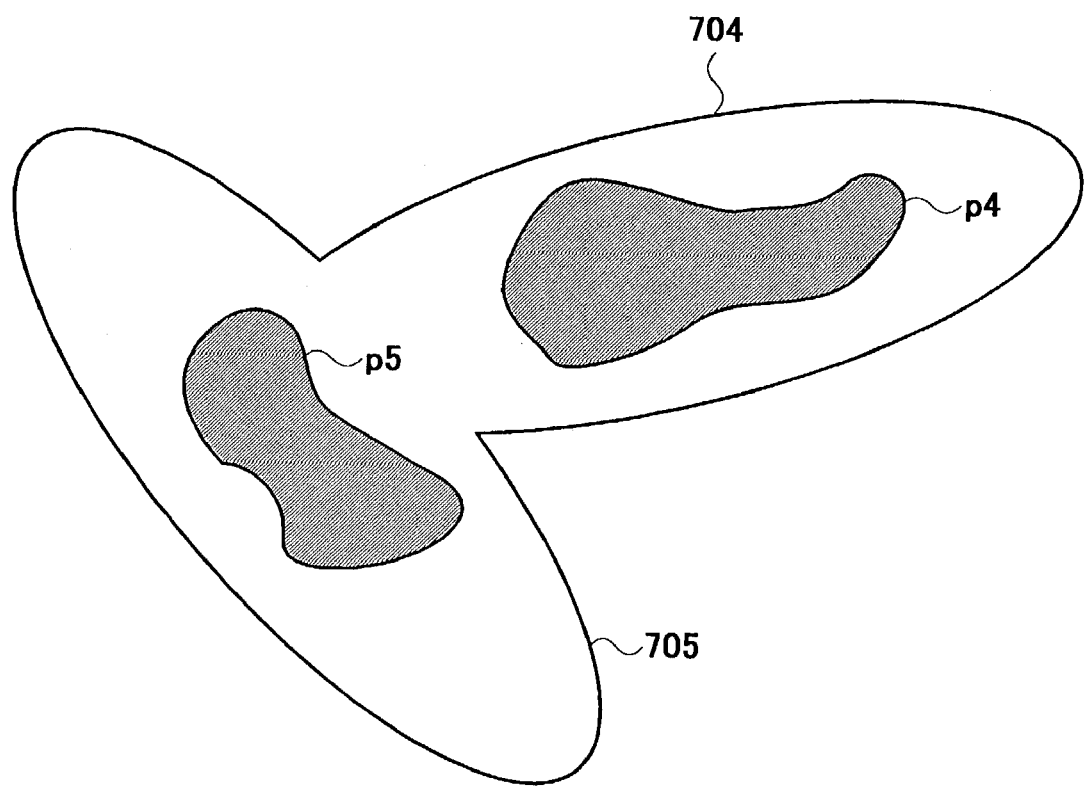
Figure 71A:
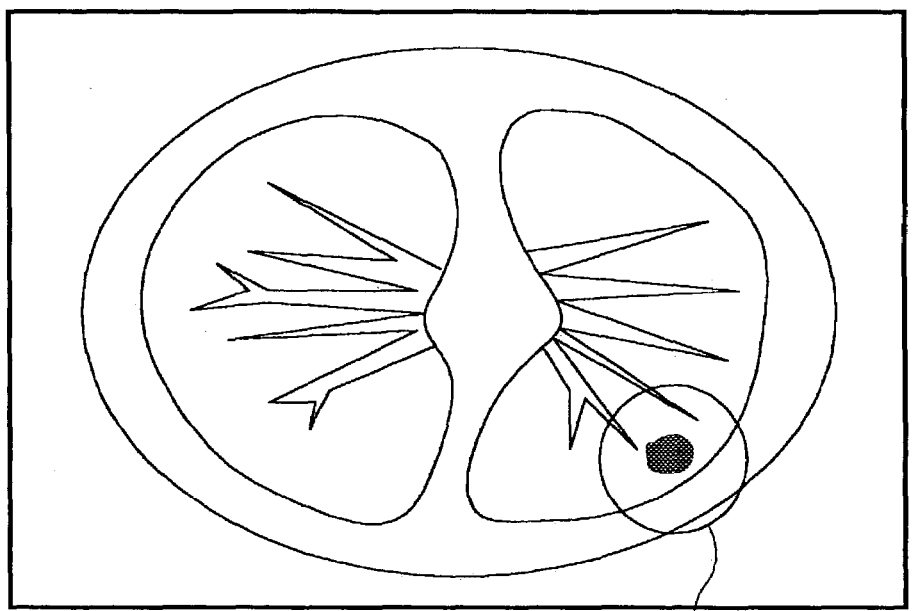
Figure 70B:
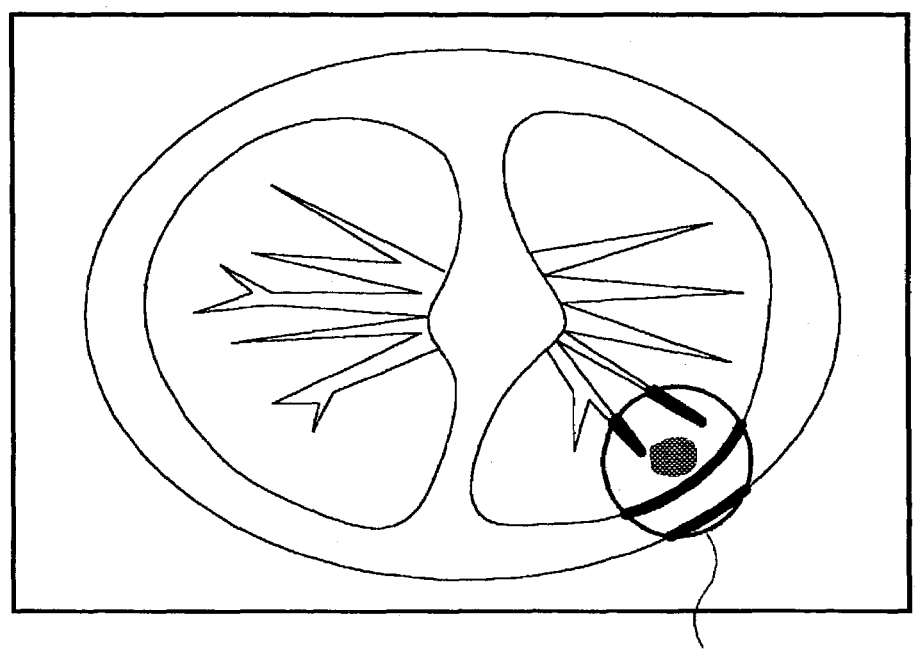

FIGS. 70a, 70b and 71a, 71b are views showing a modification of the manner of display of a marker. In the above description of the embodiment, reference has been made to the case where the shape of a marker is displayed as a circle or an ellipse. In FIG. 70a, the direction of a long diameter 701 indicative of the maximum length of a focus candidate shadow 700 and the direction of a long axis 703 of an elliptical marker 702 are made coincident with each other, and the elliptical marker 702 is displayed to surround the focus candidate shadow 700. Since the marker is displayed along the shape of the shadow, the shadow is easy to recognize. Incidentally, the length of the long axis of the elliptical marker 702 may use the value obtained by multiplying the long diameter 701 of the focus candidate shadow 700 of the focus candidate shadow by a predetermined coefficient, and the length of the short axis of the elliptical marker 702 may use the value obtained by multiplying an effective short diameter (the value obtained by dividing the area of the shadow by the maximum long diameter of the shadow) of the focus candidate shadow by a predetermined coefficient. FIG. 70b is a view showing one example of the case where an elliptical marker is displayed as an aggregation of elliptical arcs 704 and 705, similar to the case where a marker is shown as an aggregation of circular arcs, as shown in FIG. 36b. In this modification, in the case where the ellipses 704 and 705, respectively centered at focus candidate shadows p4 and p5, overlap each other, the overlapping portion of the elliptical arcs is deleted to draw the marker as an aggregation of the plurality of elliptical arcs 704 and 705, as shown in FIG. 70b. If the focus candidate shadow is only displayed by being enclosed with the marker 711, as shown in FIG. 71a, there is a case where the location of the focus candidate shadow is difficult to identify. For this reason, as shown in FIG. 71b, in, this embodiment, the contrast of the CT image in the area enclosed with the marker 711 is emphasized or the CT image is subjected to gamma processing, so that the focus candidate shadow can be displayed in a far more clearly emphasized state.

Figure 72:
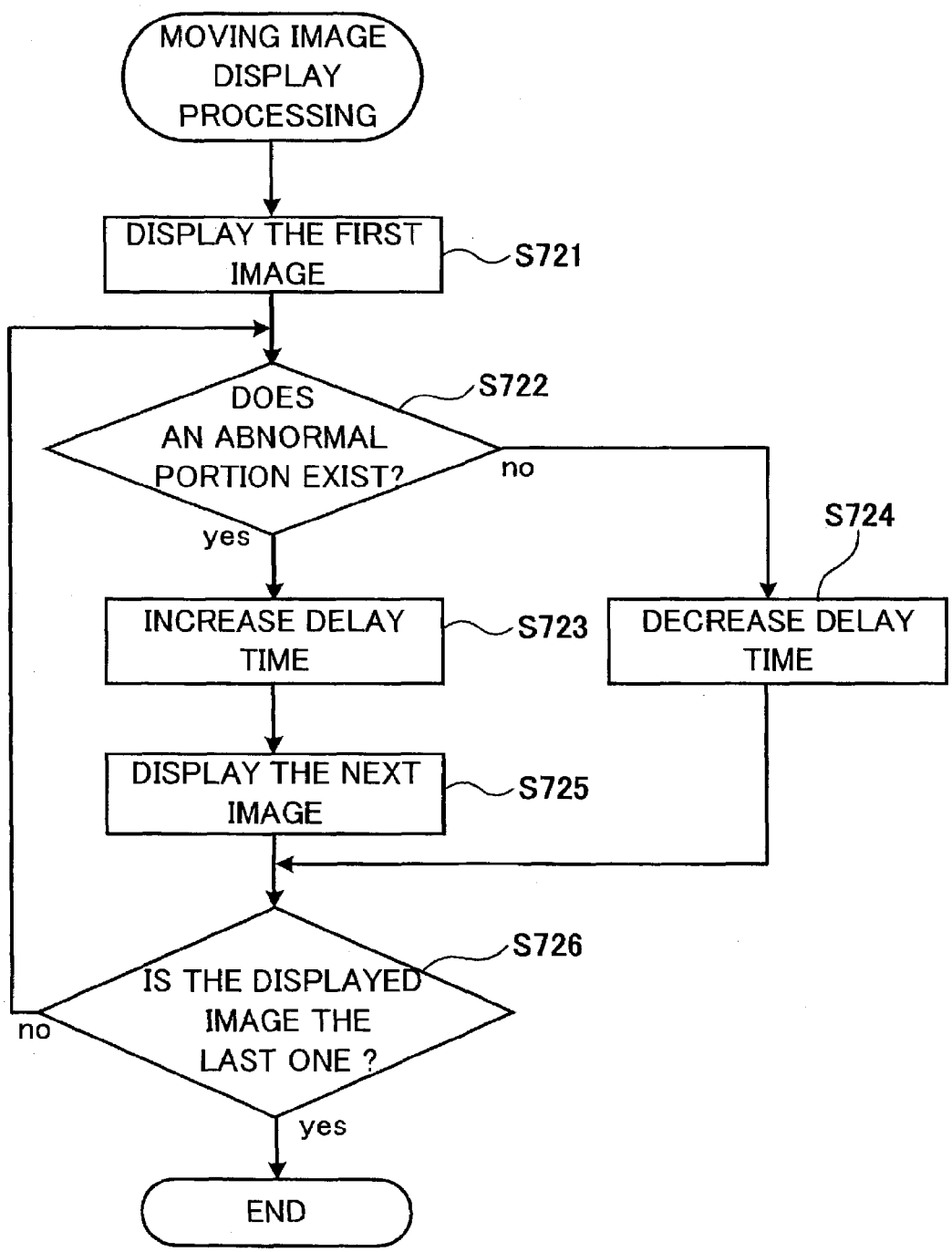
FIG. 72 is a flowchart showing a modification of a process where a CT image having an extracted focus candidate shadow and a CT image having no extracted focus candidate shadow are displayed in order as a kinematic image.

FIG. 72 is a view showing a modification in which a CT image having an extracted focus candidate shadow and a CT image having no extracted focus candidate shadow are sequentially displayed as a kinematic image. In the above description of the embodiment, reference has been made to the case where a CT image having an extracted focus candidate shadow is displayed in various display modes. However, in this embodiment, modification is applied to the manner of display, here displaying in a kinematic image, which sequentially displays a CT image at a rate of approximately 5 to 14 images/second in the order of photography irrespective of the presence or absence of an extracted focus candidate shadow. Details of this kinematic image display method will be described below with reference to the flowchart of FIG. 72.

[Step S721] The CPU 40 displays the first CT image.

[Step S722] The CPU 40 determines whether an abnormal portion, i.e., a focus candidate shadow, exists in the CT image which is presently displayed. If the decision result is yes, the CPU 40 proceeds to Step S723, whereas, if the decision result is no, the CPU 40 proceeds to Step S724.

[Step S723] Since it has been determined that the abnormal portion (focus candidate shadow) exists in the image which is presently displayed, the CPU 40 increases the delay time. The delay time is the time required to display one image during kinematic image display. As the delay time increases, the display time of the image in which the abnormal portion (focus candidate shadow) exists becomes longer than the standard display time. Accordingly, the doctor can intensively observe with ample time the image in which the abnormal portion (focus candidate shadow) exists. Incidentally, in the case where a plurality of abnormal portions (focus candidate shadows) exist in one CT image, the value of the delay time may be determined according to the number of abnormal portions (focus candidate shadows).

[Step S724] Since it has been established that an abnormal portion (focus candidate shadow) does not exist in the image which is presently being displayed, the CPU 40 decreases the delay time. As the delay time is decreased, the display of the image comes to an end earlier than the normal image display. Incidentally, the image may also be displayed with a standard delay time without decreasing the delay time. The value of the delay time in each of Step S723 and Step S724 can be arbitrarily set.

[Step S725] Since the CT image has been displayed for a period of time equivalent to the delay time, the CPU 40 starts displaying the next image.

[Step S726] The CPU 40 determines whether the image displayed in Step S725 is the last image. If the decision result is yes (the image is the last one), the CPU 40 brings the processing to an end; whereas, if the decision result is no (the image not the last one), the CPU 40 returns to Step S722 and repeats the above-described processing until the last image is displayed. In the above description, reference has been made to the case where an image in which no focus candidate shadow exists is displayed for only a short time. However, such an image may also be displayed for a longer time than the standard display time, so that the doctor can confirm whether a focus candidate shadow really does not exist.

Figure 73:
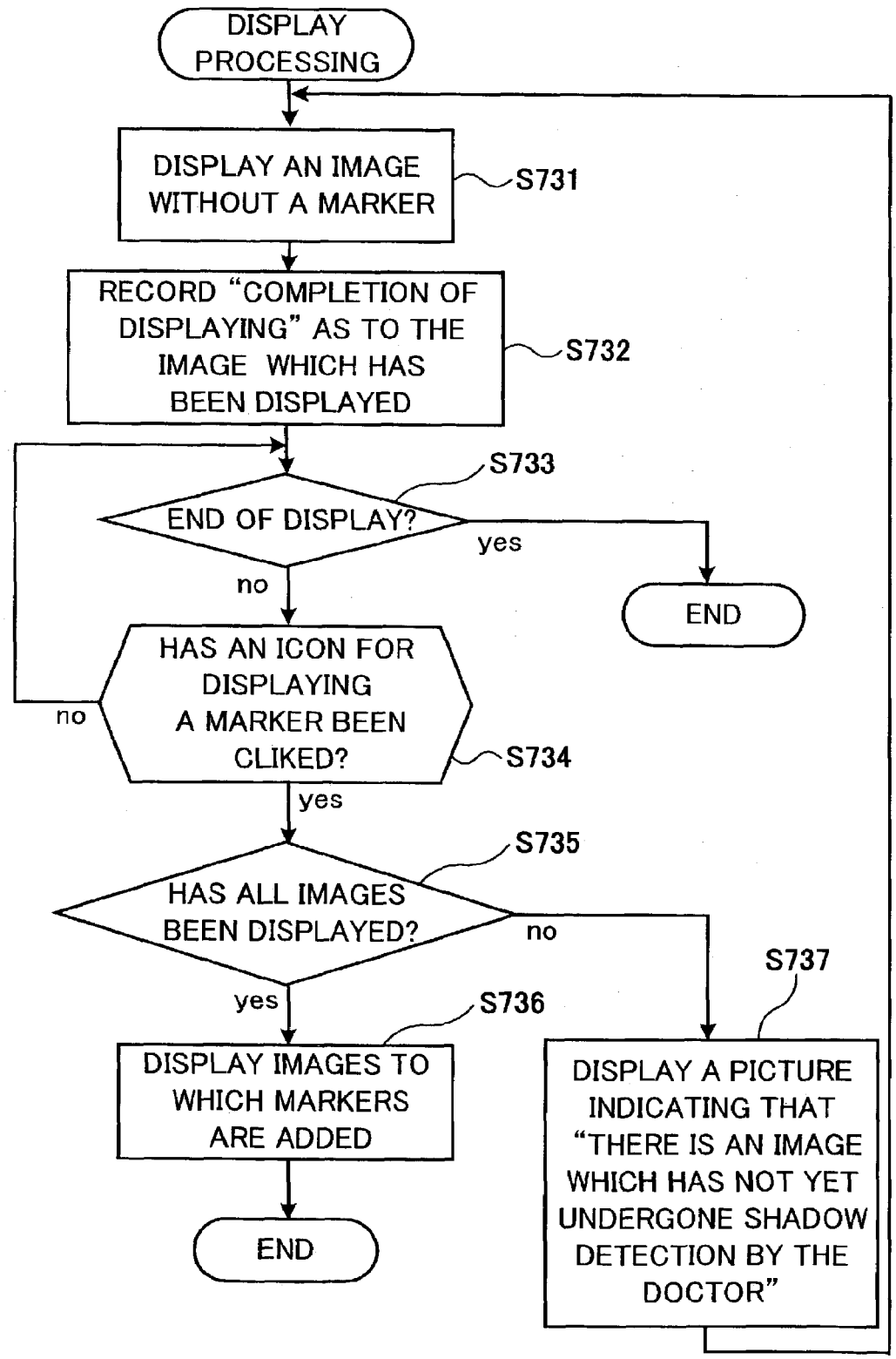
FIG. 73 is a flowchart showing one example of the display processing of displaying the diagnosis result provided by the image diagnosis supporting device according to this invention.

FIG. 73 is a view showing one example of display processing for the case where a diagnosis result provided by the image diagnosis supporting device according to this invention is displayed. In the case where a diagnosis is to be made on the basis of a medical image photographed with a CT device or the like, two doctors independently perform shadow detection as to the medical image in parallel with each other, and subsequently meet to examine the results of their shadow detections. Both doctors finally make an integrated decision as to whether the image is abnormal. If the result of this integrated decision is that the image is abnormal, the patient undergoes a thorough medical examination. On the other hand, if the result of the integrated decision is that the image is not abnormal, the doctor makes a check as to their diagnosis result or the like by using an image diagnosis supporting device. Namely, the image diagnosis supporting device must assist in the diagnosis of the doctors and detect the presence or absence of an abnormality in a medical image which has undergone shadow detection by the doctors. Accordingly, in this embodiment, display processing which does not display a marker after the shadow detection by the doctor has been completed is adopted. Details of this display processing will be described below with reference to the flowchart of FIG. 73.

[Step S731] The CPU 40 directly displays an original CT image in which a marker is not displayed.

[Step S732] The CPU 40 records "completion of displaying" as to the CT image whose displaying in Step S731 has been completed. For example, a flag indicative of "completion of displaying" is added to the field "other information", as shown in FIG. 68.

[Step S733] The CPU 40 makes a decision as to whether a display complete icon on the picture has been click-manipulated by a mouse. If the decision result is yes (the icon is manipulated), the CPU 40 brings the display processing to an end, whereas, if the decision result is no (the icon is not manipulated), the CPU 40 proceeds to Step S734.

[Step S734] The CPU 40 determines whether an icon for displaying a marker (a marker display icon) has been click-manipulated by the mouse. If the decision result is yes (the icon is manipulated), the CPU 40 proceeds to Step S735; whereas, if the decision result is no (the icon is manipulated), the CPU 40 returns to Step S733 and repeats the processing until the display complete icon or the marker display icon is manipulated.

[Step S735] The CPU 40 determines whether all CT images have been displayed by the processing of Step S731 and "completion of displaying" has been recorded by the processing of Step S732. If the decision result is yes, the CPU 40 proceeds to Step S737, whereas, if the decision result is no, the CPU 40 proceeds to Step S736.

[Step S736] Since it has been determined in the processing of Step S735 that all CT images have been displayed, the CPU 40 sequentially displays images to which markers are added. During the display of the images to which markers are added, the CPU 40 may display only marker-added CT images, each having an extracted focus candidate shadow, in a predetermined order, or it may sequentially display marker-added CT images and CT images to which no markers are added.

[Step S737] Since it has been in the processing of Step S735 that all CT images have not been displayed, the CPU 40 displays a notice indicating that "there is an image which has not yet undergone shadow detection by the doctor", and informs the operator (doctor) that a marker-added CT image is not displayed, and returns to Step S731. In this manner, shadow detection by the doctor is performed on a CT image which has not yet undergone shadow detection. In addition, when shadow detection by the doctor has been performed on a CT image, a marker-added CT image is displayed.

Figure 74A:
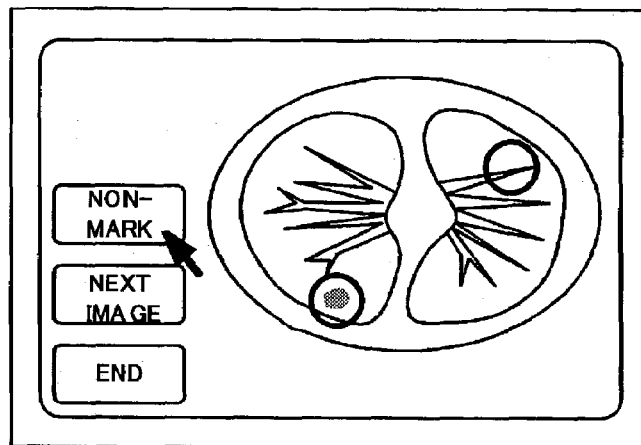
FIGS. 74a to 74c are diagrams showing another example of the display processing of displaying the diagnosis result provided by the image diagnosis supporting device according to this invention.
Figure 74B:
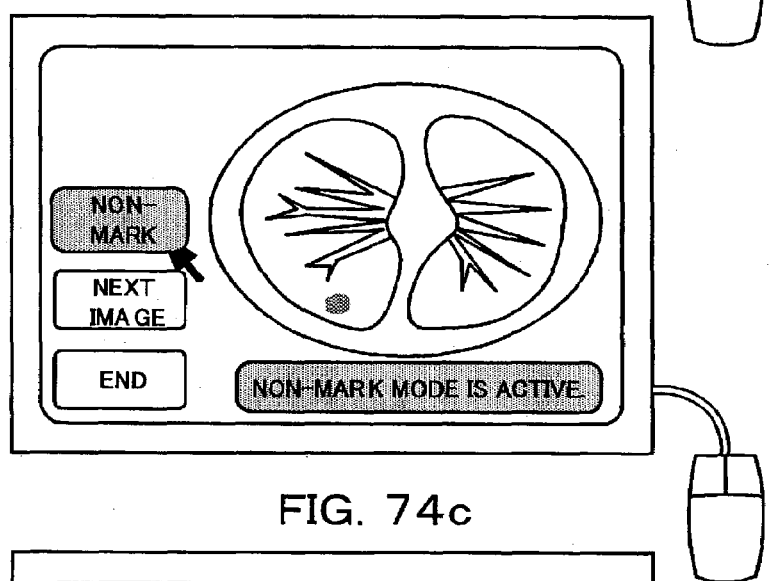
Figure 74C:
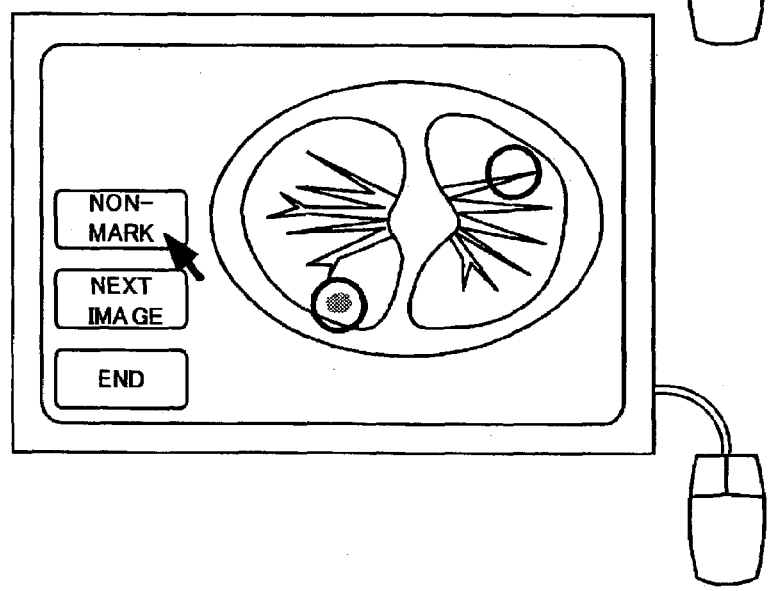

FIGS. 74a to 74c show another example of display processing for the case where a diagnosis result provided by the image diagnosis supporting device according to this invention is displayed. In the description of FIG. 73, reference has been made to the case where the presence or absence of a focus candidate shadow is detected in a medical image which has been undergone shadow detection by the doctor and a focus candidate shadow is displayed with a marker added thereto. In the following description, reference has been made to a display method for the case where a marker is removed from a marker-added CT image. FIG. 74a is a view showing one example of a display picture of a marker-added CT image. In FIG. 74a, a non-mark icon for selecting the marker-hidden mode, a next-picture icon for displaying the next picture and an end icon for bringing display to an end are displayed on the left-hand side of the picture. As shown in FIG. 74b, when the non-mark icon is click-manipulated by a mouse, a marker which has been displayed up to this time disappears and is brought to a hidden state, and the characters "NON-MARK MODE IS ACTIVE", indicative of the hidden state are displayed on the bottom side of the display. Furthermore, in this embodiment, when the non-mark mode of FIG. 74b passes a predetermined time, the picture is restored to the original marker-added CT image, as shown in FIG. 74c. This predetermined time can be set in advance as a parameter. Incidentally, a mark display icon may be provided on the upper side of the non-mark icon so that the operator can arbitrarily switch the non-mark mode and a mark mode. As shown in FIGS. 71a and 71b, an icon for switching the emphasized display and the non-emphasized display of a focus candidate shadow may be provided.

In the abnormal shadow detection processing of FIG. 9, reference has been made to the case where processing is performed in parallel in functional terms, but in sequence in temporal terms according to the kind of shadow, such as a small shadow, a large shadow, a ground glass opacity and a high-density shadow; however, each processing may also be executed in parallel by using time division processing or a plurality of computers.

Figure 75:
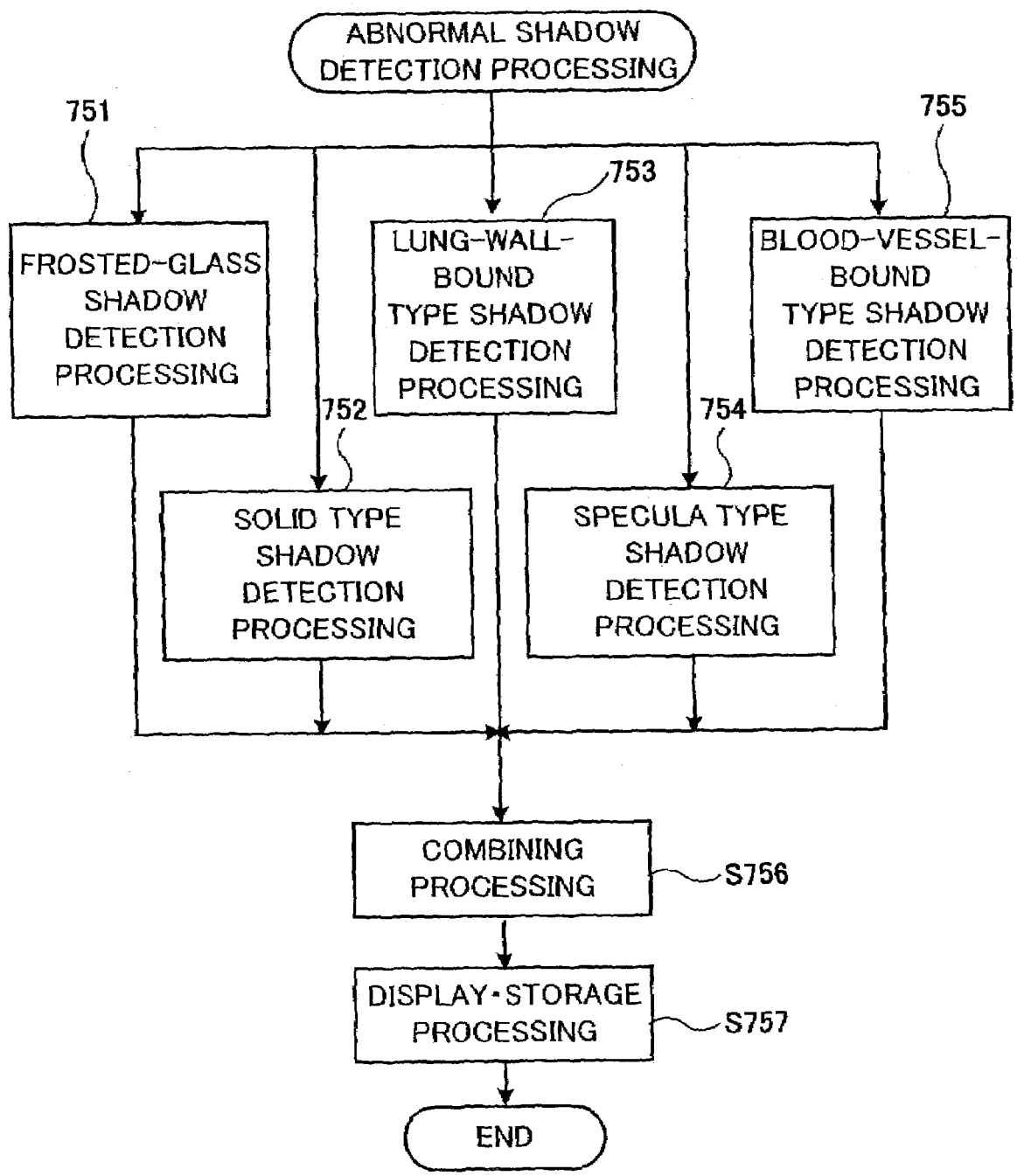
FIG. 75 is a flowchart showing a modification of a main flowchart of the abnormal shadow detection processing of FIG. 9.

FIG. 75 is a view showing a modification of the main flowchart of the abnormal shadow detection processing of FIG. 9. The abnormal shadow detection processing of FIG. 75 executes each kind of processing according to the kind of shadow in parallel. The ground glass opacity of Step S751 corresponds to the ground glass opacity processing of FIG. 9. The solid type shadow processing of Step S752 corresponds to three kinds of processing shown in FIG. 9, i.e., the small shadow detection processing, the large shadow detection processing and the high-density shadow detection processing. The lung-wall-bound type shadow processing of Step S753 corresponds to the decision making subroutines shown in FIGS. 25, 26a to 26d and 44a to 44c. The specula type shadow processing of Step S754 corresponds to the processing shown in FIGS. 63a, 63b and 64a, 64b. The blood-vessel-bound type shadow detection processing of Step S755 corresponds to the processing shown in FIGS. 50 to 53. The combining processing of Step S756 combines the results extracted by the processing of Steps S751 to S755. These extracted results include the coordinate position, the area, the maximum length and the minimum length of a shadow, as shown in FIG. 68. Accordingly, in the display storage processing of Step S757, a marker-added CT image, such as the above-described one, is displayed on the basis of the extracted result, and the extracted result is stored in a memory or a magnetic disk.

Figure 76A:
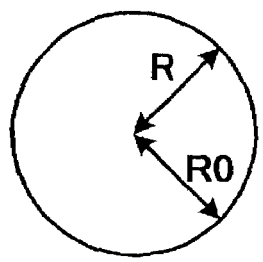
FIGS. 76a to 76d are diagrams showing a sixth modification of the decision making subroutine.
Figure 76B:
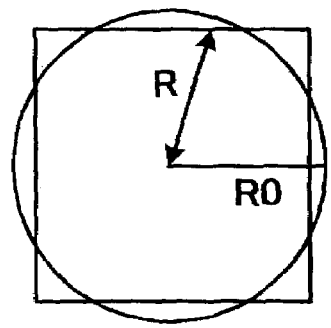
Figure 76C:
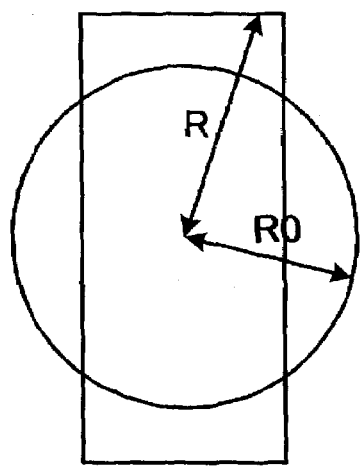
Figure 76D:
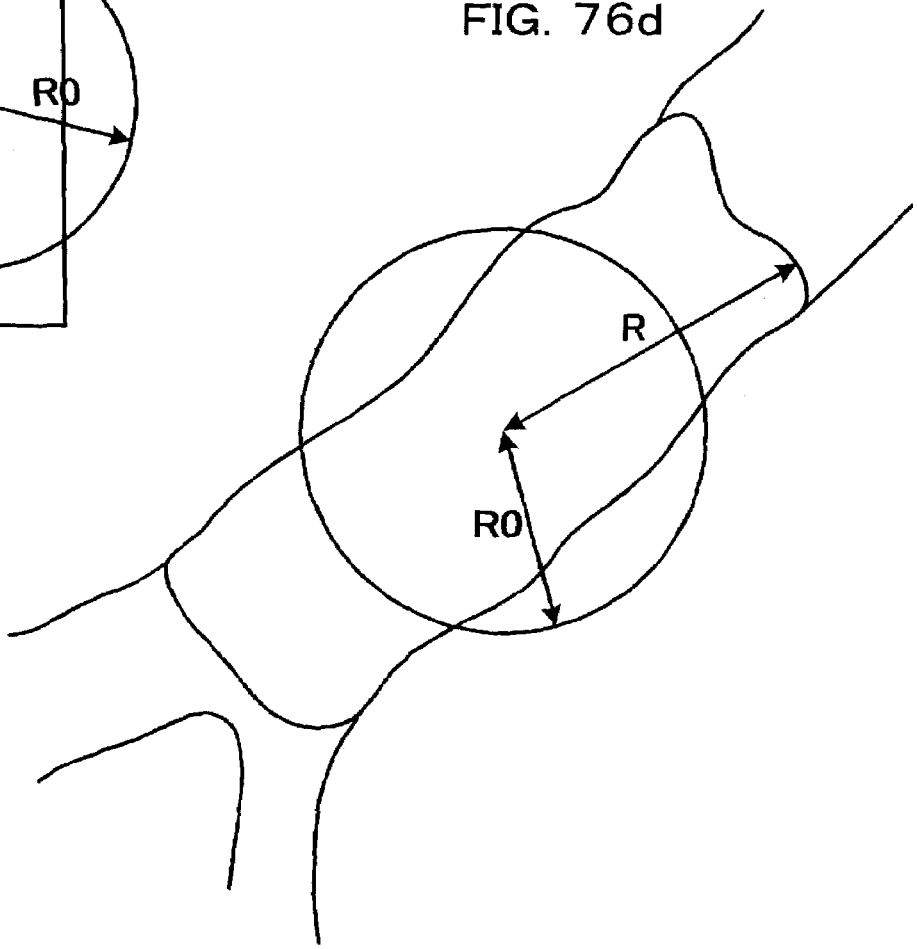
Figure 77A:
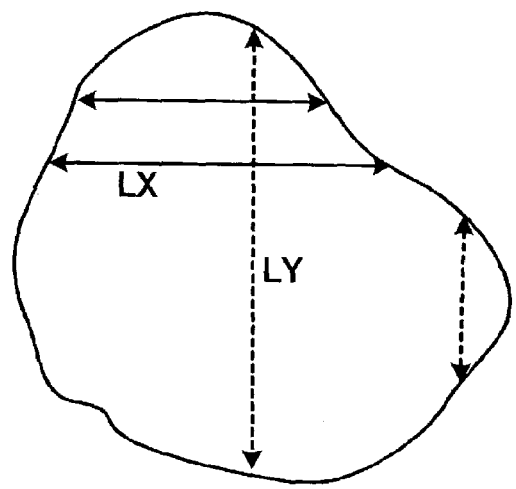
FIG. 77a is a diagram showing the sixth modification of the decision making subroutine.
Figure 77B:
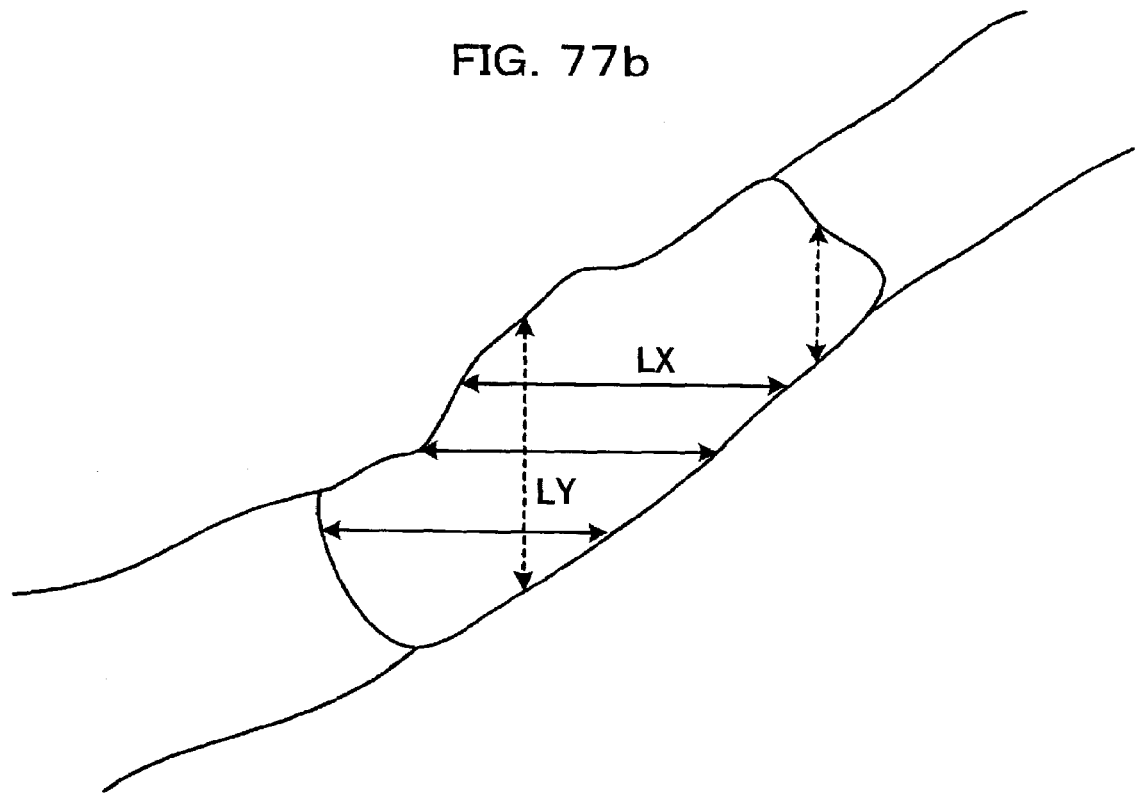
FIG. 77b is a diagram illustrating one example of how to extract a shadow which seems not to be a focus.

FIGS. 76a to 76d, 77a and 77b are views showing a sixth modification of the decision making subroutine. The decision making subroutine shown FIGS. 76a to 76d, 77a and 77b is performed in place of the decision making subroutine E1 of FIG. 27, the decision making subroutine F1 of FIG. 29 and each of the above-described decision making subroutines, or it is performed in parallel with these decision making subroutines. This decision making subroutine uses variance or standard deviation in its abnormal shadow detection processing. FIGS. 76a to 76d show the principle of a method of using a variance or standard deviation in abnormal shadow detection processing. FIGS. 77a and 77b illustrate one example of how to extract a shadow which seems not to be a focus.

It is known that the possibility that a focus candidate shadow close to a circle is a cancer shadow (abnormal shadow) is high, whereas the possibility that a focus close to a rectangle is a blood vessel shadow (normal shadow) is high. Accordingly, a decision is made by using statistical processing according to the shape of a focus candidate shadow. In this statistical processing, the weighted center point of an area indicative of a focus candidate shadow is found, and the distance from the weighted center point to the edge of the area is found along the entire periphery of the area. A variance or standard deviation of the found distance is computed; and, on the basis of the variance or standard deviation, it is determined whether the shadow is a focus candidate shadow. Namely, as shown in FIG. 76a, in the case where an extracted focus candidate shadow is an approximately circular area, since a distance R from the central point to the edge of the area is equal to a radius R0 of the circle, a variance Da in this case is 0.

As shown in FIG. 76b, in the case where an extracted focus candidate shadow is a square, for example, the weighted center point of the square area is set as the central point, and a circle of radius R0 that is centered at the central point is drawn. At this time, as shown in FIG. 76b, the length of the radius R0 is made slightly larger than the radius of a circle which touches the inside of the square area, and it is made slightly smaller then a circle which touches the outside of the square area. Namely, the length of the radius R0 is set between the maximum value and the minimum value of the distance from the central point to the edge of the shadow. In the case of FIG. 76b as well, a variance Db is found in a similar manner.

As shown in FIG. 76c, in the case where an extracted focus candidate shadow is a rectangle, a circle of radius R0 centered at the central point of the rectangular area is drawn. At this time, as shown in FIG. 76c, the length of the radius R0 is made slightly larger than the radius of a circle which touches the shorter sides of the rectangular area, and is made slightly smaller then a circle which touches the longer sides of the rectangular area. Namely, in the case of the above-described square area, the length of the radius R0 is set between the maximum value and the minimum value of the distance from the central point to the edge of the shadow. In the case of FIG. 76c as well, a variance Dc is found in a similar manner.

The relationship between the variances Db and Dc in the case of each of FIGS. 76b and 76c is Db>Dc. FIG. 76d is a view showing a specific example of the case where the above-described principle is applied to an actual blood vessel shadow. A variance D is defined as $D=(\Sigma(R-R0)^2)/N$. In this formula, R is the distance from the central point of the focus candidate shadow to the edge of the shadow area. R0 is the length of the radius of the circle centered at the central point, and corresponds to the average value of a set operation. N is the total number of pixels of the focus candidate shadow. S indicates the summation of the distances to the edge of the focus candidate shadow along the entire periphery of the area.

FIGS. 77a and 77b show a modification of the case of finding a variance or standard deviation. In FIGS. 77a and 77b, variance DX in the distances LX from one edge to the other edge of a focus candidate shadow along horizontal lines drawn thereon, and then a variance DY in the distances LY from one edge to the other edge of the focus candidate shadow along vertical lines drawn thereon, are found. Then, on the basis of the relationship in magnitude between each of the variances DX and DY and a predetermined value indicative of the shape of the shadow, a decision is made as to whether the shadow is a cancer shadow, as shown in FIG. 77a, or a blood vessel shadow, as shown in FIG. 77b. Incidentally, although the variances may be directly used, it goes without saying that the decision can be made by using a standard deviation which is the square root of each of the variances. A method of extracting the edge of a focus candidate shadow may use any of a method using threshold processing or the like for shadows, a method using particular density contours for shaded shadows, and Laplacian processing (refer to MEDICAL IMAGING TECHNOLOGY V01. 16, No. 3, May 1998, pp. 209-219), and, further, these methods may also be arbitrarily combined.

Figure 78:
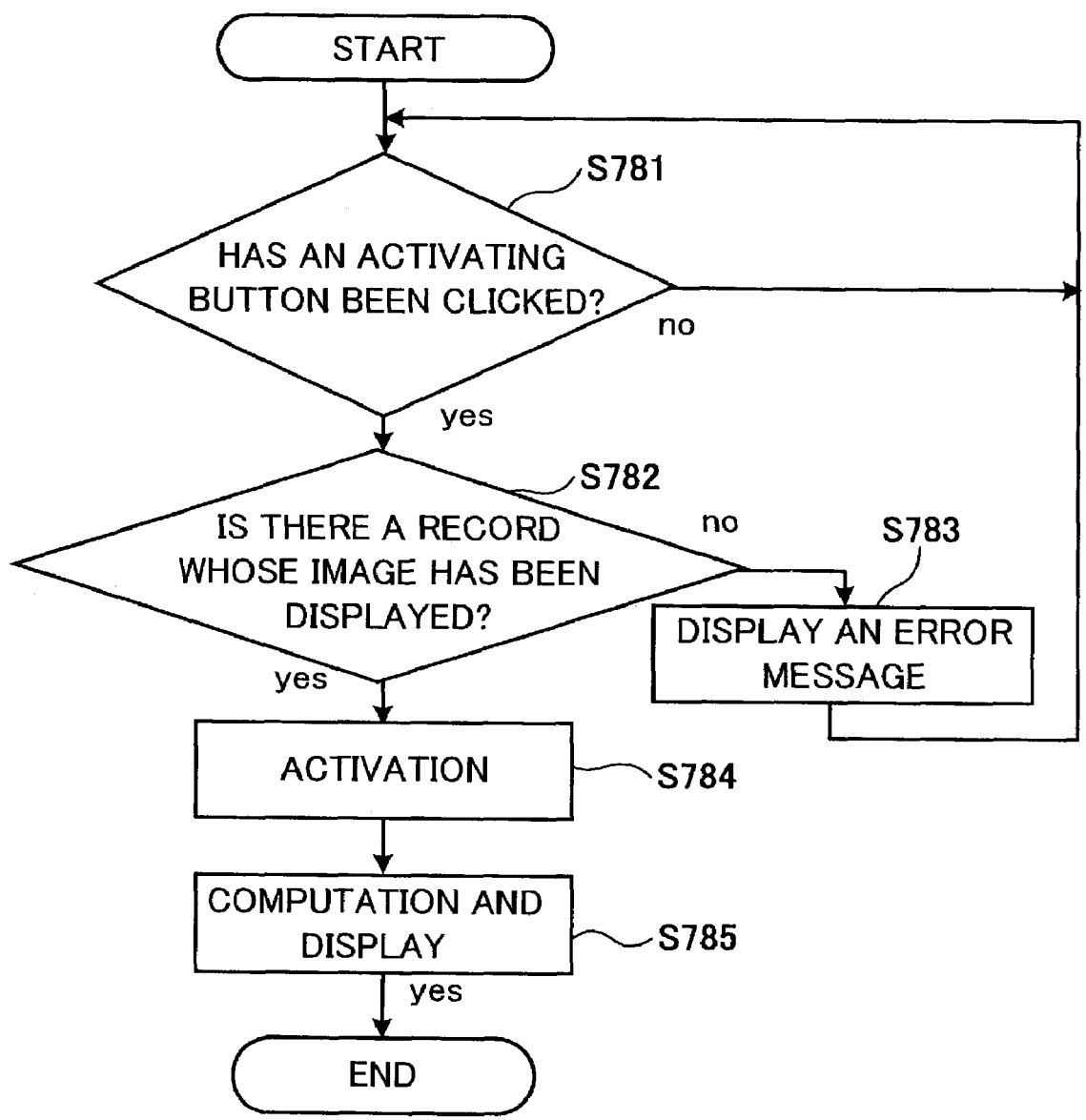
FIG. 78 is a flowchart showing a modification of the display processing of displaying the diagnosis result provided by the image diagnosis supporting device according to this invention.
Figure 79A:
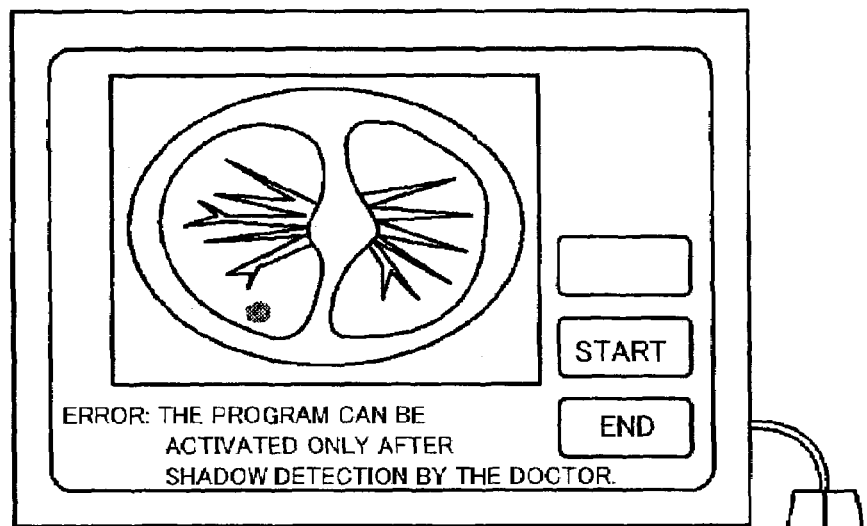
FIGS. 79a to 79c are diagrams showing one example of a display picture which accompanies the display processing of FIG. 78.
Figure 79B:
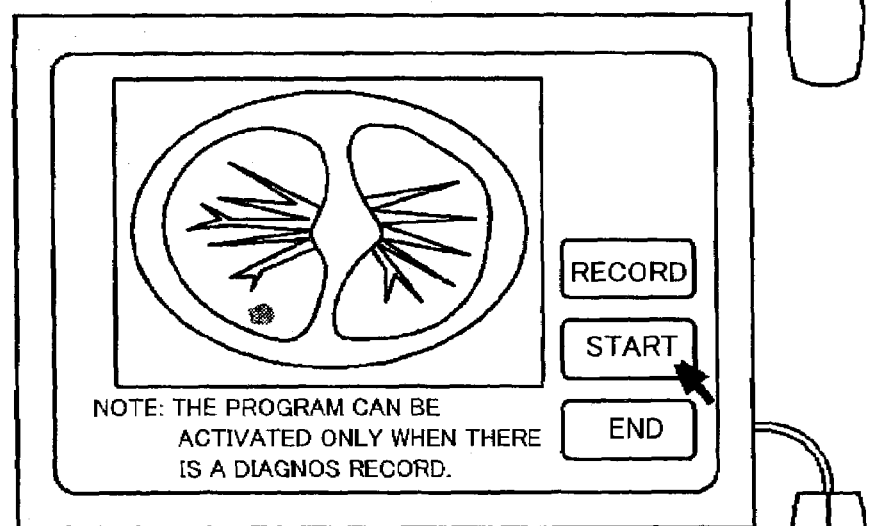
Figure 79C:
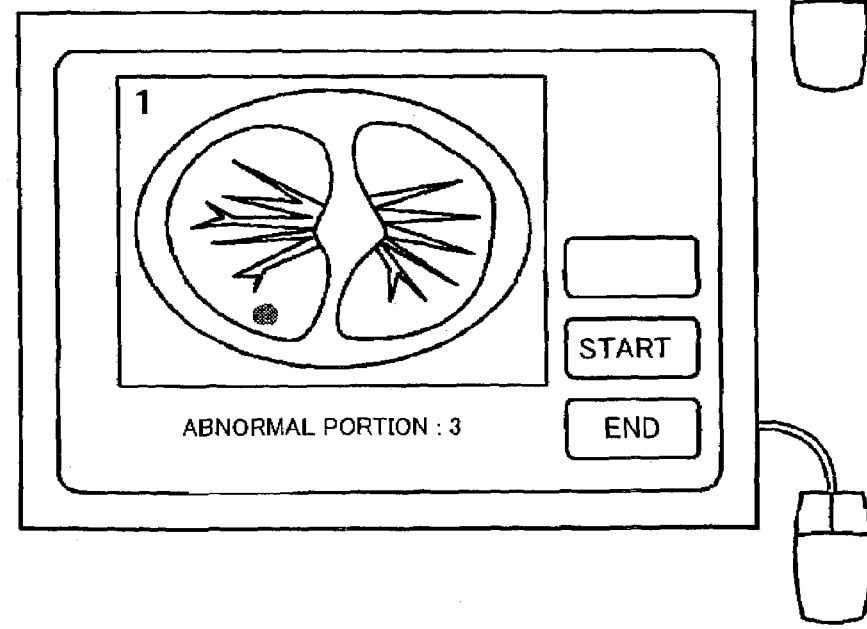

FIG. 78 is a view showing a modification of display processing for the case where a diagnosis result provided by the image diagnosis supporting device according to this invention is displayed. FIGS. 79a to 79c show one example of a display picture accompanying the display processing of FIG. 78. As described previously in connection with FIG. 73, in the case where a doctor is to make a diagnosis on the basis of a medical image photographed with a CT device or the like, if a decision result found by a computer is presented to the doctor before a diagnosis, the diagnosis has the risk of being influenced by preoccupations. Accordingly, it is desirable that the computer program of this invention not be executed before the diagnosis of the doctor. Details of this display processing will be described below with reference to the flowchart of FIG. 78.

[Step S781] The CPU 40 determines whether an activating button for activating an execution processing program for an image diagnosis supporting device according to this embodiment has been click-manipulated by a mouse. If the decision result is yes (the activating button is activated), the CPU 40 proceeds to Step S783; whereas, if the decision result is no, the CPU 40 repeats the processing of this step until the activating button is manipulated.

[Step S782] The CPU 40 determines whether there exits a record whose image has been displayed on the CRT display 48 (a flag indicative of the completion of displaying), and, if the decision result is yes (such record exists), the CPU 40 proceeds to Step S784; whereas, if the decision result is no (such record exists), the CPU 40 proceeds to Step S783. This is because the record whose image has been displayed on the CRT display 48 is regarded as diagnosed by the doctor. For a far more exact diagnosis, reference may be made to records of shadow detection by the doctor, and the decision may be made on the basis of the records. In this case, if the CPU 40 determines that there is a record of shadow detection (yes), the CPU 40 proceeds to Step S784; whereas, if the CPU 40 determines that there is not a record of shadow detection (no), the CPU 40 proceeds to Step S783.

[Step S783] Since an image which has not yet been diagnosed by the doctor is to be displayed, the CPU 40 displays an error message, and returns to Step S781. As this error message, an error message, as shown in FIG. 79a or 79b may be displayed. In FIG. 79a, an error message indicating that "error: the program can be activated only after shadow detection by the doctor" is displayed on the bottom side of a tomographic image. In FIG. 79b, an error message indicating that "note: the program can be activated only when there is a diagnosis record" is displayed on the bottom side of the tomographic image.

[Step S784] The CPU 40 activates an execution processing program.

[Step S785] The CPU 40 finds a focus candidate shadow through a computation on the basis of the execution processing program, and displays the result. The CPU 40 records the displayed information on a magnetic disk or the like as required. As shown in FIG. 79c, the display of the computation result shows the fact that, for example, the first tomographic image has one abnormal portion enclosed with a circle, and a value indicating how many abnormal portions have been found in total inclusive of those in other tomographic images. FIG. 79c shows that there are three abnormal portions in total.

Figure 80A:
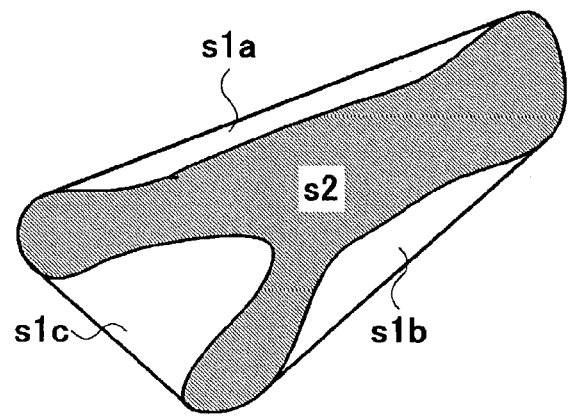
FIGS. 80a to 80c are diagrams showing a seventh modification of the decision making subroutine and showing one example of the case where the area ratio of the total area of the entire focus candidate shadow to the area of a concave portion formed in an edge portion of the shadow.
Figure 80B:
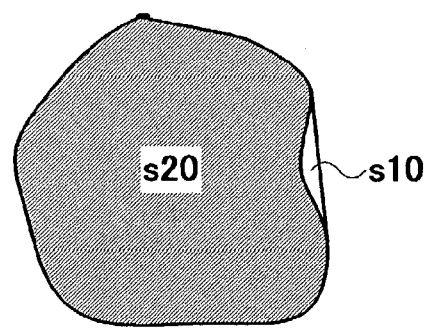
Figure 80C:
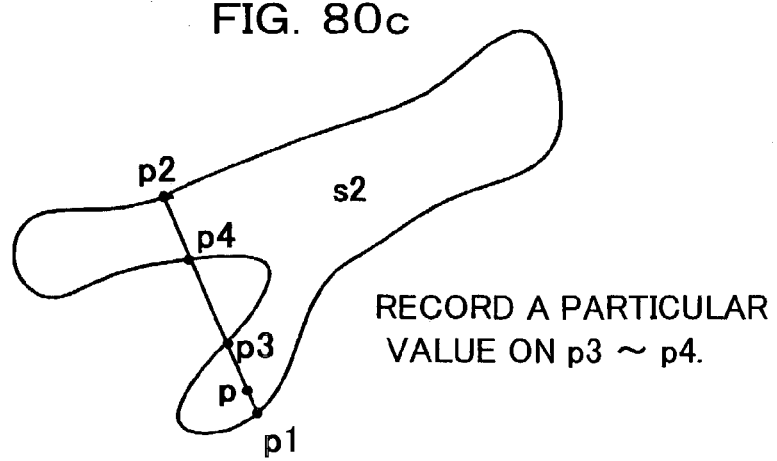
Figure 81A:
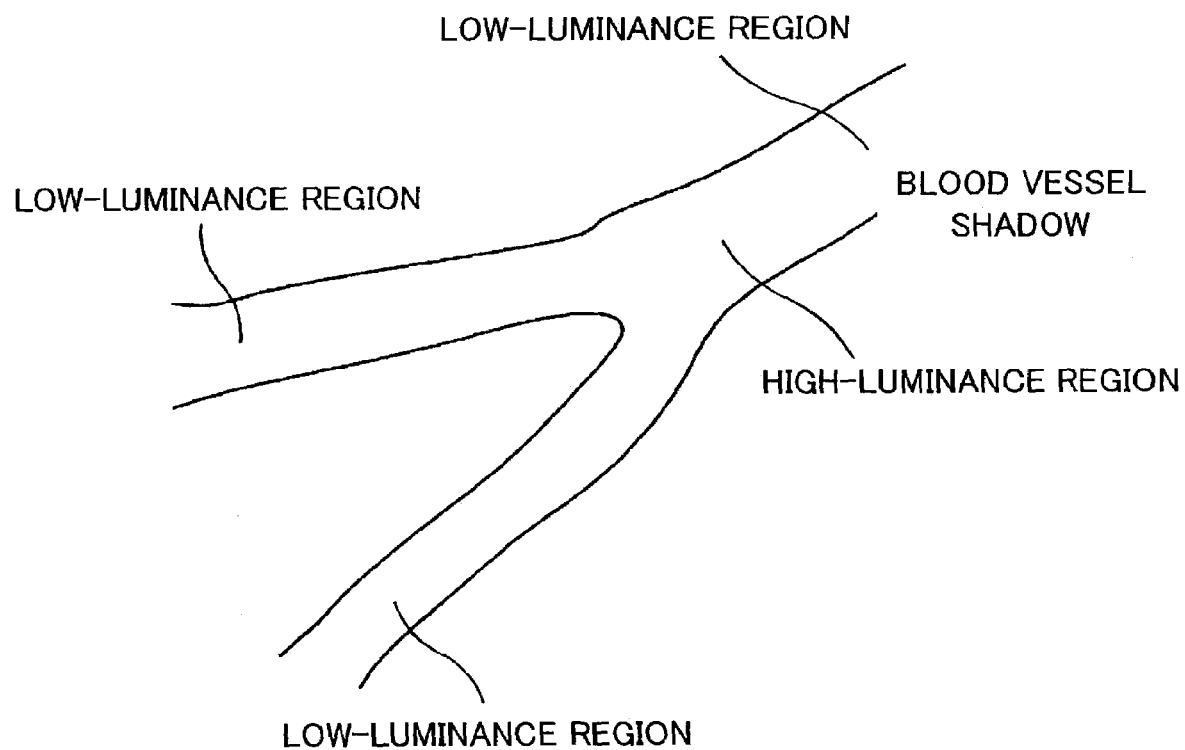
FIGS. 81a and 81b are diagrams showing a modification of the seventh modification of the decision making subroutine and showing one example of the process of how to extract a bifurcation of a blood vessel shadow.
Figure 81B:
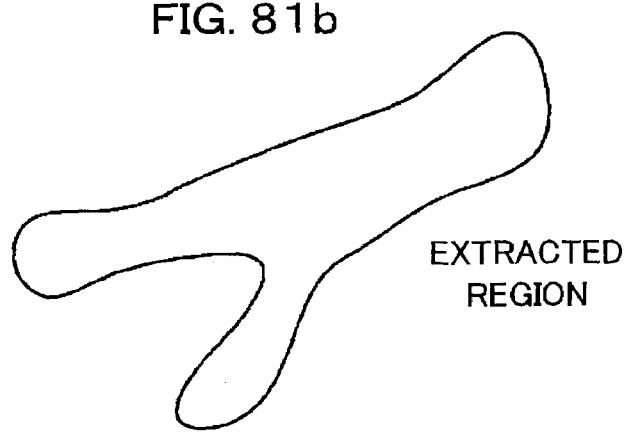
Figure 82:
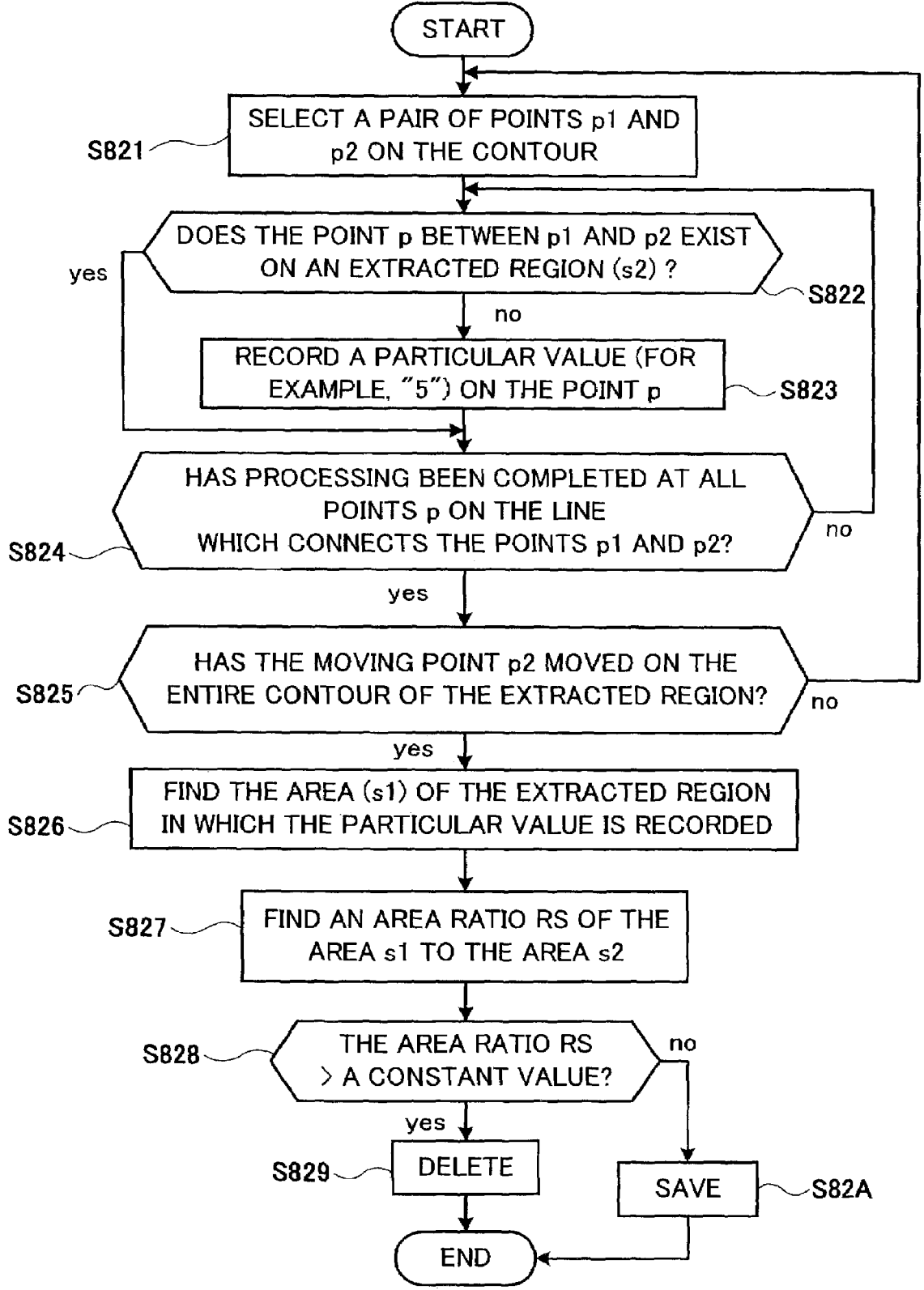
FIG. 82 is a flowchart showing the seventh modification of the decision making subroutine and a flowchart showing one example of procedures for the case of finding the area ratio of FIGS. 80a to 80c.

FIGS. 80a to 82 are views showing a seventh modification of the decision making subroutine. The decision making subroutine of FIGS. 80a to 82 is performed in place of the decision making subroutine E1 of FIG. 27, the decision making subroutine F1 of FIG. 29 and each of the above-described decision making subroutines, or it is performed in parallel with these decision making subroutines. This decision making subroutine uses the area of a shadow and the ratio of areas associated with this shadow, in abnormal shadow detection processing. FIGS. 80a to 80c show one example of the case of finding the area ratio of the total area of the entire focus candidate shadow to the area of a concave portion formed in the edge portion of the shadow. FIGS. 81a and 81b show one example of the process of how a bifurcating portion of a blood vessel shadow is extracted. FIG. 82 is a flowchart showing one example of procedures for the case of finding the area ratio of FIGS. 80a to 80c. FIG. 83 is a view showing one example of a display which accompanies the processing of FIGS. 80a to 80c.

An extracted region, as shown in FIG. 81b, is obtained by discriminating between the high and low luminances of a CT image as shown in FIG. 81a. To identify this extracted region as a blood vessel shadow, this extracted region is binarized by threshold processing. By this binarizing processing, a binarized blood vessel region as shown in FIG. 80a is extracted. FIG. 80b shows the case where a shadow of a cancer or the like is binarized. When the shadow of the cancer or the like shown in FIG. 80b is compared with the shadow or the like of the blood vessel region shown in FIG. 80a, the difference therebetween can be readily understood, and it can be understood that the shadow of the cancer or the like has a shape close to that of a circle. In the case of the blood vessel shadow shown in FIG. 80a, an area ratio SR of the sum of areas s1a, s1b and s1c of the respective concave portions of the shadow to a total area s2 of the shadow is used to make a decision as to a focus candidate shadow. The area ratio SR may be found by the following ratio formula which simply shows the ratio of the area s1 to the area s2: SR=s1/s2, or it may also be found by the following ratio formula, which shows the ratio of the total of the area s1 and the area s2 to the area s2: SR=s2/(s1+s2). In the case of the shadow of the cancer or the like shown in FIG. 80b, an area ratio SR=s10/s20 of an area 10s of the concave portion of the shadow to a total area s20 of the shadow is used to make a decision as to a focus candidate shadow. FIG. 80c shows a method of finding the area of the concave portions. Details of the processing of finding the areas of the concave portions will be described below with reference to the flowchart of FIG. 82.

[Step S821] As shown in FIG. 80c, the CPU 40 selects a pair of points p1 and p2 on the contour of the shadow, and connects both points p1 and p2 by a straight line. The pair is selected only at the first time in this processing.

[Step S822] The CPU 40 places a point p which moves by a constant length at one time from the point p1 toward the point p2, on the straight line which connects the two points p1 and p2. Each time the point p moves by the constant length, the CPU 40 determines whether the point p exists on an extracted region (s2). If the decision result is yes (the p exists on the extracted region s2), the CPU 40 proceeds to Step S824, whereas, if the decision result is no, the CPU 40 proceeds to Step S823.

[Step S823] Since the point p does not exist on the extracted region (s2), the CPU 40 records a particular value (for example, "5") on that portion.

[Step S824] The CPU 40 determines whether the point p has completely moved on the straight line which connects the points p1 and p2, and if the decision result is no (the movement of the point p has not yet been completed), the CPU 40 returns to Step S822; whereas, if the decision result is yes (the movement of the point p has been completed), the CPU 40 proceeds to Step S825. By the processing of Step S822 to Step S824, while the point p is moving from the point p1 to the point p2, the particular value (for example, "5") is recorded in a region, except for the extracted region (s2).

[Step S825] In the case where the CPU 40 sets the point p1 as a fixed point and the point p2 as a moving point, the CPU 40 determines whether the moving point p2 has moved on the entire contour of the extracted region. In the case where the CPU 40 sets the point p2 as a fixed point and the point p1 as a moving point, the CPU 40 determines whether the moving point p1 has moved on the entire contour of the extracted region. If the decision result is no (the movement of the moving point has not yet been completed), the CPU 40 returns to Step S821 and performs similar processing on the next two points. If the decision result is yes, the CPU 40 proceeds to Step S826.

[Step S826] The CPU 40 finds the area (s1) of the extracted region in which the particular value (for example, "5") is recorded. This area s1 is the area of the concave portions.

The CPU 40 finds an area ratio RS of the area s1 to the area s2 of the extracted region.

[Step S828] The CPU 40 determines whether the area ratio RS is larger than a preset constant value. If the decision result is yes (larger), the CPU 40 proceeds to Step S829, whereas, if the decision result is no (smaller or equal), the CPU 40 proceeds to Step S82A.

[Step S829] Since it has been determined in Step S828 that the area ratio RS is larger than the constant value, the possibility that the extracted shadow is a blood vessel shadow is high. Accordingly, the CPU 40 deletes the shadow from focus candidate shadows.

[Step S82A] Since it has been determined in Step S828 that the area ratio RS is not larger than the constant value, the possibility that the extracted shadow is a focus candidate shadow is high. Accordingly, the CPU 40 selects the shadow as a focus candidate shadow and saves information, such as the coordinate position thereof.

It is preferable to identifiably display the nature of a focus candidate shadow, such as a positive indication that the focus candidate shadow is a focus, a nature close to a positive indication (apparent-positive) or a negative indicating that the focus candidate shadow is not a focus, because the display of the nature supports shadow inspection by a doctor. Accordingly, in the following embodiment, reference will be made to an image diagnosis supporting device that is capable of readily, instantaneously and identifiably displaying the nature of a shadow, which seems to be an extracted focus candidate.

FIG. 83 is a view showing one example of the case where information for identifying the nature of a focus candidate shadow on the basis of the area ratio RS, such as a positive indicating that the focus candidate shadow can be determined as a focus, a nature close to a positive (apparent-positive) and a negative indicating that the focus candidate shadow is not a focus, is displayed as image supplementary information. In the display of FIG. 83, the left-hand window displays a graph in which the horizontal axis indicates a CT image having a shadow which is to be judged according to the area ratio RS, and the vertical axis corresponds to the area ratio RS. The right-hand window displays the CT image which is the decision target. In the graph, white dots (?) denote the result of a computation on the extracted shadow, and they are displayed at positions corresponding to the magnitude of the area ratio RS. Initially, all marks are displayed as white dots (?) and whether the shadow is positive is in an undetermined state. When a triangle (?) on the bottom side of the graph is moved by a mouse, an arbitrary white dot (?) can be selected on the graph. The white dot (?) selected by the triangle (?) changes to a black dot (?). At the same time, a CT image corresponding to the selected black dot (?) is displayed on the right-hand window. Accordingly, the operator (doctor) who observes this CT image determines whether the shadow is positive or negative, and if the operator (doctor) determines that the shadow is negative, the operator (doctor) clicks a "false" icon on the bottom of the CT image with the mouse. In this manner, the black dot (?) changes to a square ( ). On the other hand, if the operator (doctor) determines that the shadow is positive, the operator (doctor) clicks a "positive" icon with the mouse. In this manner, the black dot (?) changes to an X mark. At this time, the highest one of the area ratios RS indicated by X marks becomes a decision threshold value. On the basis of this decision threshold value, a threshold value is determined. The threshold value is a value obtained by multiplying the decision threshold value by a constant (for example, 1.1). Namely, the threshold=the decision threshold value× the constant. Incidentally, the constant may be found by finding the distribution of squares ( ) and using a standard deviation thereof. Incidentally, in the case where the threshold value is determined, a decision as to white dots (?) is made on the basis of this threshold value. In this case, squares ( ) or X marks to which white dots (?) have changed on the basis of the decision with the threshold value may be displayed in different colors or by dotted lines so that the operator (doctor) can recognize that a decision as to the white dots (?) has been made on the basis of the threshold value. In this embodiment, the display as shown in FIG. 83 may also be displayed as an image that is impossible to identify or a focus candidate image as shown in FIG. 33. In this case, the white dots (?) indicative of the undetermined state may be displayed as image supplementary information on the side of the decision-impossible image, and the X marks determined as positive may be displayed as image supplementary information on the side of the candidate image.

Figure 84A:
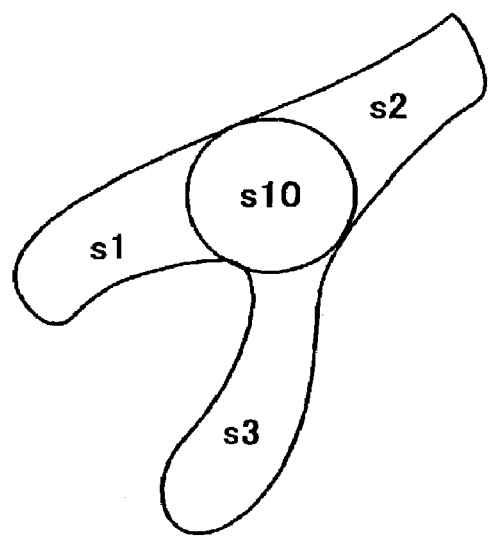
FIGS. 84a and 84b are diagrams showing a modification of the method of finding the area ratio.
Figure 84B:
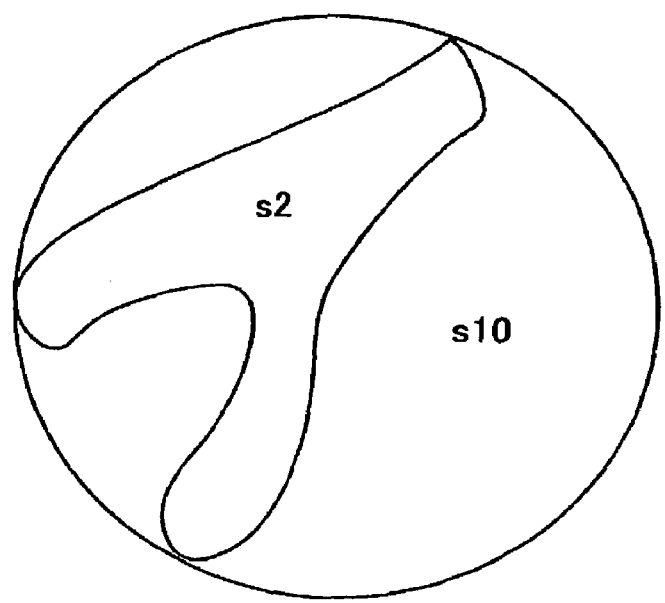

FIGS. 84*a*, 84*b*, 85*a* and 85*b* show a modification of the method of finding the area ratio. First, as shown in FIG. 84*a*, a circle is generated which is inscribed in the contour of a shadow at three points, and the area ratio RS of the total of areas s1 to s3 of individual regions into which the shadow is divided by the circle to an area s10 of the circle is found. This area ratio RS is calculated on the basis of RS=(s1+s2+s3)/s10. Then, a circle is generated which is circumscribed outside the shadow at three points, and the area ratio RS of the area s0 of the circle to the area s2 of the shadow is found. This area ratio RS is calculated on the basis of RS=s2/s10.

Figure 85A:
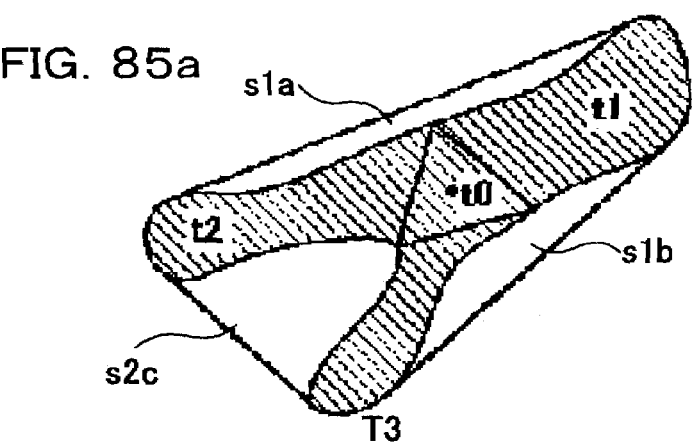
FIGS. 85a and 85b are diagrams showing a further modification of the method of finding the area ratio.
Figure 85B:
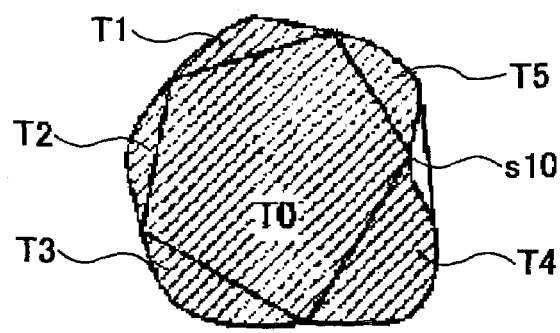

In FIG. 85*a*, a polygon (in FIG. 85*a*, a triangle) is generated which is inscribed in the adjacent lines of a blood vessel shadow, and the area ratio RS of the total of areas t1 to t3 of individual regions into which the shadow is divided by the polygon to an area t0 of the polygon is found. This area ratio RS is calculated by the formula RS=(t1+t2+t3)/t0. In FIG. 85*b*, a polygon (in FIG. 85*b*, a pentagon) which is inscribed in focus candidate shadow is generated, and the area ratio RS of the total of areas t1 to t5 of individual regions into which the shadow is divided by the polygon to an area T0 of the polygon is found. This area ratio RS is calculated by the formula RS=(t1+t2+t3+t4+t5)/T0. To find the area ratio, in addition to the above-described areas t0 to t3 and T0 to T5, the areas s1*a*, s1*b*, s1*c* and a10 of the respective concave portions formed outside the shadows may be arbitrarily used.

Furthermore, the concave portions have another feature. Namely, when a concave portion of a bifurcation of a blood vessel is found, there is a case where three separate regions are obtained. By using this fact, it is possible to delete a blood vessel bifurcation.

In the description of this embodiment, reference has been made to the case where the contour edge of a binary image is used. However, since the contour edge of a binary image corresponds to the isosbestic line of a multi-valued image shadow, it is possible to perform similar processing on the isosbestic line without binarization. Although the magnitude of this key feature quantity may be directly used in a decision, the key feature quantity may be provided as an input signal to a neural network together with other key feature quantities, and the output signal from this neural network may also be used in decision making means for selecting a suitable method from among a method using a variance and a method using an area ratio, according to the area of a sample to which the method is to be applied; for example, a selecting menu or the like may be selected with a mouse to improve the manipulability of doctor's diagnosis supporting software.

Figure 86A:
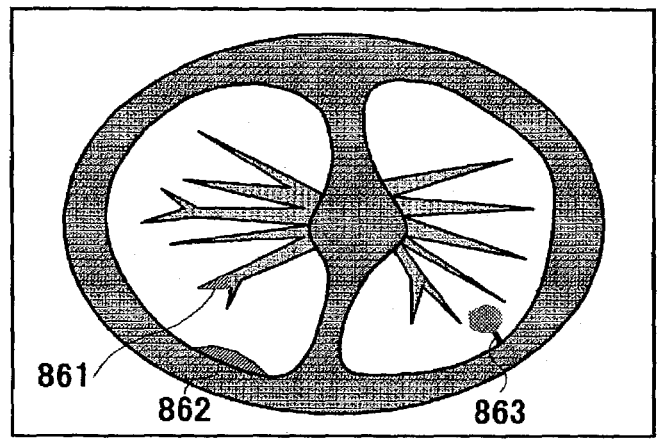
FIGS. 86a to 86c are diagrams showing one example of the case where a special shadow including a shadow of a pleural membrane is found.
Figure 86B:
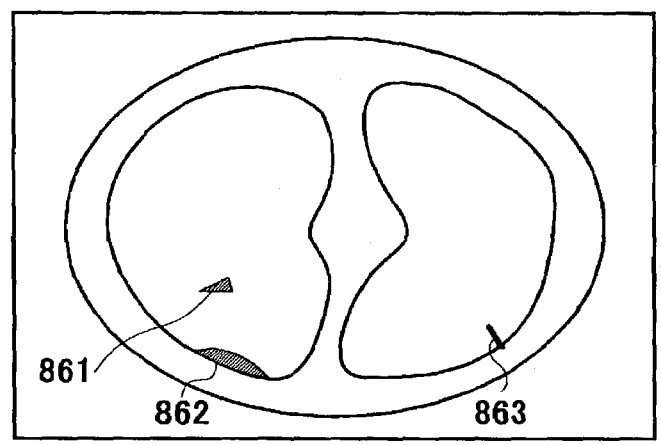
Figure 86C:
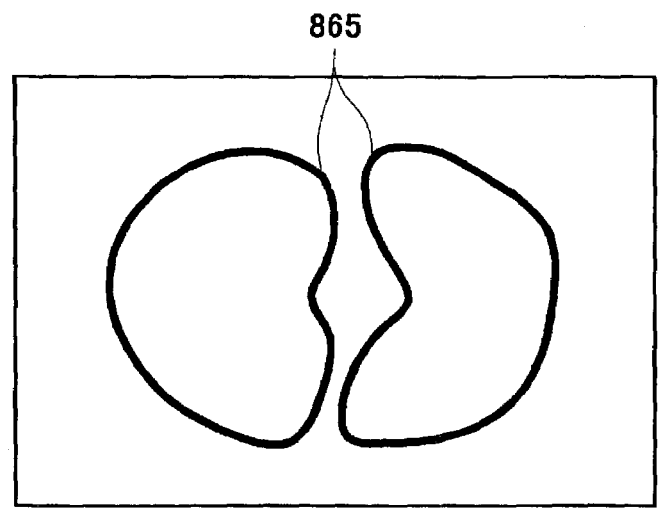

In addition, by combining a method using a variance and a method using an area ratio, it is possible to discriminate between a cancer shadow and a blood vessel shadow with far higher accuracy, whereby it is possible to improve the reliability of the diagnosis supporting software. In addition, in the extraction of a shadow, in the case where a special shadow, including a shadow of a pleural membrane, is to be found, processing which allows for specialty is needed, as shown in FIGS. 86*a* to 86*c*. FIGS. 86*a* to 86*c* show one example of the case where a special shadow, including a shadow of a pleural membrane, is found. In a CT image as shown in FIG. 86, there exist a shadow 861 due to inflammation or the like, a shadow 552 of a blood vessel or the like and a shadow 553 perpendicular to the pleural membrane. The CT image shown in FIG. 86*a* is binarized into an image as shown in FIG. 86*b*. Furthermore, as shown in FIG. 86*c*, when only a contour 865 of the pleural membrane is taken out and the relationship between the shadows 861 to 863 and the contour 865 of the pleural membrane is viewed, the normal blood vessel shadow 861 is deleted on condition that it is not in contact with the contour 865 of the pleural membrane. Furthermore, it is possible to discriminate between the wide shadow 862 due to inflammation and the shadow 863, which is in perpendicular contact with the contour 865 of the pleural membrane, because the wide shadow 862 and the shadow 863 differ in the length of contact with the contour 865 of the pleural membrane. By designating a particular range of threshold values for the CT image and emphasizing the image, it is possible to extract the contour 865, as shown in FIG. 86*c*. After the contour 865 has been extracted, the extracted contour 865 is cut and isolated to identify each of the blood vessel shadows 861 to 863 on the basis of the state of connection of the contour 865 of the pleural membrane with each of the blood vessel shadows 861 to 863. In this manner, it is possible to identify the kinds of shadows from the relationship between each of the shadows and the contour of the pleural membrane.

In the case where the above-described various feature quantities are used to make a decision as to whether a shadow is a focus candidate, even if processing, such as statistical processing or neural networks, are adopted in an intermediate step, there is a case where it is finally necessary to determine accurate parameters for thresholding processing or the like. In this case, it goes without saying that it is common practice to adopt so-called "learning" in which parameters are made more accurate through operations in an inverse direction from normal processing, from images obtained every day.

In addition, according to this invention, it is possible to provide novel feature quantities for identifying focus shadows and processing procedures using such feature quantities.

As described above, according to the image diagnosis supporting device of this invention, the above-described various kinds of shadows can be handled in an integrated manner, and so it becomes easy to adjust parameters for improving the discrimination capability, and it also becomes easy to create computer programs.

In addition, since a focus candidate shadow can be selected from shadows by simple processing, the computation time of a computer can be reduced, whereby an accurate focus candidate can be rapidly extracted and an extracted focus candidate can be instantaneously displayed for a doctor. Accordingly, the image diagnosis supporting device is useful in the early finding of cancers or the like or the inspection of the effect of treatment.

The invention claimed is:

1. An image diagnosis supporting device characterized by:
   digitizing means for applying predetermined image processing to a medical image and generating a multi-valued image comprising discrete multiple values;
   extracting means for executing at least one decision making processing routine on the multi-valued image generated by the digitizing means and extracting from among shadows a focus candidate shadow, a shadow which is likely to indicate a diseased site; and
   display means for displaying in the medical image the focus candidate shadow extracted by the extracting means so that it is easily identifiable; and
   image generating means for extracting from the medical image only pixels belonging to a pixel value range corresponding to the kind of shadow made by a target being searched and generating a medical image of the target.

2. An image diagnosis supporting device according to claim 1, characterized in that the extracting means extracts the focus candidate shadow from the multi-valued image generated by the digitizing means and the medical image.

3. An image diagnosis supporting device according to claim 1, further characterized by the digitizing means applying predetermined mage processing to the target image and generating the multi-valued image, the extracting means extracting the focus candidate shadow from the multi-valued image and the decision target medical image on the basis of the multi-valued image generated by the digitizing means.

4. An image diagnosis supporting device according to claim 1, further characterized in that the extracting means adjusts a magnification ratio or a reduction ratio of the multi-valued image according to a size of a shadow which is a target, and extracts the focus candidate shadow from the multi-valued image that has been so adjusted.

5. An image diagnosis supporting device according to claim 1, characterized in that the extracting means selects a combination of at least one of the above decision making processing routines according to the slice thickness of the medical image, and extracts the focus candidate shadow from the multi-valued image through the selected combined processing routines.

6. An image diagnosis supporting device according to claim 1, characterized in that the decision making means detects a center or a weighted center of a shadow on the basis of the multi-valued image, rotates on the shadow in the multi-valued image a radius of predetermined length about a reference point near the center or the weighted center of the shadow, samples pixels of the shadow in the multi-valued image which intersect the radius as it is rotated, and makes a decision as to whether the shadow is a focus candidate shadow, on the basis of the pixel values.

7. An image diagnosis supporting device according to claim 6, characterized by sampling the values of pixels forming a spiral or forming concentric circles as the radius rotates, finding a representative value of each of loops formed by the rotation on the basis of the individual pixel values, comparing the representative value with a reference value stored in advance, and making a decision as to the nature of the shadow.

8. An image diagnosis supporting device according to claim 6, characterized by causing a radius of predetermined length to make rotations on each of the plurality of shadows in the multi-valued image about a reference point near a detection point of each of the shadows in the multi-valued image, sampling pixel values which intersect the radius, checking correlation of the pixel values of mutually adjacent loops formed by the rotations, and making a decision as to each of the shadows on the basis of the correlation.

9. An image diagnosis supporting device according to claim 1, characterized in that the decision making means detects the center or the weighted center of a shadow on the basis of the multi-valued image, rotates two straight lines which are at a predetermined angle $\eta$ to each other about a reference point near the center or the weighted center of a shadow in the multi-valued image, the medical image or the target medical image, samples pixel values of the shadow which intersect the two straight lines, searches for anisotropy of the shadow on the basis of the pixel values corresponding to the two straight lines, and makes a decision as to whether the shadow is a focus candidate shadow.

10. An image diagnosis supporting device according to claim 1, characterized in that the decision making means detects a center or a weighted center of a shadow on the basis of the multi-valued image, causes a radius of predetermined length to make rotations about a reference point near the center or the weighted center of a shadow in the multi-valued image, samples pixel values of the shadow where it intersects the radius, detects at least two radii at which the pixel values sharply change with the rotation and finds the angle of elevation, the angle between these radii, and compares the angle of elevation with a reference value stored in advance, and makes a decision as to whether the shadow is a focus candidate shadow.

11. An image diagnosis supporting device according to claim 10, characterized in that in the case where the decision making means compares the angle of elevation with the reference value stored in advance and determines that the shadow is a focus candidate shadow, the decision making means finds the length of contact between the shadow and a wall portion and determines on the basis of the length of contact whether the shadow is a focus candidate shadow or a shadow of an object accompanying a focus.

12. An image diagnosis supporting device according to claim 1, characterized in that the decision making means detects a center or a weighted center of a shadow on the basis of the multi-valued image, rotates a straight line of predetermined length about a reference point near the center or the weighted center of a shadow in the multi-valued image to find the maximum value or minimum value, or both, of a length of the portion of the straight line which intersects the shadow in the multi-valued image, samples first and second pixel values in the multi-valued image which are located a predetermined distance outward from the shadow along an extension of a straight line which passes through the reference point and is approximately perpendicular to a straight line with the above minimum value as well as third and fourth pixel values in the multi-valued image which are located a predetermined distance outward from the shadow along an extension of the straight line of the minimum value, fifth and sixth pixel values in the multi-valued image which are located a predetermined distance outward from the shadow along an extension of a straight line which passes through the reference point and is approximately perpendicular to the straight line with the above maximum value as well as seventh and eighth pixel values in the multi-valued image which are located a predetermined distance outward from the shadow along an extension of the straight line of the maximum value, or ninth to twelfth pixel values in the multi-valued image which are located a predetermined distance outward from the shadow along the extensions of the straight lines of the maximum value and the minimum value, and makes a decision as to whether the shadow is a focus candidate shadow, on the basis of the first to fourth pixel values, the fifth to eighth pixel values or the ninth to twelfth pixel values.

13. An image diagnosis supporting device according to claim 1, characterized in that the decision making means detects a center or a weighted center of a shadow on the basis of the multi-valued image, rotates a radius of predetermined length about a reference point near the center or the weighted center of the shadow on the shadow in the multi-valued image to sample pixel values of the shadow which intersects the radius in the multi-valued image, generates a density waveform on the basis of the pixel values, finds the radii of at least two locations corresponding to angles at which peaks of the density waveform appear, finds the bisector of an angle made by the detected radii, and makes a decision as to whether the shadow is a focus candidate shadow on the basis of the sum of the pixel values on the detected radii and the sum of the pixel values on the bisector.

14. An image diagnosis supporting device according to claim 1, characterized in that the decision making means detects a center or a weighted center of a shadow on the basis of the multi-valued image, rotates a radius of predetermined length about a reference point near the center or the weighted center of the shadow on the shadow in the multi-valued image to sample pixel values of the shadow which intersect the radius, generates a density waveform on the basis of the pixel values, finds radii lying at least two locations at which peaks of the density waveform appear, and makes a decision as to whether the shadow is a focus candidate shadow on the basis of the average value of the pixel values on the detected radii and the average value of the pixel values on radii other than the detected radii.

15. An image diagnosis supporting device according to claim 1, characterized in that the decision making means detects a center or a weighted center of a shadow on the basis of the multi-valued image, rotates a straight line of predetermined length about a reference point near the center or the weighted center of the shadow on the shadow to find the length of the portion of the straight line which intersects the shadow in the multi-valued image, performs Fourier expansion on a curve describing the length of the straight line portion with varying angle of rotation, and makes a decision as to whether the shadow is a focus candidate shadow on the basis of a result of this Fourier expansion.

16. An image diagnosis supporting device according to claim 15, characterized by rotating the straight line of predetermined length on the shadow in the multi-valued image, plotting a curve where the vertical axis represents the length of the portion of the straight line which intersects the shadow and the horizontal axis represents the angle, detecting a positions of valleys of the curve, and performing interpolation between the values with a predetermined curve to draw the curve.

17. An image diagnosis supporting device according to claim 1, characterized in that the decision making means detects a center or a weighted center of a shadow on the basis of the multi-valued image, rotates a straight line of predetermined length about a reference point near the center or the weighted center of the shadow to find a minimum value of the length of the portion of the straight line which intersects the shadow, divides the area of the shadow by the second power of the minimum value, and makes a decision as to whether the shadow is a focus candidate shadow, on the basis of the divided area.

18. An image diagnosis supporting device according to claim 1, characterized in that the extracting means detects a center or a weighted center of a shadow on the basis of the multi-valued image, rotates a straight line of predetermined length about a reference point near the center or the weighted center of the shadow to find a minimum value of length of the portion of the straight line which intersects the shadow, finds a cutting length on the basis of the minimum value, and excludes an elongated shadow of the cutting length which touches the main shadow.

19. An image diagnosis supporting device according to claim 1, characterized in that the decision making means detects a center or a weighted center of a shadow on the basis of the multi-valued image, draws a closed curve corresponding to a shape of the shadow about a reference point near the center or the weighted center of the shadow, finds short curve lengths in a case where the closed curve is superposed on the shadow or short curve lengths in a case where the closed curve is not superposed on the shadow as well as the number of the short curve lengths, and makes a decision as to whether the shadow is a focus candidate shadow on the basis of the relationship between the short curve lengths and the number of the short curve lengths.

20. An image diagnosis supporting device according to claim 1, characterized in that the decision making means samples pixel values in the medical image which intersect at least one straight line passing through the shadow and extending in a predetermined direction, find a positive or negative density gradient of each pixel on the straight line on the basis of the pixel values, defines the number of pixels in which the positive gradient continues as a positive run length and defines the number of pixels by which the negative gradient continues as a negative run length, finds positive and negative run lengths and the number of the positive run lengths and the number of positive run lengths, and makes a decision as to whether the shadow is a focus candidate shadow on the basis of the relationship between the positive and negative run lengths and the number of the positive run lengths and the number of positive run lengths.

21. An image diagnosis supporting device according to claim 1, characterized in that the decision making means finds a variance or a standard deviation of pixel values of a shadow in the multi-valued image, and makes a decision as to whether the shadow is a focus candidate shadow on the basis of the variance or the standard deviation.

22. An image diagnosis supporting device according to claim 21, characterized by detecting a center or a weighted center of a shadow on the basis of the multi-valued image, rotating a straight line of predetermined length about a reference point near the center or the weighted center of the shadow to sample pixel values of the shadow which intersect the straight line in the multi-valued image, and finding the standard deviation of the pixel values which intersect the straight line at a predetermined angle, for making the decision as to the shadow.

23. An image diagnosis supporting device according to claim 21, characterized by dividing a shadow in the multi-valued image into a plurality of regions and finding a variance or a standard deviation of the pixel values in each of the regions, for making the decision as to the shadow.

24. An image diagnosis supporting device according to claim 21, characterized by finding an outside-shadow variance or an outside-shadow standard deviation of pixel values in a predetermined region outside a shadow in the multi-valued image, for making the decision as to the shadow.

25. An image diagnosis supporting device according to claim 21, characterized by detecting a center or a weighted center of a shadow in the multi-valued image and finding a variance or a standard deviation of distance from the center or the weighted center to an edge of the shadow along the entire periphery of the shadow, for making the decision as to the shadow.

26. An image diagnosis supporting device according to claim 21, characterized by finding a variance or a standard deviation of a distance from an edge to an edge of a shadow in the horizontal and vertical directions, for making the decision as to the shadow.

27. An image diagnosis supporting device according to claim 1, characterized in that the extracting means performs processing which detects a center or a weighted center of a shadow on the basis of the multi-valued image, rotates a straight line of predetermined length about a reference point near the center or the weighted center of a shadow on the multi-valued image, the medical image or the decision target medical image, finds a maximum value of length of the portion of the straight line which intersects the shadow, sets a strip-shaped extended line approximately parallel with a straight line of the maximum value, and adds a predetermined value to a pixel memory located on the strip-shaped extension, repeatedly executing this processing a number of times equal to the number of the shadows.

28. An image diagnosis supporting device according to claim 1, characterized in that the decision making means compares shadows existing in two multi-valued images adjacent to each other in a slice-thickness direction of the medical image, and makes a decision as to whether each of the shadows is a focus candidate shadow, on the basis of whether the shadows overlap each other in more than a predetermined proportion.

29. An image diagnosis supporting device according to claim 1, characterized in that the decision making means uses at least two sets from among a set of axial images, a set of sagittal images and a set of coronal images which are perpendicular to one another, and extracts a focus candidate shadow from each of the at least two sets and makes a decision as to whether the shadow is a focus candidate shadow, on the basis of the position of the focus candidate shadow extracted in each of the images.

30. An image diagnosis supporting device according to claim 29, characterized by, in the case where the shadow is a focus candidate shadow, storing in a memory the coordinate position of the focus candidate shadow and information on the focus candidate shadow.

31. An image diagnosis supporting device according to claim 1, characterized in that the decision making means finds the area of the shadow region and also finds an area of a concave region formed in an edge portion of the shadow region, finds a ratio of the area of the shadow region to the area of the concave region, and makes a decision as to whether the shadow is a focus candidate shadow, on the basis of the found ratio.

32. An image diagnosis supporting device according to claim 1, characterized in that the decision making means finds an area of a circle or a polygon inscribed in an edge of the shadow region and the area of separated regions into which the shadow is divided by the circle or the polygon, and finds the ratio of the area of the circle or the polygon to the area of the separated regions of the shadow, and makes a decision as to whether the shadow is a focus candidate shadow, on the basis of the found ratio.

33. An image diagnosis supporting device according to claim 1, characterized in that the decision making means finds an area of a circle or a polygon circumscribed to the outer edge of the shadow region, finds a ratio of the area of the circle to the area of the shadow, and makes a decision as to whether the shadow is a focus candidate shadow, on the basis of the found ratio.

34. An image diagnosis supporting device according to claim 1, characterized in that the display means displays a shadow determined as the focus candidate shadow through the decision making processing routines in the medical image or in an area other than the medical image each time one processing of the decision making processing routines is completed.

35. An image diagnosis supporting device according to claim 34, characterized in that a first display area for displaying a focus candidate shadow or image supplementary information, a second display area for displaying an undetected image in which a focus candidate is not detected or image supplementary information, and a third display area for displaying an image impossible to identify and image supplementary information are provided on a picture of the display means.

36. An image diagnosis supporting device according to claim 1, characterized in that the display means displays a magnified image of a vicinity of the focus candidate shadow in the medical image or in an area other than the medical image.

37. An image diagnosis supporting device according to claim 1, characterized in that the display means displays the medical image by controlling the order of display thereof according to the position of the focus candidate shadow in the medical image.

38. An image diagnosis supporting device according to claim 1, characterized in that the display means displays the medical images having the focus candidate shadow in an order controlled by a pointing device, according to the movement the pointing device in the medical image with the focus candidate shadow.

39. An image diagnosis supporting device according to claim 1, characterized in that the display means displays a marker line which encloses the extracted focus candidate shadow.

40. An image diagnosis supporting device according to claim 39, characterized in that the extracting means calculates the probability that a shadow is a focus, and the display means changes displays the marker line in the display on the basis of the focus certainty.

41. An image diagnosis supporting device according to claim 39, characterized in that in the case where markers overlap to enclose a plurality of focus candidate shadows, the display means displays the markers with an overlapping portion thereof erased.

42. An image diagnosis supporting device according to claim 39, characterized in that the display means performs contrast emphasis processing or gamma emphasis processing on the area enclosed with the marker and clearly displays the focus candidate shadow.

43. An image diagnosis supporting device according to claim 39, characterized in that in the case where a hidden mode in which display of the marker is disabled is selected, the display means stops displaying the marker and displays, on a picture, information indicating that the hidden mode is presently active, and automatically displays the marker when a predetermined time elapses after the hidden mode has been started.

44. An image diagnosis supporting device according to claim 1, characterized in that the extracting means finds length of contact between the extracted focus candidate shadow and a wall portion and determines on the basis of the length of contact whether the shadow is a shadow of an object accompanying a focus, the display means displaying the shadow of an object accompanying a focus enclosed with a marker.

45. An image diagnosis supporting device according to claim 1, characterized in that the display means displays focus candidate shadows respectively extracted from medical images photographed at mutually different points of time, with the respective focus candidate shadows enclosed with markers which makes it possible to discriminate between the points of time of photography.

46. An image diagnosis supporting device according to claim 1, characterized in that the display means displays a marker having an elliptical shape whose long-axis direction coincides with a long-axis direction of the extracted focus candidate shadow, with the focus candidate shadow enclosed with the marker.

47. An image diagnosis supporting device according to claim 46, characterized in that in the case where markers overlap one another to enclose a plurality of focus candidate shadows, respectively, the display means displays the markers with the overlapping portion thereof erased.

48. An image diagnosis supporting device according to claim 46, characterized in that the display means performs contrast emphasis processing or gamma emphasis processing on an area enclosed with the markers and clearly displays the focus candidate shadows.

49. An image diagnosis supporting device according to claim 46, characterized in that in the case where a hidden mode in which display of the markers is disabled is selected, the display means stops displaying the markers and displays information indicating that the hidden mode is presently active, and automatically displays the markers when a predetermined time elapses after the hidden mode has been started.

50. An image diagnosis supporting device according to claim 1, characterized in that the display means displays a medical image in which the focus candidate shadow exists and a medical image in which the focus candidate shadow does not exist, by moving image display with different display times allocated for the respective medical images.

51. An image diagnosis supporting device according to claim 1, characterized in that the display means does not display a medical image which has not yet undergone shadow detection by a doctor so that it can be identified.

* * * * *